(12) United States Patent
Barsanti et al.

(10) Patent No.: US 10,392,404 B2
(45) Date of Patent: Aug. 27, 2019

(54) COMPOUNDS AND COMPOSITIONS AS KINASE INHIBITORS

(71) Applicant: NOVARTIS AG, Basel (CH)

(72) Inventors: Paul Andrew Barsanti, Pleasant Hill, CA (US); Matthew T. Burger, Belmont, MA (US); Yan Lou, Pleasanton, CA (US); Gisele A. Nishiguchi, Arlington, MA (US); Valery Rostislavovich Polyakov, Morage, CA (US); Savithri Ramurthy, Emeryville, CA (US); Sharadha Subramanian, San Ramon, CA (US); Benjamin R. Taft, Oakland, CA (US); Huw Rowland Tanner, San Francisco, CA (US); Lifeng Wan, Union City, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/510,613

(22) PCT Filed: Sep. 11, 2015

(86) PCT No.: PCT/IB2015/056990
§ 371 (c)(1),
(2) Date: Mar. 10, 2017

(87) PCT Pub. No.: WO2016/038583
PCT Pub. Date: Mar. 17, 2016

(65) Prior Publication Data
US 2017/0260200 A1    Sep. 14, 2017

Related U.S. Application Data

(60) Provisional application No. 62/049,462, filed on Sep. 12, 2014.

(51) Int. Cl.
| | |
|---|---|
| *A61K 31/444* | (2006.01) |
| *C07D 498/08* | (2006.01) |
| *C07D 401/14* | (2006.01) |
| *C07D 413/14* | (2006.01) |
| *C07D 213/74* | (2006.01) |
| *C07D 401/04* | (2006.01) |
| *C07D 401/10* | (2006.01) |
| *C07D 407/14* | (2006.01) |
| *C07D 411/14* | (2006.01) |
| *C07D 413/12* | (2006.01) |
| *A61K 31/4418* | (2006.01) |
| *A61K 31/496* | (2006.01) |
| *A61K 31/501* | (2006.01) |
| *A61K 31/5377* | (2006.01) |

(Continued)

(52) U.S. Cl.
CPC .......... *C07D 498/08* (2013.01); *A61K 31/444* (2013.01); *A61K 31/4418* (2013.01); *A61K 31/496* (2013.01); *A61K 31/501* (2013.01); *A61K 31/5377* (2013.01); *A61K 31/541* (2013.01); *C07D 213/74* (2013.01); *C07D 213/85* (2013.01); *C07D 401/04* (2013.01); *C07D 401/10* (2013.01); *C07D 401/14* (2013.01); *C07D 405/12* (2013.01); *C07D 405/14* (2013.01); *C07D 407/14* (2013.01); *C07D 411/14* (2013.01); *C07D 413/12* (2013.01); *C07D 413/14* (2013.01); *C07D 451/02* (2013.01)

(58) Field of Classification Search
CPC ...................................................... A61K 31/444
See application file for complete search history.

(56) References Cited

U.S. PATENT DOCUMENTS

| 9,278,981 B2 | 3/2016 | Furet et al. |
| 2007/0093529 A1 | 4/2007 | Finsinger et al. |
| 2015/0183801 A1 | 7/2015 | Furet et al. |

FOREIGN PATENT DOCUMENTS

| WO | 2005058832 A1 | 6/2005 |
| WO | 2013171640 A1 | 11/2013 |

(Continued)

*Primary Examiner* — Andrew D Kosar
*Assistant Examiner* — John S Kenyon
(74) *Attorney, Agent, or Firm* — Scott W. Reid

(57) ABSTRACT

The present invention provides compounds of Formula (I) and (II) as described herein, and salts thereof and therapeutic uses of these compounds for treatment of disorders associated with Raf kinase activity. The invention further provides pharmaceutical compositions comprising these compounds, and compositions comprising these compounds and a therapeutic co-agent.

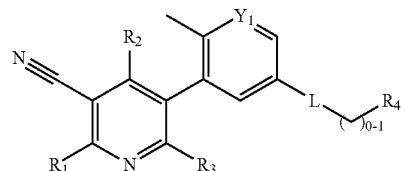

I

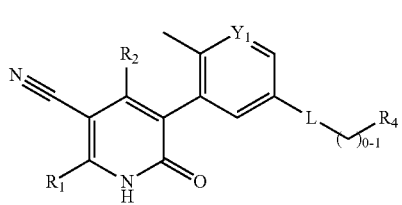

II

10 Claims, No Drawings

(51) Int. Cl.
*A61K 31/541* (2006.01)
*C07D 213/85* (2006.01)
*C07D 405/12* (2006.01)
*C07D 405/14* (2006.01)
*C07D 451/02* (2006.01)

(56) References Cited

FOREIGN PATENT DOCUMENTS

| | | | | |
|---|---|---|---|---|
| WO | 2013171641 | A1 | 11/2013 | |
| WO | WO-2013171641 | A1 * | 11/2013 | ........... C07D 213/81 |
| WO | 2015016372 | A1 | 2/2015 | |

* cited by examiner

COMPOUNDS AND COMPOSITIONS AS KINASE INHIBITORS

FIELD OF THE INVENTION

The invention provides compounds that inhibit Raf kinases, and are accordingly useful for treating certain disorders associated with excessive Raf kinase activity, including cell proliferation disorders such as cancers. The invention further provides pharmaceutical compositions containing these compounds and methods of using these compounds to treat conditions including cancer.

BACKGROUND

Protein Kinases are involved in very complex signaling cascades that regulate most cellular functions, including cell survival and proliferation. These signaling pathways have been heavily studied, particularly in the context of disorders caused by dysregulated cellular function, such as cancer. The mitogen-activated protein kinase (MAPK) cascade has been studied extensively, for example, and kinases in this pathway (e.g., RAS, RAF, MEK, and ERK) have been exploited as target sites for drug discovery. Mutated B-Raf is found in a significant fraction of malignancies (over 30% of all tumors and 40% of melanomas), and several drug candidates that inhibit a common B-Raf mutant (V600E, an activating mutation found in many cancers, particularly in cutaneous malignant melanoma, thyroid cancer, colorectal cancer, and ovarian cancer) have been reported, including GDC-0879, PLX4032, and PLX4720, while other inhibitors targeting C-Raf or B-Raf (or both) include sorafenib, XL281 RAF265, and BAY43-9006. These examples demonstrate that compounds that inhibit B-Raf or C-Raf are useful to treat various cancers.

The MAPK signaling cascade includes RAS, Raf, MEK and ERK kinases, each of which is actually a group of related proteins. These proteins function collectively as a signal transduction cascade where the number of distinct kinases and their varying substrate specificities create a complex and highly branched pathway. Raf, for example, consists of monomers referred to as A-Raf, B-Raf, and C-Raf (also called Raf-1), each of which functions primarily as a dimer. The RAF complex includes heterodimers as well as homodimers of these three species, bringing the total number of dimeric species in the Raf group to six, with each of these having a number of sites where phosphorylation at serine, threonine or tyrosine can cause either activation or inhibition. Due to the complexity of the pathway and its regulation, it has been reported that inhibitors of B-Raf can cause paradoxical activation of the pathway, apparently due to conformational effects on the kinase domain of Raf that affect dimerization, membrane localization, and interaction with RAS-GTP. In particular, ATP-competitive inhibitors can exhibit opposing effects on the signaling pathway, as either inhibitors or activators, depending on the cellular context. As a result, B-Raf inhibitors effective against tumors having the activating B-Raf mutation V600E may not be as effective as expected in tumors having wild-type B-Raf or KRas mutations.

The present invention provides novel inhibitors of Raf kinases, including A-Raf, B-Raf and/or C-Raf, and use of these compounds to treat disorders associated with excessive or undesired levels of Raf activity, such as certain cancers. The compounds of the invention minimize undesired pathway activation effects, and thus can be more efficacious and more predictable in vivo than the B-Raf inhibitors that cause paradoxical pathway activation even when they have similar in vitro potency. The compounds of the invention bind in a DFG-out mode, making them type 2 inhibitors, which have been reported to be less prone to induce paradoxical activation. The compounds are suited for treatment of BRaf wild-type and KRas mutant tumors, as well as B-RafV600E mutant tumors.

SUMMARY OF THE INVENTION

In one aspect, the invention provides compounds of formula I or II:

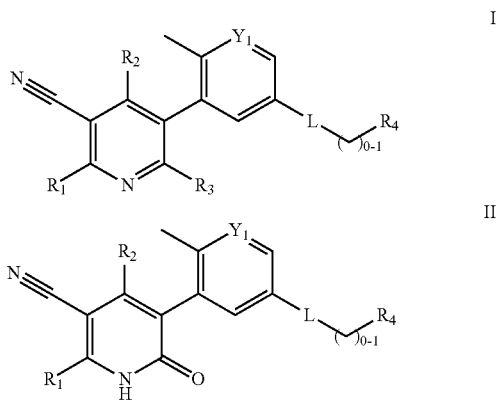

in which:
L is selected from —NHC(O)— and —C(O)NH—;
$Y_1$ is selected from N and CH;
$R_1$ is selected from H, halo, isopropyl, methyl-sulfonyl, $OR_6$, $NR_5R_6$, methoxy-ethoxy, 2-oxa-5-azabicyclo[2.2.]heptan-5-yl, 3-oxa-8-azabicyclo[3.2.1]octan-8-yl, 8-oxa-3-azabicyclo[3.2.1]octan-3-yl, 2-oxo-1,2-dihydropyridin-4-yl, tetrahydro-2H-pyranyl, 4-oxopyridin-1(4H)-yl, pyrazolyl, pyridazinyl and azetidinyl; wherein said azetidinyl, pyrazolyl or 2-oxo-1,2-dihydropyridin-4-yl is unsubstituted or substituted with 1 to 3 groups independently selected from methyl and hydroxy;
$R_2$ is selected from H and methyl;
$R_3$ is selected from H, methyl and amino;
$R_4$ is selected from:

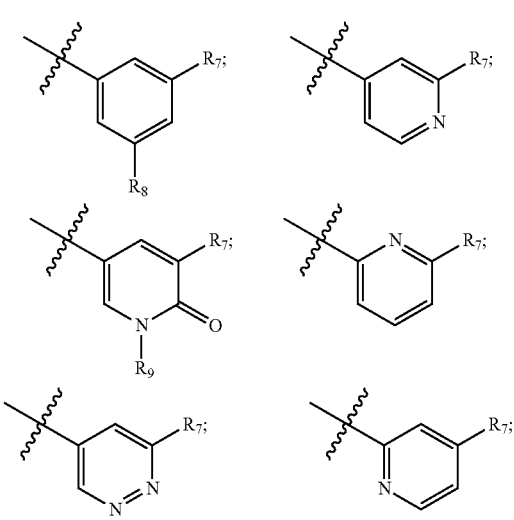

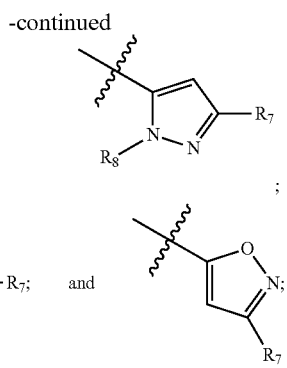

wherein

indicates the point of attachment with L;

R$_5$ is selected from H and methyl;

R$_6$ is selected from H and methyl, ethyl, propyl, isopropyl, cyclopropyl, methoxy, hydroxy-ethyl, methoxy-ethyl, tetrahydro-2H-pyranyl, pyridinyl, tetrahydrofuranyl and oxetanyl; or R$_5$ and R$_6$, together with the nitrogen to which R$_5$ and R$_6$ are attached form a group selected from morpholino, 2-oxopyridin-1(2H)-yl, 1,1-dioxidothiomorpholino, piperazinyl, pyrrolidinyl, imidazolyl and pyrazolyl; wherein said morpholino, pyrazolyl or imidazolyl can be unsubstituted or substituted with 1 to 2 methyl groups;

R$_7$ is selected from H, methyl, —CF$_3$, —C(CH$_3$)$_2$CN, —C(CH$_3$)$_2$OH, —C(CH$_3$)$_2$F, —CF$_2$CH$_3$, —CF$_2$H, isopropyl, cyclopropyl and methyl-sulfonyl; wherein said cyclopropyl is unsubstituted or substituted with cyano;

R$_8$ is selected from H, methyl, ethyl, isopropyl, —C(CH$_3$)$_2$OH and —C(CH$_3$)$_2$NH$_2$; and R$_9$ is selected from H and ethyl.

In a second aspect, the present invention provides a pharmaceutical composition which contains a compound of Formula I or II or a N-oxide derivative of Formula I or II, individual isomers and mixture of isomers thereof; or a pharmaceutically acceptable salt thereof, in admixture with one or more suitable excipients.

In another aspect, the compounds of Formula I or II are inhibitors of Raf kinases as shown by data herein, and are accordingly useful to treat conditions such as melanoma, breast cancer, sarcoma, GI tumors such as gastrointestinal stromal tumors, ovarian cancer, sarcoma, GI tumors such as gastrointestinal stromal tumors, and other malignancies associated with excessive Raf pathway activity, particularly in cancers driven by Ras mutations. In addition, the compounds of the invention exhibit low levels of paradoxical activation of the Raf pathway.

In another aspect, the invention provides pharmaceutical compositions comprising a compound of Formula I or II admixed with at least one pharmaceutically acceptable carrier or excipient, optionally admixed with two or more pharmaceutically acceptable carriers or excipients.

In addition, the invention includes combinations of a compound of Formula I or II with a co-therapeutic agent, optionally including one or more pharmaceutically acceptable carriers, and methods of treatment using a compound of Formula I or II in combination with a co-therapeutic agent.

Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like.

In another aspect, the invention provides a method to treat a condition characterized by excessive or undesired levels of activity of Raf, especially B-Raf and/or C-Raf, which comprises administering to a subject in need of such treatment an effective amount of a compound of Formula I or II or any subgenus thereof as described herein, or a pharmaceutical composition comprising such compound. The subject can be a mammal, and is preferably a human. Conditions treatable by the compounds and methods described herein include various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. The invention thus includes compounds of Formula I or II and the subgenera thereof that are disclosed herein, including each species disclosed herein, for use in therapy, particularly for use to treat cancers such as melanoma, breast cancer, lung cancer, liver cancer, sarcoma, GI tumors such as gastrointestinal stromal tumors, sarcoma, GI tumors such as gastrointestinal stromal tumors, ovarian cancer, colorectal cancer, thyroid cancer, and pancreatic cancer. The invention also includes use of such compounds for manufacture of a medicament for treating these conditions.

The invention includes compounds of Formula I or II and the subgenera of Formula I or II described herein, and all stereoisomers (including diastereoisomers and enantiomers), tautomers and isotopically enriched versions thereof (including deuterium substitutions), as well as pharmaceutically acceptable salts of these compounds. In particular, where a heteroaryl ring containing N as a ring atom is optionally substituted with hydroxyl, e.g., a 2-hydroxypyridine ring, tautomers where the hydroxyl is depicted as a carbonyl (e.g., 2-pyridone) are included. Compounds of the present invention also comprise polymorphs of compounds of formula I (or sub-formulae thereof) and salts thereof.

DETAILED DESCRIPTION

The following definitions apply unless otherwise expressly provided.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety having up to 20 carbon atoms. Unless otherwise provided, alkyl refers to hydrocarbon moieties having 1 to 10 carbon atoms, 1 to 6 carbon atoms, or 1 to 4 carbon atoms. Typically, alkyl groups have 1-6 carbon atoms. "Lower alkyl" refers to alkyl groups having 1-4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, or 1-4 substituents, up to the number of hydrogens present on the unsubstituted alkyl group. Suitable substituents for alkyl groups, if not otherwise specified, may be selected from halogen, CN, oxo, hydroxy, substituted or unsubstituted $C_{1-4}$ alkoxy, substituted or unsubstituted $C_{3-6}$ cycloalkyl, substituted or unsubstituted $C_{3-6}$ heterocycloalkyl, substituted or unsubstituted phenyl, amino, ($C_{1-4}$ alkyl)amino, di($C_{1-4}$ alkyl)amino, $C_{1-4}$ alkylthio, $C_{1-4}$ alkylsulfonyl, —C(=O)— $C_{1-4}$ alkyl, COOH, COO($C_{1-4}$ alkyl), —O(C=O)— $C_{1-4}$ alkyl, —NHC(=O)$C_{1-4}$ alkyl and —NHC(=O)O$C_{1-4}$ alkyl groups; wherein the substituents for substituted $C_{1-4}$ alkoxy, substituted $C_{3-6}$ cycloalkyl, $C_{3-6}$ heterocycloalkyl, and substituted phenyl are up to three groups selected from halo, $C_{1-4}$ alkyl, $C_{1-4}$ haloalkyl, $C_{1-4}$ alkoxy, amino, hydroxy, and CN. Preferred substituents for alkyl groups include halogen, CN, oxo, hydroxy, $C_{1-4}$ alkoxy, $C_{3-6}$ cycloalkyl, phenyl, amino, ($C_{1-4}$ alkyl)amino, di($C_{1-4}$ alkyl)amino, $C_{1-4}$ alkylthio, $C_{1-4}$ alkylsulfonyl, —C(=O)— $C_{1-4}$ alkyl, COOH, —COO($C_{1-4}$ alkyl), —O(C=O)— $C_{1-4}$ alkyl, —NHC(=O) $C_{1-4}$ alkyl and NHC (=O)O $C_{1-4}$ alkyl groups.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the substituents described as suitable and preferred for alkyl groups.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g, trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-10, or 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable and preferred substituents are selected from the substituents listed above for alkyl groups, except that hydroxyl and amino are not normally present on the carbon that is directly attached to the oxygen of the substituted 'alkyl-O' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino". "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are selected from the suitable or preferred substituents named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

DESCRIPTION OF PREFERRED EMBODIMENTS

The present invention provides compounds, compositions and methods for the treatment of kinase related disease, particularly Raf kinase related diseases; for example: various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. Various embodiments of the invention are described herein. It will be recognized that features specified in each embodiment may be combined with other specified features to provide further embodiments of the present invention. The following embodiments are representative of the invention.

In one embodiment, with reference to compounds of formula I and II are compounds of formula Ia:

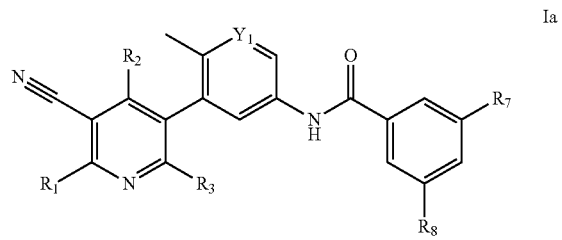

Ia in which: $Y_1$ is selected from N and CH; $R_1$ is selected from H, halo, isopropyl, methyl-sulfonyl, $OR_6$, $NR_5R_6$, methoxy-ethoxy, 2-oxa-5-azabicyclo[2.2.1]heptan-5-yl, 3-oxa-8-azabicyclo[3.2.1]octan-8-yl, 8-oxa-3-azabicyclo[3.2.1]octan-3-yl, 2-oxo-1,2-dihydropyridin-4-yl, tetrahydro-2H-pyranyl, 4-oxopyridin-1(4H)-yl, pyrazolyl, pyridazinyl and azetidinyl; wherein said azetidinyl, pyrazolyl or 2-oxo-1,2-dihydropyridin-4-yl is unsubstituted or substituted with 1 to 3 groups independently selected from methyl and hydroxy; $R_2$ is selected from H and methyl; $R_3$ is selected from H, methyl and amino; $R_7$ is selected from H, methyl, —$CF_3$, —$C(CH_3)_2CN$, —$C(CH_3)_2OH$, —$C(CH_3)_2$F, —$CF_2CH_3$, —$CF_2H$, isopropyl, cyclopropyl and methylsulfonyl; wherein said cyclopropyl is unsubstituted or substituted with cyano; R$_8$ is selected from H, methyl, ethyl, isopropyl, —C(CH$_3$)$_2$OH and —C(CH$_3$)$_2$NH$_2$; and the pharmaceutically acceptable salt thereof.
In a further embodiment are compounds, or pharmaceutically acceptable salts thereof, selected from:
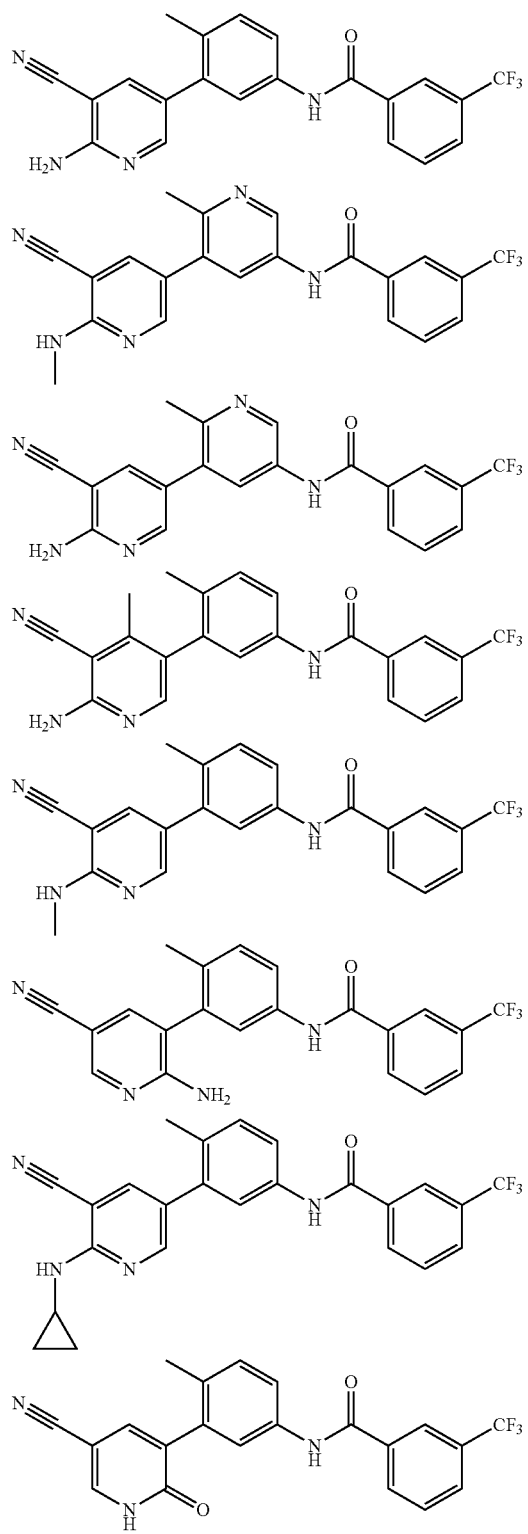
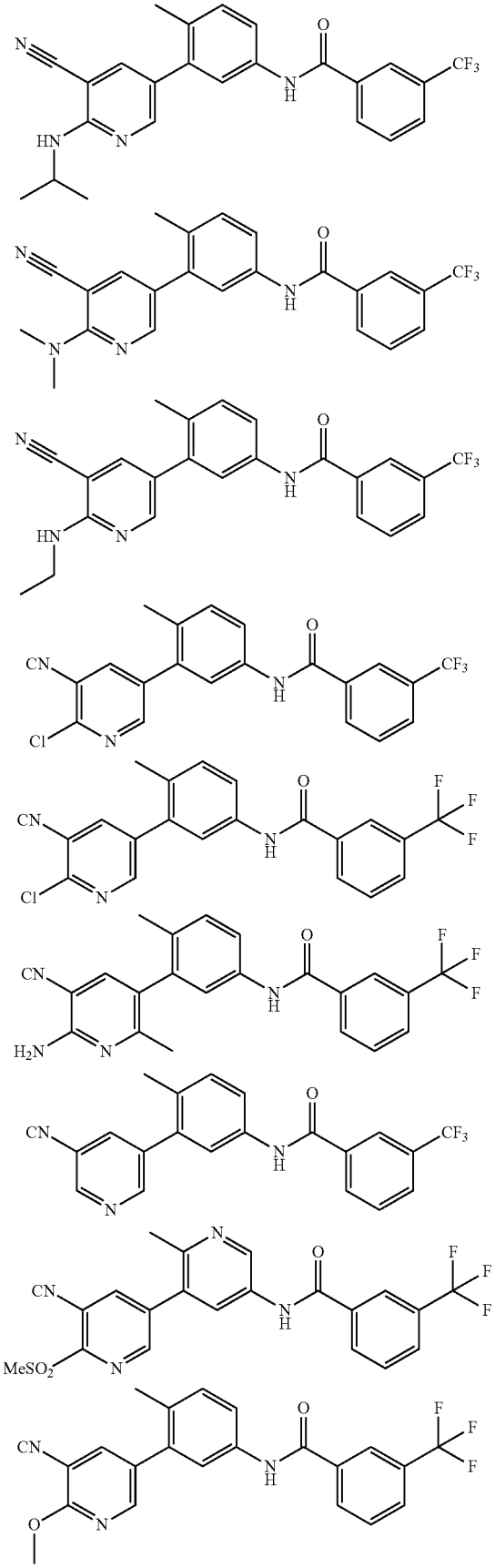

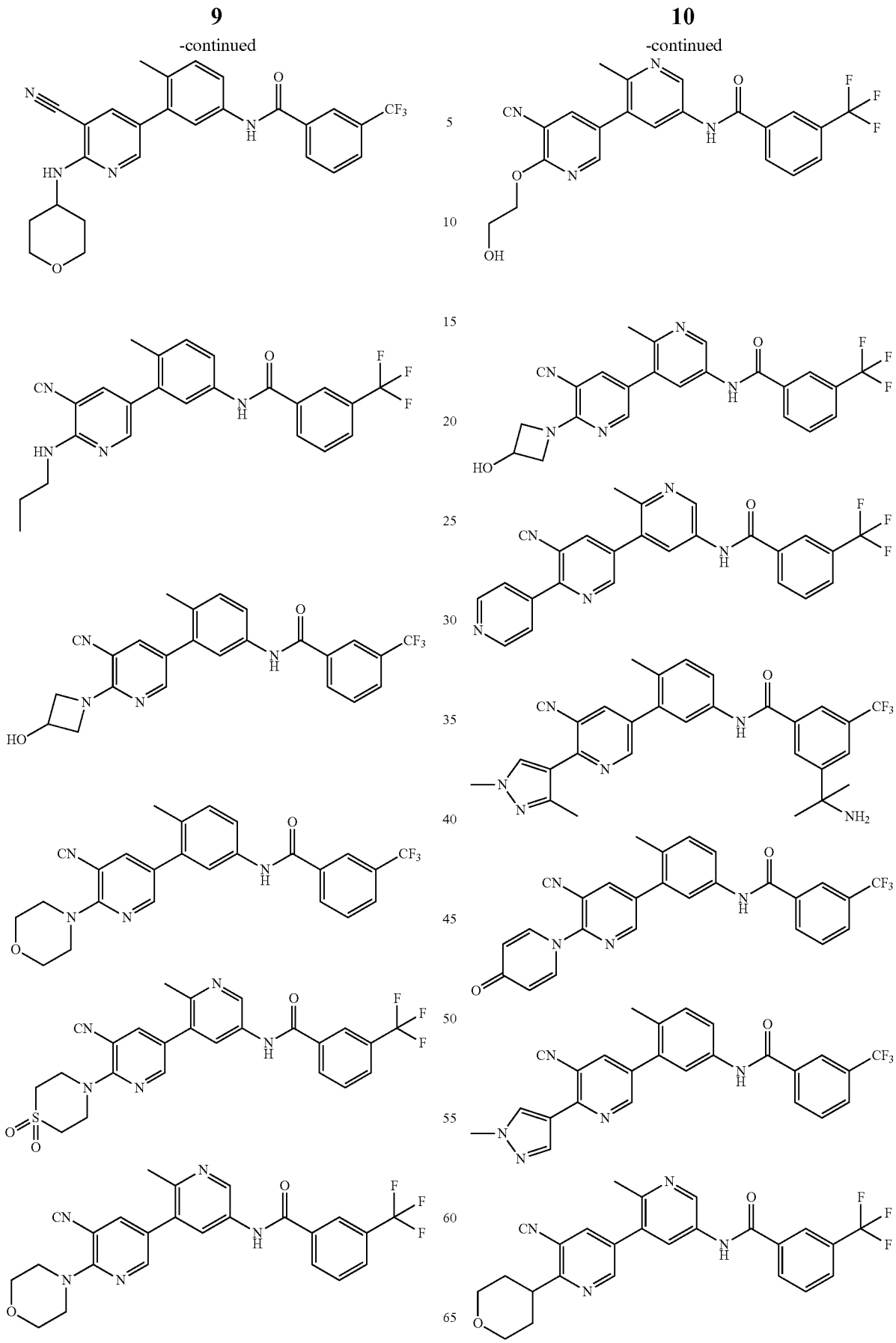

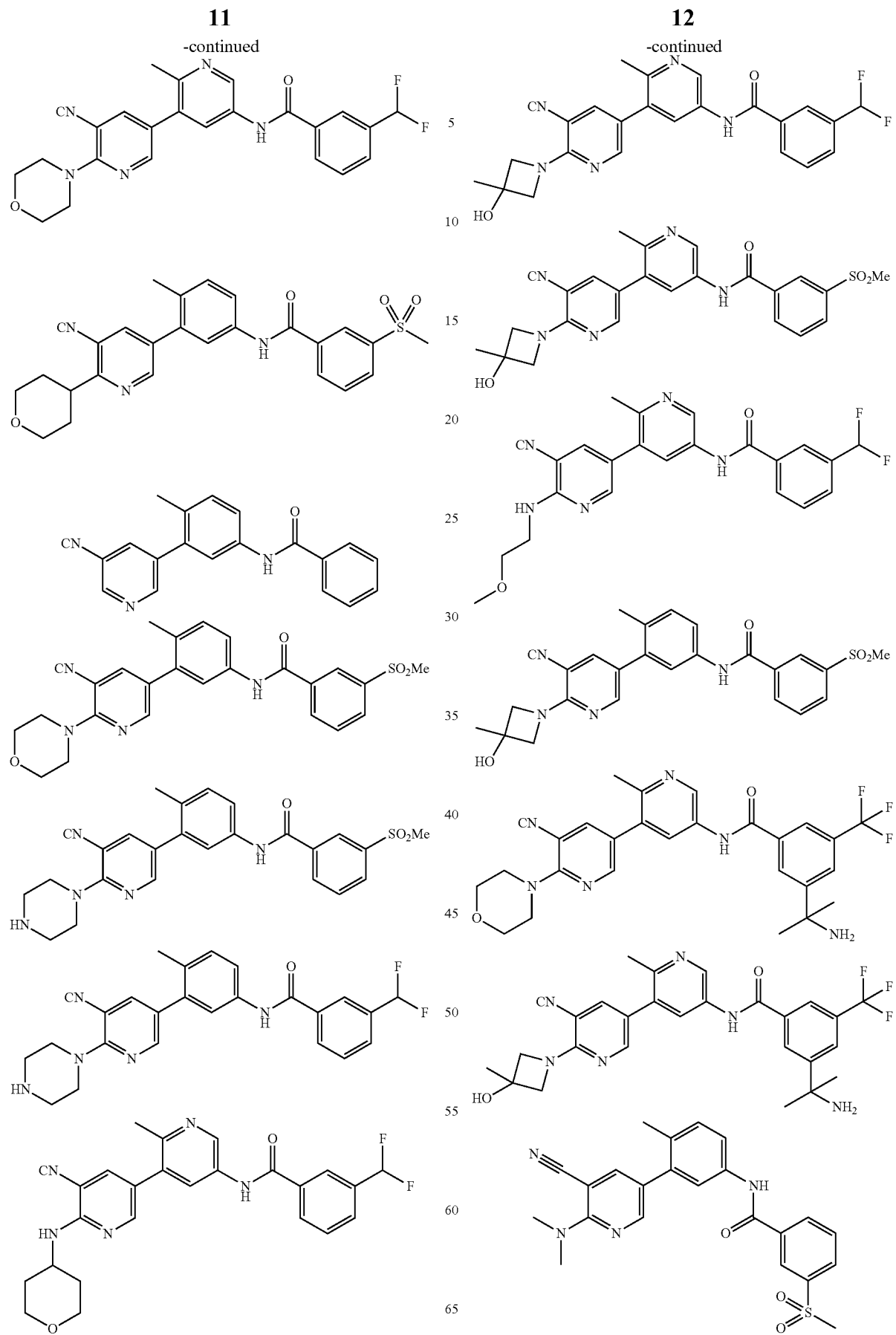

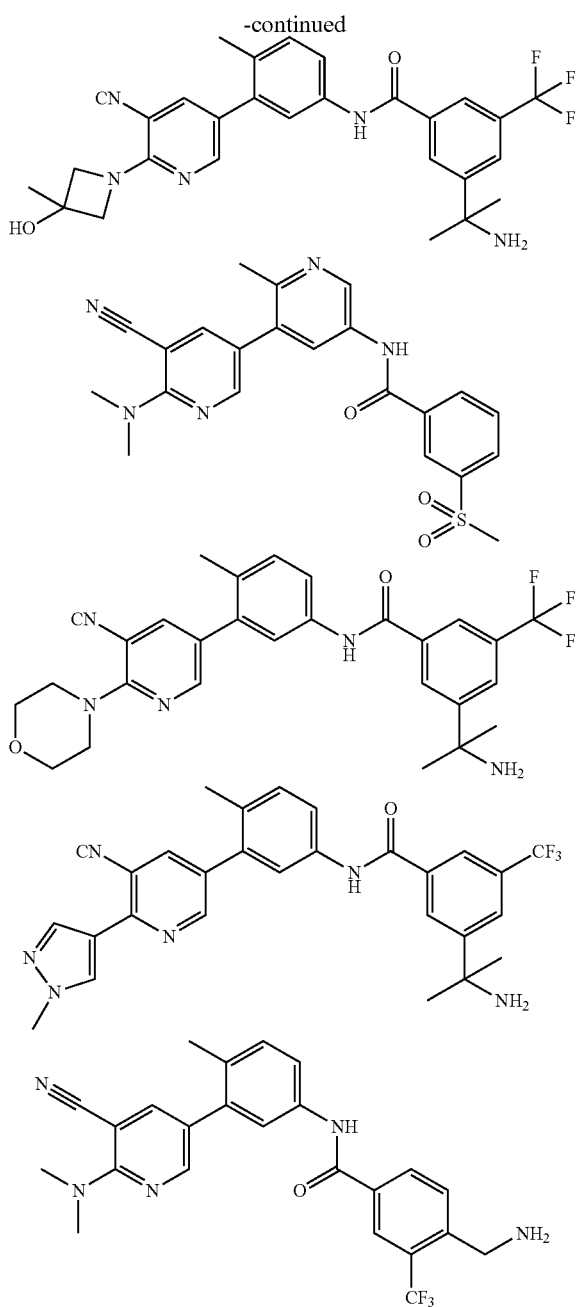

In another embodiment are compounds of formula Ib:

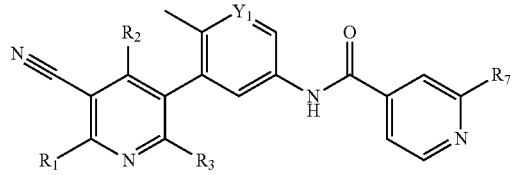

in which: $Y_1$ is selected from N and CH; $R_1$ is selected from H, halo, isopropyl, methyl-sulfonyl, $OR_6$, $NR_5R_6$, methoxy-ethoxy, 2-oxa-5-azabicyclo[2.2.1]heptan-5-yl, 3-oxa-8-azabicyclo[3.2.1]octan-8-yl, 8-oxa-3-azabicyclo[3.2.1]octan-3-yl, 2-oxo-1,2-dihydropyridin-4-yl, tetra- hydro-2H-pyranyl, 4-oxopyridin-1(4H)-yl, pyrazolyl, pyridazinyl and azetidinyl; wherein said azetidinyl, pyrazolyl or 2-oxo-1,2-dihydropyridin-4-yl is unsubstituted or substituted with 1 to 3 groups independently selected from methyl and hydroxy; $R_2$ is selected from H and methyl; $R_3$ is selected from H, methyl and amino; $R_1$ is selected from H, methyl, —$CF_3$, —$C(CH_3)_2CN$, —$C(CH_3)_2OH$, —$C(CH_3)_2F$, —$CF_2CH_3$, —$CF_2H$, isopropyl, cyclopropyl and methyl-sulfonyl; wherein said cyclopropyl is unsubstituted or substituted with cyano; and the pharmaceutically acceptable salt thereof.

In a further embodiment are compounds, or pharmaceutically acceptable salts thereof, selected from:

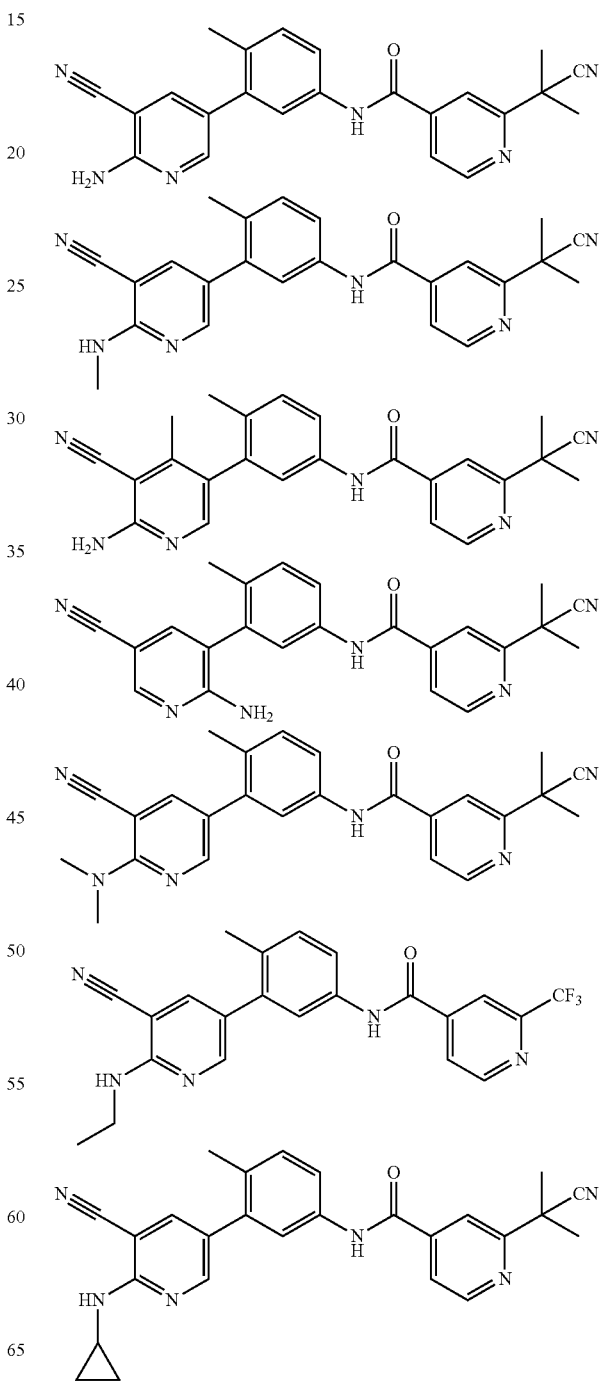

15
-continued
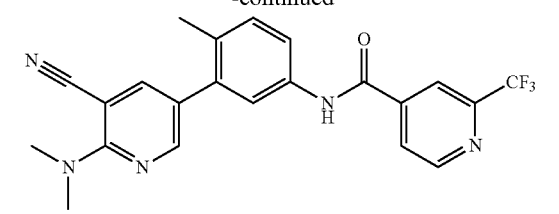
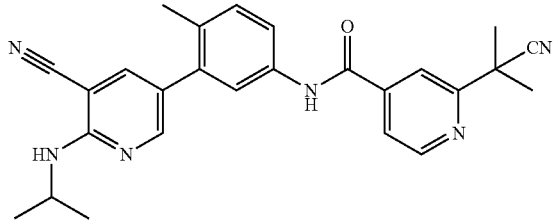
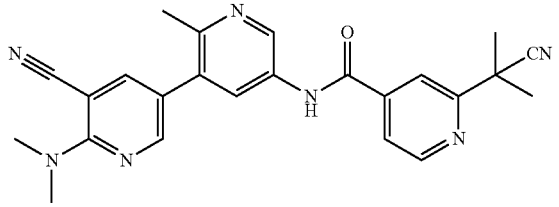
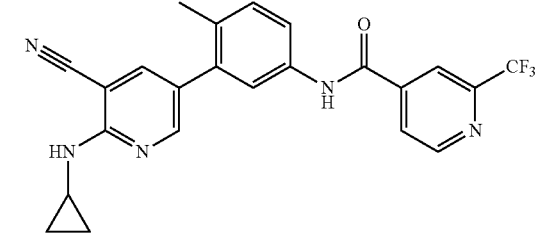
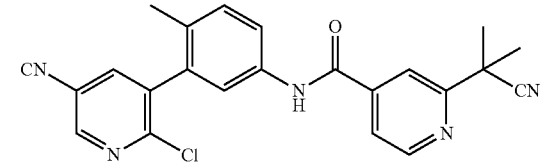
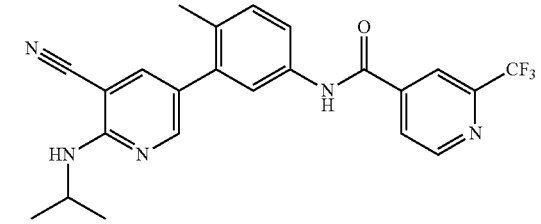
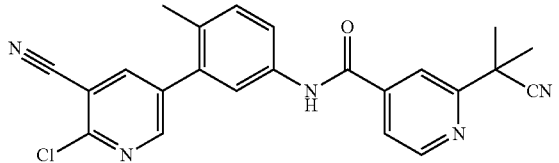
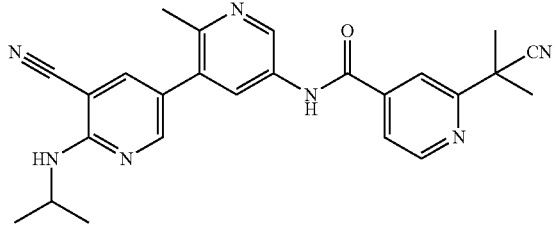
16
-continued
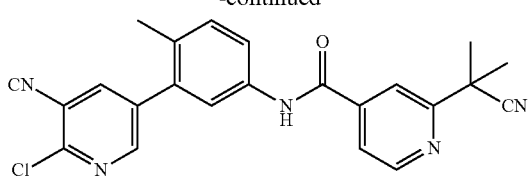
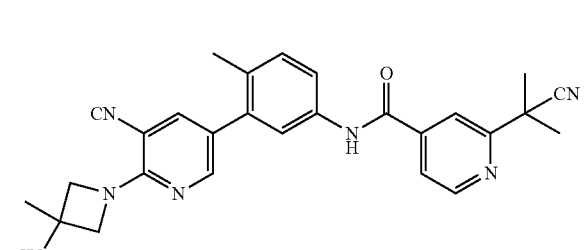
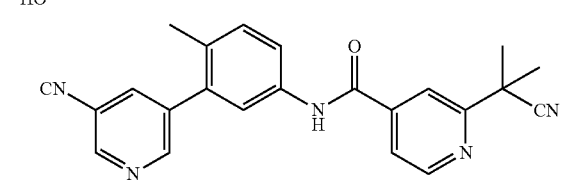
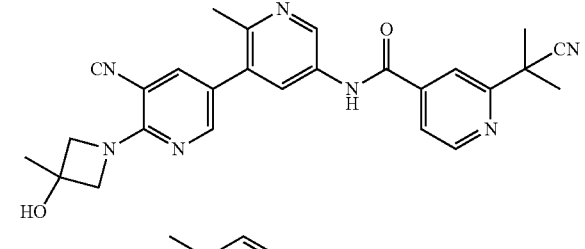
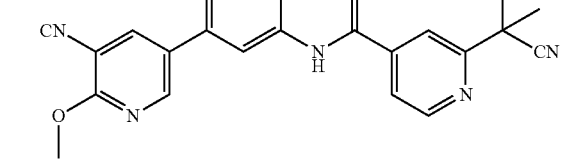
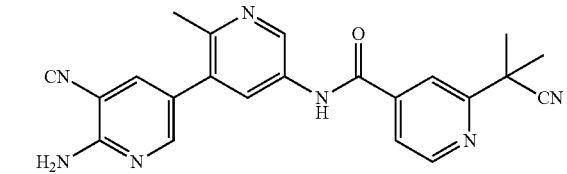
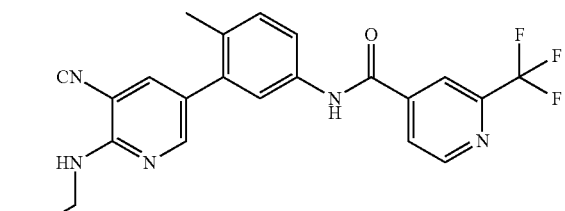
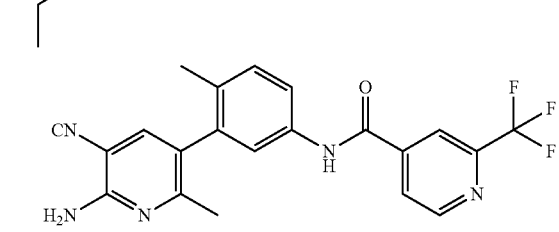

17
-continued
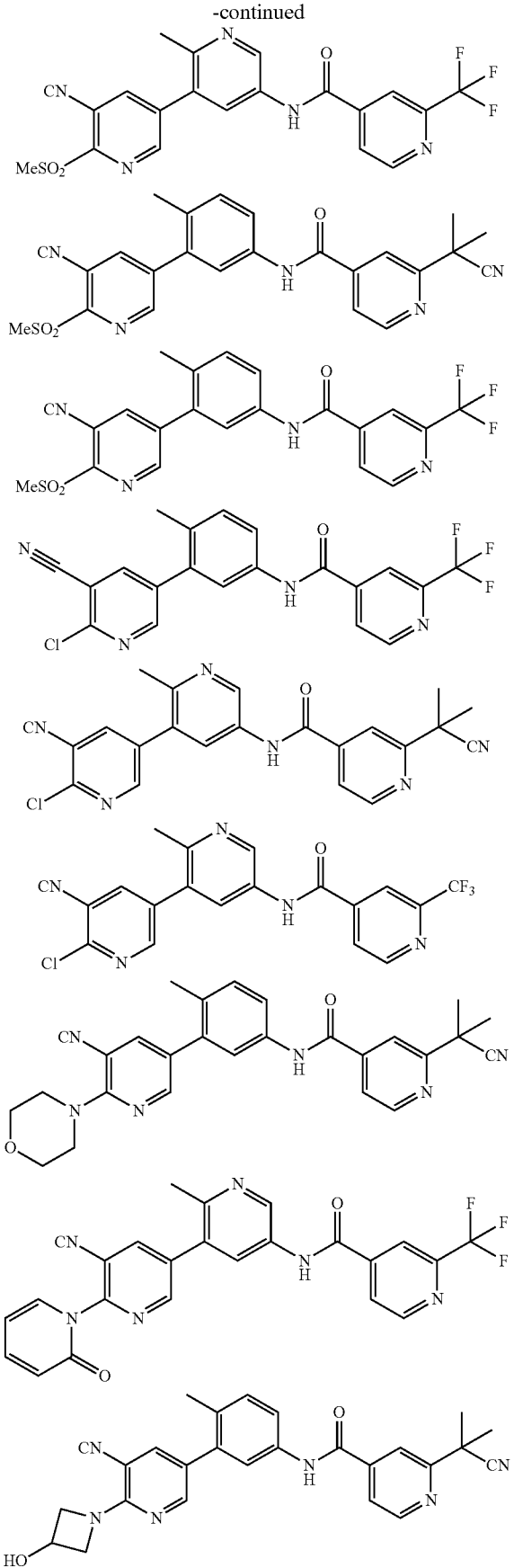
18
-continued
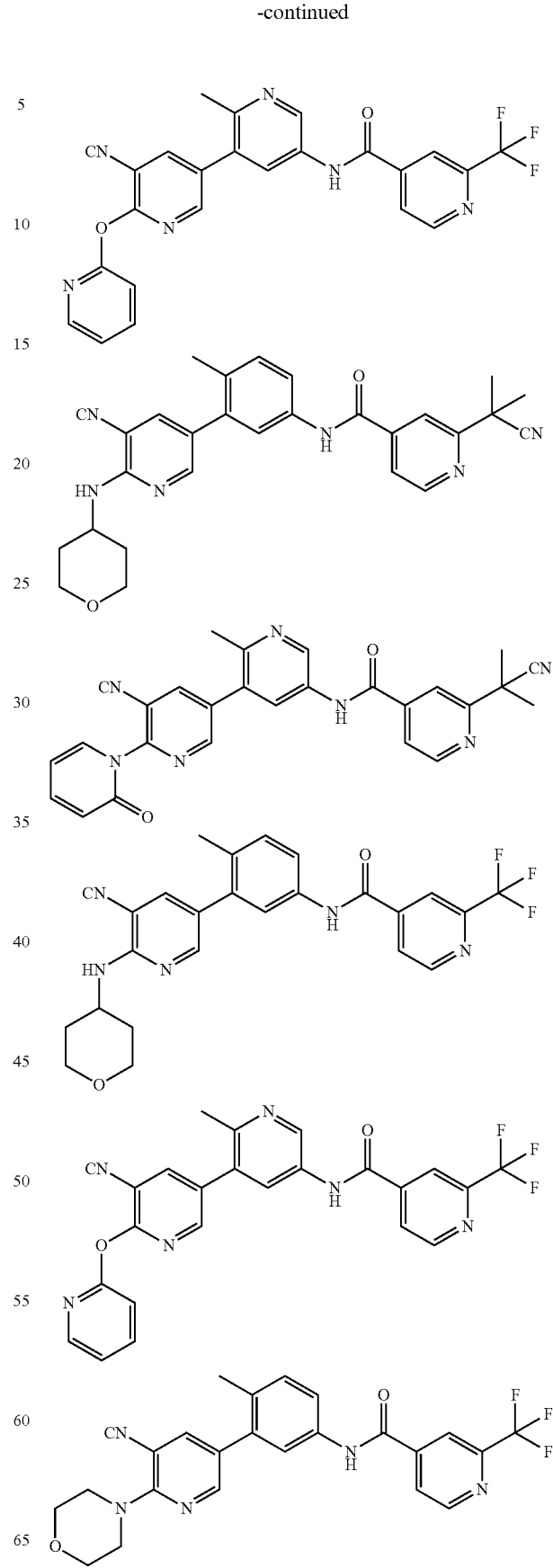

-continued
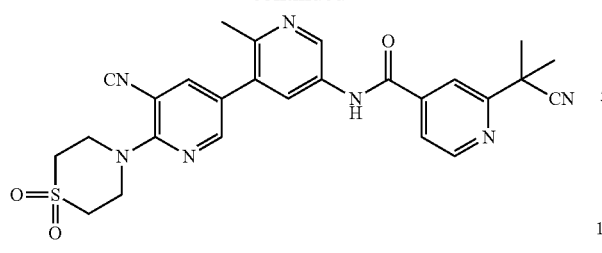
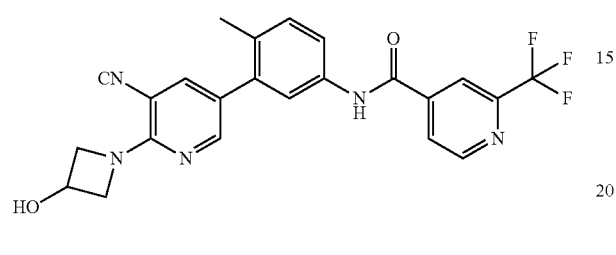
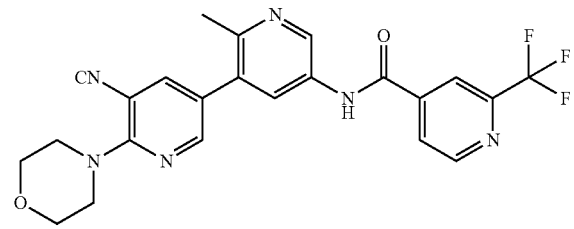
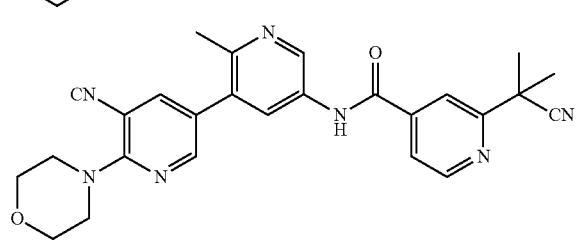
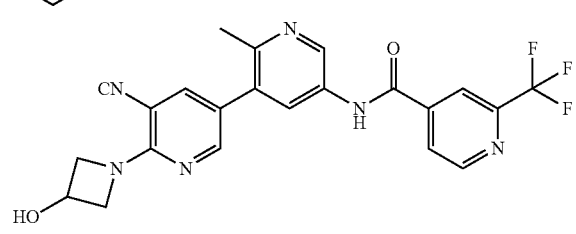
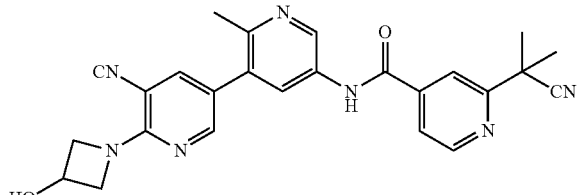
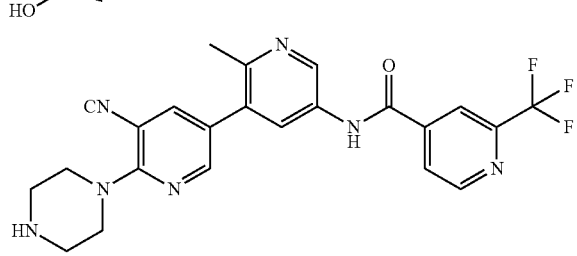
-continued
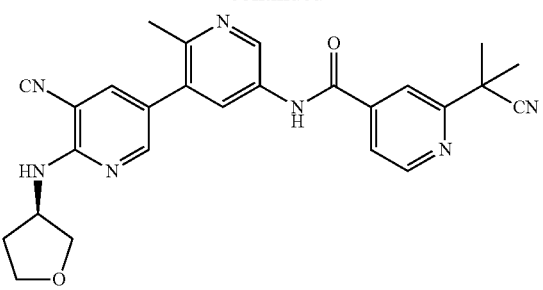
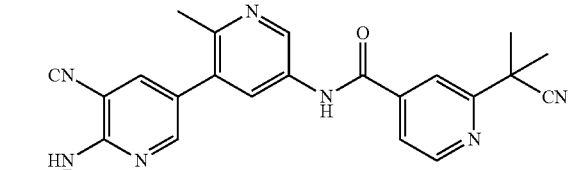
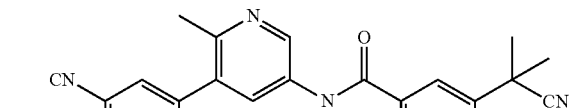
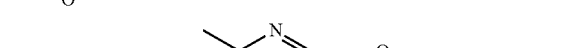
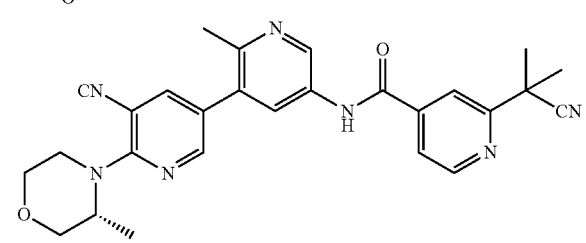
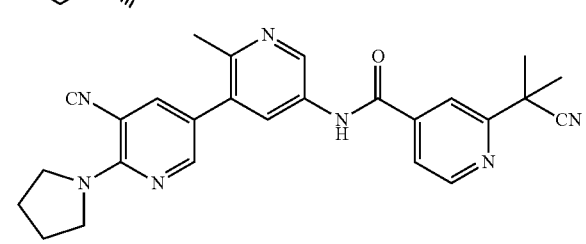

-continued
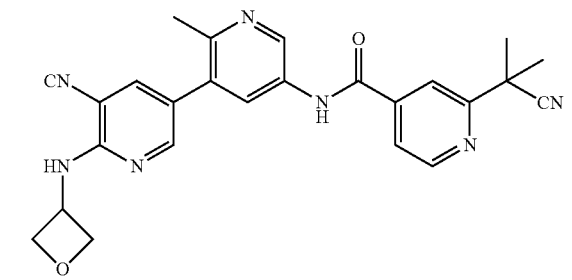
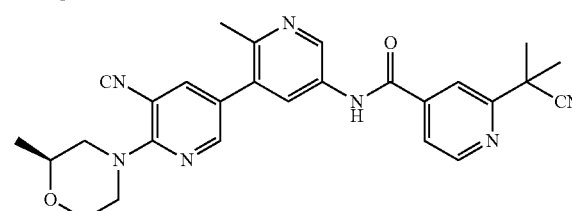
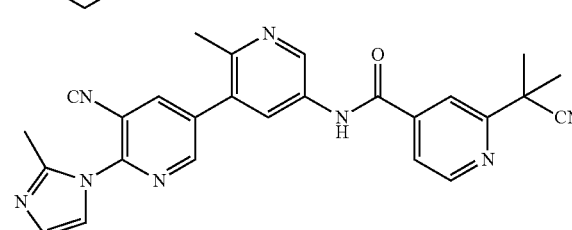
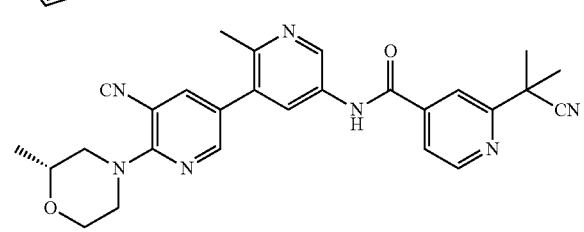
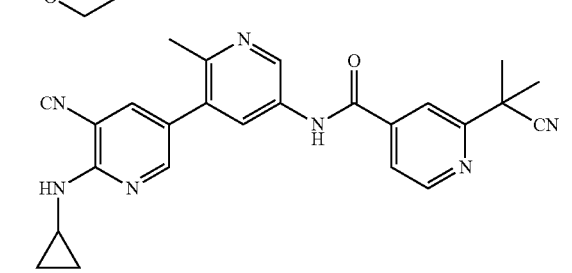
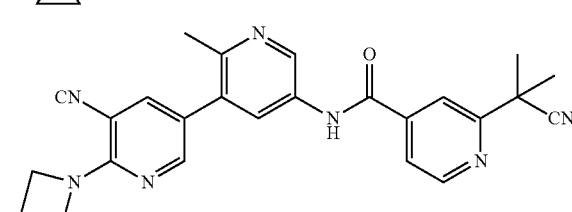
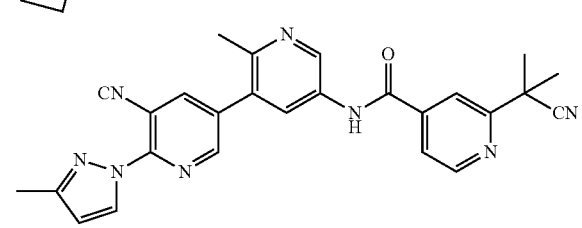
-continued
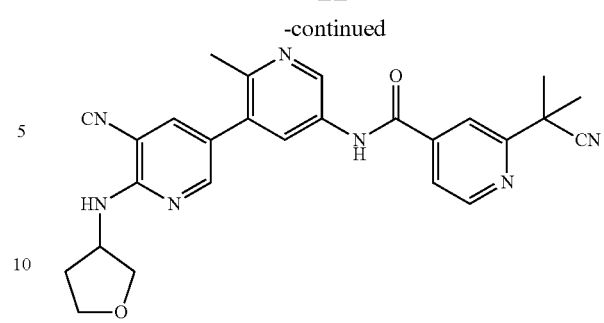
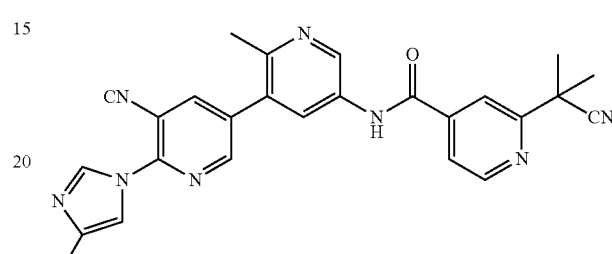
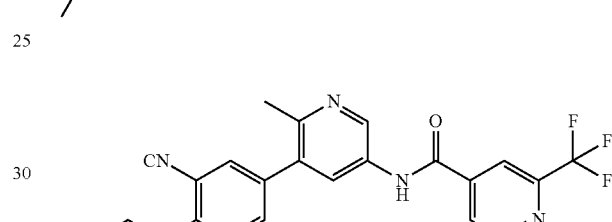
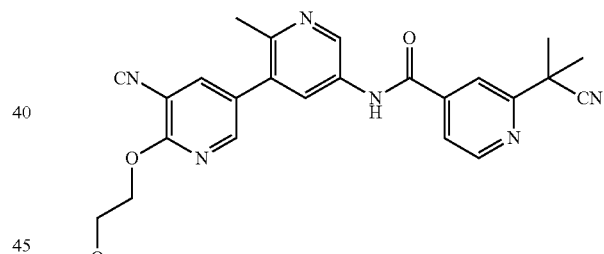
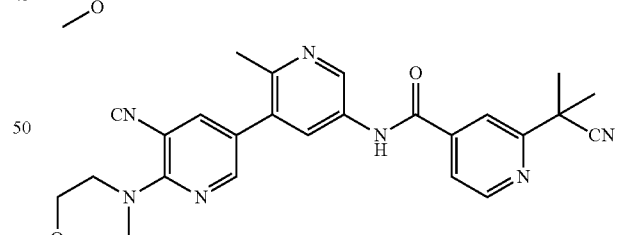
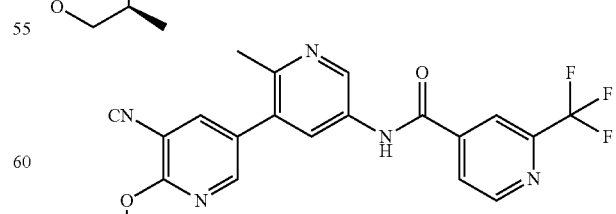

-continued
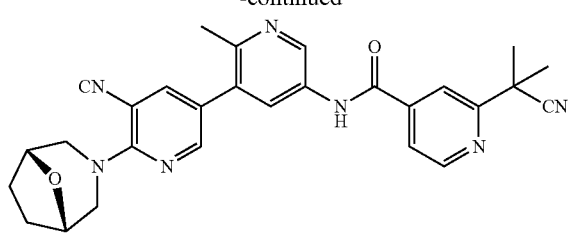
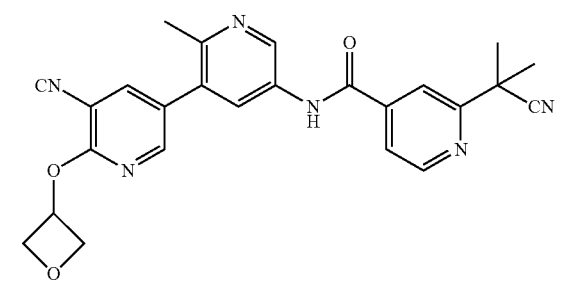
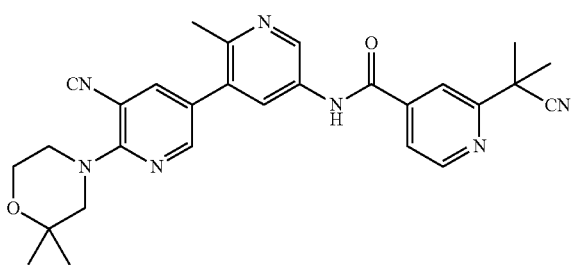
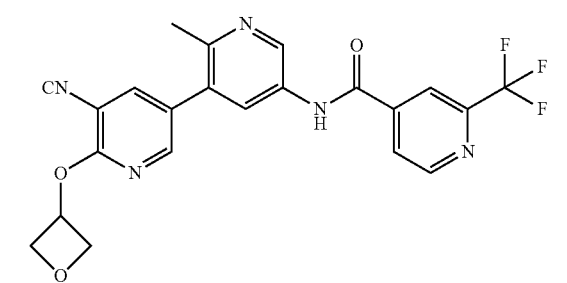
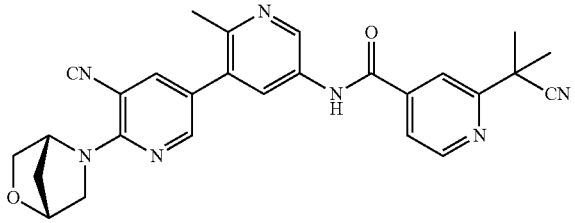
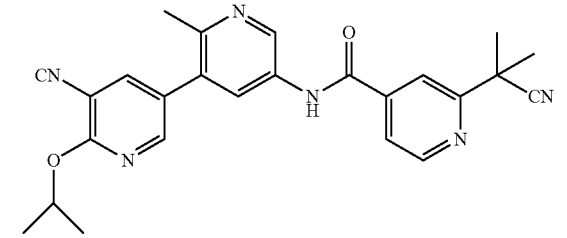
-continued
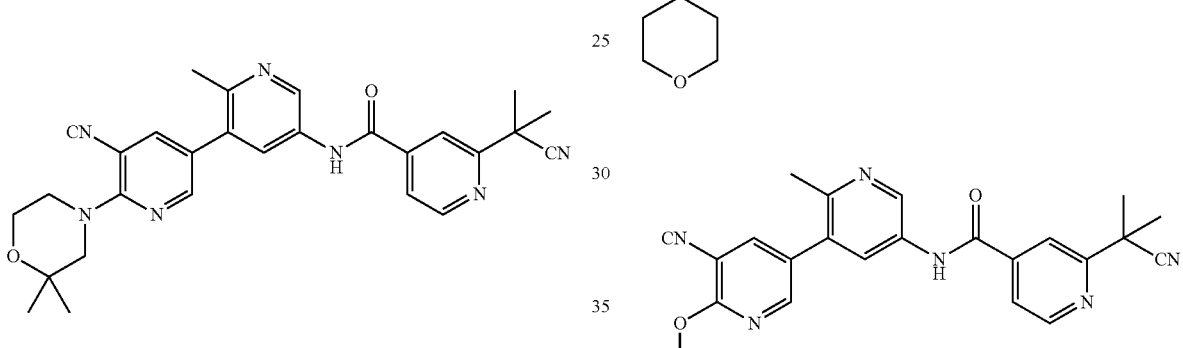
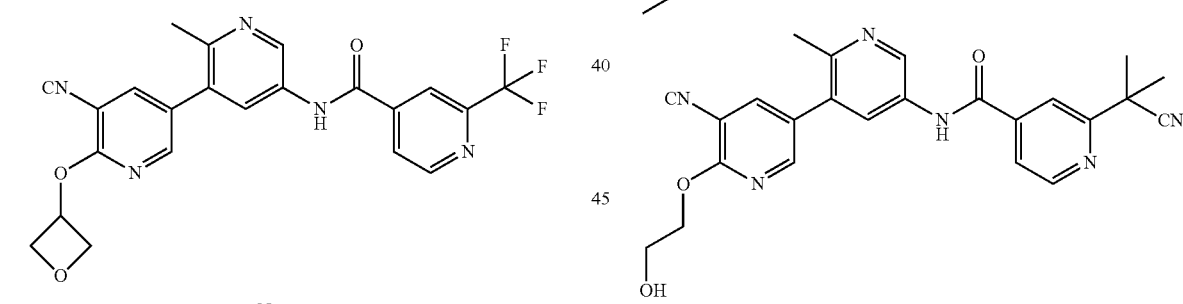
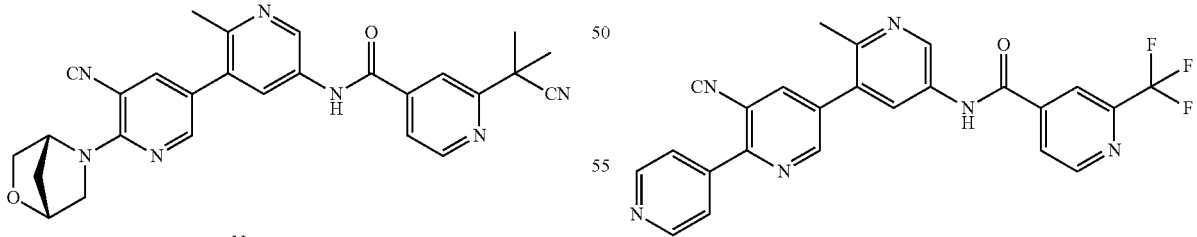
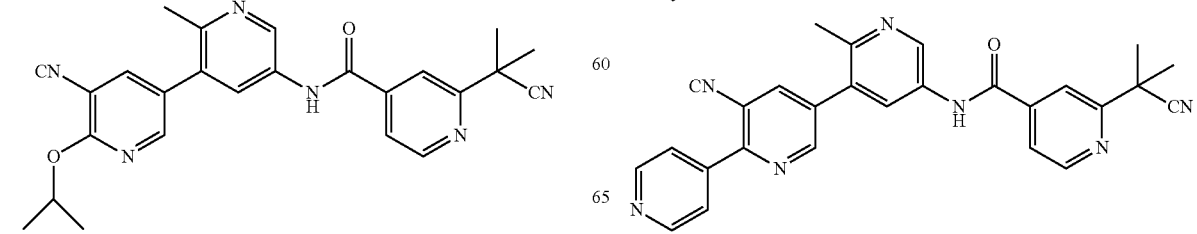

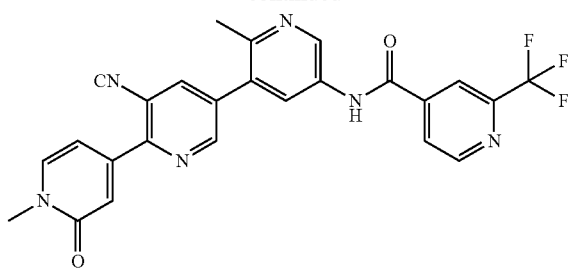
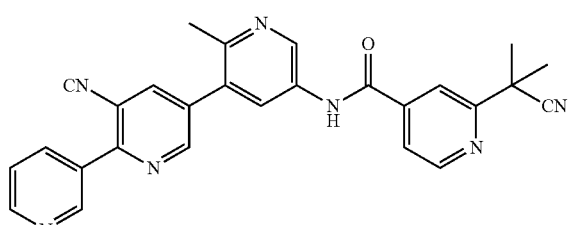
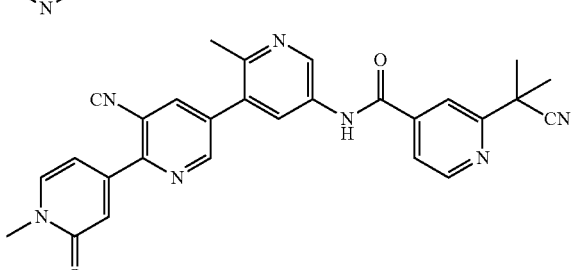
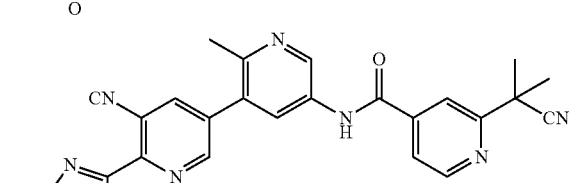
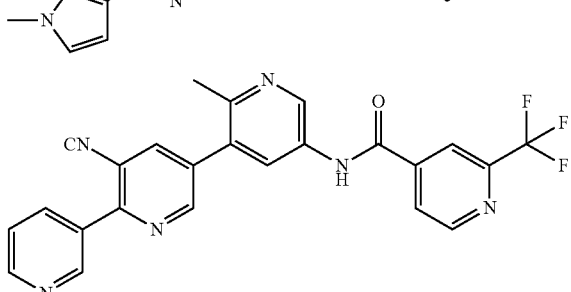
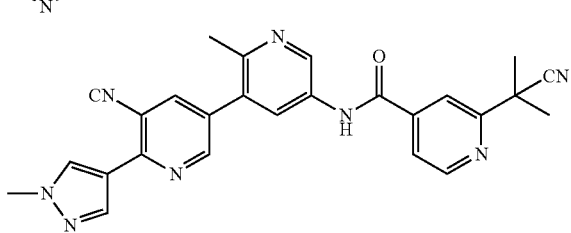
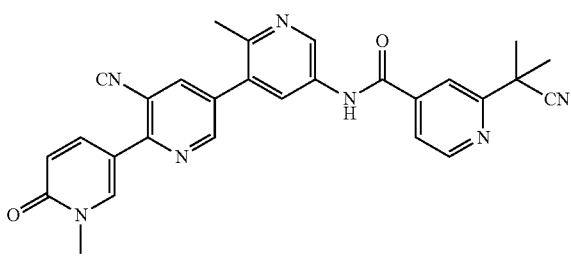
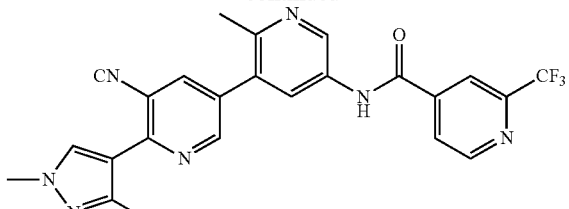
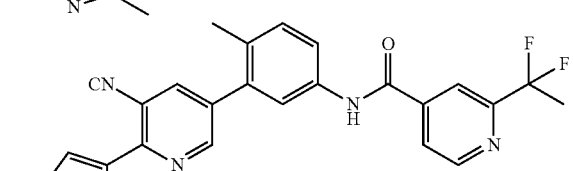
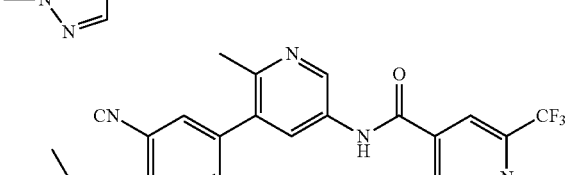
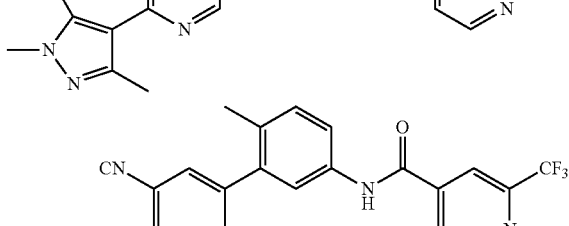
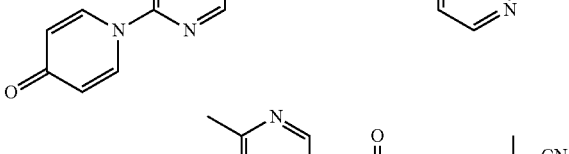
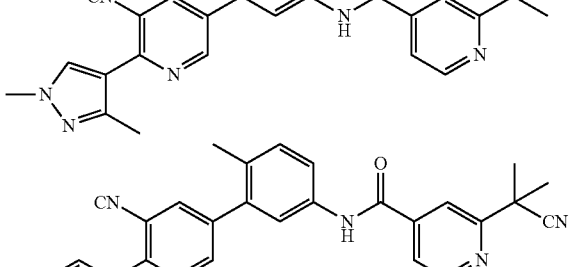
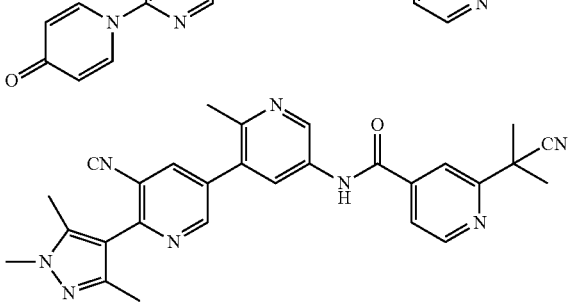
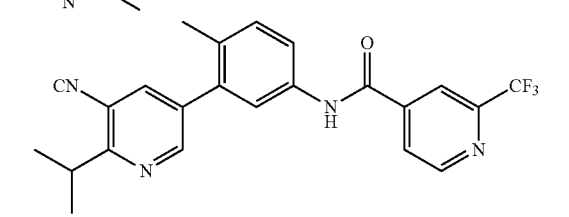

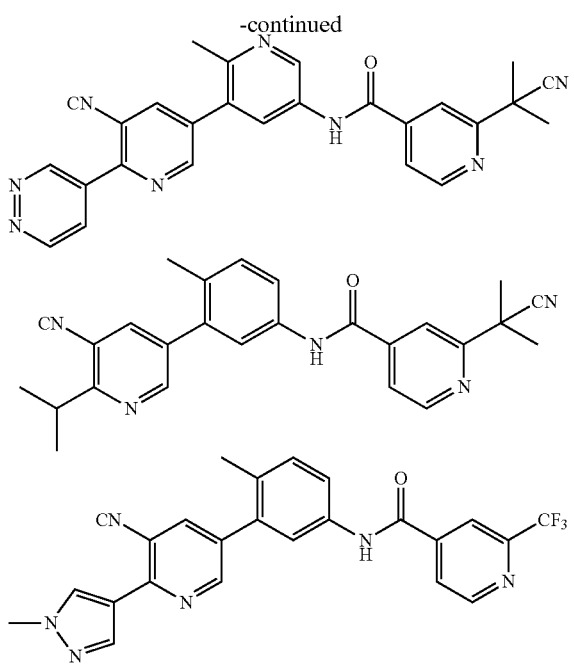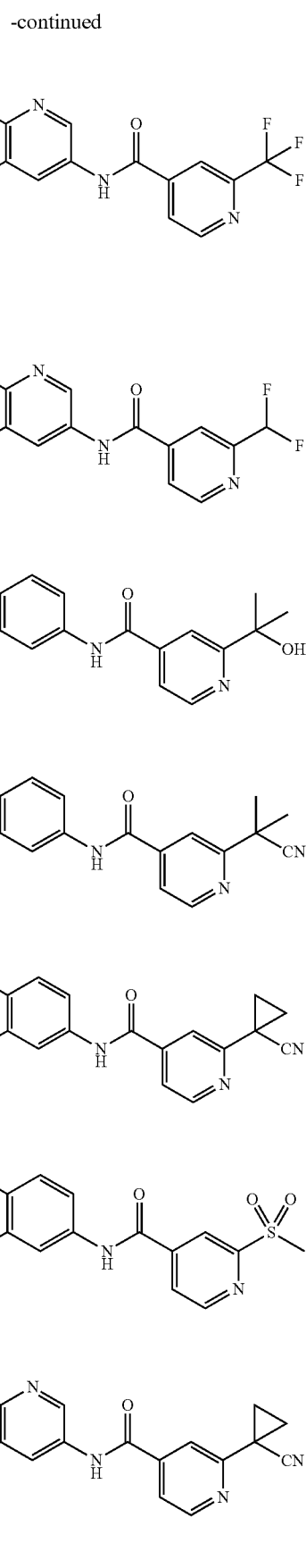

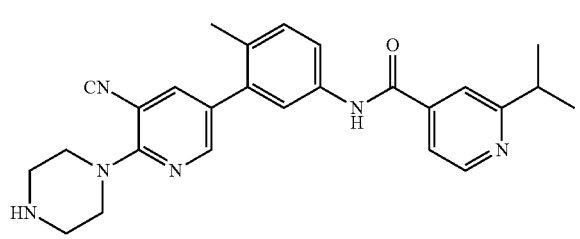
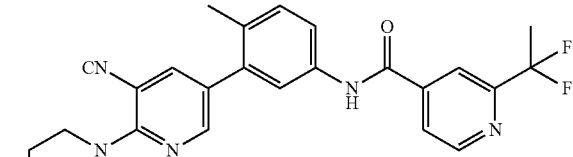
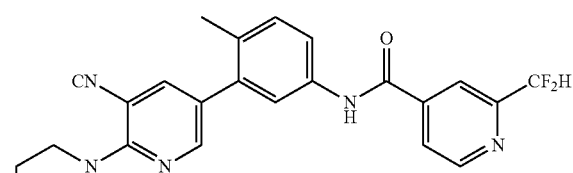
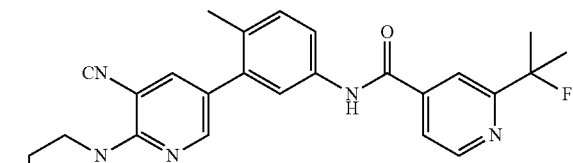
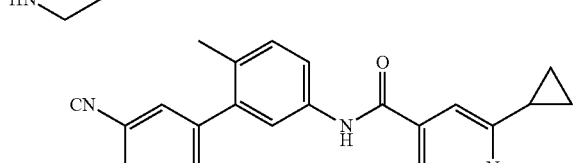
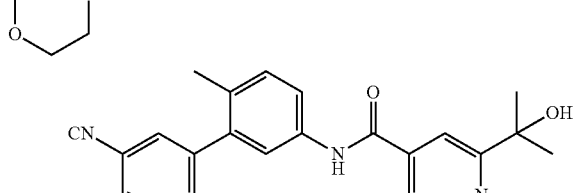
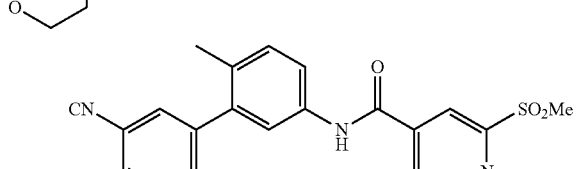
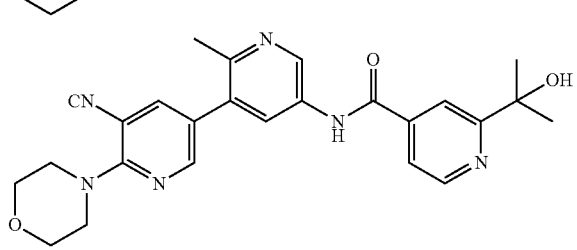

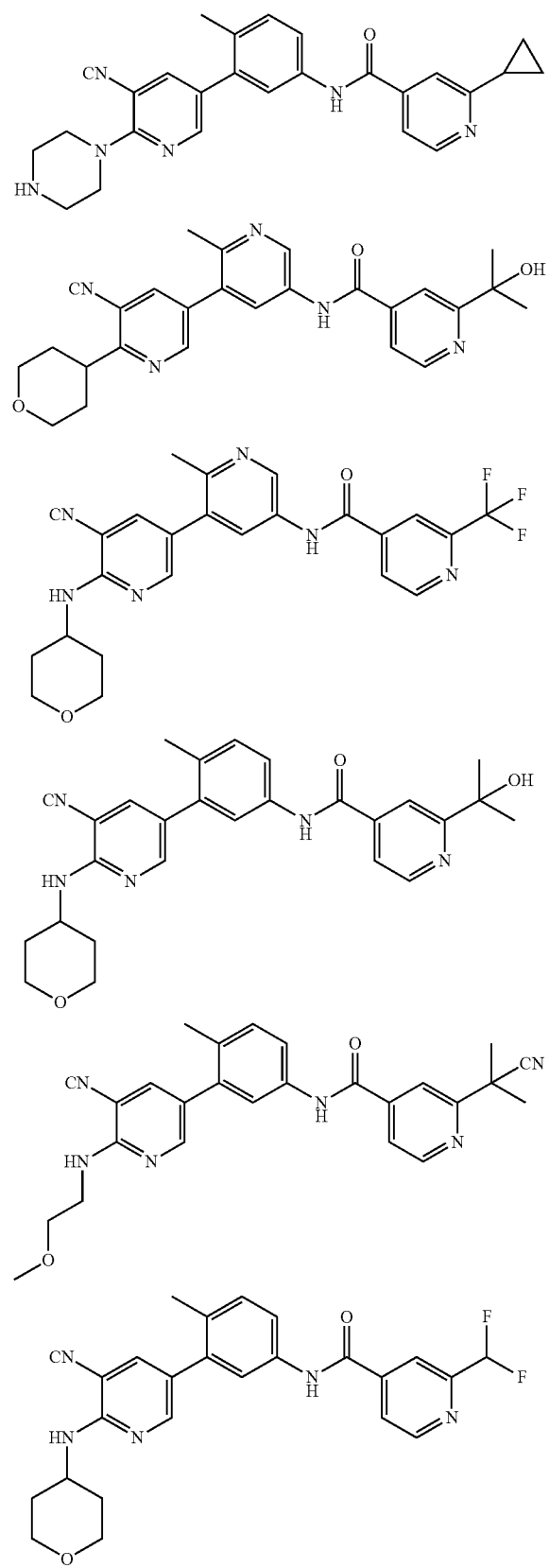
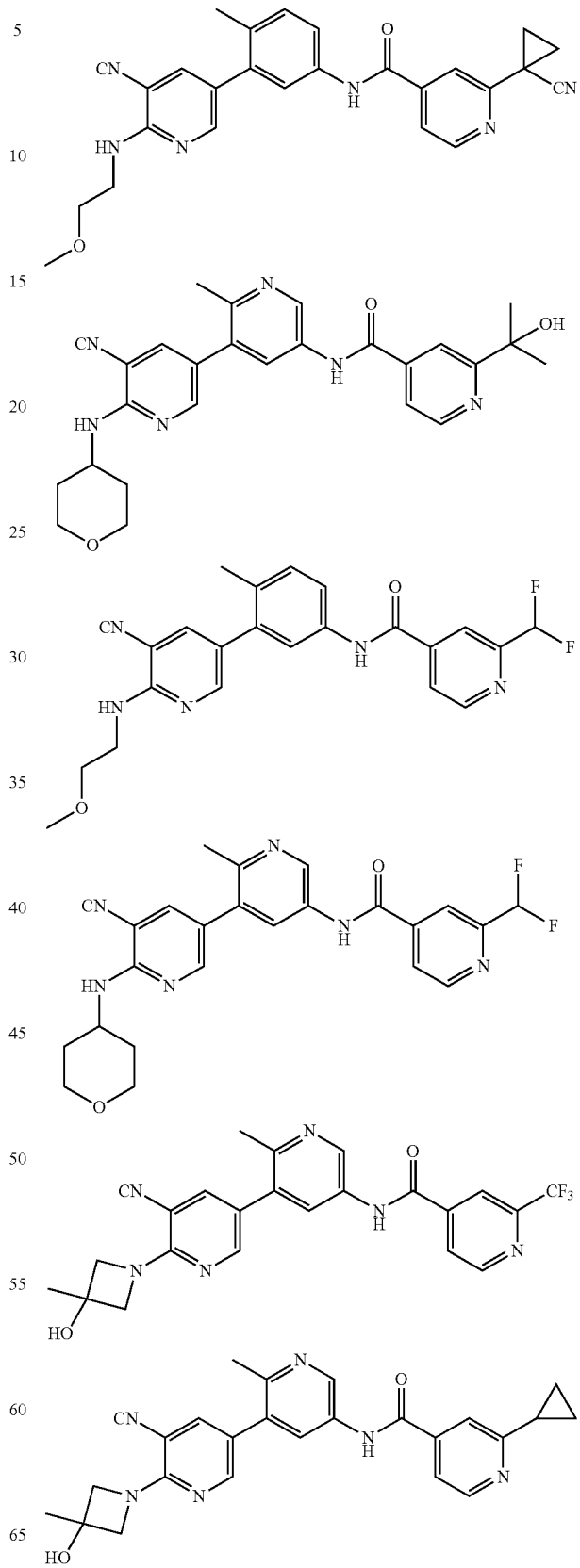

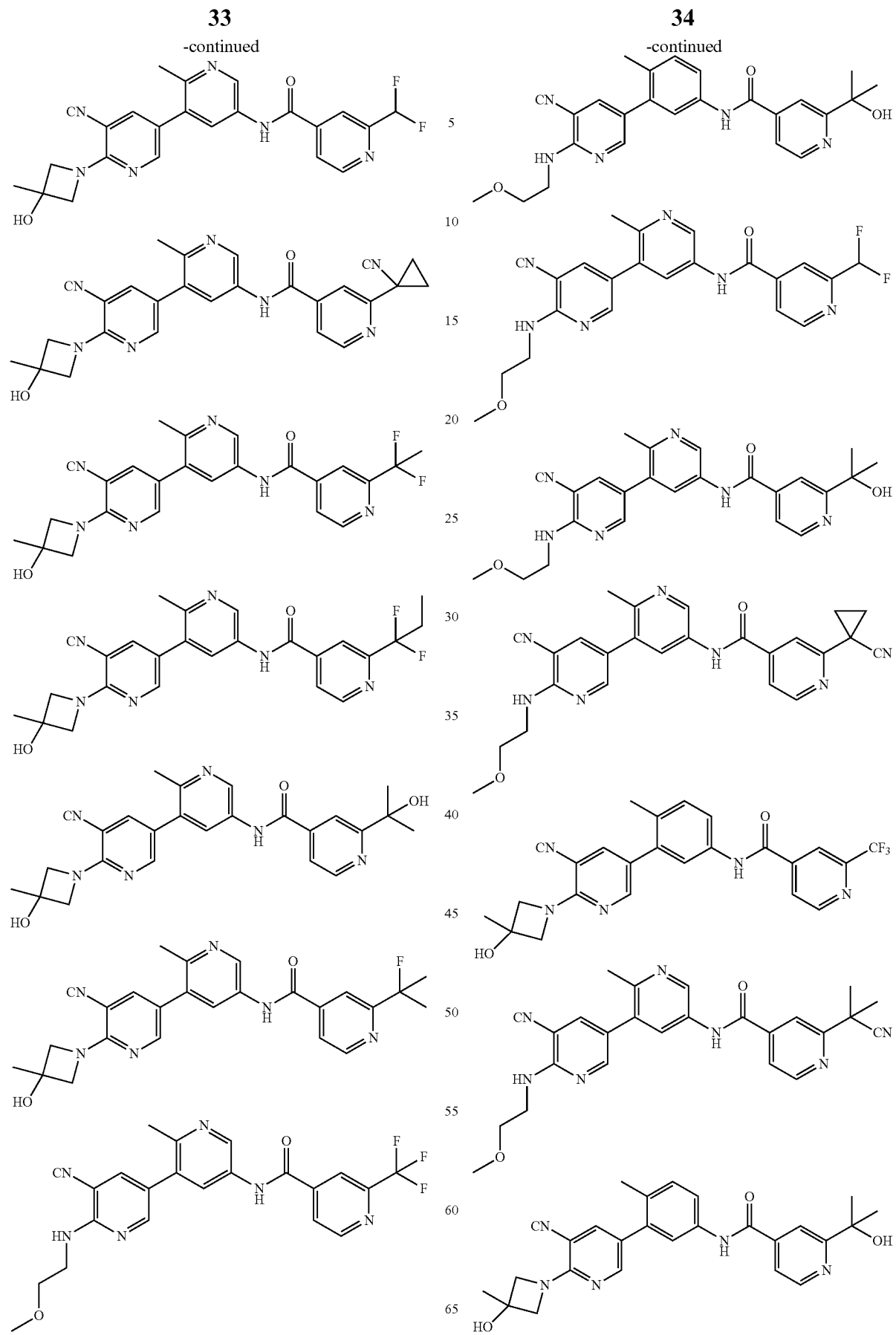

-continued
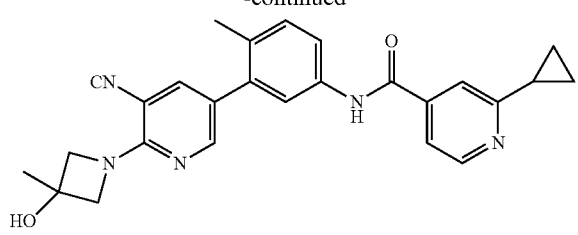
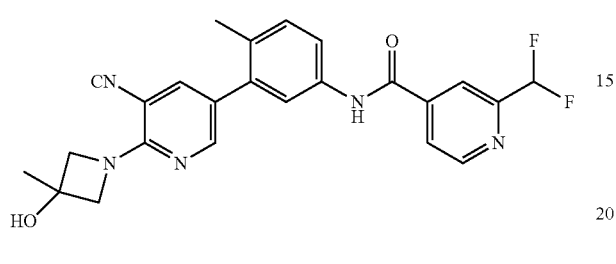
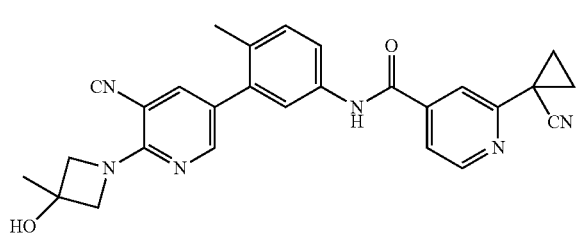
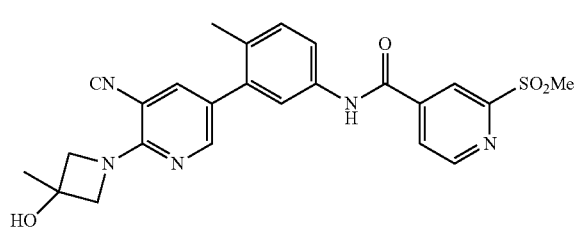
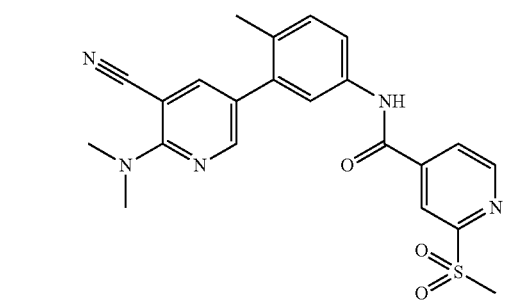
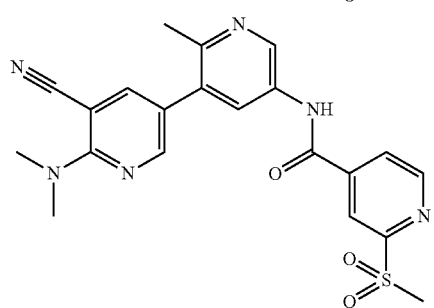
-continued
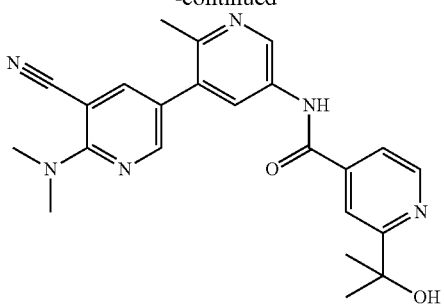
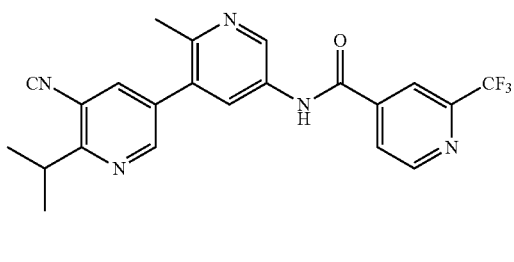
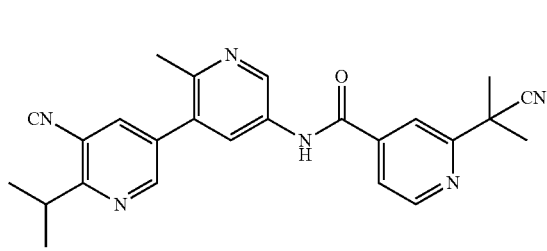
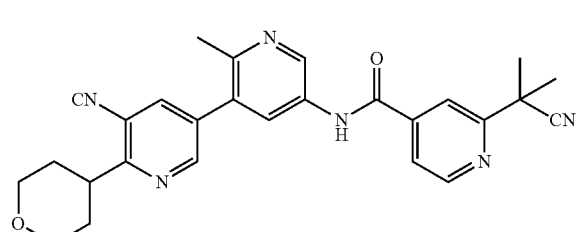
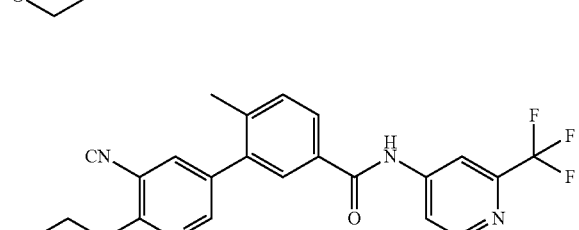
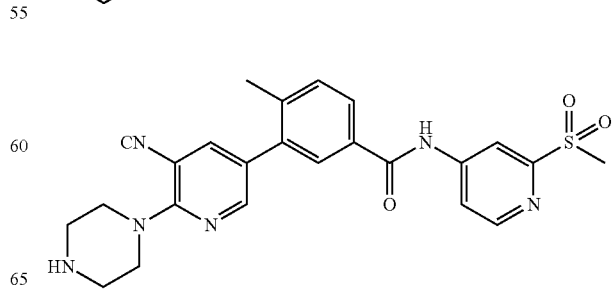

In another embodiment are compounds, or pharmaceutically acceptable salts thereof, selected from:
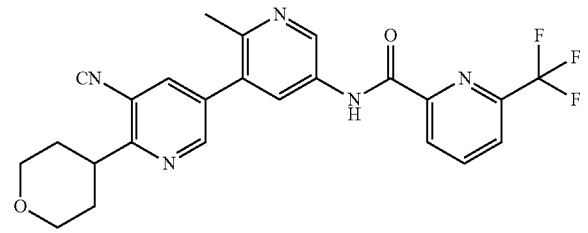
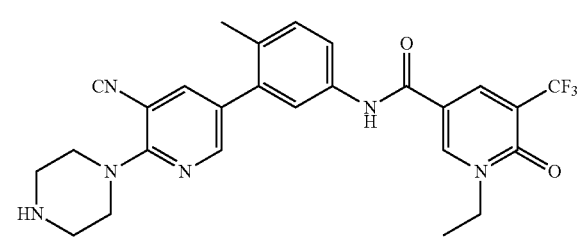
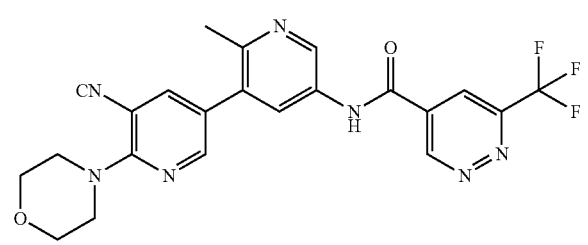
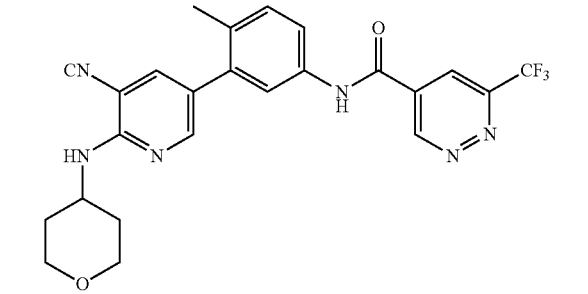
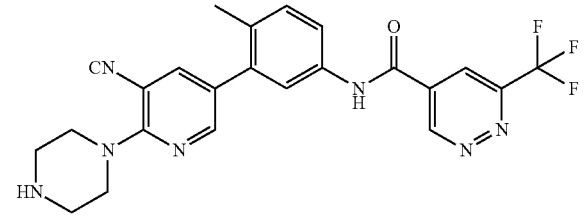
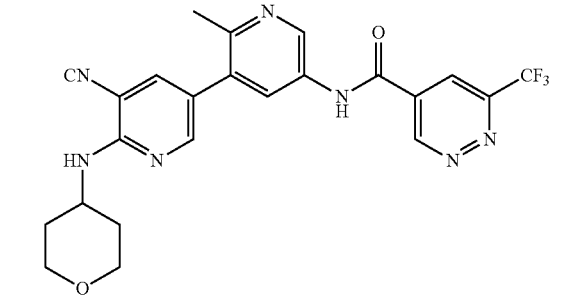
-continued
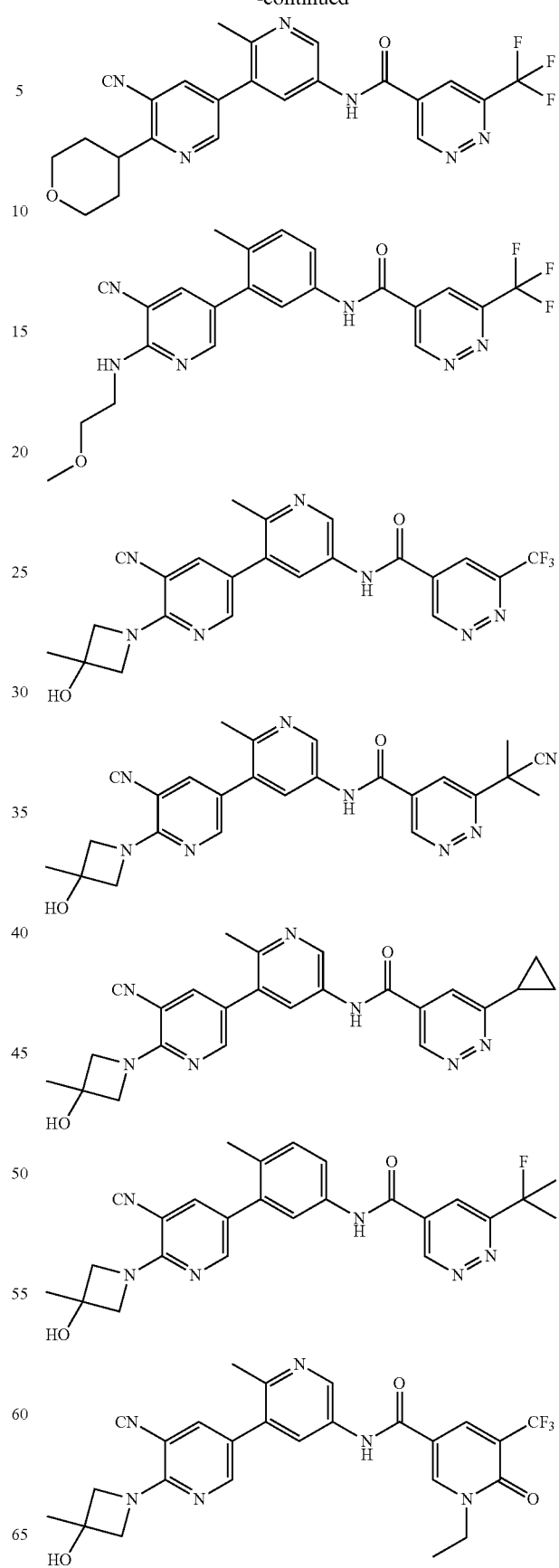

-continued
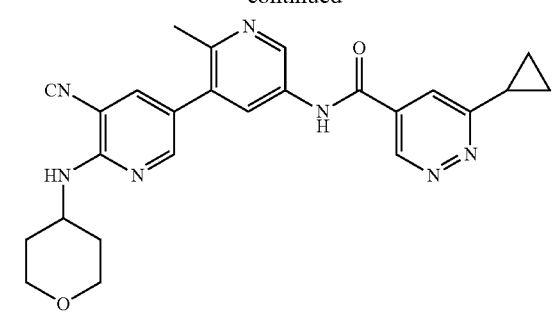
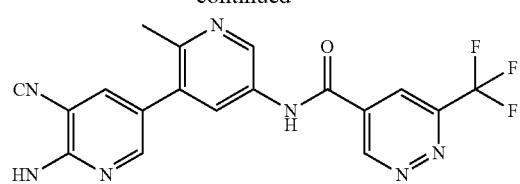
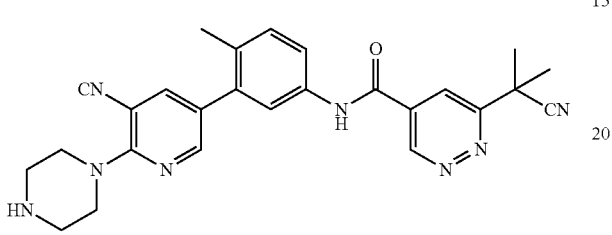
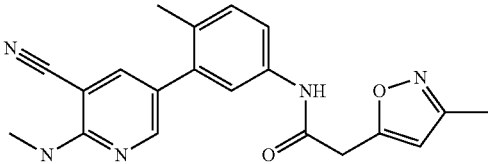
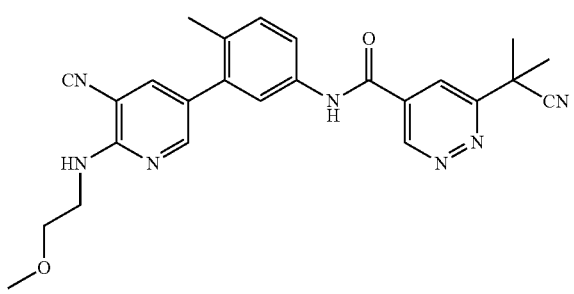
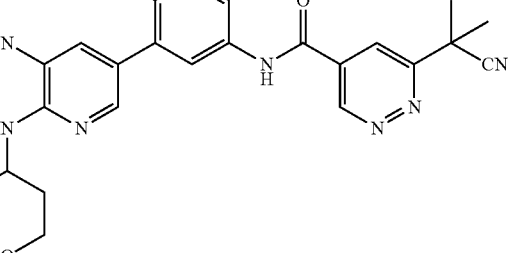
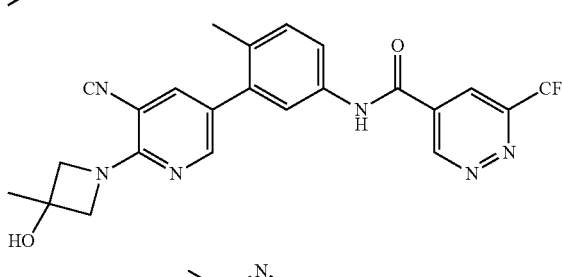
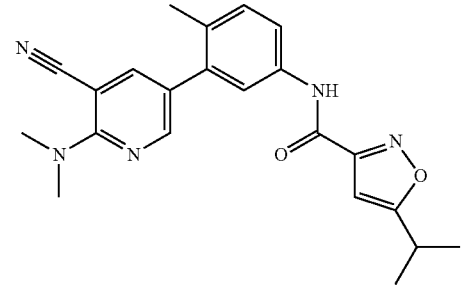
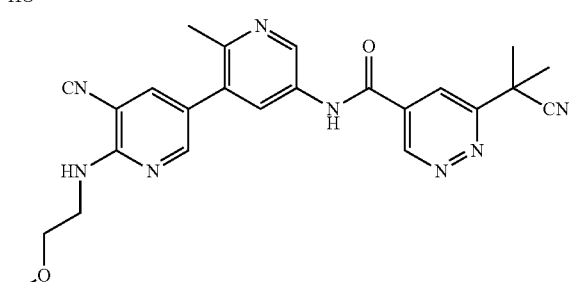
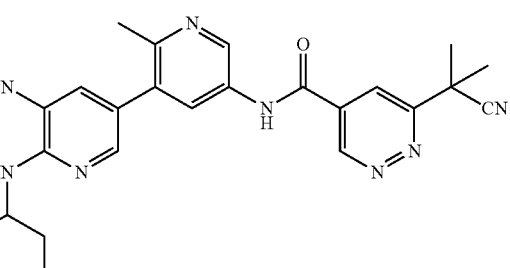
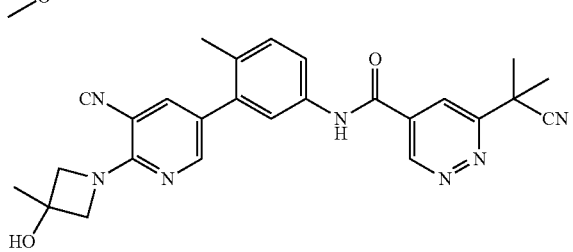
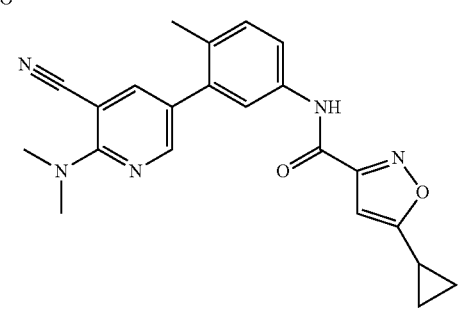

-continued
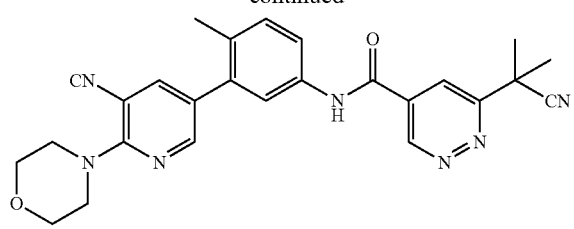
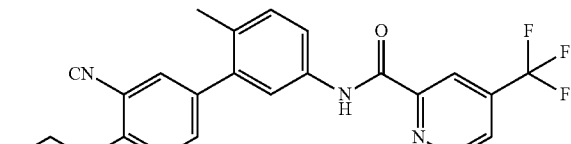
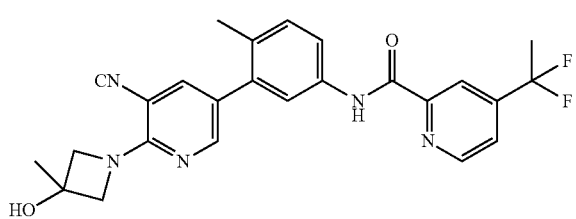
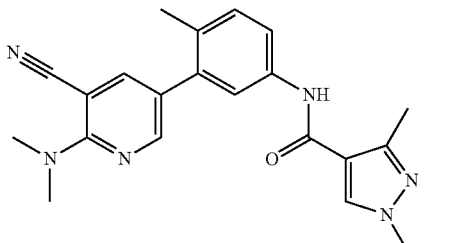
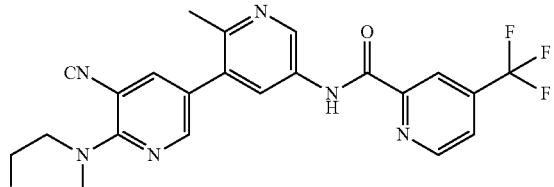
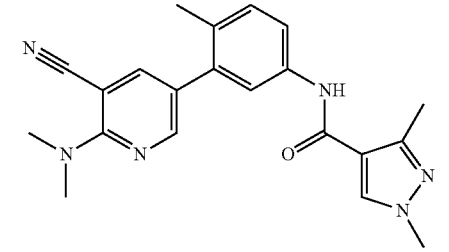
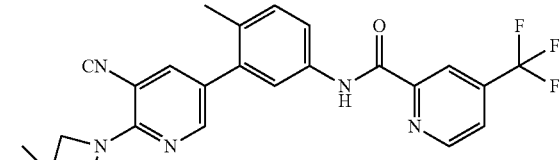
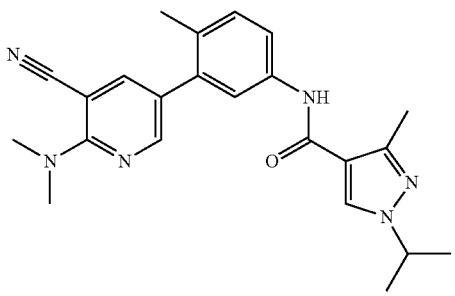
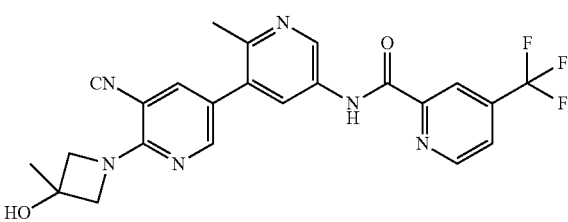

-continued
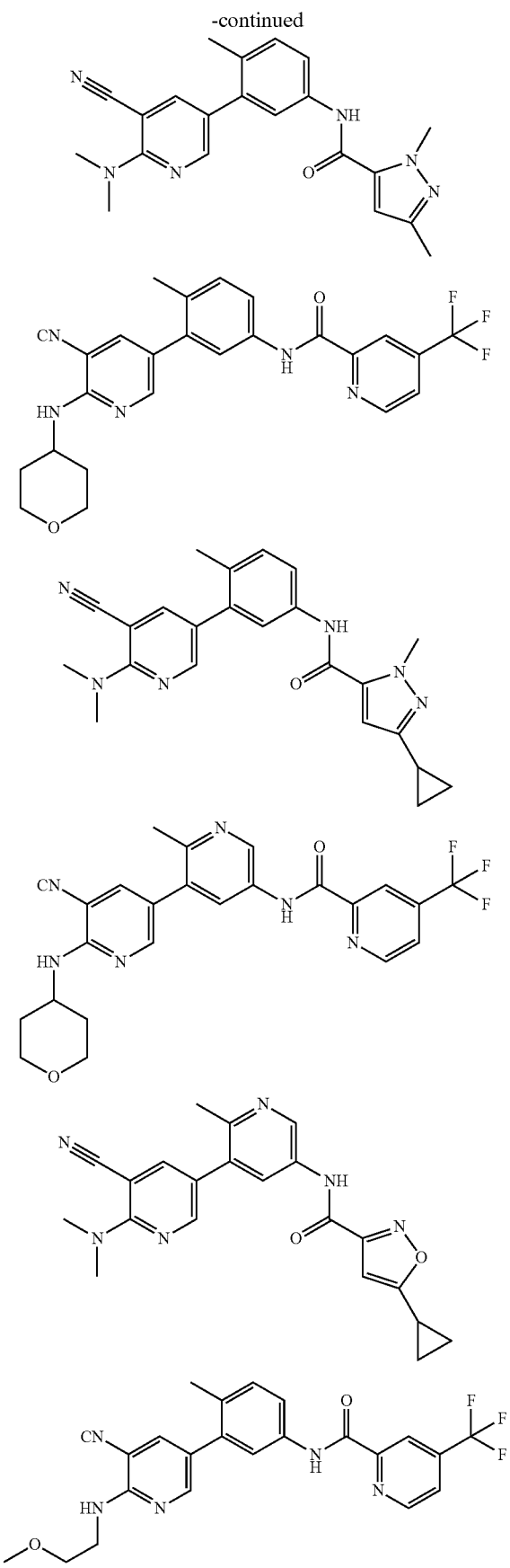
-continued
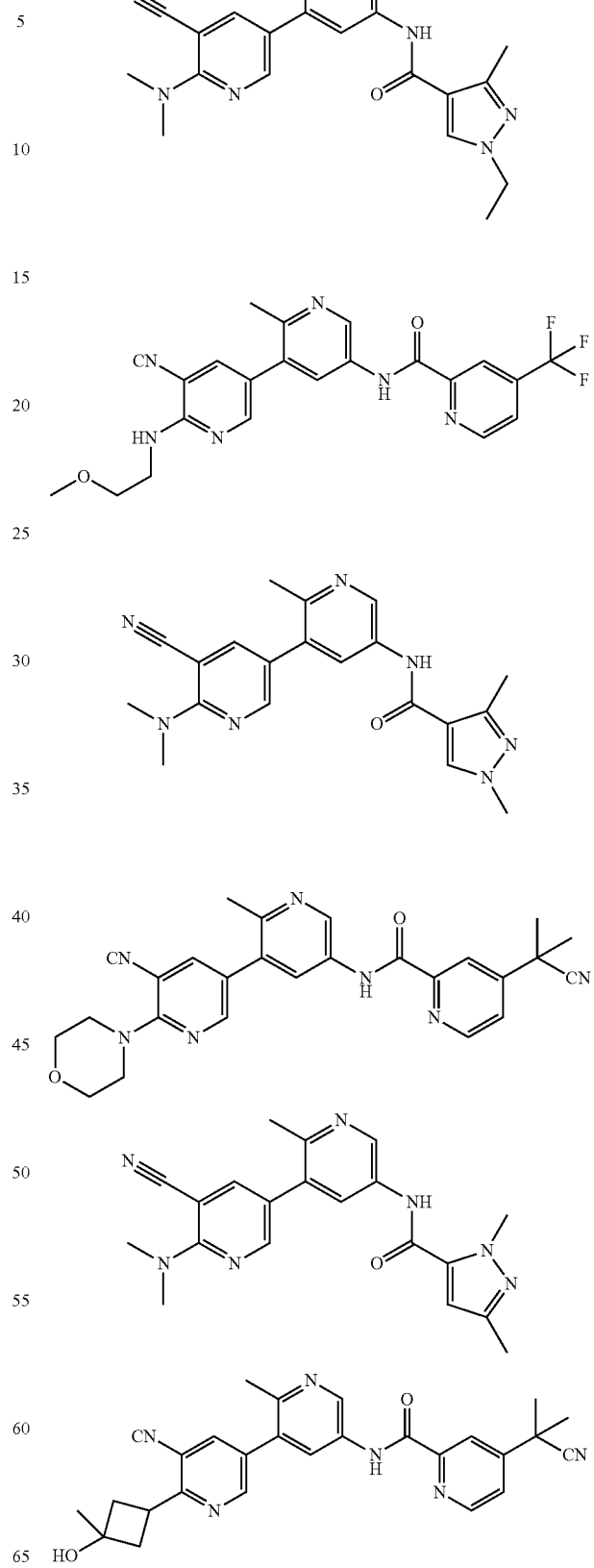

-continued
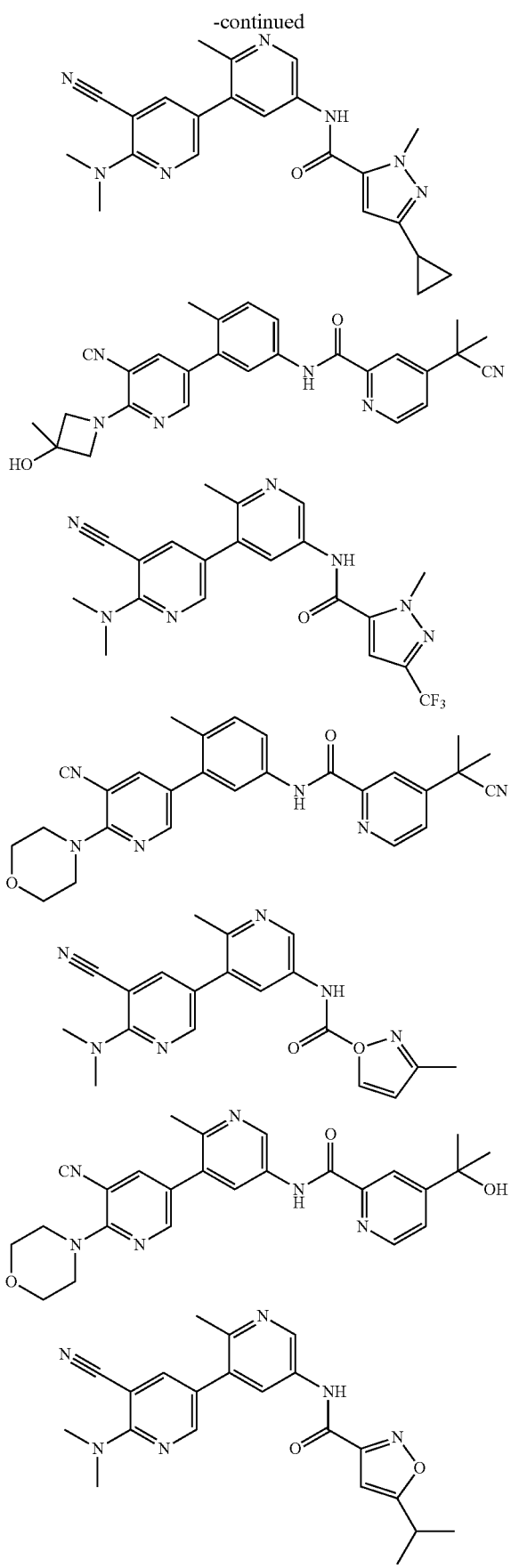
-continued
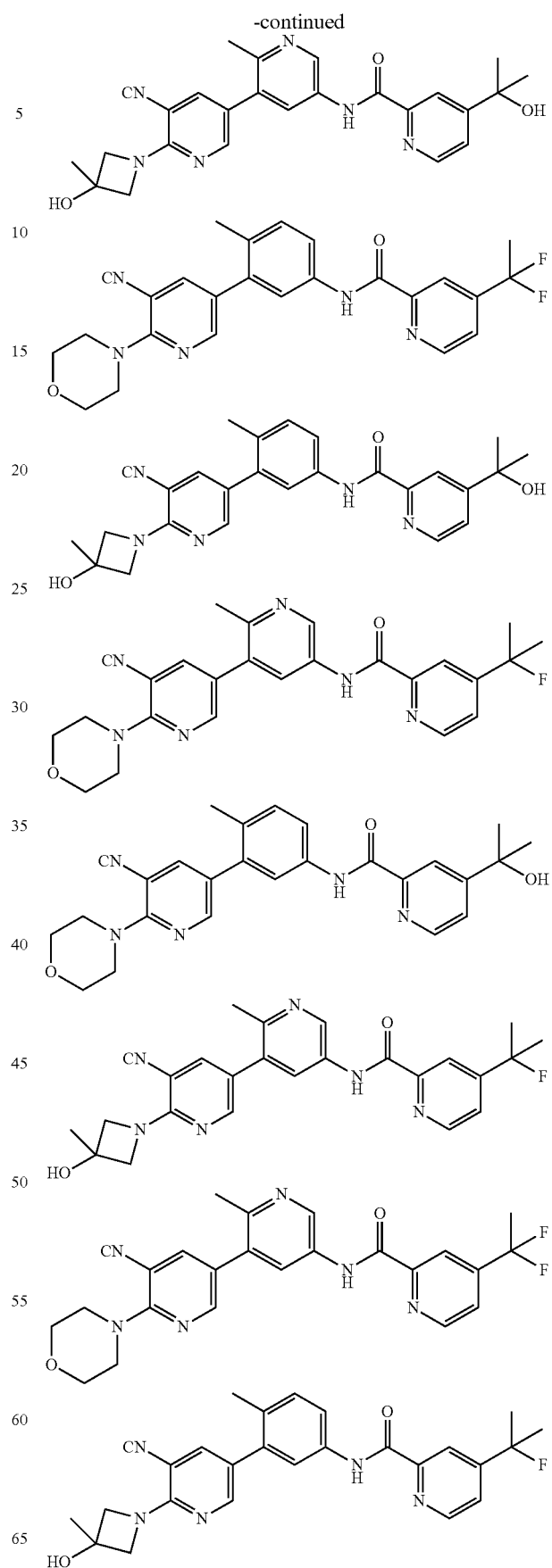

-continued

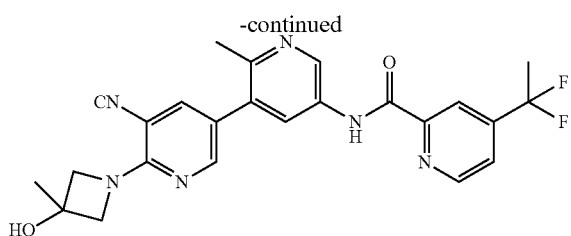

Each of the Example compounds having a measured IC-50 (B-Raf) of less than or equal to 0.01 μM, and a measured IC-50 (c-Raf) of less than 0.005 μM as shown in Table 9 is a preferred compound of the invention. The compounds of Examples having a measured IC-50 (B-Raf) of less than or equal to 0.01 μM and measured IC-50 (c-Raf) less than or equal to 0.002 μM according to Table 9 are especially preferred. Thus the use of any one of these compounds for treatment of a condition selected from melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer is an embodiment of the invention.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)- isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper, particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula I or II can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula I or II. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention. i.e. compounds of formula I or II that contain groups capable of acting as donors and/or acceptors for hydrogen bonds may be capable of forming co-crystals with suitable co-crystal formers. These co-crystals may be prepared from compounds of formula I or II by known co-crystal forming procedures. Such procedures include grinding, heating, co-subliming, co-melting, or contacting in solution compounds of formula I or II with the co-crystal former under crystallization conditions and isolating co-crystals thereby formed. Suitable co-crystal formers include those described in WO 2004/078163. Hence the invention further provides co-crystals comprising a compound of formula I or II.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by a Raf kinase such as B-Raf or C-Raf, or associated with activity of a kinase such as B-Raf or C-Raf, or (2) reduce or inhibit the activity of a kinase such as B-Raf or C-Raf in vivo.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of a kinase such as B-Raf or C-Raf, or at least partially reduce or alleviate a symptom or a condition associated with excessive Raf kinase activity.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat". "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)–, (S)– or (R,S)– configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)- configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography. e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions for compounds of Formula I or II are tablets or gelatin capsules comprising an active ingredient of Formula I or II together with at least one of the following pharmaceutically acceptable excipients:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers." include, but are not limited to, antioxidants such as ascorbic acid, pH buffers, or salt buffers, etc.

The compounds of formula I in free form or in salt form, exhibit valuable pharmacological activities, e.g. they modulate or inhibit activity of A-Raf, B-Raf and/or C-Raf, as indicated by test data provided in the next sections, and are therefore indicated for therapy or for use as research chemicals. e.g. as tool compounds. These compounds are especially useful for treatment of cancers driven by mutations in the Raf/Raf/MEK/ERK pathway, including cancers characterized by an activating Raf mutation such as Raf V600E, including but not limited to melanoma (e.g., malignant melanoma), breast cancer, lung cancer (e.g., non-small cell lung cancer), sarcoma, GI tumors such as gastrointestinal stromal tumors, ovarian cancer, colorectal cancer, thyroid cancer, and pancreatic cancer.

Thus, as a further embodiment, the present invention provides the use of a compound of formula I or II or any of the embodiments within the scope of Formula I or II as described herein, in therapy. In a further embodiment, the therapy is for a disease which may be treated by inhibition of A-Raf, B-Raf or C-Raf. In another embodiment, the compounds of the invention are useful to treat cancers, including but not limited to melanoma, breast cancer, lung cancer, sarcoma, GI tumors such as gastrointestinal stromal tumors, ovarian cancer, colorectal cancer, thyroid cancer, and pancreatic cancer.

In another embodiment, the invention provides a method of treating a disease which is treatable by inhibition of A-Raf, B-Raf or C-Raf, or a combination thereof, comprising administration of a therapeutically effective amount of a compound of formula I or II or any of the embodiments within the scope of Formula I or II as described herein. In a further embodiment, the disease is selected from the afore-mentioned list, suitably melanoma, breast cancer, lung cancer, sarcoma, GI tumors such as gastrointestinal stromal tumors, ovarian cancer, colorectal cancer, thyroid cancer, and pancreatic cancer. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula I or II or any of the embodiments of such compounds described herein for the manufacture of a medicament. In a further embodiment, the medicament is for treatment of a disease which may be treated by inhibition of A-Raf, B-Raf or C-Raf. In another embodiment, the disease is a cancer, e.g., a cancer selected from the afore-mentioned list, including melanoma, breast cancer, lung cancer, sarcoma, GI tumors such as gastrointestinal stromal tumors, ovarian cancer, colorectal cancer, thyroid cancer, and pancreatic cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s) (co-therapeutic agents). Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like. The compound of the present invention may be administered separately, by the same or different route of administration, or together in the same pharmaceutical composition as the co-agent(s).

In one embodiment, the invention provides a product comprising a compound of formula I or II and at least one other therapeutic co-agent as a combined preparation for simultaneous, separate or sequential use in therapy. In one embodiment, the therapy is the treatment of a disease or condition mediated by B-Raf or C-Raf, such as cancer. Products provided as a combined preparation include a composition comprising the compound of formula I or II and the other therapeutic co-agent(s) together in the same pharmaceutical composition, or the compound of formula I or II and the other therapeutic co-agent(s) in separate form, e.g. in the form of a kit.

In one embodiment, the invention provides a pharmaceutical composition comprising a compound of formula I or II and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula I or II. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula I or II for treating a disease or condition mediated by B-Raf or C-Raf, wherein the medicament is prepared for administration with another therapeutic agent. The invention also provides the use of another therapeutic co-agent for treating a disease or condition, wherein the medicament is administered with a compound of formula I or II.

The invention also provides a compound of formula I or II for use in a method of treating a disease or condition mediated by B-Raf or C-Raf, wherein the compound of formula I or II is prepared for administration with another therapeutic agent. The invention also provides another therapeutic co-agent for use in a method of treating a disease or condition mediated by B-Raf or C-Raf, wherein the other therapeutic co-agent is prepared for administration with a compound of formula I or II. The invention also provides a compound of formula I or II for use in a method of treating a disease or condition mediated by B-Raf or C-Raf, wherein the compound of formula I or II is administered with another therapeutic co-agent. The invention also provides another therapeutic co-agent for use in a method of treating a disease or condition mediated by B-Raf or C-Raf, wherein the other therapeutic co-agent is administered with a compound of formula I or II.

The invention also provides the use of a compound of formula I or II for treating a disease or condition mediated by B-Raf or C-Raf, wherein the patient has previously (e.g. within 24 hours) been treated with another therapeutic agent. The invention also provides the use of another therapeutic agent for treating a disease or condition mediated by B-Raf or C-Raf, wherein the patient has previously (e.g. within 24 hours) been treated with a compound of formula I or II.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme 1:

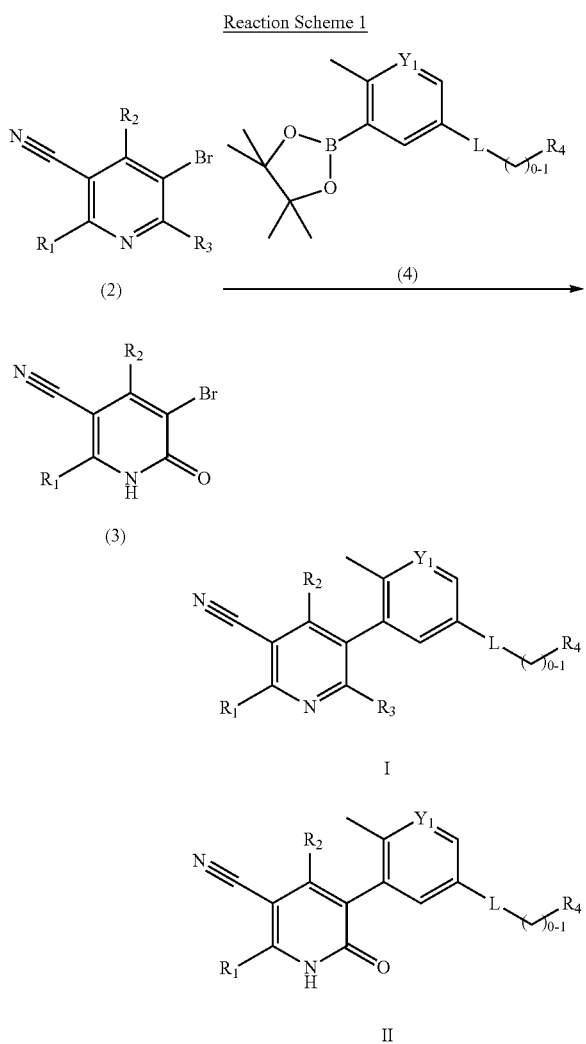

in which L, $R_1$, $R_2$, $R_3$, $R_4$ and $Y_1$ are as defined in the Summary of the Invention. A compound of formula I or II are prepared by reacting a compound of formula 2 or 3 with a compound of formula 4, respectively. The reaction takes place in the presence of s suitable catalyst (for example, $Pd(PPh_3)_4$, and the like). The reaction proceeds at a temperature of about 50° C. to about 150° C. and can take up to 4 hours to complete.

The synthetic protocol for specific examples area detailed, below.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer, for example stereoisomer, of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates and examples that illustrate the preparation of compounds of Formula I according to the invention.

The following abbreviations may be used herein:

| | |
|---|---|
| DAST | (diethylamino)sulfurtrifluoride |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| HOBt | Hydroxybenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$- DCM | Dichloro-(1,2-bis(diphenylphosphino)ethan)- Palladium(II) - dichloromothethane adduct |
| RT or rt | room temperature |
| TBDMSCl | tert-butyldimethylsilylchloride |
| TEA | Triethylamine |
| THF | tetrahydrofuran |

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Mass spectrometric analysis was performed on LCMS instruments: Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

Synthesis of
5-bromo-2-(methylamino)nicotinonitrile

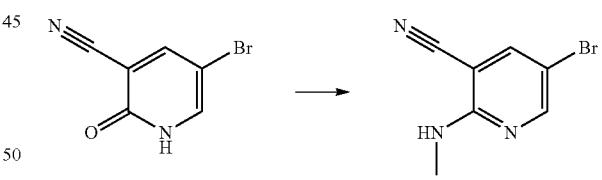

Method 1: To a solution of 5-bromo-2-oxo-1,2-dihydropyridine-3-carbonitrile in acetonitrile (0.1 M) was added DBU (2.0 equiv.), BOP (1.3 equiv.) and methyl amine (2M solution, 4.0 equiv.). The solution was stirred at room temperature for 7 hrs, the volatiles were removed in vacuo, the residue was dissolved in ethyl acetate and washed with water (2×), sodium carbonate, washed with brine and dried over magnesium sulfate. Filtered, concentrated and purified via silica gel column chromatography eluting with ethyl acetate (25%-50%) in heptanes. The pure fractions were concentrated to yield 5-bromo-2-(methylamino) nicotinonitrile in 54% yield as a white solid. LCMS (m/z) (M+H)=211.9/213.9, Rt=0.72 min.

The following intermediates were synthesized according to Method 1, using appropriate starting materials:

| Intermediate Name | Structure | Physical Data |
|---|---|---|
| 5-bromo-2-(propylamino)nicotinonitrile | 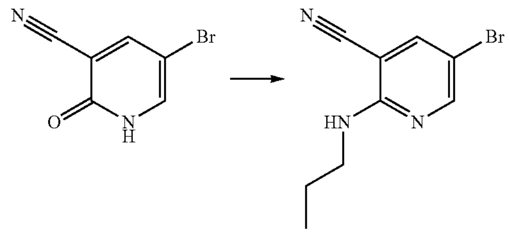 | LCMS (m/z) (M + H) = 239.9/241.9, Rt = 0.92 min. |
| 5-bromo-2-(isopropylamino)nicotinonitrile | 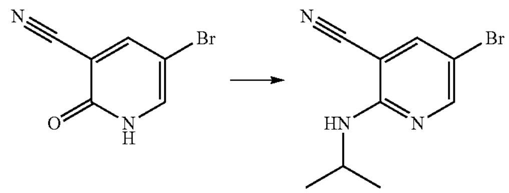 | LCMS (m/z) (M + H) = 239.9/241.9, Rt = 0.92 min. |
| 5-bromo-2-(cyclopropylamino)nicotinonitrile | 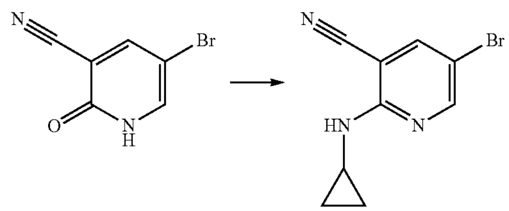 [SMILES: N#Cc1cc(Br)c[nH]c1=O ; N#Cc1cc(Br)cnc1NC1CC1] | LCMS (m/z) (M + H) = 237.9/239.9, Rt = 0.75 min. |
| 5-bromo-2-(dimethylamino)nicotinonitrile | 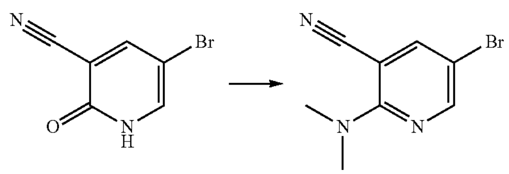 | LCMS (m/z) (M + H) = 225.9/227.9, Rt = 0.86 min. |
| 5-bromo-2-(ethylamino)nicotinonitrile | 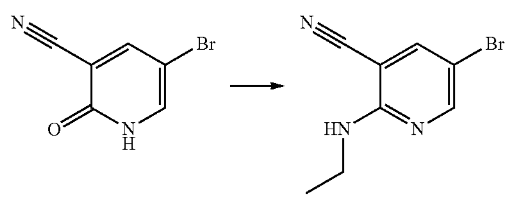 | LCMS (m/z) (M + H) = 225.9/227.9, Rt = 0.85 min. |
| 5-bromo-2-((2-methoxyethyl)amino)nicotinonitrile | 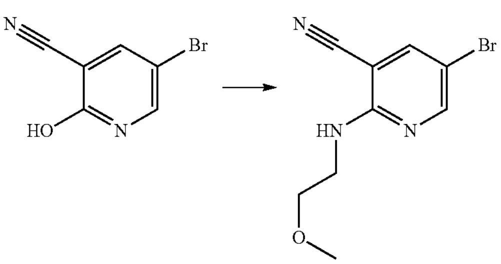 | LCMS (m/z) (M + H) = 255.9/257.9, Rt = 0.75 min. |
| 5-bromo-2-morpholinonicotinonitrile | 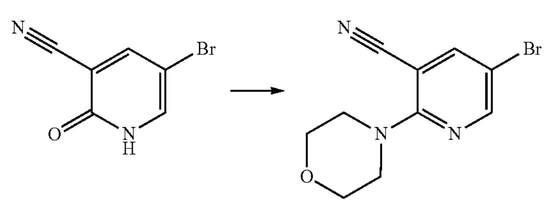 [SMILES: N#Cc1cc(Br)c[nH]c1=O ; N#Cc1cc(Br)cnc1N1CCOCC1] | LCMS (m/z) (M + H) = 267.9/269.9, Rt = 0.78 min. |

| Intermediate Name | Structure | Physical Data |
|---|---|---|
| 5-bromo-2-(3-hydroxy-3-methylazetidin-1-yl)nicotinonitrile | 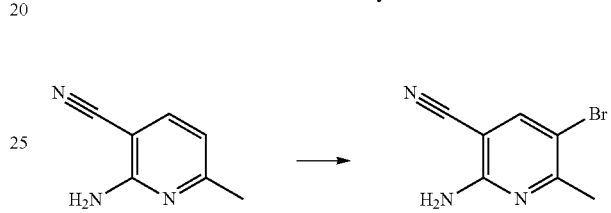 | LCMS (m/z) (M + H) = 267.8/269.8, Rt = 0.64 min. |

Synthesis of 5-bromo-2-((tetrahydro-2H-pyran-4-yl)amino)nicotinonitrile

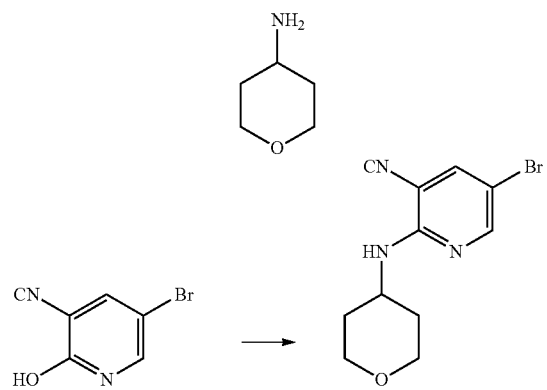

To a solution of 5-bromo-2-hydroxynicotinonitrile (1.0 equiv.) in acetonitrile (0.1M) was added 2,3,4,6,7,8,9,10-octahydropyrimido[1,2-a]azepine (2.0 equiv.), tetrahydro-2H-pyran-4-amine (2.0 equiv.) and ((1H-benzo[d][1,2,3]triazol-1-yl)oxy)tris(dimethylamino)phosphonium hexafluorophosphate(V) (1.3 equiv.) and the homogeneous solution was stirred at rt overnight. The volatiles were removed in vacuo and the residue was dissolved in ethyl acetate, washed with water, sat. sodium carbonate, sat. NaCl, dried over MgSO$_4$, filtered and concentrated. The residue was triturated in DCM and the precipitate was filtered off to give 5-bromo-2-((tetrahydro-2H-pyran-4-yl)amino)nicotinonitrile in 67% yield. LCMS (m/z) (M+H)=283.9 Rt=0.79 min.

Synthesis of 2-amino-5-bromo-4-methylnicotinonitrile

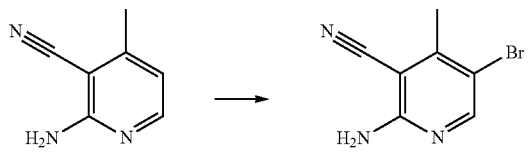

To a solution of 2-amino-4-methylnicotinonitrile (1.0 equiv.) in chloroform (0.3M) was added NBS (1.0 equiv.). The heterogeneous reaction was stirred in the dark for 16 hours. The volatiles were removed in vacuo and the residue was partitioned between ethyl acetate and water. The layers were separated, washed with 1M NaOH, brine, dried over MgSO$_4$, filtered and concentrated. Isolated 2-amino-5-bromo-4-methylnicotinonitrile as a brown solid in 88% yield. LCMS (m/z) (M+H)=211.9/213.9, Rt=0.62 min.

Synthesis of 2-amino-5-bromo-6-methylnicotinonitrile

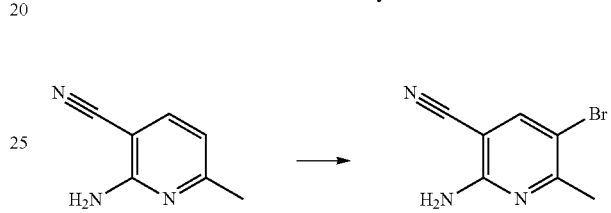

To a solution of 2-amino-6-methylnicotinonitrile (1.0 equiv.) in chloroform (0.25M) was added NBS (1.0 equiv.). The heterogeneous reaction was stirred in the dark for 16 hours. The volatiles were removed in vacuo and the residue was partitioned between ethyl acetate and water. The layers were separated, washed with 1M NaOH, brine, dried over MgSO$_4$, filtered and concentrated. Isolated 2-amino-5-bromo-6-methylnicotinonitrile as a light beige solid in 94% yield. LCMS (m/z) (M+H)=211.9/213.9, Rt=0.61 min.

Synthesis of 5-bromo-2-(methylsulfonyl)nicotinonitrile

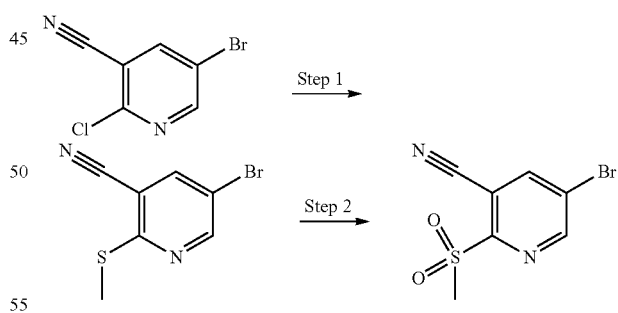

Step 1: To a solution of 5-bromo-2-chloronicotinonitrile (1.0 equiv.) in DME (0.2 M) at 0° C. was added sodium methanethiolate (1.0 equiv.). The mixture was stirred at 0° C. for 2 hours and then rt for 1 hour. Quenched by the addition of saturated ammonium chloride and extracted with ethyl acetate. The organic phase was dried with sodium sulfate, filtered and concentrated under vacuo. The crude material was used for the next step without further purification. LCMS (m/z) (M+H)=229.0/231.0, Rt=0.77 min.

Step 2: To a solution of 5-bromo-2-(methylthio)nicotinonitrile (1.0 equiv.) in ethanol (0.18 M) at 0° C. was added m-CPBA (2.1 equiv.) and the mixture was stirred at 0° C. for 2 hours then at rt overnight. The reaction was diluted with ethyl acetate and washed with sat. NaHCO₃, then sat. NaCl. The organic layer was dried with sodium sulfate, filtered and concentrated. The crude material was purified via silica gel column chromatography (ISCO, eluting with 0-100% ethyl acetate/heptanes) to give 5-bromo-2-(methylsulfonyl)nicotinonitrile in 70% yield. LCMS (m/z) (M+H)=260.9/262.9, Rt=0.39 min.

Synthesis of 5-(5-amino-2-methylphenyl)-2-(dimethylamino)nicotinonitrile

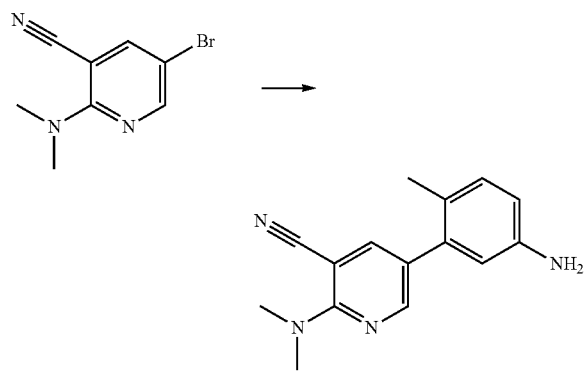

A solution of 5-bromo-2-(dimethylamino)nicotinonitrile (1.0 equiv.), 4-methyl-3-(4,4,5,5-tetramethyl-1,3,2-dioxaborolan-2-yl)aniline (1.2 equiv.), PdCl₂(dppf).CH₂Cl₂ adduct (0.05 equiv.) in DME and 2M Na₂CO₃ (2:1, 0.2 M) was degassed by bubbling Ar through for 15 mins. The stirred mixture was then heated to 95° C. for 2 hours. Allowed to cool to RT, then filtered through Celite rinsing well with EtOAc. The solvent was removed on the rotovap, then partitioned between EtOAc and 1M NaOH. The organics were separated, then washed with 1M NaOH (×2), sat. brine (×4) then dried (Na₂SO₄), filtered and evaporated under reduced pressure to give a dark brown gum. Purified on Analogix SiO₂ by dry loading, then eluted with 0-40% EtOAc/heptanes to give 5-(5-amino-2-methylphenyl)-2-(dimethylamino)nicotinonitrile in 82% yield. LCMS (m/z) (M+H)=253.0, Rt=0.53 min.

Synthesis of 5'-amino-6-(dimethylamino)-2'-methyl-[3,3'-bipyridine]-5-carbonitrile

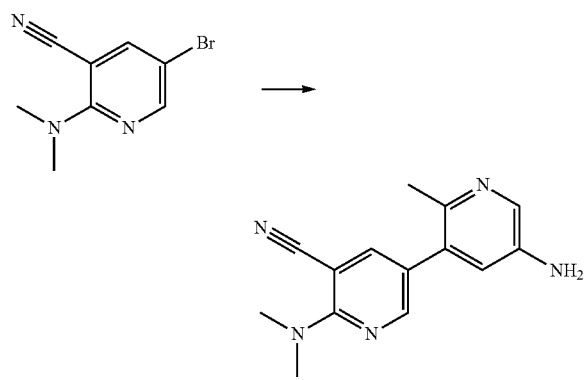

A solution of 5-bromo-2-(dimethylamino)nicotinonitrile (1.0 equiv.), 6-methyl-5-(4,4,5,5-tetramethyl-1,3,2-dioxaborolan-2-yl)pyridin-3-amine (1.2 equiv.), PdCl₂(dppf).CH₂Cl₂ adduct (0.05 equiv.) in DME and 2M Na₂CO₃ (2:1, 0.2 M) was degassed by bubbling Ar through for 15 mins. The stirred mixture was then heated to 95° C. for 3 hours. Allowed to cool to RT, then filtered through Celite rinsing well with EtOAc. The solvent was removed on the rotovap, then partitioned between EtOAc and 1M NaOH. The organics were separated, then washed with 1M NaOH (×2), sat. brine (×4) then dried (Na₂SO₄), filtered and evaporated under reduced pressure to give a dark brown gum. Purified on Analogix SiO₂ by dry loading, then eluted with 0-15% Methanol/DCM to give 5'-amino-6-(dimethylamino)-2'-methyl-[3,3'-bipyridine]-5-carbonitrile in 90% yield. LCMS (m/z) (M+H)=254.0, Rt=0.44 min.

Synthesis of 5-(5-amino-2-methylphenyl)nicotinonitrile

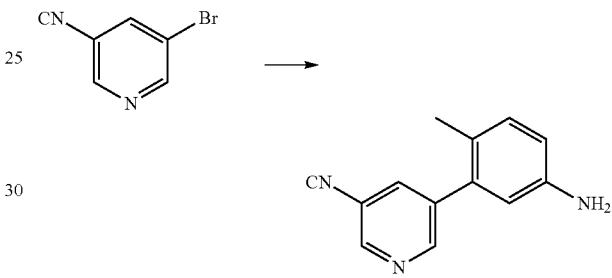

To a degassed solution of 4-methyl-3-(4,4,5,5-tetramethyl-1,3,2-dioxaborolan-2-yl)aniline (1.0 equiv.), 5-bromonicotinonitrile (1.1 equiv.) and Na₂CO₃ (5 equiv., 2M aq. sin) was added PdCl₂(dppf).CH₂Cl₂ adduct (0.15 equiv.). This mixture was heated to 120° C. for 15 min in the microwave and cooled to room temperature. Water was added, the phases were separated and the water mixture was extracted with ethyl acetate. The organic phases were pooled, dried with MgSO₄ and the volatiles removed in vacuo to give 5-(5-amino-2-methylphenyl)nicotinonitrile in 99% yield. LCMS (m/z) (M+H)=210.0, Rt=0.43 min.

Synthesis of 5'-(5-amino-2-methylphenyl)-4-oxo-4H-[1,2'-bipyridine]-3'-carbonitrile

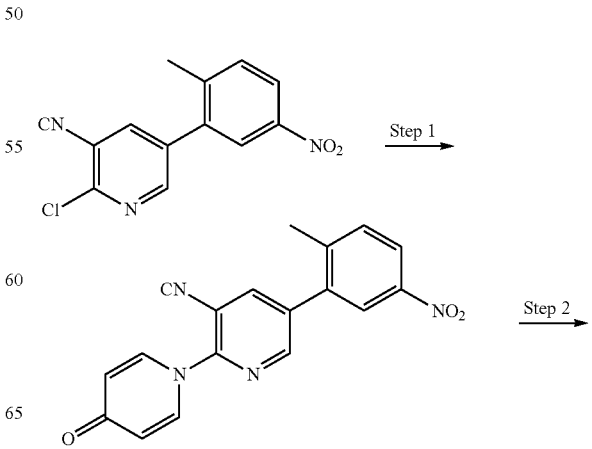

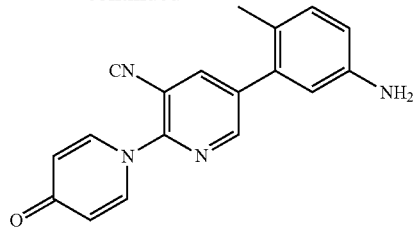

Step 1: To a solution of 2-chloro-5-(2-methyl-5-nitrophenyl)nicotinonitrile (1.0 equiv.) in water and NMP (1:1, 0.3 M) was added pyridine-4-ol (2.0 equiv.) and potassium carbonate (2.0 equiv.) and the reaction was heated at 100° C. in an oil bath for 30 min. Upon cooling to room temperature, water was added to the mixture and the precipitate was filtered off to give 5'-(2-methyl-5-nitrophenyl)-4-oxo-4H-[12'-bipyridine]-3'-carbonitrile in 70% yield. LCMS (m/z) (M+H)=333.0, Rt=0.67 min.

Step 2: To a solution of 5'-(2-methyl-5-nitrophenyl)-4-oxo-4H-[1,2'-bipyridine]-3'-carbonitrile (1.0 equiv.) in AcOH (0.1M) was added Iron (10 equiv.). The mixture was stirred at rt for 1 hr. Concentrated and worked up with EtOAc and sat. NaHCO₃ solution. The organic layer was washed with Brine, dried over Na₂SO₄ and concentrated to give 5'-(5-amino-2-methylphenyl)-4-oxo-4H-[1,2'-bipyridine]-3'-carbonitrile in 100% yield. LCMS (m/z) (M+H)=303.0, Rt=0.39 min.

Synthesis of 5-(5-amino-2-methylphenyl)-2-isopropylnicotinonitrile

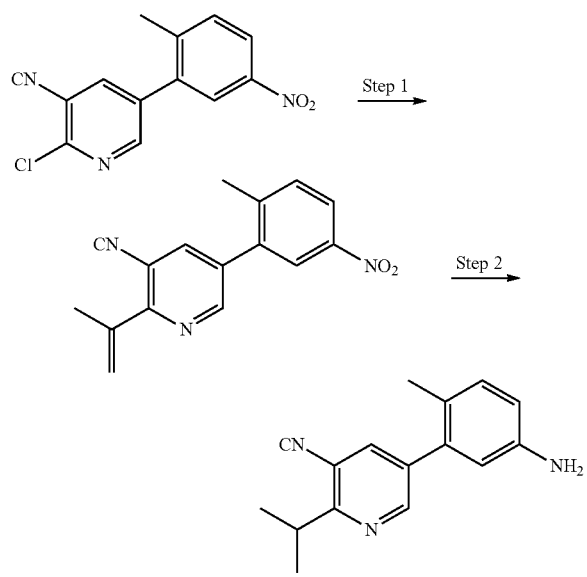

Step 1: A solution of 2-chloro-5-(2-methyl-5-nitrophenyl)nicotinonitrile (1.0 equiv.), 4,4,5,5-tetramethyl-2-(prop-1-en-2-yl)-1,3,2-dioxaborolane (3.0 equiv.), potassium carbonate (3.0 equiv.), and Pd(PPh₃)₄ (0.03 equiv.) in ethanol and toluene (1:2.5, 0.065 M) was heated in the microwave at 120° C. for 20 minutes. The reaction was partitioned between ethyl acetate and water, the layers were mixed, then separated, the organic layer was washed with sat. NaCl, dried over MgSO₄, filtered and concentrated. The crude was purified via silica gel column chromatography (ISCO, eluting with 0-100% ethyl acetate in heptanes) to give 5-(2-methyl-5-nitrophenyl)-2-(prop-1-en-2-yl)nicotinonitrile in 80% yield. LCMS (m/z) (M+H)=280.1, Rt=1.00 min.

Step 2: A heterogeneous solution of 5-(2-methyl-5-nitrophenyl)-2-(prop-1-en-2-yl)nicotinonitrile (1.0 equiv.) in MeOH (0.07M) was degassed and purged with Ar. Pd/C (Degussa type, 0.1 equiv.) was added and house vacuum was pulled on the heterogeneous solution and it was vented to an H₂ balloon. The vacuum/purge was repeated 3× and the reaction was left stirring under an H₂ atmosphere 8 hours. The solution was evacuated and purged to Ar, filtered through a 1 μM HPLC filter, rinsed with EtOAc, concentrated and pumped on to yield 5-(5-amino-2-methylphenyl)-2-isopropylnicotinonitrile in 100% yield. LCMS (m/z) (M+H)=252.1, Rt=0.63 min.

Synthesis of 5-(5-amino-2-methylphenyl)-2-(1-methyl-1H-pyrazol-4-yl)nicotinonitrile

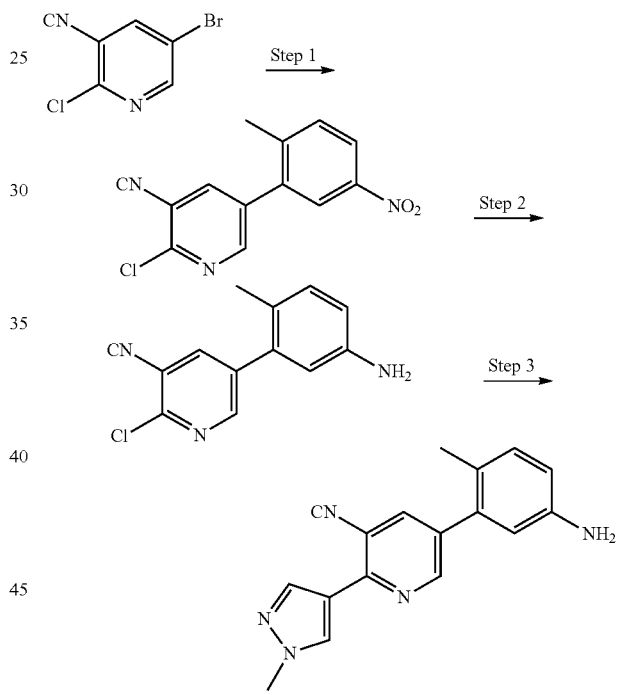

Step 1: To a degassed solution of 4,4,5,5-tetramethyl-2-(2-methyl-5-nitrophenyl)-1,3,2-dioxaborolane (1.0 equiv.), 5-bromo-2-chloronicotinonitrile (1.0 equiv.) and Na₂CO₃ (3.0 equiv., 2M aqueous solution) in toluene (0.19 M) was added PdCl₂(dppf).CH₂Cl₂ adduct (0.1 equiv.). This mixture was heated to 90° C. for 3 h, added another 0.05 equiv. of catalyst, stirred at 90° C. for 1 h and cooled to room temperature. Water was added, the phases were separated and the water mixture was extracted with ethyl acetate. The organic phases were pooled, dried with MgSO₄ and the volatiles removed in vacuo. Purified by ISCO (20% EtOAc/heptane) to give 2-chloro-5-(2-methyl-5-nitrophenyl)nicotinonitrile in 65% yield. LCMS (m/z) (M+H)=274.0, Rt=0.98 min.

Step 2: To a solution of 2-chloro-5-(2-methyl-5-nitrophenyl)nicotinonitrile (1.0 equiv) in AcOH (0.15 M) was added Iron (10 equiv.). The mixture was stirred at rt for 1 hr.

Concentrated and worked up with EtOAc and sat. NaHCO₃ solution. The organic layer was washed with Brine, dried over Na₂SO₄ and concentrated to give 5-(5-amino-2-methylphenyl)-2-chloronicotinonitrile in quantitative yield. LCMS (m/z) (M+H)=244.0, Rt=0.55 min.

Step 3: To a degassed solution of 1-methyl-4-(4,4,5,5-tetramethyl-1,3,2-dioxaborolan-2-yl)-1H-pyrazole (2.0 equiv.), 5-(5-amino-2-methylphenyl)-2-chloronicotinonitrile (1.0 equiv.) and Na₂CO₃ (5 equiv., 2M solution) in DME (0.2 M) was added PdCl₂(dppf).CH₂Cl₂ adduct (0.18 equiv.). This mixture was heated to 110° C. for 15 min in the microwave and cooled to room temperature. Water was added, the phases were separated and the water mixture was extracted with ethyl acetate. The organic phases were pooled, dried with MgSO₄ and the volatiles removed in vacuo. The material was purified by ISCO (65% EtOAc/heptanes) to yield 5-(5-amino-2-methylphenyl)-2-(1-methyl-1H-pyrazol-4-yl)nicotinonitrile in 77% yield. LCMS (m/z) (M+H)=290.0, Rt=0.53 min.

Synthesis of 5-(5-amino-2-methylphenyl)-2-chloronicotinonitrile

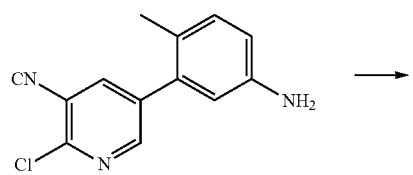

To a solution of 5-bromo-2-chloronicotinonitrile (1.0 equiv.) in THF and water (4:1, 0.2M) was added potassium carbonate (3.0 equiv.) and 4-methyl-3-(4,4,5,5-tetramethyl-1,3,2-dioxaborolan-2-yl)aniline (1.0 equiv.) and the solution was degassed with Argon. PdCl₂(dppf)-DCM (0.1 equiv.) was added and the solution was refluxed at 90° C. for 24 hours. Upon cooling to room temperature, the reaction was partitioned between 1:1 EtOAc/n-heptanes and H₂O, mixed, separated, washed with NaCl$_{(sat.)}$, dried over MgSO₄, filtered, concentrated and purified by ISCO SiO₂ chromatography (0-80%/o EtOAc/n-heptanes) to yield 5-(5-amino-2-methylphenyl)-2-chloronicotinonitrile in 82% yield. LCMS (m/z) (M+H)=243.9, Rt=0.56 min.

Synthesis of tert-butyl 4-(5-(5-amino-2-methylphenyl)-3-cyanopyridin-2-yl)piperazine-1-carboxylate

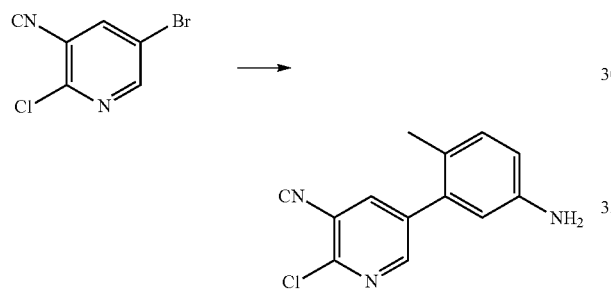

A solution of tert-butyl piperazine-1-carboxylate (1.4 equiv.), 5-(5-amino-2-methylphenyl)-2-chloronicotinonitrile (1.0 equiv.), and potassium carbonate (3.0 equiv.) in DMF (0.4M) was heated at 75° C. for 5 hours. Upon cooling to rt, the reaction was partitioned between ethyl acetate and water, the organic phase was washed with water, then sat. NaCl, dried over MgSO₄, filtered and concentrated to dryness. The crude material was purified via silica gel chromatography (ISCO, eluting with 0-80% ethylacetate/n-heptanes) to yield tert-butyl 4-(5-(5-amino-2-methylphenyl)-3-cyanopyridin-2-yl)piperazine-1-carboxylate in 62% yield. LCMS (m/z) (M+H)=338.2, Rt=0.73 min.

Synthesis of 5-(5-amino-2-methylphenyl)-2-morpholinonicotinonitrile

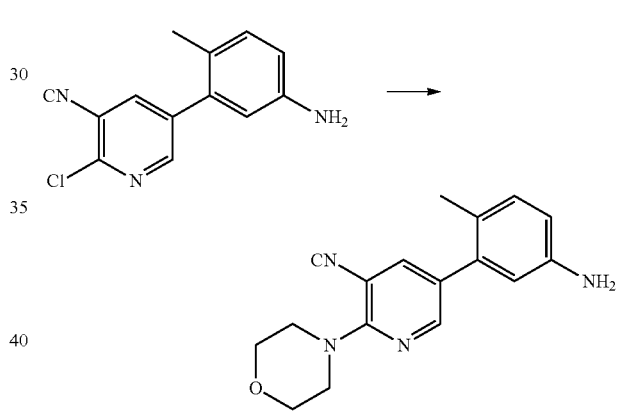

A solution of morpholine (1.4 equiv.), 5-(5-amino-2-methylphenyl)-2-chloronicotinonitrile (1.0 equiv.), and potassium carbonate (3.0 equiv.) in DMF (0.4M) was heated at 75° C. for 5 hours. Upon cooling to rt, the reaction was partitioned between ethyl acetate and water, the organic phase was washed with water, then sat. NaCl, dried over MgSO₄, filtered and concentrated to dryness. The crude material was purified via silica gel chromatography (ISCO, eluting with 0-80% ethylacetate/n-heptanes) to yield 5-(5-amino-2-methylphenyl)-2-morpholinonicotinonitrile in 67% yield. LCMS (m/z) (M+H)=295.1, Rt=0.55 min.

Synthesis of 5'-amino-2'-methyl-6-morpholino-[3,3'-bipyridine]-5-carbonitrile

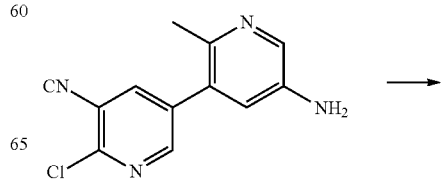

-continued

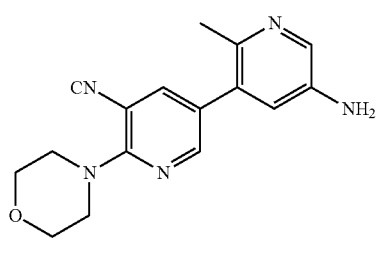

A solution of 5'-amino-6-chloro-2'-methyl-[3,3'-bipyridine]-5-carbonitrile (1.0 equiv.), morpholine (1.2 equiv.) and sodium carbonate (3.0 equiv.) was stirred at rt in DMSO for 48 hours. The mixture was diluted with ethyl acetate, washed with water, sat. NaCl, dried over $Na_2SO_4$, filtered and concentrated. The residue was purified via silica gel chromatography (ISCO, eluting with 0-100% ethyl acetate/heptanes) to give 5'-amino-2'-methyl-6-morpholino-[3,3'-bipyridine]-5-carbonitrile in 91% yield. LCMS (m/z) (M+H)=295.1, Rt=0.42 min.

Synthesis of 5-(5-amino-2-methylphenyl)-2-((tetrahydro-2H-pyran-4-yl)amino)nicotinonitrile

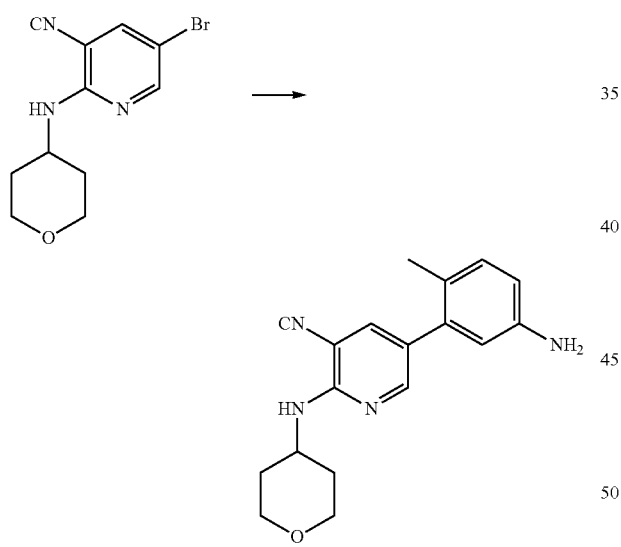

A solution of 5-bromo-2-((tetrahydro-2H-pyran-4-yl)amino)nicotinonitrile (1.0 equiv.), 4-methyl-3-(4,4,5,5-tetramethyl-1,3,2-dioxaborolan-2-yl)aniline (1.0 equiv.), sodium carbonate (3.0 equiv., 2M aqueous solution), and $PdCl_2(dppf)$-DCM (0.03 equiv.) in DME (0.13M) was heated in the microwave at 130° C. for 30 min. The solution was partitioned between ethyl acetate and water, the organic phase was washed with sat. NaCl, dried over $MgSO_4$, filtered and concentrated to dryness. Purification via silica gel chromatography (ISCO, eluting with 0-100% ethyl acetate/heptanes) afforded 5-(5-amino-2-methylphenyl)-2-((tetrahydro-2H-pyran-4-yl)amino)nicotinonitrile in 65% yield. LCMS (m/z) (M+H)=309.1 Rt=0.53 min.

Synthesis of 5'-amino-2'-methyl-6-((tetrahydro-2H-pyran-4-yl)amino)-[3,3'-bipyridine]-5-carbonitrile

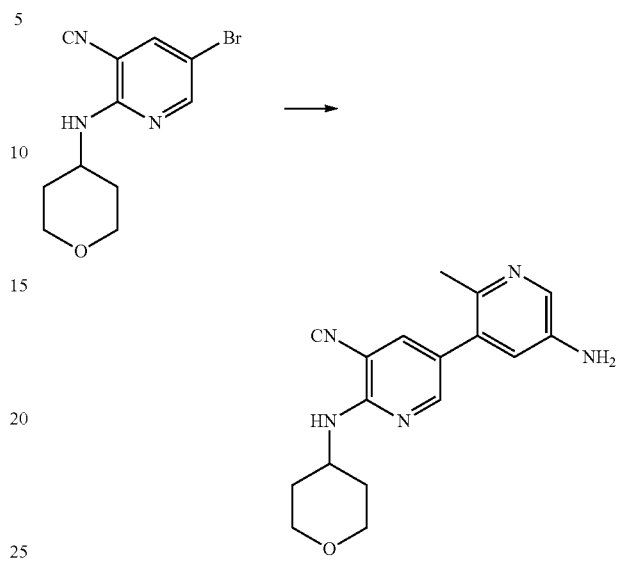

A solution of 5-bromo-2-((tetrahydro-2H-pyran-4-yl)amino)nicotinonitrile (1.0 equiv.), 6-methyl-5-(4,4,5,5-tetramethyl-1,3,2-dioxaborolan-2-yl)pyridin-3-amine (1.4 equiv.), sodium carbonate (3.0 equiv., 2M aqueous solution), and $PdCl_2(dppf)$-DCM (0.03 equiv.) in DME (0.12 M) was heated in the microwave at 130° C. for 30 min. The solution was partitioned between ethyl acetate and water, the organic phase was washed with sat. NaCl, dried over $MgSO_4$, filtered and concentrated to dryness. Purification via silica gel chromatography (ISCO, eluting with 0-5% methanol/DCM with 0.1% DIEA to 25% methanol/DCM with 0.1% DIEA) afforded 5'-amino-2'-methyl-6-((tetrahydro-2H-pyran-4-yl)amino)-[3,3'-bipyridine]-5-carbonitrile in 59% yield. LCMS (m/z) (M+H)=310.0 Rt=0.44 min.

Synthesis of 5-(5-amino-2-methylphenyl)-2-((2-methoxyethyl)amino)nicotinonitrile

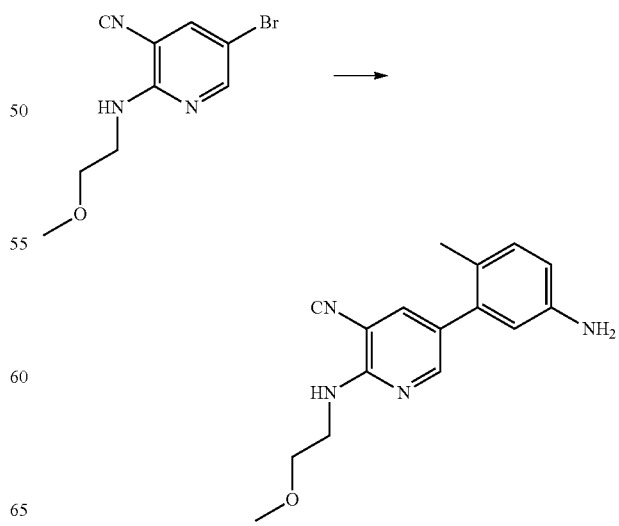

A solution of 5-bromo-2-((2-methoxyethyl)amino)nicotinonitrile (1.0 equiv.), 4-methyl-3-(4,4,5,5-tetramethyl-1,3,2-dioxaborolan-2-yl)aniline (1.0 equiv.), sodium carbonate (3.0 equiv., 2M solution), and PdCl$_2$(dppf)-DCM (0.03 equiv.) in DME (0.13 M) was heated in the microwave at 130° C. for 30 min. The solution was partitioned between ethyl acetate and water, the organic phase was washed with sat. NaCl, dried over MgSO$_4$, filtered and concentrated to dryness. Purification via silica gel chromatography (ISCO, eluting with 0-100% ethyl acetate/heptanes) afforded 5-(5-amino-2-methylphenyl)-2-((2-methoxyethyl)amino)nicotinonitrile in 88% yield. LCMS (m/z) (M+H)=283.0 Rt=0.51 min.

Synthesis of 5'-amino-6-((2-methoxyethyl)amino)-2'-methyl-[3,3'-bipyridine]-5-carbonitrile

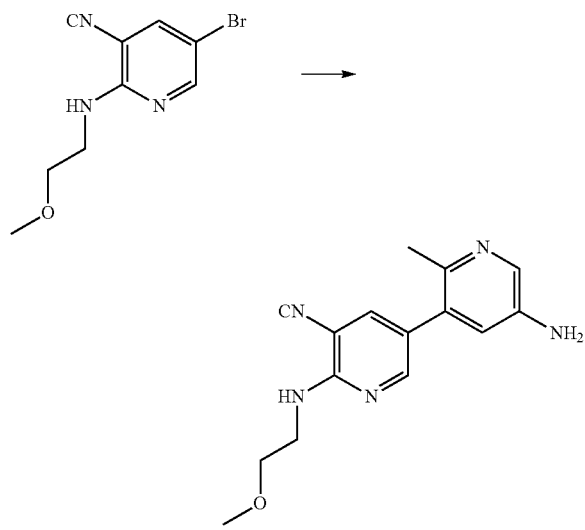

A solution of 5-bromo-2-((2-methoxyethyl)amino)nicotinonitrile (1.0 equiv.), 6-methyl-5-(4,4,5,5-tetramethyl-1,3,2-dioxaborolan-2-yl)pyridin-3-amine (1.4 equiv.), sodium carbonate (3.0 equiv., 2M solution), and PdCl$_2$(dppf)-DCM (0.03 equiv.) in DME (0.15 M) was heated in the microwave at 130° C. for 30 min. The solution was partitioned between ethyl acetate and water, the organic phase was washed with sat. NaCl, dried over MgSO$_4$, filtered and concentrated to dryness. Purification via silica gel chromatography (ISCO, eluting with 0-5% methanol/DCM with 0.1% DIEA to 25% methanol/DCM with 0.1% DIEA) afforded 5'-amino-6-((2-methoxyethyl)amino)-2'-methyl-[3,3'-bipyridine]-5-carbonitrile in 63% yield. LCMS (m/z) (M+H)=284.0 Rt=0.42 min.

Synthesis of 5-(5-amino-2-methylphenyl)-2-(3-hydroxy-3-methylazetidin-1-yl)nicotinonitrile

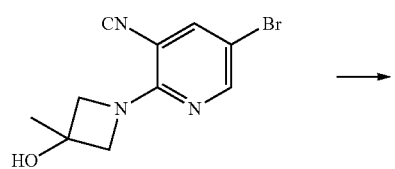

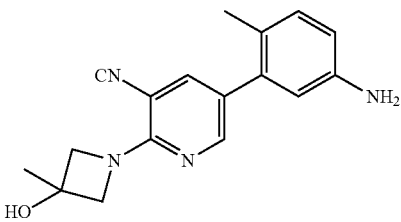

A solution of 5-bromo-2-(3-hydroxy-3-methylazetidin-1-yl)nicotinonitrile (1.0 equiv.), 4-methyl-3-(4,4,5,5-tetramethyl-1,3,2-dioxaborolan-2-yl)aniline (1.4 equiv.), sodium carbonate (3.0 equiv., 2M aq. solution), and PdCl$_2$(dppf)-DCM (0.03 equiv.) in DME (0.22 M) was heated in the microwave at 110° C. for 15 min. The solution was partitioned between ethyl acetate and water, the organic phase was dried over Na$_2$SO$_4$, filtered and concentrated to dryness. Purification via silica gel chromatography (ISCO, eluting with 0-100% ethyl acetate/heptanes) afforded 5-(5-amino-2-methylphenyl)-2-(3-hydroxy-3-methylazetidin-1-yl)nicotinonitrile in 90% yield. LCMS (m/z) (M+H)=295.0 Rt=0.48 min.

Synthesis of 5'-amino-6-(3-hydroxy-3-methylazetidin-1-yl)-2'-methyl-[3,3'-bipyridine]-5-carbonitrile

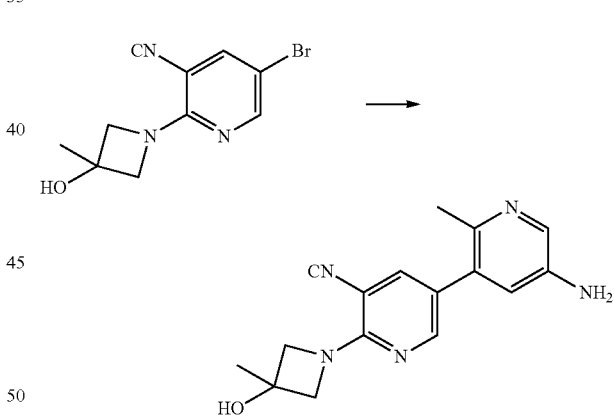

A solution of 5-bromo-2-(3-hydroxy-3-methylazetidin-1-yl)nicotinonitrile (1.0 equiv.), 6-methyl-5-(4,4,5,5-tetramethyl-1,3,2-dioxaborolan-2-yl)pyridin-3-amine (1.4 equiv.), sodium carbonate (3.0 equiv., 2M aq. solution), and PdCl$_2$(dppf)-DCM (0.15 equiv.) in DME (0.22 M) was heated in the microwave at 110° C. for 15 min. The solution was partitioned between ethyl acetate and water, the organic phase was dried over Na$_2$SO$_4$, filtered and concentrated to dryness. Purification via silica gel chromatography (ISCO, eluting with 0-8% methanol/DCM) afforded 5'-amino-6-(3-hydroxy-3-methylazetidin-1-yl)-2'-methyl-[3,3'-bipyridine]-5-carbonitrile in 91% yield. LCMS (m/z) (M+H)=296.0 Rt=0.40 min.

Synthesis of 5-(5-amino-2-methylphenyl)-2-(tetrahydro-2H-pyran-4-yl)nicotinonitrile

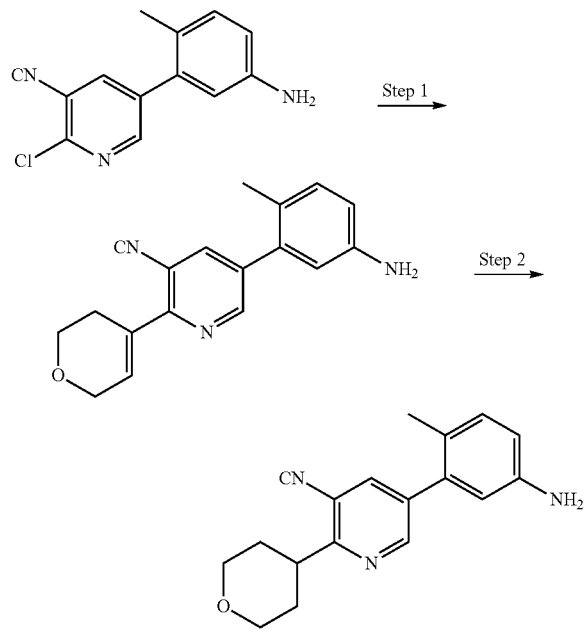

Step 1: A solution of 5-(5-amino-2-methylphenyl)-2-chloronicotinonitrile (1.0 equiv.), 2-(3,6-dihydro-2H-pyran-4-yl)-4,4,5,5-tetramethyl-1,3,2-dioxaborolane (1.4 equiv.), PdCl₂(dppf)-DCM (0.1 equiv.) and sodium carbonate (3.8 equiv, 2M solution) in DME (0.18 M) was heated in the microwave at 120° C. for 40 min. Partitioned between water and ethyl acetate, the organic phase was washed with sat. NaCl, dried over MgSO₄, filtered and concentrated to dryness. The residue was purified via silica gel chromatography (ISCO, eluting with 0-100% ethyl acetate/heptanes) to yield 5-(5-amino-2-methylphenyl)-2-(3,6-dihydro-2H-pyran-4-yl)nicotinonitrile in 91% yield. LCMS (m/z) (M+H)=292.0 Rt=0.55 min.

Step 2: To a solution of 5-(5-amino-2-methylphenyl)-2-(3,6-dihydro-2H-pyran-4-yl)nicotinonitrile (1.0 equiv.) in ethanol/DCM (5:1) was added Pd(OH)₂ (0.7 equiv.) and the mixture was purged with hydrogen and stirred for 3 hours. The solution was filtered and the filtrate was concentrated to dryness to give 5-(5-amino-2-methylphenyl)-2-(tetrahydro-2H-pyran-4-yl)nicotinonitrile in 72% yield. LCMS (m/z) (M+H)=294.0 Rt=0.55 min.

Synthesis of 5'-amino-6-(3,6-dihydro-2H-pyran-4-yl)-2'-methyl-[3,3'-bipyridine]-5-carbonitrile

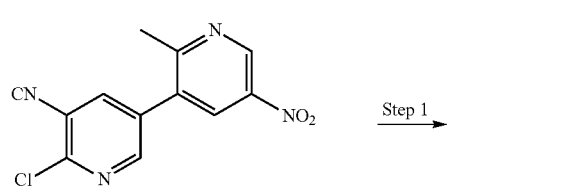

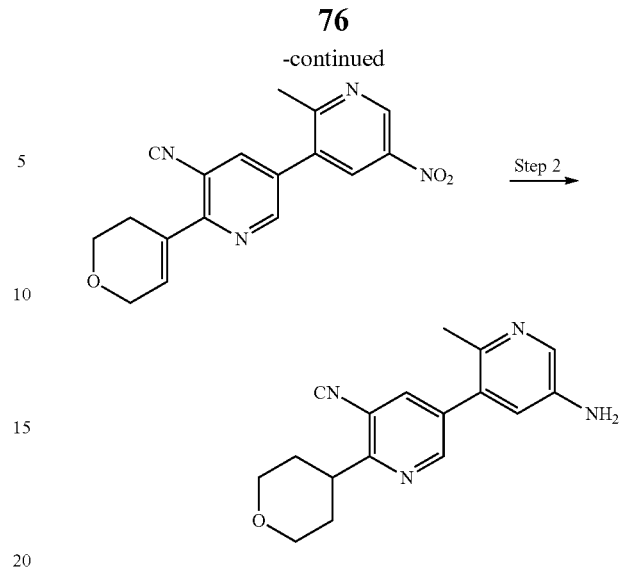

Step 1: To a solution of 6-chloro-2'-methyl-5'-nitro-[3,3'-bipyridine]-5-carbonitrile (1.0 equiv.) in DME (0.18 M) was added 2-(3,6-dihydro-2H-pyran-4-yl)-4,4,5,5-tetramethyl-1,3,2-dioxaborolane (2.0 equiv.), sodium carbonate (1.0 equiv, 2M aq. solution) and PdCl₂(dppf)-DCM (0.15 equiv.) and the reaction was heated in the microwave at 110° C. for 15 min. The solution was diluted with ethyl acetate and washed with water, then sat. NaCl. The organic layer was dried with Na₂SO₄, filtered and concentrated. The crude residue was purified via silica gel chromatography (ISCO, eluting with 0-30% ethyl acetate/heptanes) to give 6-(3,6-dihydro-2H-pyran-4-yl)-2'-methyl-5'-nitro-[3,3'-bipyridine]-5-carbonitrile in 100% yield. LCMS (m/z) (M+H)=323.2 Rt=0.68 min.

Step 2: To a suspension of 6-(3,6-dihydro-2H-pyran-4-yl)-2'-methyl-5'-nitro-[3,3'-bipyridine]-5-carbonitrile (1.0 equiv.) in EtOH/DCM (1:1, 0.03 M) was added Pd(OH)₂ (1.0 equiv.). The mixture was purged with H₂ and stirred under H₂ for 3 hr. Filter off the catalyst and concentrated to give 5'-amino-6-(3,6-dihydro-2H-pyran-4-yl)-2'-methyl-[3,3'-bipyridine]-5-carbonitrile in 79% yield. LCMS (m/z) (M+H)=295.2 Rt=0.47 min.

Synthesis of 3-(6-(4-(tert-butoxycarbonyl)piperazin-1-yl)-5-cyanopyridin-3-yl)-4-methylbenzoic acid

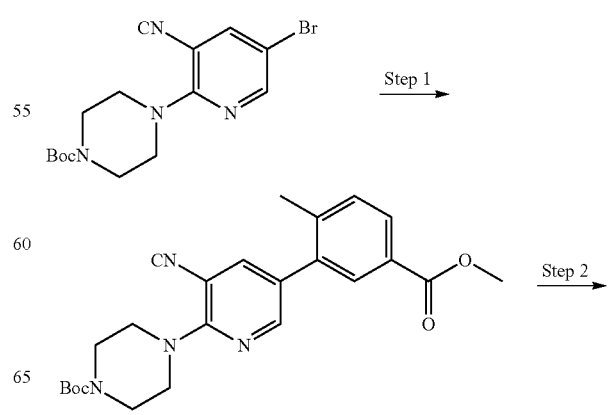

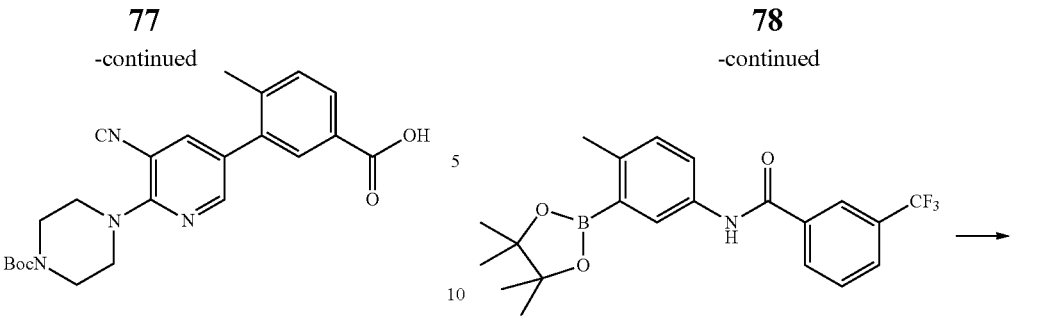

Step 1: To a mixture of tert-butyl 4-(5-bromo-3-cyano-pyridin-2-yl)piperazine-1-carboxylate (1.0 equiv.), methyl 4-methyl-3-(4,4,5,5-tetramethyl-1,3,2-dioxaborolan-2-yl)benzoate (1.1 equiv.) and PdCl$_2$(dppf).CH$_2$Cl$_2$ adduct (0.08 equiv.) in DME (0.36 M) was added Na$_2$CO$_3$ (3.0 equiv, 2M aqueous solution). The mixture was stirred at 120° C. in the microwave for 15 min. LC-MS showed complete conversion. Added brine and EtOAc, the organic layer was dried over sodium sulfate and concentrated and purified by ISCO (0-100% EtOAc/Heptane) to give tert-butyl 4-(3-cyano-5-(5-(methoxycarbonyl)-2-methylphenyl)pyridin-2-yl)piperazine-1-carboxylate in 74% yield. LCMS (m/z) (M+H)=381.2, Rt=1.13 min.

Step 2: To a solution of tert-butyl 4-(3-cyano-5-(5-(methoxycarbonyl)-2-methylphenyl)pyridin-2-yl)piperazine-1-carboxylate (1.0 equiv.) in THF (0.13 M) was added LiOH (5.5 equiv.). The mixture was stirred at rt for 4 hr. Concentrated to remove most of THF and the residue was neutralized with 6 N HCl to pH=3 and extracted with EtOAc. The organic layer was washed with brine, dried with sodium sulfate and concentrated to yield 3-(6-(4-(tert-butoxycarbonyl)piperazin-1-yl)-5-cyanopyridin-3-yl)-4-methylbenzoic acid in 22% yield. LCMS (m/z) (M+H)=367.1, Rt=0.99 min.

Example 1

N-(3-(6-amino-5-cyanopyridin-3-yl)-4-methylphenyl)-3-(trifluoromethyl)benzamide

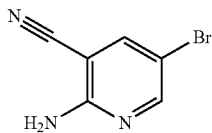

Method 2: To a solution of 2-amino-5-bromonicotinonitrile (1.4 equiv.) in toluene and ethanol (2.5:1) was added N-(4-methyl-3-(4,4,5,5-tetramethyl-1,3,2-dioxaborolan-2-yl)phenyl)-3-(trifluoromethyl)benzamide (1.0 equiv.), Pd(PPh$_3$)$_4$ (0.1 equiv.) and aqueous potassium carbonate (3M, 3.0 equiv.). The reaction was heated in the microwave at 120° C. for 40 min. The organic layer was separated and concentrated to dryness under vacuo. The residue was dissolved in DMSO and purified via reverse phase HPLC. The pure fractions were lyophilized to give N-(3-(6-amino-5-cyanopyridin-3-yl)-4-methylphenyl)-3-(trifluoromethyl)benzamide as the TFA salt in 48% yield. $^1$H NMR (400 MHz, DMSO$_{d6}$) δ 10.45 (s, 1H), 8.30 (s, 1H), 8.25 (d, J=2.0, 1H), 8.23 (d, J=2.0, 1H), 7.97 (d, J=8.0, 1H), 7.95 (d, J=4.0, 1H), 7.79 (t, J=8.0, 1H), 7.72 (dd, J=8.0, 2.0, 1H), 7.61 (d, J=4.0, 1H), 7.30 (d, J=12.0, 1H), 2.23 (s, 3H). LCMS (m/z) (M+H)=397.1, Rt=0.91 min.

The compounds listed in Table 1, below, were prepared using methods similar to those described for the preparation of Example 1 (Method 2) using the appropriate starting materials.

TABLE 1

| Example | Structure | Name | Physical Data |
|---|---|---|---|
| 2 | 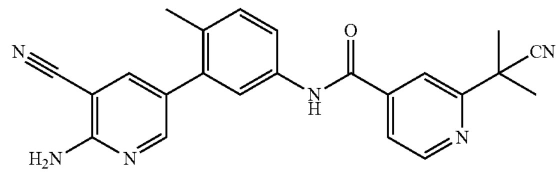 [SMILES: Cc1ccc(NC(=O)c2ccnc(C(C)(C)C#N)c2)cc1-c1cnc(N)c(C#N)c1] | N-(3-(6-amino-5-cyanopyridin-3-yl)-4-methylphenyl)-2-(2-cyanopropan-2-yl)isonicotinamide | $^1$H NMR (400 MHz, DMSO$_{d6}$) δ 10.54 (s, 1H), 8.80 (d, J = 4.0, 1H), 8.22 (d, J = 4.0, 1H), 8.00 (s, 1H), 7.95 (d, J = 4.0, 1H), 7.86 (dd, J = 8.0, 4.0, 1H), 7.69 (dd, J = 8.0, 4.0, 1H), 7.59 (d, J = 4.0), 7.31 (d, J = 8.0, 1H), 2.23 (s, 3H), 1.77 (s, 6H). LCMS (m/z) (M + H) = 397.2, Rt = 0.77 min. |
| 3 | 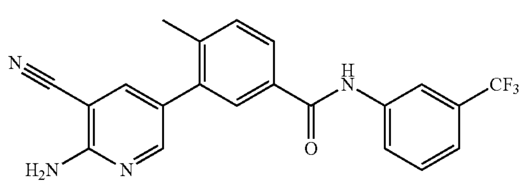 [SMILES: Cc1ccc(C(=O)Nc2cccc(C(F)(F)F)c2)cc1-c1cnc(N)c(C#N)c1] | 3-(6-amino-5-cyanopyridin-3-yl)-4-methyl-N-(3-(trifluoromethyl)phenyl)benzamide | $^1$H NMR (400 MHz, DMSO$_{d6}$) δ 10.45 (s, 1H), 8.30 (d, J = 4.0, 1H), 8.22 (s, 1H), 8.06 (d, J = 8.0, 1H), 8.03 (d, J = 2.0, 1H), 7.87-7.90 (m, 2H), 7.60 (t, J = 8.0, 1H), 7.44-7.49 (m, 2H), 2.34 (s, 3H). LCMS (m/z) (M + H) = 397.1, Rt = 0.95 min. |

TABLE 1-continued

| Example | Structure | Name | Physical Data |
|---|---|---|---|
| 4 | 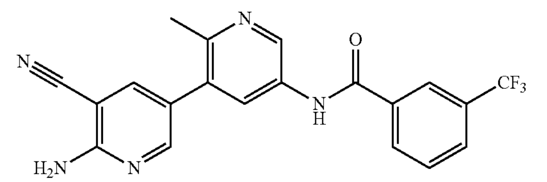 [SMILES: Cc1ncc(NC(=O)c2cccc(C(F)(F)F)c2)cc1-c1cnc(N)c(C#N)c1] | N-(6'-amino-5'-cyano-2-methyl-[3,3'-bipyridin]-5-yl)-3-(trifluoromethyl)benzamide | $^1$H NMR (400 MHz, DMSO$_{d6}$) δ 10.87 (s, 1H), 8.99 (d, J = 2.0, 1H), 8.34 (s, 1H), 8.32 (d, J = 2.0, 1H), 8.30 (d, J = 8.0, 1H), 8.20 (s, J = 4.0, 1H), 8.08 (d, J = 2.0, 1H), 8.03 (d, J = 8.0, 1H), 7.84 (t, J = 9.0, 1H), 2.52 (s, 3H). LCMS (m/z) (M + H) = 398.1, Rt = 0.65 min. |
| 5 | 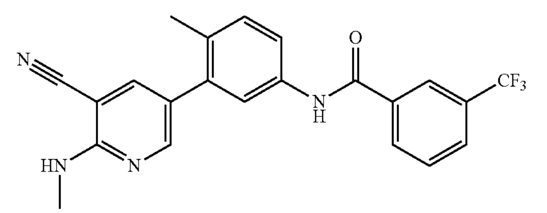 [SMILES: CNc1ncc(-c2cc(NC(=O)c3cccc(C(F)(F)F)c3)ccc2C)cc1C#N] | N-(3-(5-cyano-6-(methylamino)pyridin-3-yl)-4-methylphenyl)-3-(trifluoromethyl)benzamide | $^1$H NMR (400 MHz, DMSO$_{d6}$) δ 10.45 (s, 1H), 8.32 (d, J = 2.0, 1H), 8.30 (s, 1H), 8.26 (d, J = 8.0, 1H), 7.96-7.98 (m, 2H), 7.79 (t, J = 8.0, 1H), 7.71 (dd, J = 8.0, 2.0, 1H), 7.62 (d, J = 2.0, 1H), 7.29 (d, J = 8.0, 1H), 2.91 (s, 3H), 2.23 (s, 3H). LCMS (m/z) (M + H) = 411.1, Rt = 0.98 min. |
| 6 | 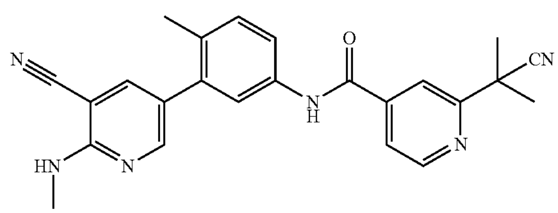 [SMILES: CNc1ncc(-c2cc(NC(=O)c3ccnc(C(C)(C)C#N)c3)ccc2C)cc1C#N] | N-(3-(5-cyano-6-(methylamino)pyridin-3-yl)-4-methylphenyl)-2-(2-cyanopropan-2-yl)isonicotinamide | $^1$H NMR (400 MHz, DMSO$_{d6}$) δ 10.54 (s, 1H), 8.81 (d, J = 4.0, 1H), 8.32 (d, J = 4.0, 1H), 8.00 (s, 1H), 7.96 (d, J = 4.0, 1H), 7.86 (dd, J = 4.0, 2.0, 1H), 7.68 (dd, J = 8.0, 2.0, 1H), 7.60 (d, J = 2.0, 1H), 7.31 (d, J = 8.0, 1H), 2.91 (s, 3H), 2.22 (s, 3H), 1.77 (s, 6H). LCMS (m/z) (M + H) = 411.2, Rt = 0.85 min. |
| 7 | 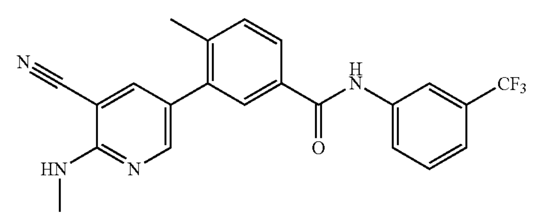 [SMILES: CNc1ncc(-c2cc(C(=O)Nc3cccc(C(F)(F)F)c3)ccc2C)cc1C#N] | 3-(5-cyano-6-(methylamino)pyridin-3-yl)-4-methyl-N-(3-(trifluoromethyl)phenyl)benzamide | $^1$H NMR (400 MHz, DMSO$_{d6}$) δ 10.45 (s, 1H), 8.40 (d, J = 2.0, 1H), 8.22 (s, 1H), 8.06 (d, J = 4.0, 1H), 8.05 (d, J = 4.0, 1H), 7.89 (dd, J = 8.0, 2.0, 1H), 7.88 (s, 1H), 7.60 (t, J = 8.0, 1H), 7.48 (d, J = 8.0, 1H), 7.45 (d, J = 8.0, 1H), 7.29 (m, 1H), 2.92 (d, J = 4.0, 3H), 2.34 (s, 3H). LCMS (m/z) (M + H) = 411.1, Rt = 1.02 min. |
| 8 | 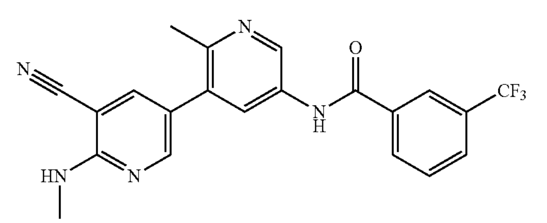 [SMILES: CNc1ncc(-c2cc(NC(=O)c3cccc(C(F)(F)F)c3)cnc2C)cc1C#N] | N-(5'-cyano-2-methyl-6'-(methylamino)-[3,3'-bipyridin]-5-yl)-3-(trifluoromethyl)benzamide | $^1$H NMR (400 MHz, DMSO$_{d6}$) δ 10.81 (s, 1H), 8.93 (d, J = 2.0, 1H), 8.40 (d, J = 2.0, 1H), 8.34 (s, 1H), 8.29 (d, J = 8.0, 1H), 8.15 (d, J = 2.0, 1H), 8.08 (d, J = 4.0, 1H), 8.02 (d, J = 8.0, 1H), 7.83 (t, J = 8.0, 1H), 7.40 (d, J = 4.0, 1H), 2.92 (d, J = 4.0, 3H), 2.50 (s, 3H). LCMS (m/z) (M + H) = 412.1, Rt = 0.71 min. |
| 9 | 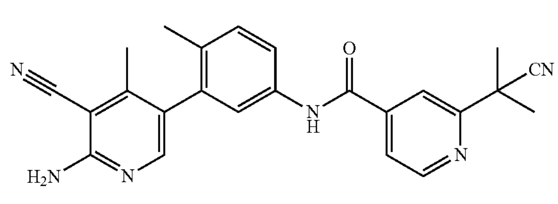 [SMILES: Cc1ccc(NC(=O)c2ccnc(C(C)(C)C#N)c2)cc1-c1cnc(N)c(C#N)c1C] | N-(3-(6-amino-5-cyano-4-methylpyridin-3-yl)-4-methylphenyl)-2-(2-cyanopropan-2-yl)isonicotinamide | 1H NMR (400 MHz, DMSO$_{d6}$) δ 10.54 (s, 1H), 879 (d, J = 4.0, 1H), 7.99 (s, 1H), 7.94 (s, 1H), 7.85 (dd, J = 4.0, 1.0, 1H), 7.71 (dd, J = 8.0, 2.0, 1H), 7.51 (d, J = 4.0, 1H), 7.34 (d, J = 8.0, 1H), 2.11 (s, 3H), 2.02 (s, 3H), 1.76 (s, 6H). LCMS (m/z) (M + H) = 411.1, Rt = 0.74 min. |
| 10 | 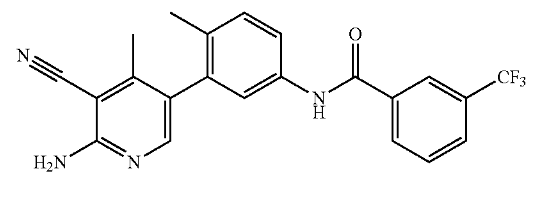 [SMILES: Cc1ccc(NC(=O)c2cccc(C(F)(F)F)c2)cc1-c1cnc(N)c(C#N)c1C] | N-(3-(6-amino-5-cyano-4-methylpyridin-3-yl)-4-methylphenyl)-3-(trifluoromethyl)benzamide | $^1$H NMR (400 MHz, DMSO$_{d6}$) δ 10.46 (s, 1H), 8.28 (s, 1H), 8.25 (d, J = 8.0, 1H), 7.96 (d, J = 8.0, 1H), 7.94 (s, 1H), 7.78 (t, J = 8.0, 1H), 7.73 (dd, J = 8.0, 4.0, 1H), 7.52 (d, J = 4.0, 1H), 7.32 (d, J = 8.0, 1H), 2.12 (s, 3H), 2.02 (s, 3H). LCMS (m/z) (M + H) = 411.1, Rt = 0.87 min. |

TABLE 1-continued

| Example | Structure | Name | Physical Data |
|---|---|---|---|
| 11 | 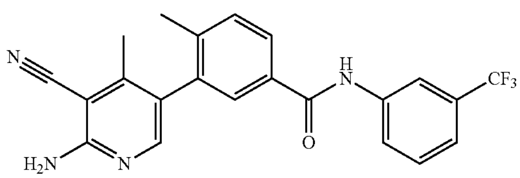 [SMILES: Cc1ccc(C(=O)Nc2cccc(C(F)(F)F)c2)cc1-c1cnc(N)c(C#N)c1C] | 3-(6-amino-5-cyano-4-methylpyridin-3-yl)-4-methyl-N-(3-(trifluoromethyl)phenyl)benzamide | $^1$H NMR (400 MHz, DMSO$_{d6}$) δ 10.42 (s, 1H), 8.21 (s, 1H), 8.06 (d, J = 8.0, 1H), 7.98 (s, 1H), 7.95 (dd, J = 8.0, 4.0, 1H), 7.78 (d, J = 4.0, 1H), 7.59 (t, J = 8.0, 1H), 7.51 (d, J = 8.0, 1H), 7.45 (d, J = 8.0, 1H), 2.13 (s, 3H), 2.10 (s, 3H). LCMS (m/z) (M + H) = 411.0, Rt = 0.89 min. |
| 12 | 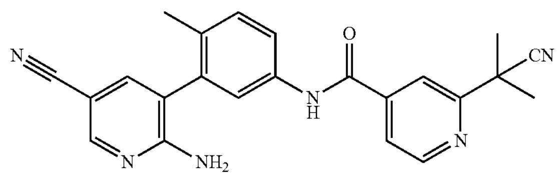 [SMILES: Cc1ccc(NC(=O)c2ccnc(C(C)(C)C#N)c2)cc1-c1cc(C#N)cnc1N] | N-(3-(2-amino-5-cyanopyridin-3-yl)-4-methylphenyl)-2-(2-cyanopropan-2-yl)isonicotinamide | $^1$H NMR (400 MHz, DMSO$_{d6}$) δ 10.56 (s, 1H), 8.81 (d, J = 4.0, 1H), 8.41 (d, J = 4.0, 1H), 7.99 (s, 1H), 7.85 (dd, J = 4.0, 2.0, 1H), 7.79 (d, J = 8.0, 4.0, 1H), 7.61 (d, J = 4.0, 1H), 7.56 (d, J = 2.0, 1H), 7.35 (d, J = 8.0, 1H), 2.09 (s, 3H), 1.76 (s, 6H). LCMS (m/z) (M + H) = 397.1, Rt = 0.72 min. |
| 13 | 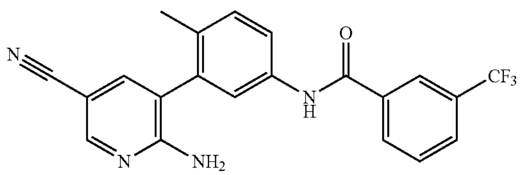 [SMILES: Cc1ccc(NC(=O)c2cccc(C(F)(F)F)c2)cc1-c1cc(C#N)cnc1N] | N-(3-(2-amino-5-cyanopyridin-3-yl)-4-methylphenyl)-3-(trifluoromethyl)benzamide | $^1$H NMR (400 MHz, DMSO$_{d6}$) δ 10.48 (s, 1H), 8.41 (d, J = 2.0, 1H), 8.29 (s, 1H), 8.26 (d, J = 8.0, 1H), 7.97 (d, J = 8.0, 1H), 7.77-7.82 (m, 2H), 7.61 (d, J = 2.0, 1H), 7.58 (d, J = 4.0, 1H), 7.33 (d, J = 8.0, 1H), 2.08 (s, 3H). LCMS (m/z) (M + H) = 397.1, Rt = 0.85 min. |
| 14 | 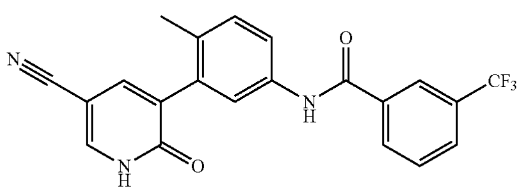 [SMILES: Cc1ccc(NC(=O)c2cccc(C(F)(F)F)c2)cc1-c1cc(C#N)c[nH]c1=O] | N-(3-(5-cyano-2-oxo-1,2-dihydropyridin-3-yl)-4-methylphenyl)-3-(trifluoromethyl)benzamide | $^1$H NMR (400 MHz, DMSO$_{d6}$) δ 10.44 (s, 1H), 8.32 (d, J = 12.0, 1H), 8.30 (s, 1H), 8.26 (d, J = 8.0, 1H), 7.97 (d, J = 8.0, 1H), 7.79 (t, J = 8.0, 1H), 7.70 (dd, J = 8.0, 2.0, 1H), 7.65 (d, J = 2.0, 1H), 7.75 (d, J = 4.0, 1H), 7.24 (d, J = 12.0, 1H), 2.12 (s, 3H). LCMS (m/z) (M + H) = 398.1, Rt = 0.85 min. |
| 15 | 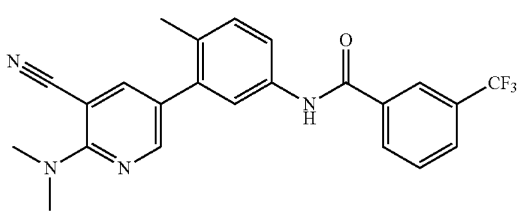 [SMILES: Cc1ccc(NC(=O)c2cccc(C(F)(F)F)c2)cc1-c1cnc(N(C)C)c(C#N)c1] | N-(3-(5-cyano-6-(dimethylamino)pyridin-3-yl)-4-methylphenyl)-3-(trifluoromethyl)benzamide | $^1$H NMR (400 MHz, DMSO$_{d6}$) δ 10.46 (s, 1H), 8.37 (d, J = 4.0, 1H), 8.29 (s, 1H), 8.26 (d, J = 8.0, 1H), 8.00 (d, J = 4.0, 1H), 7.97 (d, J = 8.0, 1H), 7.79 (t, J = 8.0, 1H), 7.72 (dd, J = 8.0, 4.0, 1H), 7.65 (d, J = 2.0, 1H), 7.30 (d, J = 8.0, 1H), 3.27 (s, 6H), 2.24 (s, 3H). LCMS (m/z) (M + H) = 425.1, Rt = 1.07 min. |
| 16 | 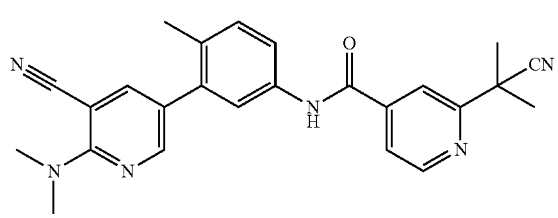 [SMILES: Cc1ccc(NC(=O)c2ccnc(C(C)(C)C#N)c2)cc1-c1cnc(N(C)C)c(C#N)c1] | N-(3-(5-cyano-6-(dimethylamino)pyridin-3-yl)-4-methylphenyl)-2-(2-cyanopropan-2-yl)isonicotinamide | $^1$H NMR (400 MHz, DMSO$_{d6}$) δ 10.55 (s, 1H), 8.81 (d, J = 8.0, 1H), 8.37 (s, J = 4.0, 1H), 8.0-8.01 (m, 2H), 7.86 (dd, J = 8.0, 2.0, 1H), 7.70 (dd, J = 8.0, 4.0, 1H), 7.63 (d, J = 4.0, 1H), 7.32 (d, J = 12.0, 1H), 3.27 (s, 6H), 2.24 (s, 3H), 1.77 (s, 6H). LCMS (m/z) (M + H) = 425.1, Rt = 0.94 min. |
| 17 | 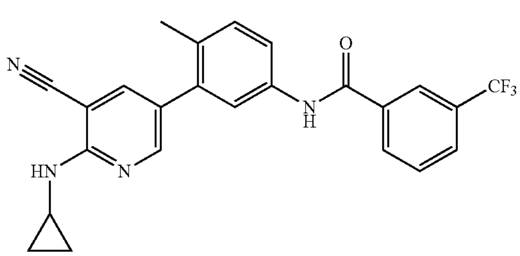 [SMILES: Cc1ccc(NC(=O)c2cccc(C(F)(F)F)c2)cc1-c1cnc(NC2CC2)c(C#N)c1] | N-(3-(5-cyano-6-(cyclopropylamino)pyridin-3-yl)-4-methylphenyl)-3-(trifluoromethyl)benzamide | $^1$H NMR (400 MHz, DMSO$_{d6}$) δ 10.46 (s, 1H), 8.36 (d, J = 2.0, 1H), 8.30 (s, 1H), 8.26 (d, J = 8.0, 1H), 7.96-7.98 (m, 2H), 7.79 (t, J = 8.0, 1H), 7.72 (dd, J = 8.0, 4.0, 1H), 7.64 (d, J = 2.0, 1H), 7.45 (bs, 1H), 7.30 (d, J = 8.0, 1H), 2.81-2.87 (m, 1H), 2.24 (s, 3H), 0.72-0.76 (m, 2H), 0.61-0.64 (m, 2H). LCMS (m/z) (M + H) = 437.1, Rt = 1.01 min. |

TABLE 1-continued

| Example | Structure | Name | Physical Data |
|---|---|---|---|
| 18 | 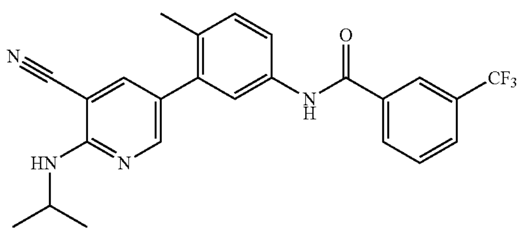 [SMILES: Cc1ccc(NC(=O)c2cccc(C(F)(F)F)c2)cc1-c1cnc(NC(C)C)c(C#N)c1] | N-(3-(5-cyano-6-(isopropylamino)pyridin-3-yl)-4-methylphenyl)-3-(trifluoromethyl)benzamide | $^1$H NMR (400 MHz, DMSO$_{d6}$) δ 10.45 (s, 1H), 8.31 (d, J = 2.0, 1H), 8.30 (s, 1H), 8.26 (d, J = 8.0, 1H), 7.95-7.98 (m, 2H), 7.79 (t, J = 8.0, 1H), 7.72 (dd, J = 8.0, 2.0, 1H), 7.63 (d, J = 2.0, 1H), 7.29 (d, J = 8.0, 1H), 6.83 (d, J = 4.0, 1H), 4.31-4.37 (m, 1H), 2.24 (s, 3H), 1.23 (d, J = 4.0, 6H). LCMS (m/z) (M + H) = 439.1, Rt = 1.07 min. |
| 19 | 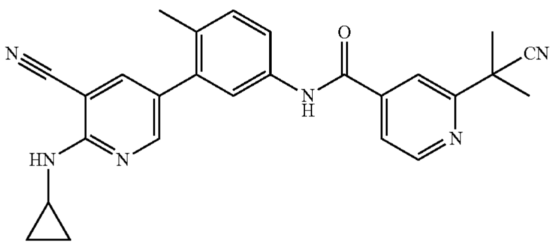 [SMILES: Cc1ccc(NC(=O)c2ccnc(C(C)(C)C#N)c2)cc1-c1cnc(NC2CC2)c(C#N)c1] | N-(3-(5-cyano-6-(cyclopropylamino)pyridin-3-yl)-4-methylphenyl)-2-(2-cyanopropan-2-yl)isonicotinamide | $^1$H NMR (400 MHz, DMSO$_{d6}$) δ 10.54 (s, 1H), 8.81 (d, J = 8.0, 1H), 8.36 (d, J = 2.0, 1H), 8.00 (s, 1H), 7.97 (d, J = 2.0, 1H), 7.86 (dd, J = 8.0, 4.0, 1H), 7.69 (dd, J = 8.0, 2.0, 1H), 7.62 (d, J = 2.0, 1H), 7.45 (d, J = 4.0, 1H), 7.30 (d, J = 8.0, 1H), 2.81-2.87 (m, 1H), 2.24 (s. 3H), 1.77 (s, 6H), 0.72-0.76 (m, 2H), 0.61-0.64 (m, 2H). LCMS (m/z) (M + H) = 437.1, Rt = 0.88 min. |
| 20 | 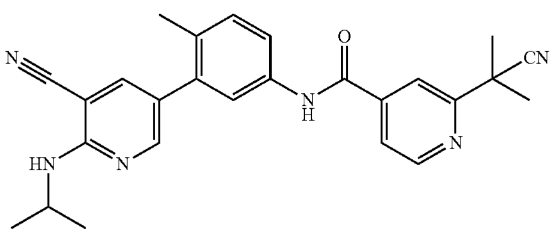 [SMILES: Cc1ccc(NC(=O)c2ccnc(C(C)(C)C#N)c2)cc1-c1cnc(NC(C)C)c(C#N)c1] | N-(3-(5-cyano-6-(isopropylamino)pyridin-3-yl)-4-methylphenyl)-2-(2-cyanopropan-2-yl)isonicotinamide | $^1$H NMR (400 MHz, DMSO$_{d6}$) δ 10.54 (s, 1H), 8.81 (d, J = 4.0, 1H), 8.30 (d, J = 4.0, 1H), 8.00 (s, 1H), 7.96 (d, J = 4.0, 1H), 7.85 (dd, J = 8.0, 2.0, 1H), 7.68 (dd, J = 8.0, 4.0, 1H), 7.60 (d, J = 4.0, 1H), 7.31 (d, J = 8.0, 1H), 6.84 (d, J = 4.0, 1H), 4.31-4.37 (m, 1H), 2.24 (s, 3H), 1.77 (s, 6H), 1.22 (d, J = 4.0, 6H). LCMS (m/z) (M + H) = 439.1, Rt = 0.99 min. |
| 21 | 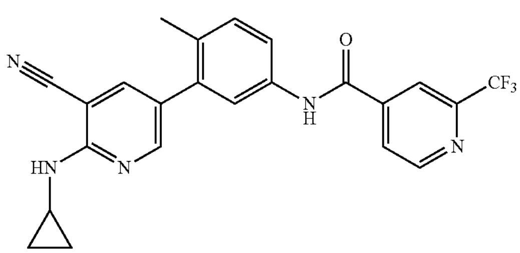 [SMILES: Cc1ccc(NC(=O)c2ccnc(C(F)(F)F)c2)cc1-c1cnc(NC2CC2)c(C#N)c1] | N-(3-(5-cyano-6-(cyclopropylamino)pyridin-3-yl)-4-methylphenyl)-2-(trifluoromethyl)isonicotinamide | $^1$H NMR (400 MHz, DMSO$_{d6}$) δ 10.67 (s, 1H), 8.99 (d, J = 4.0, 1H), 8.36-8.37 (m, 2H), 8.19 (d, J = 8.0, 1H), 7.96 (d, J = 4.0, 1H), 7.71 (dd, J = 8.0, 2.0, 1H), 7.63 (d, J = 2.0, 1H), 7.45 (d, J = 2.0, 1H), 7.33 (d, J = 8.0, 1H), 2.81-2.87 (m, 1H), 2.25 (s, 3H), 0.72-0.76 (m, 2H), 0.62-0.65 (m, 2H). LCMS (m/z) (M + H) = 438.1, Rt = 0.94 min. |
| 22 | 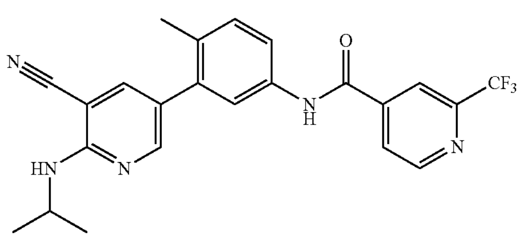 [SMILES: Cc1ccc(NC(=O)c2ccnc(C(F)(F)F)c2)cc1-c1cnc(NC(C)C)c(C#N)c1] | N-(3-(5-cyano-6-(isopropylamino)pyridin-3-yl)-4-methylphenyl)-2-(trifluoromethyl)isonicotinamide | $^1$H NMR (400 MHz, DMSO$_{d6}$) δ 10.67 (s, 1H), 8.99 (d, J = 4.0, 1H), 8.36 (s, 1H), 8.30 (d, J = 4.0, 1H), 8.19 (d, J = 4.0, 1H), 7.95 (d, J = 4.0, 1H), 7.70 (dd, J = 8.0, 4.0, 1H), 7.62 (d, J = 2.0, 1H), 7.32 (d, J = 8.0, 1H), 6.85 (d, J = 8.0, 1H), 4.30-4.38 (m, 1H), 2.24 (s, 3H), 1.22 (d, J = 4.0, 6H). LCMS (m/z) (M + H) = 440.1, Rt = 1.10 min. |
| 23 | 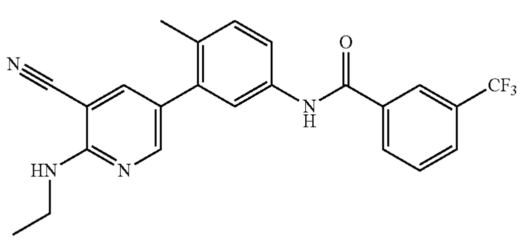 [SMILES: CCNc1ncc(-c2cc(NC(=O)c3cccc(C(F)(F)F)c3)ccc2C)cc1C#N] | N-(3-(5-cyano-6-(ethylamino)pyridin-3-yl)-4-methylphenyl)-3-(trifluoromethyl)benzamide | $^1$H NMR (400 MHz, DMSO$_{d6}$) δ 10.45 (s, 1H), 8.29-8.31 (m, 2H), 8.26 (d, J = 8.0, 1H), 7.95-7.98 (m, 2H), 7.79 (t, J = 8.0, 1H), 7.71 (dd, J = 8.0, 2.0, 1H), 7.62 (d, J = 4.0, 1H), 7.29 (d, J = 8.0, 1H), 7.25 (m, 1H), 3.42-3.48 (m, 2H), 2.23 (s, 3H), 1.17 (t, J = 8.0, 3H). LCMS (m/z) (M + H) = 425.0, Rt = 1.09 min. |

TABLE 1-continued

| Example | Structure | Name | Physical Data |
|---|---|---|---|
| 24 | 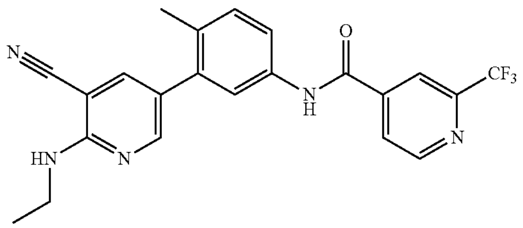 [SMILES: CCNc1ncc(-c2cc(NC(=O)c3ccnc(C(F)(F)F)c3)ccc2C)cc1C#N] | N-(3-(5-cyano-6-(ethylamino)pyridin-3-yl)-4-methylphenyl)-2-(trifluoromethyl)isonicotinamide | $^1$H NMR (400 MHz, DMSO$_{d6}$) δ 10.67 (s, 1H), 8.99 (d, J = 4.0, 1H), 8.36 (s, 1H), 8.30 (d, J = 2.0, 1H), 8.19 (d, J = 4.0, 1H), 7.95 (d, J = 4.0, 1H), 7.70 (dd, J = 8.0, 4.0, 1H), 7.62 (d, J = 2.0, 1H), 7.32 (d, J = 8.0, 1H), 7.26 (m, 1H), 3.42-3.48 (m, 2H), 2.24 (s, 3H), 1.17 (t, J = 8.0, 3H). LCMS (m/z) (M + H) = 426.0, Rt = 1.02 min. |
| 25 | 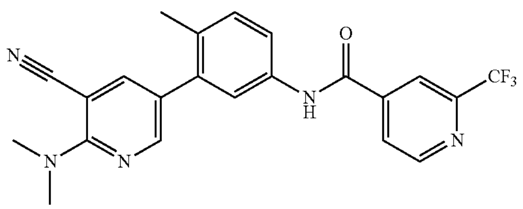 | N-(3-(5-cyano-6-(dimethylamino)pyridin-3-yl)-4-methylphenyl)-2-(trifluoromethyl)isonicotinamide | $^1$H NMR (400 MHz, DMSO$_{d6}$) δ 10.68 (s, 1H), 8.99 (d, J = 2.0, 1H), 8.36-8.38 (m, 2H), 8.19 (dd, J = 4.0, 2.0, 1H), 8.01 (d, J = 2.0, 1H), 7.71 (dd, J = 8.0, 4.0, 1H), 7.65 (d, J = 2.0, 1H), 7.33 (d, J = 8.0, 1H), 3.27 (s, 6H), 2.25 (s, 3H). LCMS (m/z) (M + H) = 426.1, Rt = 1.06 min. |
| 26 | 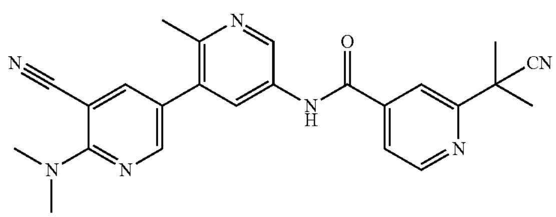 [SMILES: Cc1ncc(NC(=O)c2ccnc(C(C)(C)C#N)c2)cc1-c1cnc(N(C)C)c(C#N)c1] | N-(5'-cyano-6'-(dimethylamino)-2-methyl-[3,3'-bipyridin]-5-yl)-2-(2-cyanopropan-2-yl)isonicotinamide | $^1$H NMR (400 MHz, DMSO$_{d6}$) δ 10.89 (s, 1H), 8.90 (d, J = 4.0, 1H), 8.85 (dd, J = 8.0, 1.0, 1H), 8.44 (d, J = 4.0, 1H), 8.14 (d, J = 4.0, 2H), 8.04 (s, 1H), 7.99 (dd, J = 9.0, 2.0, 1H), 3.29 (s, 6H), 2.50 (s, 3H), 1.77 (s, 6H). LCMS (m/z) (M + H) = 426.1, Rt = 0.78 min. |
| 27 | 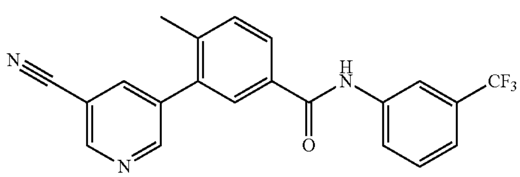 [SMILES: Cc1ccc(C(=O)Nc2cccc(C(F)(F)F)c2)cc1-c1cncc(C#N)c1] | 3-(5-cyanopyridin-3-yl)-4-methyl-N-(3-(trifluoromethyl)phenyl)benzamide | $^1$H NMR (400 MHz, DMSO$_{d6}$) δ 10.50 (s, 1H), 9.10 (d, J = 4.0, 1H), 8.98 (d, J = 2.0, 1H), 8.50 (t, J = 2.0, 1H), 8.22 (s, 1H), 8.06 (d, J = 8.0, 1H), 7.99 (dd, J 8.0, 1.0, 1H), 7.96 (s, 1H), 7.61 (t, J = 8.0, 1H), 7.56 (d, J = 8.0, 1H), 7.46 (d, J = 8.0, 1H), 2.35 (s, 3H). LCMS (m/z) (M + H) = 382.0, Rt = 1.03 min. |
| 28 | 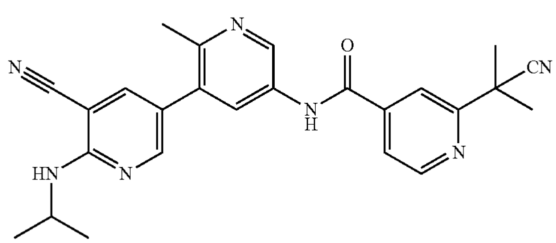 [SMILES: Cc1ncc(NC(=O)c2ccnc(C(C)(C)C#N)c2)cc1-c1cnc(NC(C)C)c(C#N)c1] | N-(5'-cyano-6'-(isopropylamino)-2-methyl-[3,3'-bipyridin]-5-yl)-2-(2-cyanopropan-2-yl)isonicotinamide | 1H NMR (400 MHz, DMSO$_{d6}$) δ 10.88 (s, 1H), 8.90 (d, J = 4.0, 1H), 8.85 (d, J = 8.0, 1H), 8.38 (d, J = 2.0, 1H), 8.11 (s, 1H), 8.08 (s, 1H), 8.04 (d, J = 4.0, 1H), 7.89 (dd, J = 4.0, 2.0, 1H), 7.02 (d, J = 8.0, 1H), 4.30-4.42 (m, 1H), 2.50 (s, 3H), 1.77 (s, 6H), 1.23 (d, J = 8.0, 3H). LCMS (m/z) (M + H) = 440.1, Rt = 0.72 min. |
| 29 | 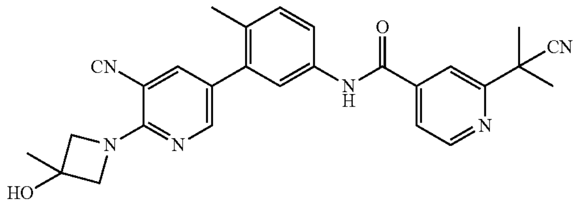 | N-(3-(5-cyano-6-(3-hydroxy-3-methylazetidin-1-yl)pyridin-3-yl)-4-methylphenyl)-2-(2-cyanopropan-2-yl)isonicotinamide | $^1$H NMR (400 MHz, <dmso>) δ ppm 1.47 (s, 3 H) 1.77 (s, 6 H) 2.23 (s, 3 H) 4.09-4.20 (m, 4 H) 7.32 (d, J = 8.71 Hz, 1 H) 7.61 (d, J = 2.20 Hz, 1 H) 7.69 (dd, J = 8.0, 2.0, 1H) 7.86 (d, J = 5.09 Hz, 1 H) 7.99-8.00 (m, 1 H) 8.01 (d, J = 2.40 Hz, 1 H) 8.34 (d, J = 2.35 Hz, 1 H) 8.81 (dd, J = 5.04, 0.88 Hz, 1 H) 10.55 (s, 1 H). LCMS (m/z) (M + H) = 467.2, Rt = 0.83 min. |

TABLE 1-continued

| Example | Structure | Name | Physical Data |
|---|---|---|---|
| 30 | 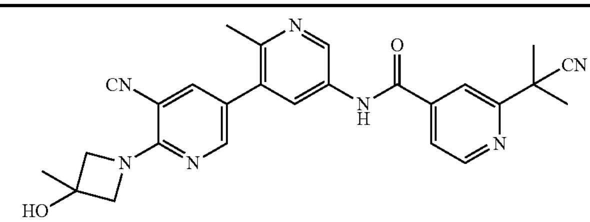 | N-(5'-cyano-6'-(3-hydroxy-3-methylazetidin-1-yl)-2-methyl-[3,3'-bipyridin]-5-yl)-2-(2-cyanopropan-2-yl)isonicotinamide | ¹H NMR (400 MHz, <dmso>) δ ppm ¹H NMR (400 MHz, <dmso>) □ ppm 1.47 (s, 3 H) 1.77 (s, 6 H) 2.48 (s, 3 H) 4.14-4.20 (m, 4H) 7.89 (dd, J = 4.0, 2.0, 1H) 8.03 (s, 1 H) 8.10 (d, J = 2.0, 1H) 8.13 (d, J = 2.35 Hz, 1 H) 8.41 (d, J = 2.40 Hz, 1 H) 8.84 (d, J = 4.0, 1H), 8.90 (d, J = 2.0, 1H), 10.88 (s, 1H). LCMS (m/z) (M + H) = 468.2, Rt = 0.59 min. |

Example 31

N-(3-(2-chloro-5-cyanopyridin-3-yl)-4-methylphenyl)-2-(2-cyanopropan-2-yl)isonicotinamide

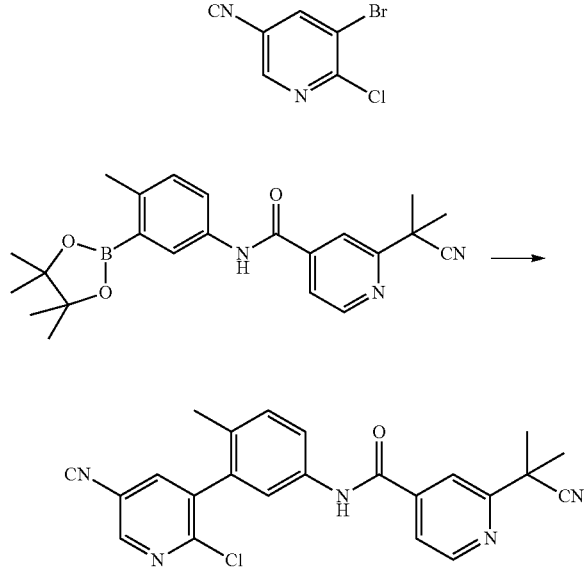

Method 3: To a degassed solution of 5-bromo-6-chloronicotinonitrile (1.0 equiv.) was added 2-(2-cyanopropan-2-yl)-N-(4-methyl-3-(4,4,5,5-tetramethyl-1,3,2-dioxaborolan-2-yl)phenyl)isonicotinamide (1.1 equiv.) followed by sodium carbonate (5.0 equiv., 2M solution) and PdCl₂(dppf)-DCM adduct (0.15 equiv.). The mixture was heated to 90° C. for 1 hour and then cooled to room temperature. Water was added, the phases were separated and the water mixture was extracted with ethyl acetate. The organics were combined, dried with magnesium sulfate, filtered and concentrated under vacuo. The material was purified via silica gel column chromatography eluting with 40% ethyl acetate in heptanes. The pure fractions were concentrated and further purified via reverse phase HPLC. The pure fractions were lyophilized to yield N-(3-(2-chloro-5-cyanopyridin-3-yl)-4-methylphenyl)-2-(2-cyanopropan-2-yl)isonicotinamide as the TFA salt in 23% yield. ¹H NMR (400 MHz, <cd3od>) □□ ppm 1.80 (s, 6 H) 2.12 (s, 3 H) 7.34-7.41 (m, 1 H) 7.55-7.62 (m, 1 H) 7.69-7.76 (m, 1 H) 7.77-7.83 (m, 1 H) 8.02-8.08 (m, 1 H) 8.19 (s, 1 H) 8.73-8.78 (m, 1 H) 8.80 (s, 1H). LCMS (m/z) (M+H)=416.1, Rt=0.94 min.

Example 32

N-(3-(6-chloro-5-cyanopyridin-3-yl)-4-methylphenyl)-2-(2-cyanopropan-2-yl)isonicotinamide

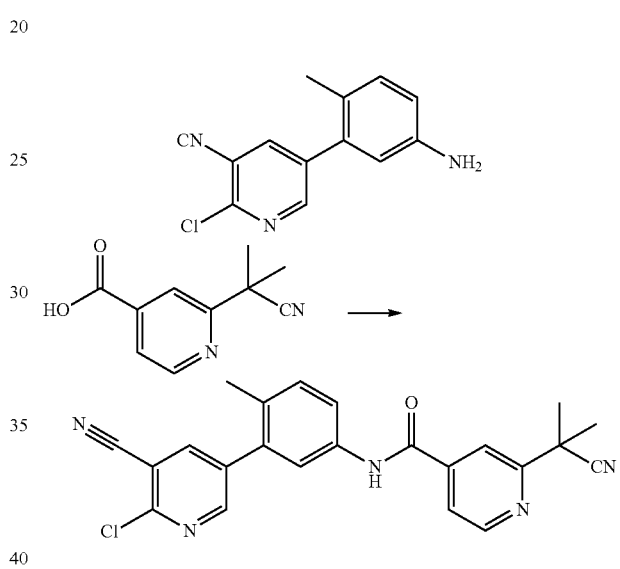

EDC (2.0 equiv.) was added to a solution of 5-(5-amino-2-methylphenyl)-2-chloronicotinonitrile (1.0 equiv.), 2-(2-cyanopropan-2-yl)isonicotinic acid (1.1 equiv.), HOAt (2.0 equiv.) in DMF (0.2 M). The mixture was stirred at ambient temperature for 3 hrs. The reaction mixture was diluted with water and extracted with ethyl acetate. The combined extracts were washed sequentially with 1M aqueous sodium hydroxide and brine, dried over sodium sulfate, filtered, and concentrated. Purified by ISCO (26% EtOAc/Heptane) to give N-(3-(6-chloro-5-cyanopyridin-3-yl)-4-methylphenyl)-2-(2-cyanopropan-2-yl)isonicotinamide in 76% yield. LCMS (m/z) (M+H)=416.0, Rt=0.93 min.

Example 33

N-(3-(6-chloro-5-cyanopyridin-3-yl)-4-methylphenyl)-3-(trifluoromethyl)benzamide

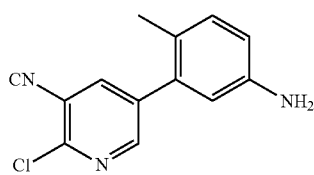

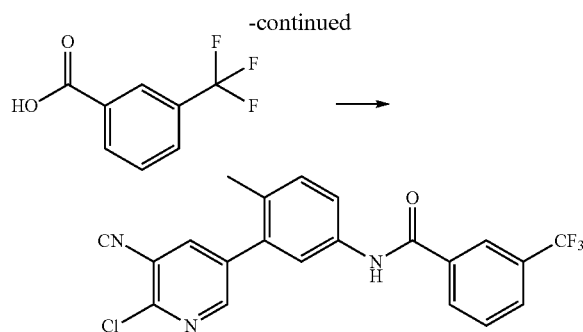

EDC (1.3 equiv.) was added to a solution of 5-(5-amino-2-methylphenyl)-2-chloronicotinonitrile (1.0 equiv.), 3-(trifluoromethyl)benzoic acid (1.1 equiv.), HOAt (1.3 equiv.) in DMF (0.2 M). The mixture was stirred at ambient temperature for 3 hrs. LC-MS showed 100% conversion. The reaction mixture was diluted with water and extracted with ethyl acetate. The combined extracts were washed sequentially with 1M aqueous sodium hydroxide and brine, dried over sodium sulfate, filtered, and concentrated. Purified by ISCO (26% EtOAc/Heptane) to give N-(3-(6-chloro-5-cyanopyridin-3-yl)-4-methylphenyl)-3-(trifluoromethyl)benzamide in 78% yield. LCMS (m/z) (M+H)=416.0, Rt=1.06 min.

The compounds listed in Table 2, below, were prepared using methods similar to those described for the preparation of Example 31 (Method 3) using the appropriate starting materials.

TABLE 2

| Example | Structure | Name | Physical Data |
|---|---|---|---|
| 32 | 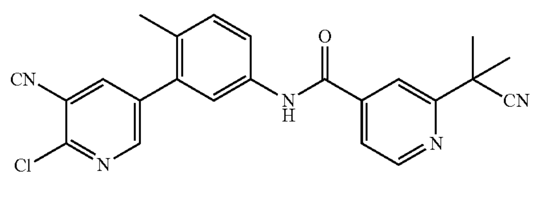 | N-(3-(6-chloro-5-cyanopyridin-3-yl)-4-methylphenyl)-2-(2-cyanopropan-2-yl)isonicotinamide | $^1$H NMR (400 MHz, <cd3od>) δ ppm 1.81 (s, 6 H) 2.28 (s, 3 H) 7.38 (d, J = 8.22 Hz, 1 H) 7.67 (d, J = 2.35 Hz, 2 H) 7.81 (s, 1 H) 8.06 (s, 1 H) 8.34 (d, J = 2.35 Hz, 1 H) 8.65 (d, J = 2.35 Hz, 1 H) 8.76 (d, J = 5.09 Hz, 1 H). LCMS (m/z) (M + H) = 416.1, Rt = 0.96 min. |
| 33 | 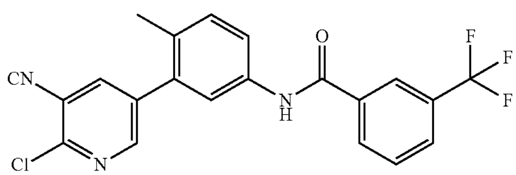 | N-(3-(6-chloro-5-cyanopyridin-3-yl)-4-methylphenyl)-3-(trifluoromethyl)benzamide | $^1$H NMR (400 MHz, <cd3od>) δ ppm 2.28 (s, 3 H) 7.33-7.41 (m, 1 H) 7.66 (s, 3 H) 7.85-7.92 (m, 1 H) 8.16-8.36 (m, 3 H) 8.66 (d, J = 2.35 Hz, 1H). LCMS (m/z) (M + H) = 416.0, Rt = 1.09 min. |
| 34 | 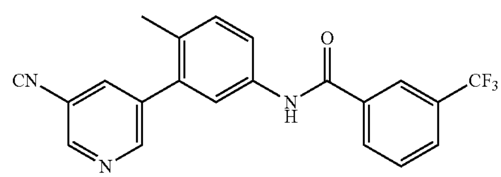 | N-(3-(5-cyanopyridin-3-yl)-4-methylphenyl)-3-(trifluoromethyl)benzamide | $^1$H NMR (400 MHz, <cdcl3>) δ ppm 2.27 (s, 3 H) 7.36 (d, J = 8.22 Hz, 1 H) 7.55 (s, 1 H) 7.66 (s, 2 H) 7.83 (br. s., 2 H) 7.93-7.99 (m, 1 H) 8.06 (s, 1 H) 8.12 (s, 1 H) 8.83 (d, J = 1.96 Hz, 1 H) 8.90 (d, J = 1.57 Hz, 1 H). LCMS (m/z) (M + H) = 382.1, Rt = 0.99 min. |
| 35 | 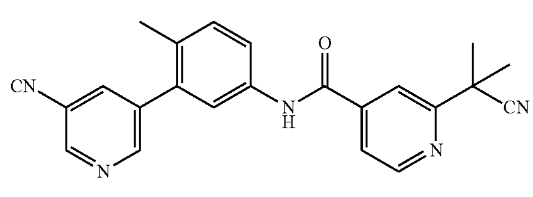 | 2-(2-cyanopropan-2-yl)-N-(3-(5-cyanopyridin-3-yl)-4-methylphenyl)isonicotinamide | $^1$H NMR (400 MHz, <cd3od>) δ ppm 1.73-1.88 (m, 6 H) 2.27 (s, 3 H) 7.35-7.44 (m, 1 H) 7.63-7.75 (m, 2 H) 7.77-7.84 (m, 1 H) 8.01-8.10 (m, 1 H) 8.21-8.30 (m, 1 H) 8.69-8.79 (m, 1 H) 8.80-8.87 (m, 1 H) 8.89-8.97 (m, 1 H). LCMS (m/z) (M + H) = 382.0, Rt = 0.86 min. |
| 36 | 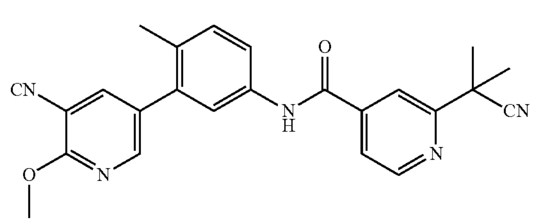 | N-(3-(5-cyano-6-methoxypyridin-3-yl)-4-methylphenyl)-2-(2-cyanopropan-2-yl)isonicotinamide | $^1$H NMR (400 MHz, <cd3od>) δ ppm 1.71 (s, 6 H) 2.17 (s, 3 H) 4.02 (s, 3 H) 7.26 (s, 1 H) 7.52 (s, 2 H) 7.68-7.75 (m, 1 H) 7.94-8.05 (m, 2 H) 8.31 (d, J = 2.35 Hz, 1 H) 8.66 (d, J = 5.09 Hz, 1 H). LCMS (m/z) (M + H) = 412.1, Rt = 0.97 min. |

TABLE 2-continued

| Example | Structure | Name | Physical Data |
|---|---|---|---|
| 37 | 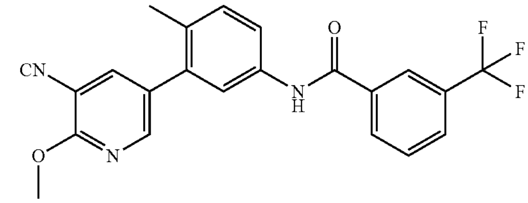 | N-(3-(5-cyano-6-methoxypyridin-3-yl)-4-methylphenyl)-3-(trifluoromethyl)benzamide | $^1$H NMR (400 MHz, <cd3od>) δ ppm 2.26 (s, 3H) 4.11 (s, 3 H) 7.33 (d, J = 8.22 Hz, 1 H) 7.59-7.69 (m, 2 H) 7.69-7.76 (m, 1 H) 7.89 (d, J = 7.83 Hz, 1 H) 8.11 (d, J = 2.35 Hz, 1 H) 8.20 (d, J = 8.22 Hz, 1 H) 8.25 (s, 1 H) 8.41 (d, J = 2.35 Hz, 1 H). LCMS (m/z) (M + H) = 412.0, Rt = 1.09 min. |
| 38 | 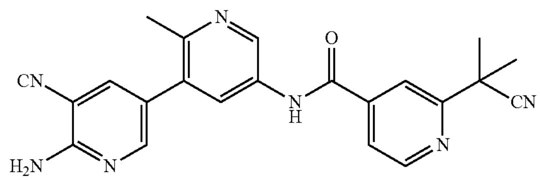 | N-(6'-amino-5'-cyano-2-methyl-[3,3'-bipyridin]-5-yl)-2-(2-cyanopropan-2-yl)isonicotinamide | $^1$H NMR (400 MHz, <cd3od>) δ ppm 1.77-1.86 (m, 6 H) 2.67 (s, 3 H) 7.82-7.90 (m, 1 H) 7.99-8.05 (m, 1 H) 8.09-8.16 (m, 1 H) 8.30-8.42 (m, 2 H) 8.77-8.85 (m, 1 H) 9.25-9.31 (m, 1 H). LCMS (m/z) (M + H) = 398.1, Rt = 0.53 min |
| 39 | 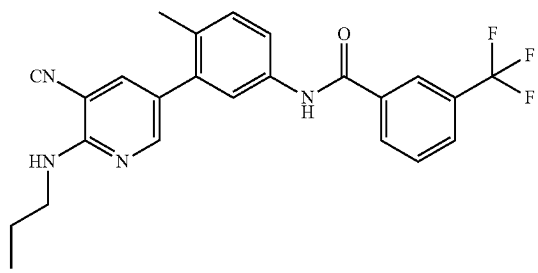 | N-(3-(5-cyano-6-(propylamino)pyridin-3-yl)-4-methylphenyl)-3-(trifluoromethyl)benzamide | $^1$H NMR (400 MHz, <cd3od>) δ ppm 1.00 (t, J = 7.43 Hz, 3 H) 1.69 (d, J = 7.43 Hz, 2 H) 2.28 (s, 3 H) 3.47 (t, J = 7.43 Hz, 2 H) 7.31 (d, J = 8.22 Hz, 1H) 7.58 (d, J = 1.96 Hz, 2 H) 7.72 (s, 1 H) 7.90 (d, J = 2.35 Hz, 2 H) 8.16-8.27 (m, 3H). LCMS (m/z) (M + H) = 439.1, Rt = 1.09 min. |
| 40 | 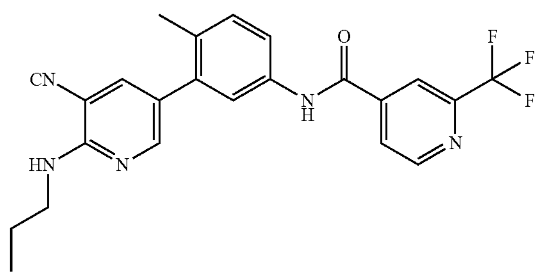 | N-(3-(5-cyano-6-(propylamino)pyridin-3-yl)-4-methylphenyl)-2-(trifluoromethyl)isonicotinamide | $^1$H NMR (400 MHz, <cd3od>) δ ppm 1.00 (t, J = 7.43 Hz, 3 H) 1.69 (d, J = 7.43 Hz, 2 H) 2.28 (s, 3 H) 3.47 (t, J = 7.24 Hz, 2 H) 7.33 (s, 1 H) 7.60 (d, J = 1.96 Hz, 2 H) 7.89 (d, J = 2.35 Hz, 1 H) 8.09-8.15 (m, 1 H) 8.23 (d, J = 2.35 Hz, 1 H) 8.29 (s, 1 H) 8.84-8.95 (m, 1 H). LCMS (m/z) (M + H) = 440.1, Rt = 1.11 min. |
| 41 | 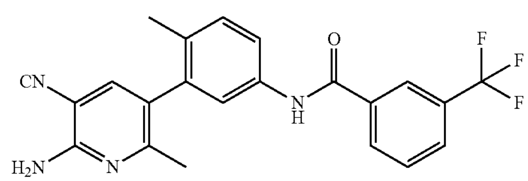 | N-(3-(6-amino-5-cyano-2-methylpyridin-3-yl)-4-methylphenyl)-3-(trifluoromethyl)benzamide | $^1$H NMR (400 MHz, <cd3od>) δ ppm 2.11 (s, 3 H) 2.26 (s, 3 H) 7.34 (d, J = 8.22 Hz, 1 H) 7.55 (d, J = 1.96 Hz, 1 H) 7.59-7.66 (m, 1 H) 7.72 (s, 1 H) 7.87 (s, 2 H) 8.24 (s, 2 H). LCMS (m/z) (M + H) = 411.1, Rt = 0.89 min. |
| 42 | 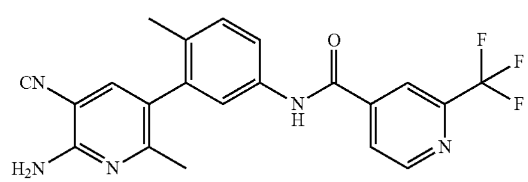 | N-(3-(6-amino-5-cyano-2-methylpyridin-3-yl)-4-methylphenyl)-2-(trifluoromethyl)isonicotinamide | $^1$H NMR (400 MHz, <cd3od>) δ ppm 2.12 (s, 3 H) 2.26 (s, 3 H) 7.37 (s, 1 H) 7.57 (d, J = 1.96 Hz, 1 H) 7.61-7.72 (m, 1 H) 7.87 (s, 1 H) 8.07-8.16 (m, 1 H) 8.28 (s, 1 H) 8.90 (d, J = 5.09 Hz, 1 H) LCMS (m/z) (M + H) = 412.0, Rt = 0.81 min. |
| 43 | 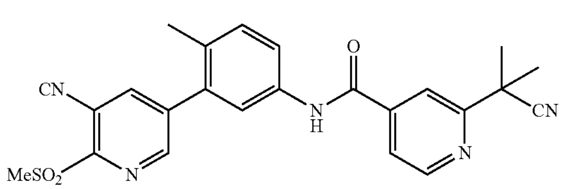 | N-(3-(5-cyano-6-(methylsulfonyl)pyridin-3-yl)-4-methylphenyl)-2-(2-cyanopropan-2-yl)isonicotinamide | $^1$H NMR (400 MHz, <dmso>) δ ppm 1.71 (s, 6 H) 2.39 (s, 3 H) 3.45 (s, 3 H) 7.36-7.54 (m, 3 H) 7.66 (br. s., 1 H) 7.78 (s, 3 H) 8.69-8.82 (m, 2 H) 9.02 (d, J = 1.57 Hz, 1 H) 10.42 (s, 1 H). LCMS (m/z) (M + H) = 460.0, Rt = 0.82 min. |

TABLE 2-continued

| Example | Structure | Name | Physical Data |
|---|---|---|---|
| 44 | 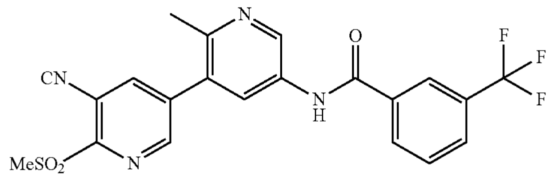 | N-(5'-cyano-2-methyl-6'-(methylsulfonyl)-[3,3'-bipyridin]-5-yl)-3-(trifluoromethyl)benzamide | $^1$H NMR (400 MHz, <dmso>) δ ppm 2.46 (s, 3 H) 3.51 (s, 3 H) 7.71-7.89 (m, 1 H) 7.96-8.07 (m, 1 H) 8.19-8.35 (m, 3 H) 8.84 (d, J = 1.96 Hz, 1H) 8.92 (d, J = 2.35 Hz, 1 H) 9.10 (d, J = 1.96 Hz, 1 H) 10.79 (s, 1 H). LCMS (m/z) (M + H) = 461.1, Rt = 0.69 min. |
| 45 | 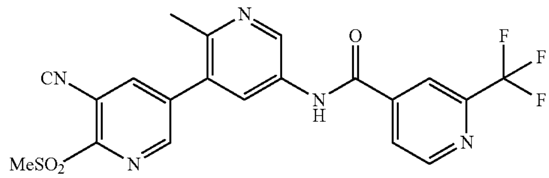 | N-(5'-cyano-2-methyl-6'-(methylsulfonyl)-[3,3'-bipyridin]-5-yl)-2-(trifluoromethyl)isonicotinamide | LCMS (m/z) (M + H) = 462.0, Rt = 0.65 min. |
| 46 | 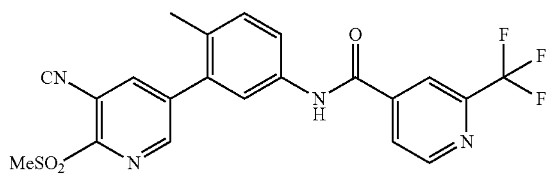 | N-(3-(5-cyano-6-(methylsulfonyl)pyridin-3-yl)-4-methylphenyl)-2-(trifluoromethyl)isonicotinamide | $^1$H NMR (400 MHz, <dmso>) δ ppm 2.26 (s, 4 H) 3.50 (s, 3 H) 7.34-7.48 (m, 1 H) 7.78 (s, 2 H) 8.13-8.22 (m, 1 H) 8.35 (s, 1 H) 8.66-8.81 (m, 1H) 8.94-9.08 (m, 2 H) 10.70-10.83 (m, 1 H). LCMS (m/z) (M + H) = 461.1, Rt = 0.83 min. |

Example 47

N-(3-(6-chloro-5-cyanopyridin-3-yl)-4-methylphenyl)-2-(trifluoromethyl)isonicotinamide

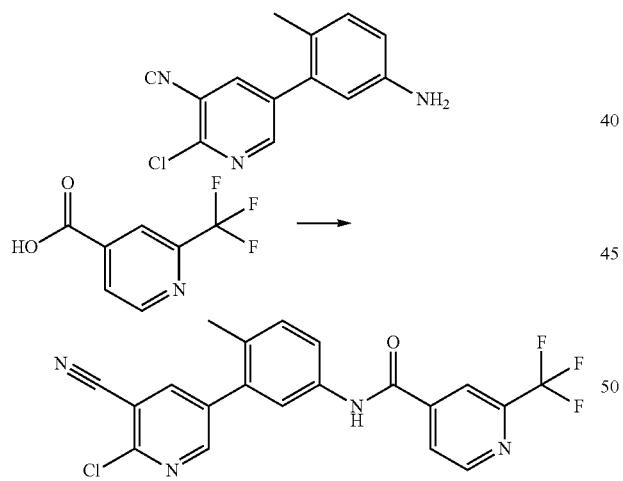

Example 48

N-(6'-chloro-5'-cyano-2-methyl-[3,3'-bipyridin]-5-yl)-2-(2-cyanopropan-2-yl)isonicotinamide

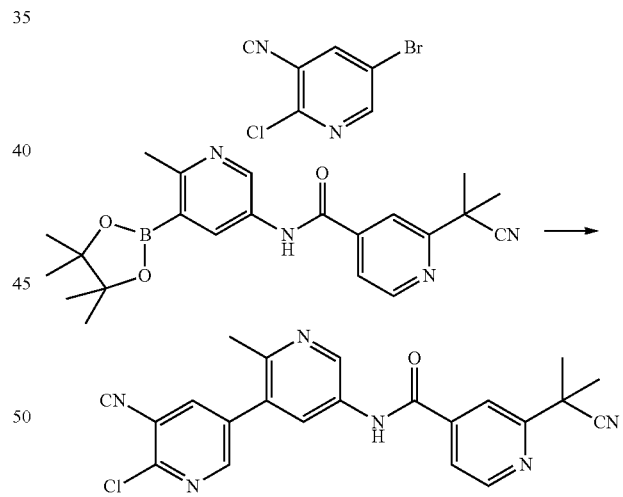

EDC (2.0 equiv.) was added to a solution of 5-(5-amino-2-methylphenyl)-2-chloronicotinonitrile (1.0 equiv.), 2-(trifluoromethyl)isonicotinic acid (1.1 equiv.), HOAt (2.0 equiv.) in DMF (0.2 M). The mixture was stirred at ambient temperature for 3 hrs. The reaction mixture was diluted with water and extracted with ethyl acetate. The combined extracts were washed sequentially with 1M aqueous sodium hydroxide and brine, dried over sodium sulfate, filtered, and concentrated. Purified by ISCO (26% EtOAc/Heptane) to give N-(3-(6-chloro-5-cyanopyridin-3-yl)-4-methylphenyl)-2-(trifluoromethyl)isonicotinamide in 100% yield. LCMS (m/z) (M+H)=417.0, Rt=1.03 min.

To a degassed solution of 2-(2-cyanopropan-2-yl)-N-(6-methyl-5-(4,4,5,5-tetramethyl-1,3,2-dioxaborolan-2-yl)pyridin-3-yl)isonicotinamide (1.0 equiv.), 5-bromo-2-chloronicotinonitrile (1.05 equiv.) and sodium carbonate (3.0 equiv, 2M aqueous solution) was added PdCl$_2$(dppf)-DCM adduct (0.15 equiv.) and this mixture was heated to 90° C. for 2 hours. Upon cooling to rt, water was added, the phases were separated and the aqueous phase was extracted with ethyl acetate. The combined organics were dried with MgSO$_4$, filtered and concentrated. The crude material was purified via silica gel chromatography (ISCO, 0-100% ethyl acetate in heptanes) and the pure fractions were concentrated to give N-(6'-chloro-5'-cyano-2-methyl-[3,3'-bipyridin]-5- yl)-2-(2-cyanopropan-2-yl)isonicotinamide in 63% yield. LCMS (m/z) (M+H)=417.0, Rt=0.69 min.

Example 49

N-(6'-chloro-5'-cyano-2-methyl-[3,3'-bipyridin]-5-yl)-2-(trifluoromethyl)isonicotinamide

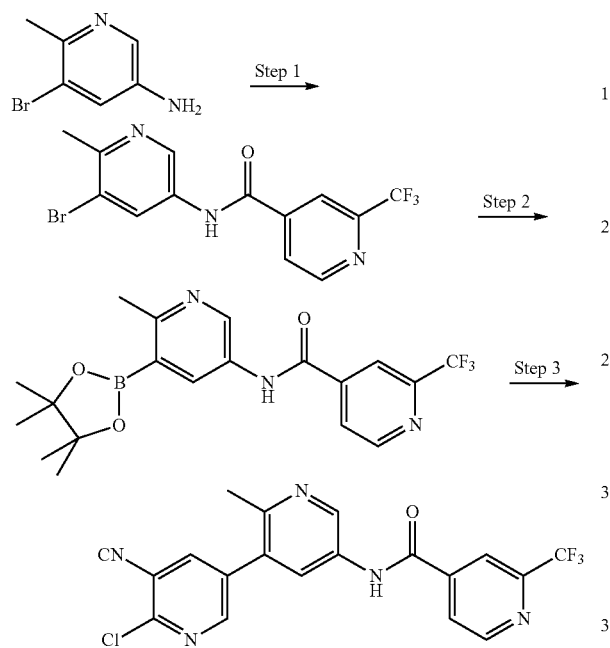

Step 1: A solution of 5-bromo-6-methylpyridin-3-amine (1.0 equiv.), 2-(trifluoromethyl)isonicotinic acid (1.05 equiv.), N1-((ethylimino)methylene)-N3,N3-dimethylpropane-1,3-diamine hydrochloride (1.2 equiv.) and 3H-[1,2,3]triazolo[4,5-b]pyridin-3-ol (1.2 equiv.) in DMF (0.35 M) was stirred overnight at rt. The reaction was partitioned between ethyl acetate and water, mixed, the organic layer was separated, washed with water, 1N NaOH, NaCl (sat.), dried over $MgSO_4$, filtered, concentrated and dried under vacuum to give N-(5-bromo-6-methylpyridin-3-yl)-2-(trifluoromethyl)isonicotinamide in quantitative yield. LCMS (m/z) (M+H)=361.9, Rt=0.78 min.

Step 2: To a solution of N-(5-bromo-6-methylpyridin-3-yl)-2-(trifluoromethyl)isonicotinamide (1.0 equiv.), 4,4,4',4',5,5,5',5'-octamethyl-2,2'-bi(1,3,2-dioxaborolane) (1.1 equiv.) and potassium acetate (3.0 equiv.) was added $PdCl_2$(dppf)-DCM adduct (0.05 equiv.) and the solution was heated to 125° C. for 3 hours. Upon cooling to rt, the solution was diluted with ethyl acetate, filtered and the solid was rinsed further with ethyl acetate. The combined organics were washed with water, sat. sodium chloride, dried over $MgSO_4$, filtered and concentrated to yield a brown oil. This oil was triturated in n-heptanes and sonicated for 30 min. The resulting brown solid was filtered and dried under high vacuum to give N-(6-methyl-5-(4,4,5,5-tetramethyl-1,3,2-dioxaborolan-2-yl)pyridin-3-yl)-2-(trifluoromethyl)isonicotinamide in 94% yield as a beige solid. LCMS (m/z) (M+H)=326.0, Rt=0.48 min.

Step 3: To a solution of N-(6-methyl-5-(4,4,5,5-tetramethyl-1,3,2-dioxaborolan-2-yl)pyridin-3-yl)-2-(trifluoromethyl)isonicotinamide (1.0 equiv.) and 5-bromo-2-chloronicotinonitrile (1.5 equiv.) in toluene (0.1 M) was added 2M $Na_2CO_3$ (3.0 equiv.) and argon was bubbled through for 5 minutes. $PdCl_2$(dppf)-DCM adduct (0.1 equiv.) was added and the reaction was heated to 90° C. for 3 hours. Upon cooling to rt, the solution was partitioned between ethyl acetate and water, the organic layer was separated, washed with sat. sodium chloride, dried over $MgSO_4$, filtered and concentrated. The crude material was purified via silica gel chromatography (ISCO, 0-100% ethyl acetate in heptanes) to give N-(6'-chloro-5'-cyano-2-methyl-[3,3'-bipyridin]-5-yl)-2-(trifluoromethyl)isonicotinamide in 69% yield. LCMS (m/z) (M+H)=418.0, Rt=0.72 min.

Example 50

N-(3-(5-cyano-6-((tetrahydro-2H-pyran-4-yl)amino)pyridin-3-yl)-4-methylphenyl)-3-(trifluoromethyl)benzamide

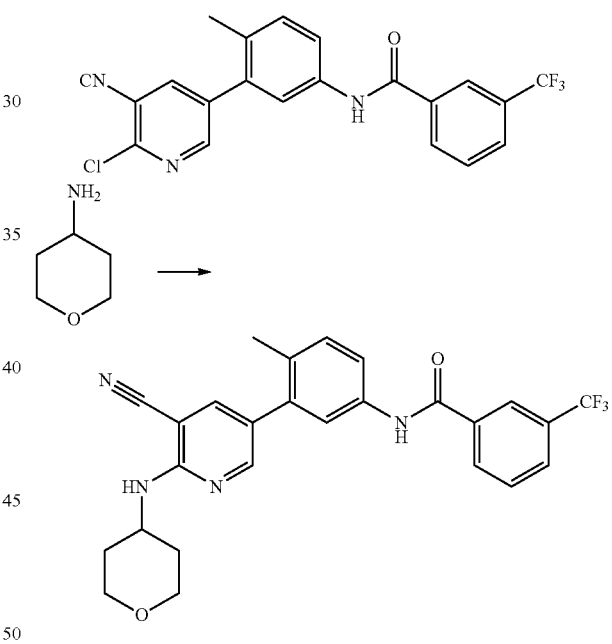

Method 4: To a solution of N-(3-(6-chloro-5-cyanopyridin-3-yl)-4-methylphenyl)-3-(trifluoromethyl)benzamide (1.0 equiv.) in DMSO (0.07 M) was added $Cs_2CO_3$ (3.0 equiv.), Huenig's base (3.0 equiv.) and tetrahydro-2H-pyran-4-amine (2.0 equiv.). The reaction was heated in the oil bath at 50° C. overnight. Upon cooling to room temperature, the solution was purified via prep-HPLC. Upon lyophilization, isolated N-(3-(5-cyano-6-((tetrahydro-2H-pyran-4-yl)amino)pyridin-3-yl)-4-methylphenyl)-3-(trifluoromethyl)benzamide in 23% yield as the TFA salt. LCMS (m/z) (M+H)=481.1, Rt=1.04 min.

The compounds listed in Table 3, below, were prepared using methods similar to those described for the preparation of Example 50 (Method 4) using the appropriate starting materials.

TABLE 3

| Example | Structure | Name | Physical Data |
|---|---|---|---|
| 51 | 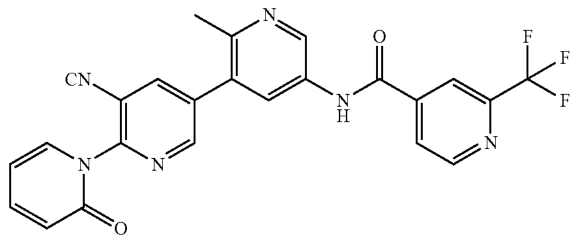 | N-(3'-cyano-2''-methyl-2-oxo-2H-[1,2':5',3''-terpyridin]-5''-yl)-2-(trifluoromethyl)isonicotinamide | $^1$H NMR (400 MHz, <dmso>) δ ppm 2.50 (br. s., 3 H) 6.46 (t, J = 6.65 Hz, 1 H) 6.59 (d, J = 9.39 Hz, 1 H) 7.63 (ddd, J = 9.19, 6.85, 1.96 Hz, 1 H) 7.84 (dd, J = 6.65, 1.57 Hz, 1 H) 8.13-8.29 (m, 2 H) 8.38 (s, 1 H) 8.77 (d, J = 2.35 Hz, 1 H) 8.91 (d, J = 2.35 Hz, 1 H) 8.97-9.05 (m, 2H) 11.02 (s, 1 H). LCMS (m/z) (M + H) = 477.1, Rt = 0.60 min. |
| 52 | 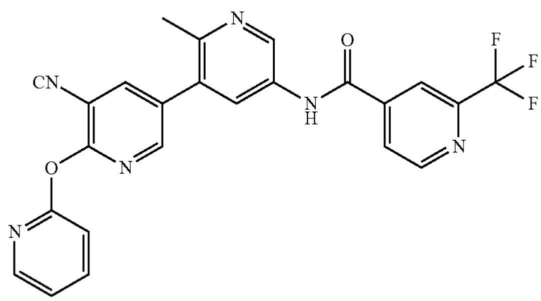 | N-(5'-cyano-2-methyl-6'-(pyridin-2-yloxy)-[3,3'-bipyridin]-5-yl)-2-(trifluoromethyl)isonicotinamide | $^1$H NMR (400 MHz, <dmso>) δ ppm 2.45 (s, 3H) 7.37 (d, J = 7.83 Hz, 2 H) 7.94-8.05 (m, 1 H) 8.10-8.24 (m, 2 H) 8.37 (s, 2 H) 8.56 (d, J = 2.35 Hz, 1 H) 8.65 (d, J = 2.35 Hz, 1 H) 8.88 (d, J = 1.96 Hz, 1 H) 9.01 (d, J = 4.70 Hz, 1 H) 10.97 (s, 1 H). LCMS (m/z) (M + H) = 477.0, Rt = 0.69 min. |
| 53 | 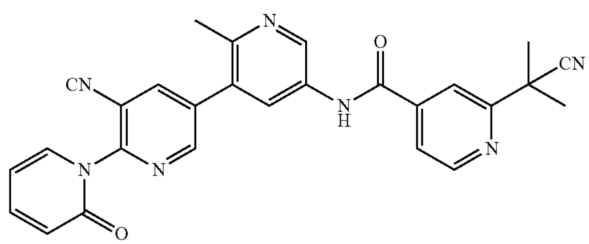 | N-(3'-cyano-2''-methyl-2-oxo-2H-[1,2':5',3''-terpyridin]-5''-yl)-2-(2-cyanopropan-2-yl)isonicotinamide | $^1$H NMR (400 MHz, <dmso>) δ ppm 1.76 (s, 6H) 2.50 (s, 3 H) 6.46 (t, J = 6.46 Hz, 1 H) 6.59 (d, J = 9.39 Hz, 1 H) 7.63 (ddd, J = 9.19, 6.85, 1.96 Hz, 1 H) 7.79-7.94 (m, 2 H) 8.02 (s, 1 H) 8.23 (d, J = 2.35 Hz, 1 H) 8.70-9.06 (m, 4 H) 10.90 (s, 1 H). LCMS (m/z) (M + H) = 476.1, Rt = 0.60 min. |
| 54 | 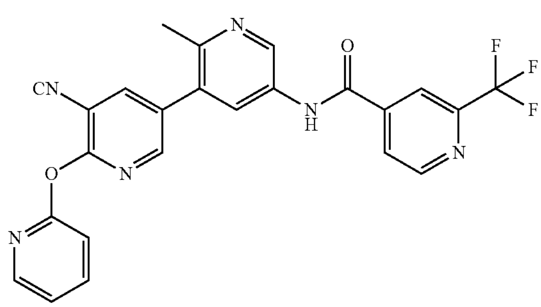 | N-(5'-cyano-2-methyl-6'-(pyridin-2-yloxy)-[3,3'-bipyridin]-5-yl)-2-(2-cyanopropan-2-yl)isonicotinamide | $^1$H NMR (400 MHz, <dmso>) δ ppm 1.71 (s, 6 H) 2.42 (br. s., 3 H) 7.22-7.42 (m, 2 H) 7.74-7.89 (m, 1 H) 7.92-8.03 (m, 2 H) 8.12 (d, J = 1.96 Hz, 1 H) 8.25-8.36 (m, 1 H) 8.51 (d, J = 2.35 Hz, 1 H) 8.61 (d, J = 2.35 Hz, 1 H) 8.78 (d, J = 4.70 Hz, 1 H) 8.86 (d, J = 1.96 Hz, 1 H) 10.85 (s, 1 H). LCMS (m/z) (M + H) = 476.1, Rt = 0.68 min. |
| 55 | 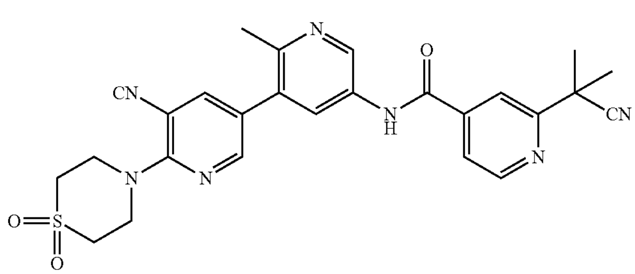 | N-(5'-cyano-6'-(1,1-dioxidothiomorpholino)-2-methyl-[3,3'-bipyridin]-5-yl)-2-(2-cyanopropan-2-yl)isonicotinamide | $^1$H NMR (400 MHz, <dmso>) δ ppm 1.75 (s, 6 H) 2.46 (br. s., 3 H) 3.34 (br. s., 4H) 4.15 (br. s., 4 H) 7.82-7.92 (m, 1 H) 8.01 (s, 1H) 8.09-8.16 (m, 1 H) 8.31 (d, J = 1.96 Hz, 1 H) 8.53 (d, J = 2.35 Hz, 1 H) 8.79-8.88 (m, 2 H) 10.80-10.88 (m, 1 H). LCMS (m/z) (M + H) = 516.1, Rt = 0.59 min. |

Example 56

N-(3-(5-cyano-6-morpholinopyridin-3-yl)-4-methylphenyl)-2-(2-cyanopropan-2-yl)isonicotinamide

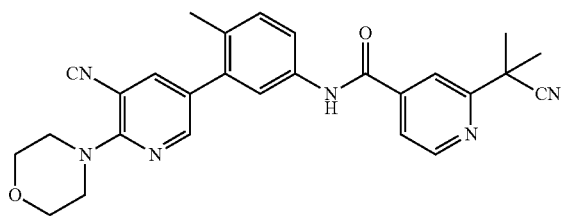

To a solution of N-(3-(6-chloro-5-cyanopyridin-3-yl)-4-methylphenyl)-2-(2-cyanopropan-2-yl)isonicotinamide (1.0 equiv.) in DMSO (0.07M) was added sodium carbonate (3.0 equiv.) and morpholine (2.0 equiv.) and the solution was stirred at 50° C. in the oil bath for 1 hour. The mixture was purified via prep-HPLC and the pure fractions were lyophilized for two days to give N-(3-(5-cyano-6-morpholinopyridin-3-yl)-4-methylphenyl)-2-(2-cyanopropan-2-yl)isonicotinamide as the TFA salt in 30% yield. $^1$H NMR (400 MHz, <dmso>) δ ppm 1.75 (s, 6 H) 2.23 (s, 3 H) 3.60-3.70 (m, 4 H) 3.71-3.80 (m, 4H) 7.32 (d, J=−8.61 Hz, 1 H) 7.59-7.74 (m, 2 H) 7.84 (d, J=5.09 Hz, 1 H) 7.99 (s, 1 H) 8.14 (d, J=2.35 Hz, 1 H) 8.44 (d, J=2.35 Hz, 1 H) 8.79 (d, J=5.09 Hz, 1 H) 10.55 (s, 1H). LCMS (m/z) (M+H)=467.2, Rt=0.97 min.

Example 57

N-(3-(5-cyano-6-(3-hydroxyazetidin-1-yl)pyridin-3-yl)-4-methylphenyl)-2-(2-cyanopropan-2-yl)isonicotinamide

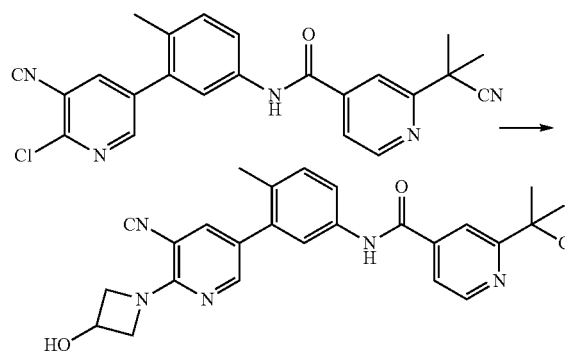

To a solution of N-(3-(6-chloro-5-cyanopyridin-3-yl)-4-methylphenyl)-2-(2-cyanopropan-2-yl)isonicotinamide (1.0 equiv.) in DMSO (0.07M) was added sodium carbonate (2.0 equiv.) and azetidin-3-ol (2.0 equiv.) and the solution was stirred at 50° C. in the oil bath for 1 hour. The mixture was purified via prep-HPLC and the pure fractions were lyophilized for two days to give N-(3-(5-cyano-6-(3-hydroxyazetidin-1-yl)pyridin-3-yl)-4-methylphenyl)-2-(2-cyanopropan-2-yl)isonicotinamide as the TFA salt in 40% yield. 1H NMR (400 MHz, <dmso>) ☐☐ ppm 1.75 (s, 6 H) 2.21 (s, 3 H) 3.99 (dd, J=9.39, 4.30 Hz, 2 H) 4.42-4.65 (m, 3 H) 7.30 (d, J=8.61 Hz, 1 H) 7.59 (d, J=1.57 Hz, 1 H) 7.67 (d, J=8.61 Hz, 1H) 7.84 (d, J=4.70 Hz, 1 H) 7.94-8.03 (m, 2 H) 8.32 (d, J=1.96 Hz, 1 H) 8.79 (d, J=4.70 Hz, 1 H) 10.53(s, 1 H). LCMS (m/z) (M+H)=453.1, Rt=0.77 min.

Example 58

N-(3-(5-cyano-6-(3-hydroxyazetidin-1-yl)pyridin-3-yl)-4-methylphenyl)-3-(trifluoromethyl)benzamide

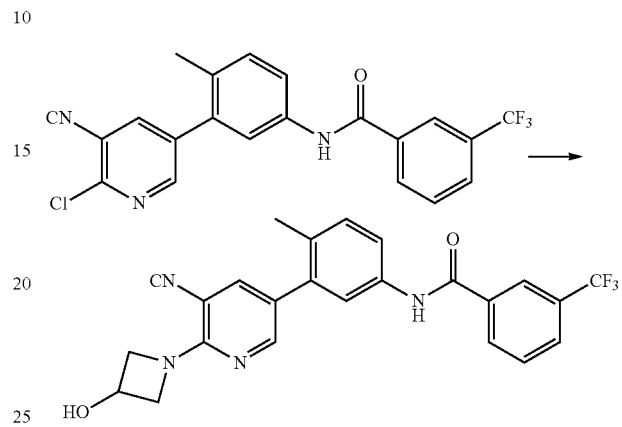

To a solution of N-(3-(6-chloro-5-cyanopyridin-3-yl)-4-methylphenyl)-3-(trifluoromethyl)benzamide (1.0 equiv.) in DMSO (0.07M) was added potassium carbonate (2.0 equiv.) and azetidin-3-ol (2.0 equiv.) and the solution was stirred at rt for 18 hours. The mixture was purified via prep-HPLC and the pure fractions were lyophilized for two days to give N-(3-(5-cyano-6-(3-hydroxyazetidin-1-yl)pyridin-3-yl)-4-methylphenyl)-3-(trifluoromethyl)benzamide as the TFA salt in 37% yield. $^1$H NMR (400 MHz, <dmso>) δ ppm 2.21 (s, 3 H) 3.93-4.06 (m, 2 H) 4.47 (s, 2 H) 4.53-4.64 (m, 1 H) 7.30 (s, 1 H) 7.61 (d, J=2.35 Hz, 1 H) 7.66-7.82 (m, 2 H) 7.99 (d, J=2.35 Hz, 2 H) 8.19-8.38 (m, 3 H) 10.44 (s, 1 H). LCMS (m/z) (M+H)=453.1, Rt=0.88 min.

Example 59

N-(3-(5-cyano-6-morpholinopyridin-3-yl)-4-methylphenyl)-3-(trifluoromethyl)benzamide

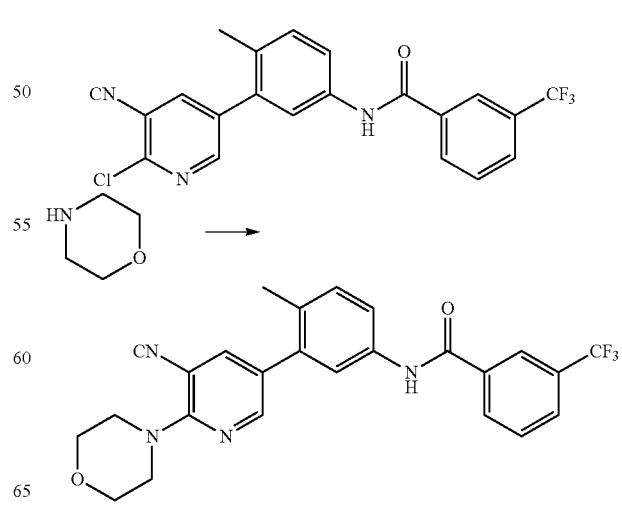

Method 5: To a solution of N-(3-(6-chloro-5-cyanopyridin-3-yl)-4-methylphenyl)-3-(trifluoromethyl)benzamide (1.0 equiv.) in DMSO (0.07M) was added sodium carbonate (3.0 equiv.) and morpholine (2.0 equiv.) and the solution was stirred at 50° C. in the oil bath for 1 hour. The mixture was purified via prep-HPLC and the pure fractions were lyophilized for two days to give N-(3-(5-cyano-6-morpholinopyridin-3-yl)-4-methylphenyl)-3-(trifluoromethyl)benzamide as the TFA salt in 42% yield. $^1$H NMR (400 MHz, <dmso>) δ ppm 2.23 (s, 3 H) 3.58-3.69 (m, 4 H) 3.72-3.80 (m, 4 H) 7.31 (d, J=8.61 Hz, 1 H) 7.63-7.84 (m, 3 H) 7.95 (d, J=7.83 Hz, 1 H) 8.14 (d, J=2.35 Hz, 1 H) 8.20-8.34 (m, 2 H) 8.45 (d, J=2.35 Hz, 1 H) 10.46 (s, 1 H). LCMS (m/z) (M+H)=467.0, Rt=1.05 min.

The compounds listed in Table 4, below, were prepared using methods similar to those described for the preparation of Example 59 (Method 5) using the appropriate starting materials. If a BOC protecting group was present, it was deprotected by stirring the crude material in TFA and DCM (1:2) until completion, then purified by concentrating under vacuo and purified via reverse phase prep-HPLC. The pure fractions were lyophilized to give the desired product as the TFA salt.

TABLE 4

| Example | Structure | Name | Physical Data |
|---|---|---|---|
| 60 | 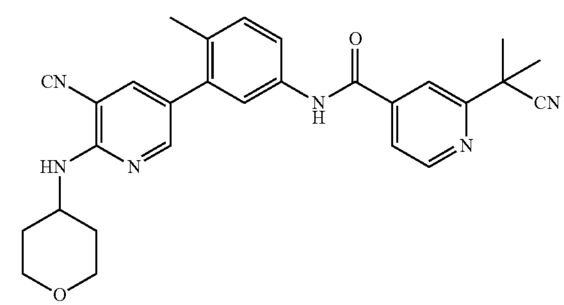 | N-(3-(5-cyano-6-((tetrahydro-2H-pyran-4-yl)amino)pyridin-3-yl)-4-methylphenyl)-2-(2-cyanopropan-2-yl)isonicotinamide | $^1$H NMR (400 MHz, <dmso>) δ ppm 1.62-1.84 (m, 10 H) 2.22 (s, 3 H) 3.37 (s, 2 H) 3.81-3.99 (m, 2 H) 4.10-4.30 (m, 1 H) 6.95-7.05 (m, 1 H) 7.31 (s, 1 H) 7.59 (s, 2 H) 7.80-7.90 (m, 1 H) 7.92-8.02 (m, 2 H) 8.29 (d, J = 2.35 Hz, 1 H) 8.79 (d, J = 4.70 Hz, 1 H) 10.52 (s, 1 H). LCMS (m/z) (M + H) = 481.1, Rt = 0.94 min. |
| 61 | 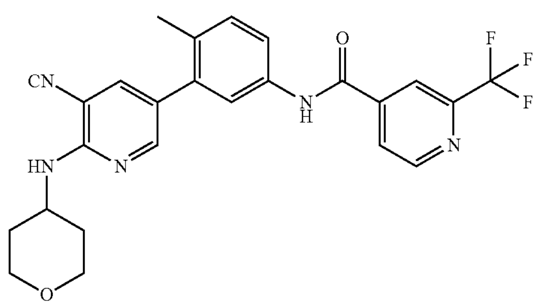 | N-(3-(5-cyano-6-((tetrahydro-2H-pyran-4-yl)amino)pyridin-3-yl)-4-methylphenyl)-2-(trifluoromethyl)isonicotinamide | $^1$H NMR (400 MHz, <dmso>) δ ppm 1.78 (br. s., 4 H) 2.18-2.27 (m, 3 H) 3.37 (s, 2H) 3.89 (br. s., 2 H) 6.97-7.07 (m, 1 H) 7.30 (d, J = 8.22 Hz, 1H) 7.61 (d, J = 1.96 Hz, 2 H) 7.96 (d, J = 2.35 Hz, 1 H) 8.17 (d, J = 4.70 Hz, 1 H) 8.25-8.41 (m, 2 H) 8.98 (d, J = 4.70 Hz, 1 H) 10.66 (s, 1 H). LCMS (m/z) (M + H) = 482.1, Rt = 0.99 min. |
| 62 | 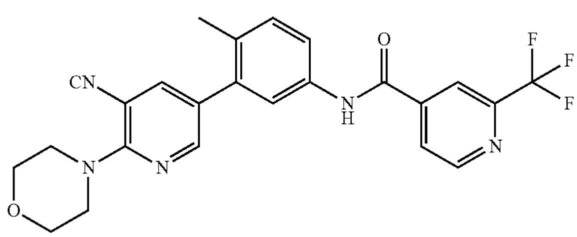 | N-(3-(5-cyano-6-morpholinopyridin-3-yl)-4-methylphenyl)-2-(trifluoromethyl)isonicotinamide | $^1$H NMR (400 MHz, <dmso>) δ ppm 2.23 (s, 3 H) 3.60-3.81 (m, 8 H) 7.33 (d, J = 8.61 Hz, 1 H) 7.61-7.75 (m, 2 H) 8.09-8.24 (m, 2 H) 8.35 (s, 1 H) 8.44 (d, J = 2.35 Hz, 1 H) 8.98 (d, J = 5.09 Hz, 1 H) 10.68 (s, 1 H). LCMS (m/z) (M + H) = 468.0, Rt = 1.02 min. |
| 63 | 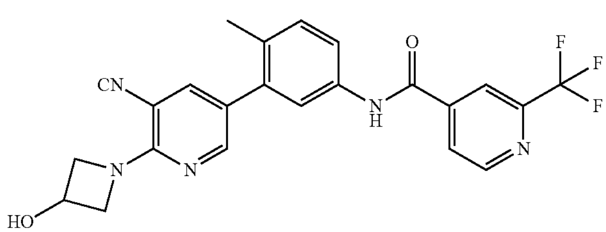 | N-(3-(5-cyano-6-(3-hydroxyazetidin-1-yl)pyridin-3-yl)-4-methylphenyl)-2-(trifluoromethyl)isonicotinamide | $^1$H NMR (400 MHz, <dmso>) δ ppm 2.16-2.26 (m, 3 H) 3.99 (dd, J = 9.39, 4.30 Hz, 2 H) 4.43-4.52 (m, 2 H) 4.58 (d, J = 6.26 Hz, 1 H) 7.31 (d, J = 8.61 Hz, 1 H) 7.61 (d, J = 1.57 Hz, 1 H) 7.69 (dd, J = 8.22, 1.96 Hz, 1 H) 7.99 (d, J = 2.35 Hz, 1 H) 8.17 (d, J = 4.70 Hz, 1 H) 8.29-8.40 (m, 2 H) 8.98 (d, J = 5.09 Hz, 1 H) 10.66 (s, 1 H). LCMS (m/z) (M + H) = 454.0, Rt = 0.85 min. |

TABLE 4-continued

| Example | Name | Physical Data |
|---|---|---|
| 64 | N-(5'-cyano-2-methyl-6'-morpholino-[3,3'-bipyridin]-5-yl)-2-(2-cyanopropan-2-yl)isonicotinamide | ¹H NMR (400 MHz, <dmso>) δ ppm 1.75 (s, 6 H) 2.42-2.47 (m, 3 H) 3.63-3.80 (m, 8 H) 7.87 (d, J = 3.91 Hz, 1 H) 8.02 (s, 1 H) 8.12 (d, J = 1.96 Hz, 1 H) 8.25 (d, J = 2.35 Hz, 1 H) 8.51 (d, J = 2.35 Hz, 1 H) 8.78-8.91 (m, 2H) 10.86 (s, 1 H). LCMS (m/z) (M + H) = 468.1, Rt = 0.66 min. |
| 65 | N-(5'-cyano-6'-(3-hydroxyazetidin-1-yl)-2-methyl-[3,3'-bipyridin]-5-yl)-2-(2-cyanopropan-2-yl)isonicotinamide | ¹H NMR (400 MHz, <dmso>) δ ppm 1.66-1.76 (m, 6 H) 2.41 (br. s., 3H) 3.96 (dd, J = 9.59, 4.11 Hz, 2 H) 4.38-4.49 (m, 2 H) 4.50-4.60 (m, 1 H) 7.82 (d, J = 4.30 Hz, 1 H) 7.97 (s, 1 H) 8.02-8.11 (m, 2 H) 8.34 (d, J = 2.35 Hz, 1 H) 8.73-8.87 (m, 2 H) 10.82 (s, 1 H). LCMS (m/z) (M + H) = 454.1, Rt = 0.56 min. |
| 66 | N-(5'-cyano-2-methyl-6'-morpholino-[3,3'-bipyridin]-5-yl)-3-(trifluoromethyl)benzamide | ¹H NMR (400 MHz, <dmso>) δ ppm 2.46 (br. s., 3 H) 3.74 (d, J = 5.09 Hz, 8 H) 7.76-7.87 (m, 1 H) 7.95-8.04 (m, 1 H) 8.13 (s, 1 H) 8.22-8.35 (m, 3 H) 8.51 (d, J = 2.35 Hz, 1 H) 8.89 (d, J = 2.35 Hz, 1 H) 10.75 (s, 1 H). LCMS (m/z) (M + H) = 468.1, Rt = 0.77 min. |
| 67 | N-(5'-cyano-6'-(3-hydroxyazetidin-1-yl)-2-methyl-[3,3'-bipyridin]-5-yl)-3-(trifluoromethyl)benzamide | ¹H NMR (400 MHz, <dmso>) δ ppm 2.43-2.47 (m, 3 H) 4.01 (dd, J = 9.59, 4.11 Hz, 3 H) 4.45-4.55 (m, 2 H) 4.56-4.64 (m, 1 H) 7.81 (s, 1 H) 7.99 (s, 1 H) 8.08-8.17 (m, 2 H) 8.24-8.35 (m, 2 H) 8.40 (d, J = 2.35 Hz, 1 H) 8.92 (d, J = 1.96 Hz, 1 H) 10.79 (s, 1 H). LCMS (m/z) (M + H) = 454.0, Rt = 0.67 min. |
| 68 | N-(5'-cyano-2-methyl-6'-morpholino-[3,3'-bipyridin]-5-yl)-2-(trifluoromethyl)isonicotinamide | ¹H NMR (400 MHz, <dmso>) δ ppm 2.47 (br. s., 3 H) 3.66-3.78 (m, 8 H) 8.12 (d, J = 1.96 Hz, 1 H) 8.16-8.27 (m, 2 H) 8.37 (s, 1 H) 8.50 (d, J = 2.35 Hz, 1 H) 8.87 (d, J = 1.96 Hz, 1 H) 9.01 (d, J = 5.09 Hz, 1 H) 10.97 (s, 1 H). LCMS (m/z) (M + H) = 469.1, Rt = 0.67 min. |
| 69 | N-(5'-cyano-6'-(3-hydroxyazetidin-1-yl)-2-methyl-[3,3'-bipyridin]-5-yl)-2-(trifluoromethyl)isonicotinamide | ¹H NMR (400 MHz, <dmso>) δ ppm 2.46 (s, 3 H) 4.01 (dd, J = 9.59, 4.11 Hz, 2 H) 4.44-4.54 (m, 2 H) 4.59 (br. s., 1 H) 8.04-8.15 (m, 2 H) 8.20 (d, J = 4.70 Hz, 1 H) 8.34-8.41 (m, 2 H) 8.88 (d, J = 2.35 Hz, 1 H) 9.01 (d, J = 5.09 Hz, 1 H) 10.98 (s, 1 H). LCMS (m/z) (M + H) = 455.0, Rt = 0.57 min. |

TABLE 4-continued

| Example | Structure | Name | Physical Data |
|---|---|---|---|
| 70 | 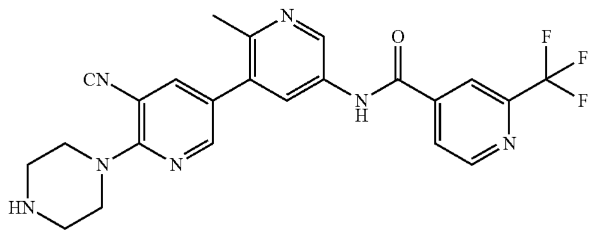 | N-(5'-cyano-2-methyl-6'-(piperazin-1-yl)-[3,3'-bipyridin]-5-yl)-2-(trifluoromethyl)isonicotinamide | $^1$H NMR (400 MHz, <dmso>) δ ppm 2.44 (s, 3 H) 3.28 (br. s., 4 H) 3.81-3.91 (m, 4 H) 8.12 (d, J = 2.35 Hz, 1 H) 8.16-8.23 (m, 1 H) 8.29-8.40 (m, 2 H) 8.54 (d, J = 2.35 Hz, 1 H) 8.81 (d, J = 2.35 Hz, 2 H) 9.01 (d, J = 5.09 Hz, 1 H) 10.94 (s, 1 H). LCMS (m/z) (M + H) = 468.1, Rt = 0.51 min. |
| 71 | 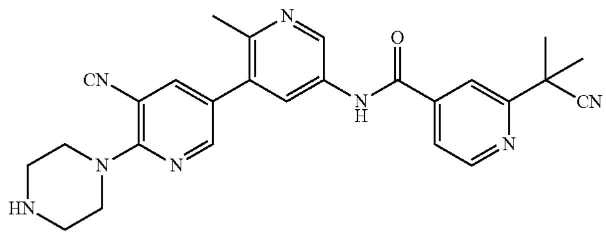 | N-(5'-cyano-2-methyl-6'-(piperazin-1-yl)-[3,3'-bipyridin]-5-yl)-2-(2-cyanopropan-2-yl)isonicotinamide | $^1$H NMR (400 MHz, <dmso>) δ ppm 1.75 (s, 6 H) 2.44 (s, 3 H) 3.29 (br. s., 4 H) 3.79-3.90 (m, 4 H) 7.80-7.92 (m, 1 H) 8.01 (s, 1 H) 8.11 (d, J = 1.96 Hz, 1 H) 8.32 (d, J = 1.96 Hz, 1 H) 8.54 (d, J = 2.35 Hz, 1 H) 8.78-8.85 (m, 3 H) 10.83 (s, 1 H). LCMS (m/z) (M + H) = 467.1, Rt = 0.49 min. |
| 72 | 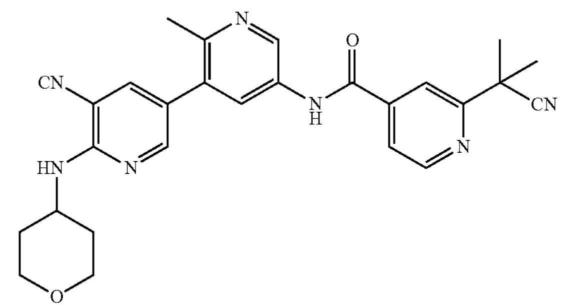 | N-(5'-cyano-6'-((tetrahydro-2H-pyran-4-yl)amino)-[3,3'-bipyridin]-5-yl)-2-(2-cyanopropan-2-yl)isonicotinamide | $^1$H NMR (400 MHz, <dmso>) δ ppm 1.57-1.80 (m, 10 H) 2.44-2.46 (m, 3 H) 3.21-3.42 (m, 2 H) 3.83 (dd, J = 11.35, 2.74 Hz, 2 H) 4.08-4.26 (m, 1 H) 7.14 (d, J = 7.43 Hz, 1 H) 7.83 (d, J = 5.09 Hz, 1 H) 7.94-8.11 (m, 3 H) 8.33 (d, J = 2.35 Hz, 1 H) 8.74-8.S9 (m, 2 H) 10.86 (s, 1 H). LCMS (m/z) (M + H) = 482.2, Rt = 0.65 min. |
| 73 | 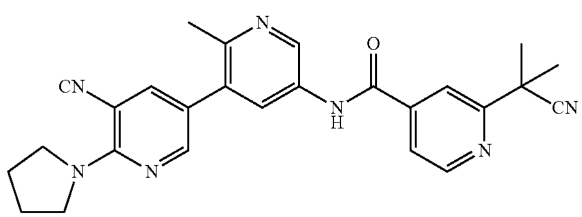 | N-(5'-cyano-2-methyl-6'-(pyrrolidin-1-yl)-[3,3'-bipyridin]-5-yl)-2-(2-cyanopropan-2-yl)isonicotinamide | $^1$H NMR (400 MHz, <dmso>) δ ppm 1.76 (s, 6 H) 1.95 (br. s., 4 H) 2.46-2.47 (m, 3 H) 3.72 (br. s., 4 H) 7.83-7.91 (m, 1 H) 8.07 (d, J = 2.35 Hz, 3 H) 8.37-8.46 (m, 1 H) 8.79-8.90 (m, 2 H) 10.74-10.88 (m, 1 H). LCMS (m/z) (M + H) = 452.2, Rt = 0.73 min. |
| 74 | 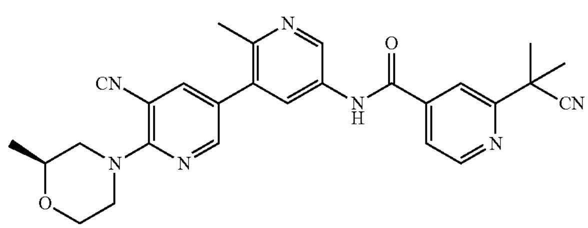 | (S)-N-(5'-cyano-2-methyl-6'-(2-methylmorpholino)-[3,3'-bipyridin]-5-yl)-2-(2-cyanopropan-2-yl)isonicotinamide | $^1$H NMR (400 MHz, <dmso>) δ ppm 1.15 (d, J = 6.26 Hz, 3 H) 1.72-1.81 (m, 6 H) 2.46 (s, 3 H) 2.74-2.94 (m, 1 H) 3.09-3.25 (m, 1 H) 3.61 (d, J = 2.35 Hz, 2 H) 3.91-3.96 (m, 1 H) 4.09-4.33 (m, 2 H) 7.83-7.92 (m, 1 H) 8.02 (s, 1 H) 8.09 (d, J = 1.96 Hz, 1 H) 8.23 (d, J = 2.35 Hz, 1 H) 8.49 (d, J = 2.35 Hz, 1 H) 8.77-8.89 (m, 2 H) 10.84 (s, 1 H). LCMS (m/z) (M + H) = 482.2, Rt = 0.70 min. |
| 75 | 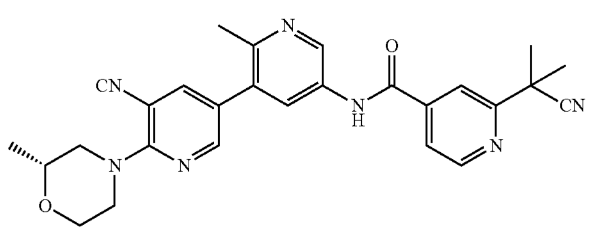 | (R)-N-(5'-cyano-2-methyl-6'-(2-methylmorpholino)-[3,3'-bipyridin]-5-yl)-2-(2-cyanopropan-2-yl)isonicotinamide | $^1$H NMR (400 MHz, <dmso>) δ ppm 1.15 (d, J = 6.26 Hz, 3 H) 1.75 (s, 6 H) 2.46 (br. s., 3 H) 2.76-2.91 (m, 1 H) 3.08-3.23 (m, 1 H) 3.56-3.70 (m, 2 H) 3.92-3.96 (m, 1 H) 4.15-4.27 (m, 2 H) 7.78-7.92 (m, 1 H) 8.02 (s, 1 H) 8.06-8.13 (m, 1 H) 8.23 (d, J = 2.74 Hz, 1 H) 8.49 (d, J = 2.35 Hz, 1 H) 8.76-8.93 (m, 2 H) 10.84 (s, 1 H). LCMS (m/z) (M + H) = 482.1, Rt = 0.71 min. |

TABLE 4-continued

| Example | Name | Physical Data |
|---|---|---|
| 76 | N-(6'-(azetidin-1-yl)-5'-cyano-2-methyl-[3,3'-bipyridin]-5-yl)-2-(2-cyanopropan-2-yl)isonicotinamide | ¹H NMR (400 MHz, <dmso>) δ ppm 1.75 (s, 6 H) 2.37 (s, 2 H) 2.46 (s, 3 H) 4.30 (t, J = 7.63 Hz, 4 H) 7.79-7.93 (m, 1 H) 7.97-8.13 (m, 3 H) 8.38 (d, J = 2.35 Hz, 1 H) 8.78-8.92 (m, 2 H) 10.85 (s, 1 H). LCMS (m/z) (M + H) = 438.1, Rt = 0.67 min. |
| 77 | N-(5'-cyano-2-methyl-6'-((tetrahydrofuran-3-yl)amino)-[3,3'-bipyridin]-5-yl)-2-(2-cyanopropan-2-yl)isonicotinamide | LCMS (m/z) (M + H) = 468.1, Rt = 0.63 min. |
| 78a & b | (S)-N-(5'-cyano-2-methyl-6'-((tetrahydrofuran-3-yl)amino)-[3,3'-bipyridin]-5-yl)-2-(2-cyanopropan-2-yl)isonicotinamide & (R)-N-(5'-cyano-2-methyl-6'-((tetrahydrofuran-3-yl)amino)-[3,3'-bipyridin]-5-yl)-2-(2-cyanopropan-2-yl)isonicotinamide | LCMS (m/z) (M + H) = 468.2, Rt = 0.63 min. |
| 79 | (R)-N-(5'-cyano-2-methyl-6'-(3-methylmorpholino)-[3,3'-bipyridin]-5-yl)-2-(2-cyanopropan-2-yl)isonicotinamide | ¹H NMR (400 MHz, <dmso>) δ ppm 1.29 (d, J = 6.65 Hz, 3 H) 1.75 (s, 6 H) 2.45 (br. s., 3 H) 3.41-3.44 (m, 2 H) 3.66-3.73 (m, 2 H) 3.87-4.07 (m, 2 H) 4.47-4.60 (m, 1 H) 7.83-7.91 (m, 1 H) 7.98-8.03 (m, 1 H) 8.05-8.11 (m, 1 H) 8.15-8.23 (m, 1 H) 8.47-8.54 (m, 1 H) 8.77-8.88 (m, 2 H) 10.74-10.84 (m, 1 H). LCMS (m/z) (M + H) = 482.1, Rt = 0.70 min. |

TABLE 4-continued

| Example | Structure | Name | Physical Data |
|---|---|---|---|
| 80 | 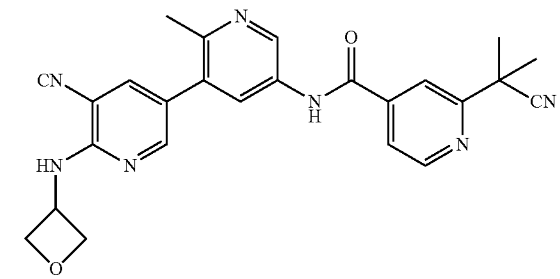 | N-(5'-cyano-2-methyl-6'-(oxetan-3-ylamino)-[3,3'-bipyridin]-5-yl)-2-(2-cyanopropan-2-yl)isonicotinamide | $^1$H NMR (400 MHz, <dmso>) δ ppm 1.75 (s, 6 H) 2.42 (s, 3 H) 4.57-4.68 (m, 2 H) 4.76 (t, J = 6.65 Hz, 2 H) 4.96-5.08 (m, 1 H) 7.86 (d, J = 4.70 Hz, 1 H) 7.96-8.05 (m, 3 H) 8.11 (d, J = 2.35 Hz, 1 H) 8.33 (d, J = 2.35 Hz, 1 H) 8.78-8.84 (m, 2 H) 10.75 (s, 1 H). LCMS (m/z) (M + H) = 454.1, Rt = 0.59 min. |
| 81 | 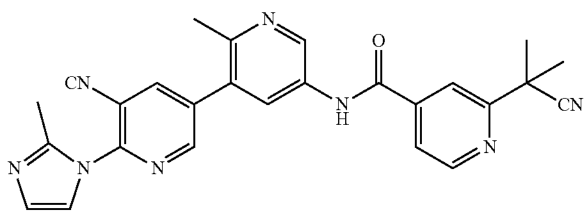 | N-(5'-cyano-2-methyl-6'-(2-methyl-1H-imidazol-1-yl)-[3,3'-bipyridin]-5-yl)-2-(2-cyanopropan-2-yl)isonicotinamide | $^1$H NMR (500 MHz, DMSO-d6) δ ppm 1.78 (s, 6 H) 2.53 (s, 3 H) 2.71 (s, 3 H) 7.77-7.86 (m, 1 H) 7.91 (d, J = 5.04 Hz, 1 H) 8.05 (s, 1 H) 8.20 (s, 1 H) 8.31 (d, J = 2.21 Hz, 1 H) 8.83-8.92 (m, 2 H) 9.00 (d, J = 1.58 Hz, 1 H) 9.05-9.11 (m, 1 H) 10.95 (s, 1 H). LCMS (m/z) (M + H) = 463.1, Rt = 0.51 min. |
| 82 | 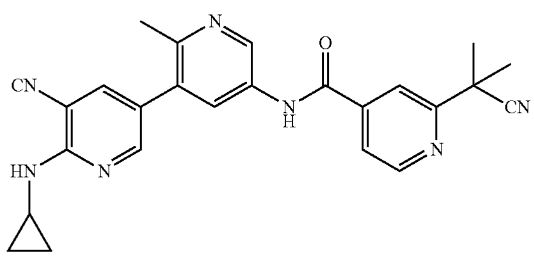 | N-(5'-cyano-6'-(cyclopropylamino)-2-methyl-[3,3'-bypyridin]-5-yl)-2-(2-cyanopropan-2-yl)isonicotinamide | $^1$H NMR (400 MHz, <dmso>) δ ppm 0.53-0.78 (m, 4 H) 1.75 (s, 6 H) 2.43 (s, 3 H) 2.76-2.91 (m, 1 H) 7.43-7.56 (m, 1 H) 7.82-7.91 (m, 1 H) 7.96-8.07 (m, 3 H) 8.32-8.44 (m, 1 H) 8.75-8.86 (m, 2 H) 10.70-10.82 (m, 1 H). LCMS (m/z) (M + H) = 438.2, Rt = 0.65 min. |
| 83 | 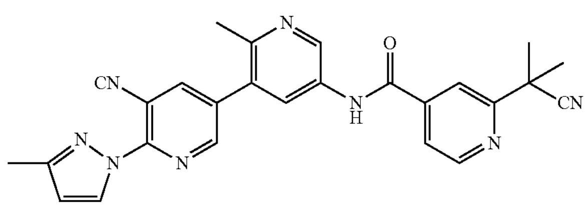 | N-(5'-cyano-2-methyl-6'-(3-methyl-1H-pyrazol-1-yl)-[3,3'-bipyridin]-5-yl)-2-(2-cyanopropan-2-yl)isonicotinamide | $^1$H NMR (500 MHz, DMSO-d6) δ ppm 1.78 (s, 6 H) 2.36 (s, 3 H) 2.50-2.50 (m, 3 H) 6.54 (d, J = 2.52 Hz, 1 H) 7.84-7.97 (m, 1 H) 8.06 (s, 1 H) 8.20 (d, J = 1.89 Hz, 1 H) 8.55-8.66 (m, 2 H) 8.81-8.90 (m, 2 H) 8.95 (d, J = 1.89 Hz, 1 H) 10.91 (s, 1 H). LCMS (m/z) (M + H) = 463.1, Rt = 0.75 min. |
| 84 | 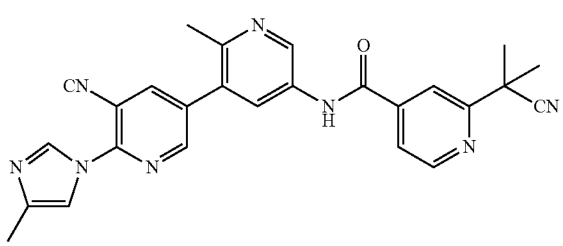 | N-(5'-cyano-2-methyl-6'-(4-methyl-1H-imidazol-1-yl)-[3,3'-bipyridin]-5-yl)-2-(2-cyanopropan-2-yl)isonicotinamide | $^1$H NMR (500 MHz, DMSO-d6) δ ppm 1.78 (s, 6 H) 2.34 (s, 3 H) 2.50-2.50 (m, 3 H) 7.92 (d, J = 5.36 Hz, 2 H) 8.05 (s, 1 H) 8.24 (d, J = 2.21 Hz, 1 H) 8.84-8.95 (m, 3 H) 8.99-9.02 (m, 1 H) 9.10-9.18 (m, 1 H) 10.94 (s, 1 H). LCMS (m/z) (M + H) = 463.1, Rt = 0.62 min. |
| 85 | 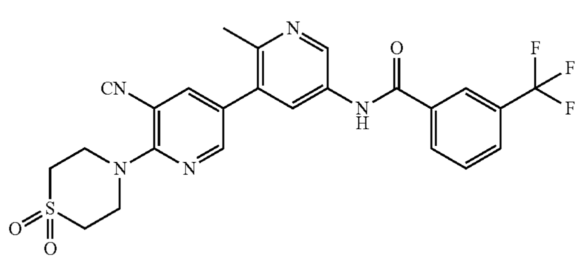 | N-(5'-cyano-6'-(1,1-dioxidothiomorpholino)-2-methyl-[3,3'-bipyridin]-5-yl)-3-(trifluoromethyl)benzamide | $^1$H NMR (400 MHz, <dmso>) δ ppm 2.42-2.42 (m, 3 H) 3.29 (br. s., 4 H) 4.11 (br. s., 4 H) 7.70-7.82 (m, 1 H) 7.91-7.98 (m, 1 H) 8.11 (d, J = 1.96 Hz, 1 H) 8.26 (d, J = 1.96 Hz, 3 H) 8.49 (d, J = 2.35 Hz, 1 H) 8.83 (d, J = 1.96 Hz, 1 H) 10.71 (s, 1 H). LCMS (m/z) (M + H) = 516.0, Rt = 0.72 min. |

TABLE 4-continued

| Example | Structure | Name | Physical Data |
|---|---|---|---|
| 86 | 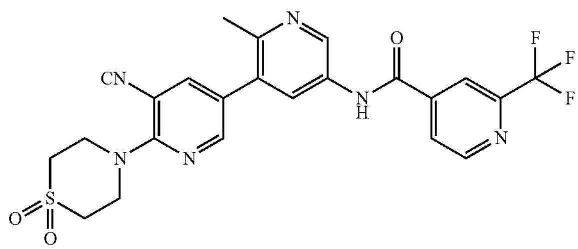 | N-(5'-cyano-6'-(1,1-dioxidothiomorpholino)-2-methyl-[3,3'-bipyridin]-5-yl)-2-(trifluoromethyl)isonicotinamide | $^1$H NMR (400 MHz, <dmso>) δ ppm 2.42 (br. s., 3 H) 3.29 (br. s., 4 H) 4.11 (br. s., 4 H) 8.08 (d, J = 2.35 Hz, 1 H) 8.15 (d, J = 4.70 Hz, 1 H) 8.26 (d, J = 2.35 Hz, 1 H) 8.32 (s, 1 H) 8.48 (d, J = 2.35 Hz, 1 H) 8.80 (d, J = 1.96 Hz, 1 H) 8.96 (d, J = 5.09 Hz, 1 H) 10.91 (s, 1 H). LCMS (m/z) (M + H) = 517.1, Rt = 0.63 min. |
| 87 | 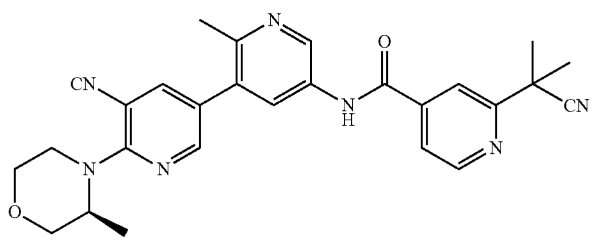 | (S)-N-(5'-cyano-2-methyl-6'-(3-methylmorpholino)-[3,3'-bipyridin]-5-yl)-2-(2-cyanopropan-2-yl)isonicotinamide | $^1$H NMR (400 MHz, <dmso>) δ ppm 130 (d, J = 6.65 Hz, 3 H) 1.72-1.79 (m, 6 H) 2.47-247 (m, 3 H) 3.39-3.59 (m, 2 H) 3.65-3.74 (m, 2 H) 3.93 (d, J = 10.17 Hz, 1 H) 4.03 (d, J = 13.30 Hz, 1 H) 4.49-4.58 (m, 1 H) 7.87 (dd, J = 5.09, 1.17 Hz, 1 H) 8.02 (s, 1 H) 8.11 (d, J = 1.96 Hz, 1 H) 8.22 (d, J = 2.35 Hz, 1 H) 8.50 (d, J = 2.35 Hz, 1 H) 8.80-8.93 (m, 2 H) 10.85 (s, 1 H). LCMS (m/z) (M + H) = 482.3, Rt = 0.70 min. |
| 88 | 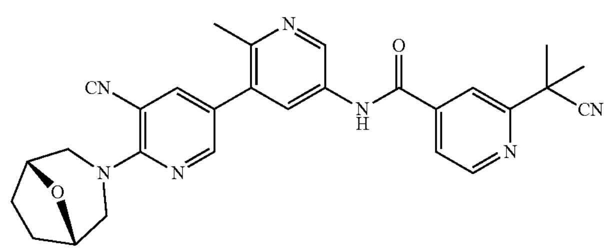 | N-(6'-((1R,5S)-8-oxa-3-azabicyclo[3,2,1]octan-3-yl)-5'-cyano-2-methyl-[3,3'-bipyridin]-5-yl)-2-(2-cyanopropan-2-yl)isonicotinamide | $^1$H NMR (400 MHz, <dmso>) δ ppm 1.71 (s, 6 H) 1.80 (s, 4 H) 2.47 (s, 3 H) 3.22 (d, J = 10.96 Hz, 2 H) 4.01 (d, J = 12.52 Hz, 2 H) 4.40 (br. s., 2H) 7.83 (d, J = 1.57 Hz, 1 H) 7.97 (s, 1 H) 8.06 (d, J = 1.96 Hz, 1 H) 8.15 (d, J = 2.35 Hz, 1 H) 8.43 (d, J = 2.35 Hz, 1 H) 8.74-8.86 (m, 2 H) 10.81 (s, 1 H). LCMS (m/z) (M + H) = 494.3, Rt = 0.66 min. |
| 89 | 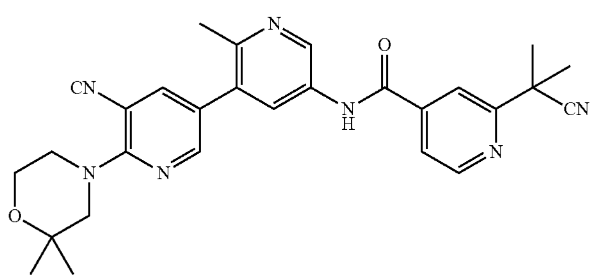 | N-(5'-cyano-6'-(2,2-dimethylmorpholino)-2-methyl-[3,3'-bipyridin]-5-yl)-2-(2-cyanopropan-2-yl)isonicotinamide | $^1$H NMR (400 MHz, <dmso>) δ ppm 1.23 (s, 6 H) 1.75 (s, 6 H) 2.45 (s, 3 H) 3.55 (br. s., 4 H) 3.75-3.83 (m, 2 H) 7.77-7.93 (m, 1 H) 8.02 (s, 2 H) 8.16-8.28 (m, 1 H) 8.43-8.54 (m, 1 H) 8.77-8.91 (m, 2 H) 10.74-10.86 (m, 1 H). LCMS (m/z) (M + H) = 496.2, Rt = 0.73 min. |
| 90 | 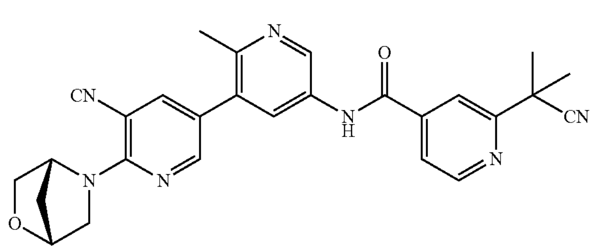 | N-(6'-((1R,4R)-2-oxa-5-azabicyclo[2.2.1]heptan-5-yl)-5'-cyano-2-methyl-[3,3'-bipyridin]-5-yl)-2-(2-cyanopropan-2-yl)isonicotinamide | LCMS (m/z) (M + H) = 480.2, Rt = 0.62 min. |

TABLE 4-continued

| Example | Structure | Name | Physical Data |
|---|---|---|---|
| 91 | 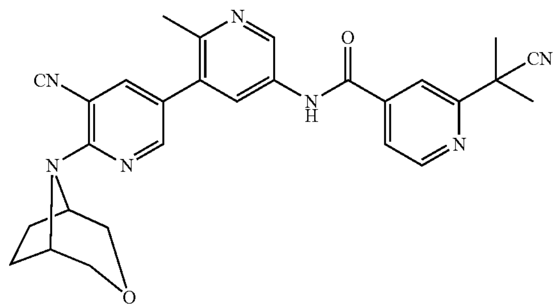 | N-(6'-((1R,5S)-3-oxa-8-azabicyclo[3.2.1]octan-8-yl)-5'-cyano-2-methyl-[3,3'-bipyridin]-5-yl)-2-(2-cyanopropan-2-yl)isonicotinamide | $^1$H NMR (400 MHz, <dmso>) δ ppm 1.75 (s, 6 H) 1.89-2.04 (m, 4 H) 2.46-2.47 (m, 3 H) 3.67 (s, 2 H) 3.74-3.77 (m, 2 H) 4.71-4.82 (m, 2 H) 7.82-7.90 (m, 1 H) 8.02 (s, 1 H) 8.06-8.12 (m, 1 H) 8.18-8.24 (m, 1 H) 8.43-8.50 (m, 1 H) 8.80-8.88 (m, 2 H) 10.78-10.85 (m, 1 H). LCMS (m/z) (M + H) = 494.3, Rt = 0.67 min. |

Example 92

N-(5'-cyano-6'-(2-methoxyethoxy)-2-methyl-[3,3'-bipyridin]-5-yl)-2-(2-cyanopropan-2-yl)isonicotinamide

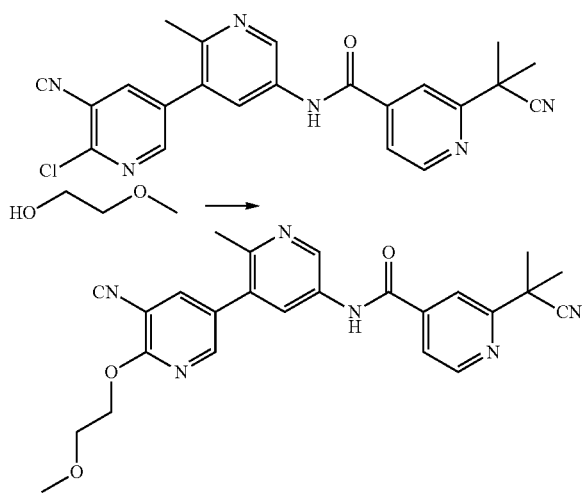

Method 6: To a solution of 2-methoxyethanol (1.2 equiv.) in THF (0.12 M) was added sodium hydride (2.5 equiv.) and the solution was stirred at room temperature for 1 hour. N-(6'-chloro-5'-cyano-2-methyl-[3,3'-bipyridin]-5-yl)-2-(2-cyanopropan-2-yl)isonicotinamide (1.0 equiv.) was added into the mixture and the solution was stirred at rt for 2 hours. Upon quenching with water and concentration under vacuo, the crude residue was purified via reverse phase prep-HPLC. The pure fractions were lyophilized to yield N-(5'-cyano-6'-(2-methoxyethoxy)-2-methyl-[3,3'-bipyridin]-5-yl)-2-(2-cyanopropan-2-yl)isonicotinamide in 38% yield as the TFA salt. $^1$H NMR (400 MHz, <dmso>) δ ppm 1.75 (s, 6 H) 2.45 (s, 3 H) 3.33 (s, 3 H) 3.68-3.80 (m, 2 H) 4.52-4.65 (m, 2 H) 7.87 (d, J=5.09 Hz, 1 H) 8.02 (s, 1 H) 8.12 (d, J=−1.96 Hz, 1 H) 8.45 (d, =2.35 Hz, 1 H) 8.53 (d, J=2.35 Hz, 1H) 8.79-8.94 (m, 2 H) 10.87 (s, 1 H). LCMS (m/z) (M+H)=457.1, Rt=0.65 min.

The compounds listed in Table 5, below, were prepared using methods similar to those described for the preparation of Example 92 (Method 6) using the appropriate starting materials.

TABLE 5

| Example | Structure | Name | Physical Data |
|---|---|---|---|
| 93 | 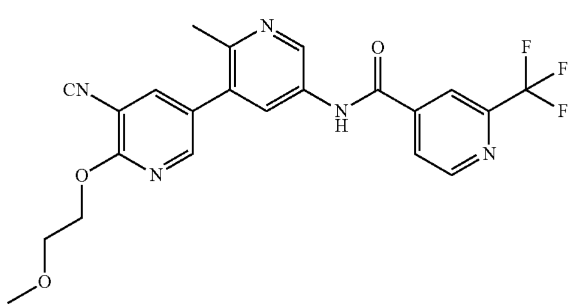 | N-(5'-cyano-6'-(2-methoxyethoxy)-2-methyl-[3,3'-bipyridin]-5-yl)-2-(trifluoromethyl)isonicotinamide | $^1$H NMR (400 MHz, <dmso>) δ ppm 2.44 (s, 3 H) 3.33 (s, 3 H) 3.64-3.79 (m, 2 H) 4.53-4.65 (m, 2 H) 8.11 (d, J = 1.96 Hz, 1 H) 8.20 (d, J = 4.70 Hz, 1 H) 8.37 (s, 1 H) 8.45 (d, J = 2.35 Hz, 1 H) 8.53 (d, J = 2.35 Hz, 1 H) 8.89 (d, J = 2.35 Hz, 1 H) 9.01 (d, J = 5.09 Hz, 1 H) 10.97 (s, 1 H). LCMS (m/z) (M + H) = 458.0, Rt = 0.70 min. |

TABLE 5-continued

| Example | Structure | Name | Physical Data |
| --- | --- | --- | --- |
| 94 | 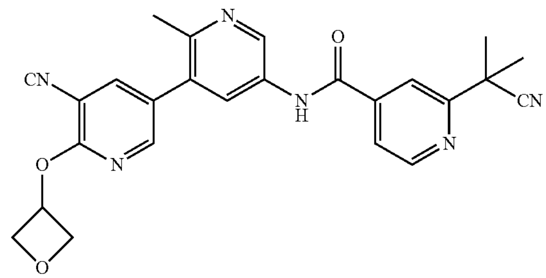 | N-(5'-cyano-2-methyl-6'-(oxetan-3-yloxy)-[3,3'-bipyridin]-5-yl)-2-(2-cyanopropan-2-yl)isonicotinamide | ¹H NMR (400 MHz, <dmso>) δ ppm 1.75 (s, 6 H) 2.42 (s, 3 H) 4.66 (dd, J = 7.83, 5.09 Hz, 2 H) 4.94 (t, J = 6.85 Hz, 2 H) 5.73 (s, 1 H) 7.86 (d, J = 3.91 Hz, 1 H) 7.98-8.11 (m, 2 H) 8.44-8.54 (m, 2 H) 8.78-8.89 (m, 2 H) 10.81 (s, 1 H). LCMS (m/z) (M + H) = 455.0, Rt = 0.65 min. |
| 95 | 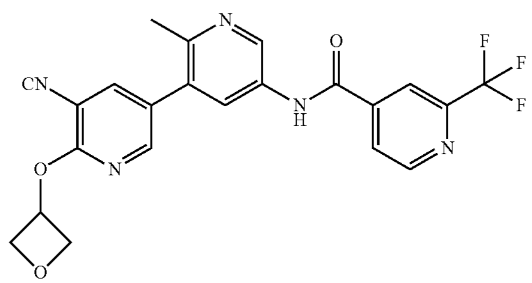 | N-(5'-cyano-2-methyl-6'-(oxetan-3-yloxy)-[3,3'-bipyridin]-5-yl)-2-(trifluoromethyl)isonicotinamide | ¹H NMR (400 MHz, <dmso>) δ ppm 2.42 (s, 3 H) 4.66 (dd, J = 7.83, 5.09 Hz, 2 H) 4.94 (t, J = 7.04 Hz, 2 H) 5.73 (t, J = 5.48 Hz, 1 H) 8.09 (d, J = 2.35 Hz, 1 H) 8.19 (d, J = 4.70 Hz, 1 H) 8.37 (s, 1 H) 8.45-8.55 (m, 2 H) 8.85 (d, J = 2.35 Hz, 1 H) 9.01 (d, J = 5.09 Hz, 1 H) 10.94 (s, 1 H). LCMS (m/z) (M + H) = 456.1, Rt = 0.67 min. |
| 96 | 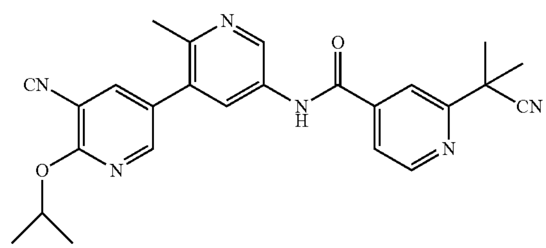 | N-(5'-cyano-6'-isopropoxy-2-methyl-[3,3'-bipyridin]-5-yl)-2-(2-cyanopropan-2-yl)isonicotinamide | ¹H NMR (400 MHz, <dmso>) δ ppm 1.38 (d, J = 6.26 Hz, 6 H) 1.75 (s, 6 H) 2.44 (s, 3 H) 5.35-5.51 (m, 1 H) 7.82-7.94 (m, 1 H) 7.97-8.15 (m, 2H) 8.41 (d, J = 2.35 Hz, 1 H) 8.52 (d, J = 2.35 Hz, 1 H) 8.79-8.91 (m, 2 H) 10.83 (s, 1 H). LCMS (m/z) (M + H) = 441.1, Rt = 0.78 min. |
| 97 | 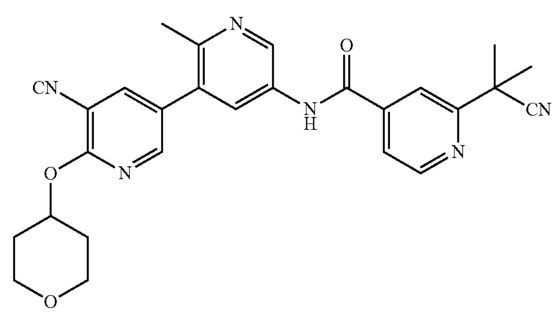 | N-(5'-cyano-2-methyl-6'-((tetrahydro-2H-pyran-4-yl)oxy)-[3,3'-bipyridin]-5-yl)-2-(2-cyanopropan-2-yl)isonicotinamide | ¹H NMR (400 MHz, <dmso>) δ ppm 1.71-1.78 (m, 8 H) 2.01-2.13 (m, 2 H) 2.45 (s, 3 H) 3.47-3.59 (m, 2 H) 3.82-3.92 (m, 2 H) 5.34-5.45 (m, 1 H) 7.83-7.92 (m, 1 H) 8.02 (s, 1 H) 8.13 (d, J = 1.96 Hz, 1 H) 8.45 (d, J = 2.35 Hz, 1 H) 8.53 (d, J = 2.35 Hz, 1 H) 8.79-8.93 (m, 2 H) 10.88 (s, 1 H). LCMS (m/z) (M + H) = 483.1, Rt = 0.70 min. |
| 98 | 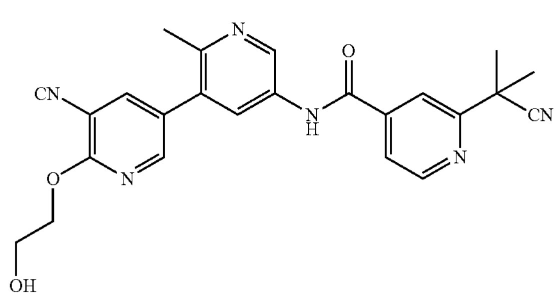 | N-(5'-cyano-6'-(2-hydroxyethoxy)-2-methyl-[3,3'-bipyridin]-5-yl)-2-(2-cyanopropan-2-yl)isonicotinamide | ¹H NMR (400 MHz, <dmso>) δ ppm 1.75 (s, 6 H) 2.43 (s, 3 H) 3.77 (t, J = 4.89 Hz, 2 H) 4.49 (t, J = 4.89 Hz, 2 H) 7.84-7.91 (m, 1 H) 8.02 (s, 1 H) 8.09 (d, J = 1.96 Hz, 1 H) 8.44 (d, J = 2.35 Hz, 1 H) 8.52 (d, J = 2.35 Hz, 1 H) 8.80-8.91 (m, 2H) 10.83 (s, 1 H). LCMS (m/z) (M + H) = 443.1, Rt = 0.57 min. |

TABLE 5-continued

| Example | Structure | Name | Physical Data |
|---|---|---|---|
| 99 | 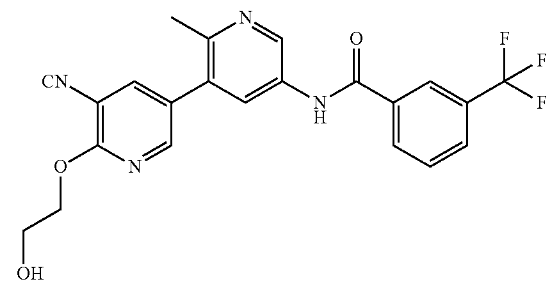 | N-(5'-cyano-6'-(2-hydroxyethoxy)-2-methyl-[3,3'-bipyridin]-5-yl)-3-(trifluoromethyl)benzamide | ¹H NMR (400 MHz, <dmso>) δ ppm 2.44 (s, 3 H) 3.77 (t, J = 5.09 Hz, 2 H) 4.49 (t, J = 4.89 Hz, 2 H) 7.81 (s, 1 H) 7.98 (s, 1 H) 8.13 (d, J = 1.96 Hz, 1 H) 8.24-8.36 (m, 2 H) 8.44 (d, J = 2.35 Hz, 1 H) 8.52 (d, J = 2.35 Hz, 1 H) 8.91 (d, J = 2.35 Hz, 1 H) 10.76 (s, 1 H). LCMS (m/z) (M + H) = 443.1, Rt = 0.68 min. |

Example 100

N-(5'-cyano-6'-ethoxy-2-methyl-[3,3'-bipyridin]-5-yl)-2-(2-cyanopropan-2-yl)isonicotinamide

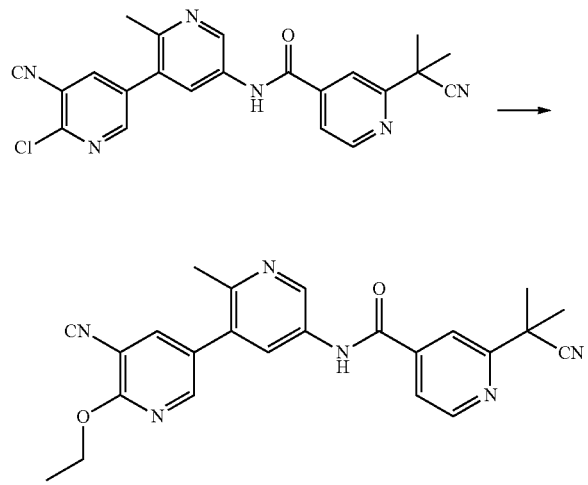

To a solution of N-(6'-chloro-5'-cyano-2-methyl-[3,3'-bipyridin]-5-yl)-2-(2-cyanopropan-2-yl)isonicotinamide (1.0 equiv.) in THF (0.12 M) was added sodium ethoxide (2.5 equiv., 30% solution in ethanol) and the reaction was stirred at rt for 2 hours. Upon quenching with water and concentration under vacuo, the crude residue was purified via reverse phase prep-HPLC. The pure fractions were lyophilized to yield N-(5'-cyano-6'-ethoxy-2-methyl-[3,3'-bipyridin]-5-yl)-2-(2-cyanopropan-2-yl)isonicotinamide in 35% yield. ¹H NMR (400 MHz, <dmso>) δ ppm 1.39 (t, J=7.04 Hz, 3 H) 1.75 (s, 6 H) 2.44 (s, 3 H) 4.52 (q, J=7.04 Hz, 2 H) 7.87 (d, J=5.09 Hz, 1 H) 8.02 (s, 1 H) 8.11 (d, J=1.57 Hz, 1 H) 8.43 (d, J=2.35 Hz, 1 H) 8.53 (d, J=2.74 Hz, 1 H) 8.79-8.91 (m, 2 H) 10.86 (s, 1 H). LCMS (m/z) (M+H)=427.1, Rt=0.72 min.

Example 101

N-(5'-cyano-2-methyl-[3,3':6',4''-terpyridin]-5-yl)-2-(trifluoromethyl)isonicotinamide

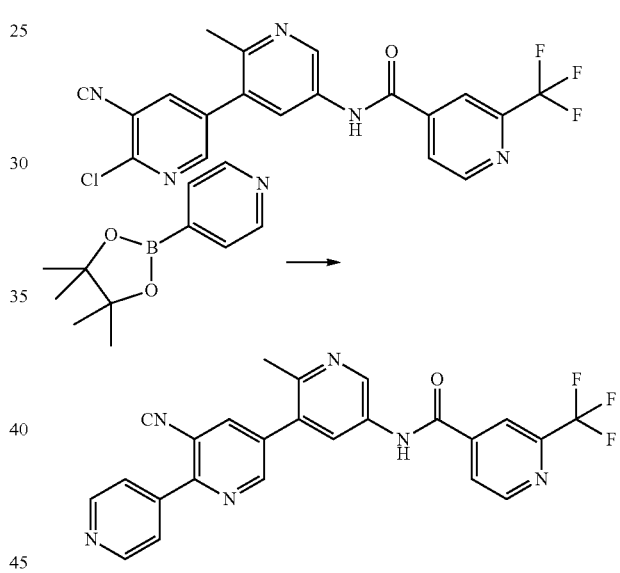

Method 7: To a degassed solution of 4-(4,4,5,5-tetramethyl-1,3,2-dioxaborolan-2-yl)pyridine (1.3 equiv.) in DME (0.03 M) was added N-(6'-chloro-5'-cyano-2-methyl-[3,3'-bipyridin]-5-yl)-2-(trifluoromethyl)isonicotinamide (1.0 equiv.), sodium carbonate (5.0 equiv., 2M aqueous solution) and PdCl₂(dppf)-DCM adduct (0.15 equiv.). This mixture was heated to 110° C. for 15 min in the microwave and cooled to rt. Diluted with ethyl acetate and the organic layer was concentrated to dryness under vacuo. The residue was purified via reverse phase prep-HPLC and the pure fractions were lyophilized to give N-(5'-cyano-2-methyl-[3,3':6',4''-terpyridin]-5-yl)-2-(trifluoromethyl)isonicotinamide as the TFA salt in 72% yield. ¹H NMR (400 MHz, <dmso>) δ ppm 2.46-2.48 (m, 3 H) 7.98 (d, J=5.87 Hz, 2 H) 8.13-8.23 (m, 2 H) 8.34 (s, 1 H) 8.67 (d, J=1.96 Hz, 1 H) 8.82-8.90 (m, 3 H) 8.97 (d, J=4.70 Hz, 1 H) 9.05 (d, J=1.96 Hz, 1 H) 10.98 (s, 1 H). LCMS (m/z) (M+H)=461.0, Rt=0.53 min.

The compounds listed in Table 6, below, were prepared using methods similar to those described for the preparation of Example 101 (Method 7) using the appropriate starting materials.

TABLE 6

| Example | Structure | Name | Physical Data |
|---|---|---|---|
| 102 | 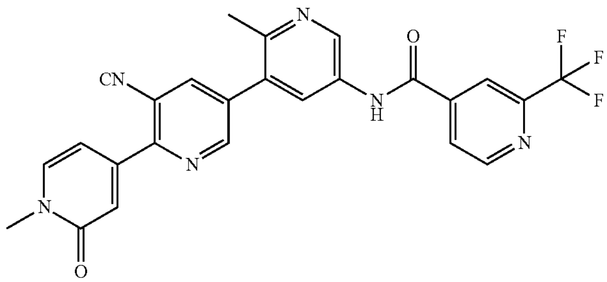 | N-(5'-cyano-1",2-dimethyl-2"-oxo-1",2"-dihydro-[3,3':6',4"-terpyridin]-5-yl)-2-(trifluoromethyl)isonicotinamide | $^1$H NMR (400 MHz, <dmso>) δ ppm 2.45-2.48 (m, 3 H) 3.50 (s, 3 H) 6.66 (dd, J = 7.04, 1.96 Hz, 1 H) 6.93 (d, J = 3.96 Hz, 1 H) 7.90 (d, J = 7.04 Hz, 1 H) 8.15-8.27 (m, 2 H) 8.38 (s, 1 H) 8.65 (d, J = 1.96 Hz, 1 H) 8.92 (d, J = 2.35 Hz, 1 H) 8.99-9.07 (m, 2 H) 11.02 (s, 1 H). LCMS (m/z) (M + H) = 491.1, Rt = 0.60 min. |
| 103 | 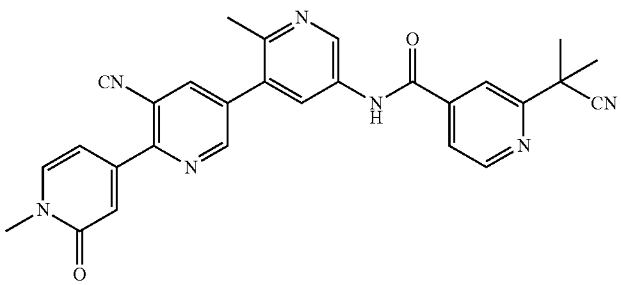 | N-(5'-cyano-1",2-dimethyl-2"-oxo-1",2"-dihydro-[3,3':6',4"-terpyridin]-5-yl)-2-(2-cyanopropan-2-yl)isonicotinamide | $^1$H NMR (400 MHz, <dmso>) δ ppm 1.76 (s, 6 H) 2.46-2.47 (m, 3 H) 3.50 (s, 3 H) 6.55-6.72 (m, 1 H) 6.89-6.97 (m, 1 H) 7.90 (d, J = 7.43 Hz, 2 H) 8.02 (s, 1 H) 8.18 (d, J = 1.96 Hz, 1 H) 8.64 (d, J = 1.96 Hz, 1 H) 8.90 (d, J = 2.35 Hz, 2 H) 9.04 (d, J = 1.96 Hz, 1 H) 10.87 (s, 1 H). LCMS (m/z) (M + H) = 490.1, Rt = 0.56 min. |
| 104 | 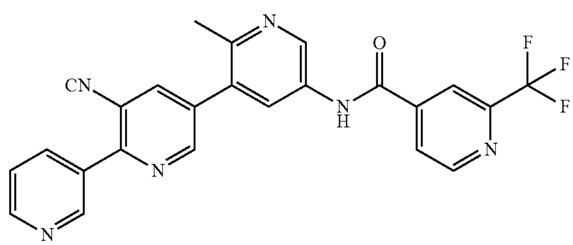 | N-(3'-cyano-2"-methyl-[3,2':5',3"-terpyridin]-5'-yl)-2-(trifluoromethyl)isonicotinamide | $^1$H NMR (400 MHz, <dmso>) δ ppm 2.52 (s, 3 H) 7.71 (dd, J = 8.02, 4.89 Hz, 1 H) 8.18-8.29 (m, 2 H) 8.35-8.48 (m, 2 H) 8.69 (d, J = 1.96 Hz, 1 H) 8.80 (dd, J = 4.70, 1.17 Hz, 1 H) 8.91-9.20 (m, 4 H) 11.05 (s, 1 H). LCMS (m/z) (M + H) = 461.0, Rt = 0.55 min. |
| 105 | 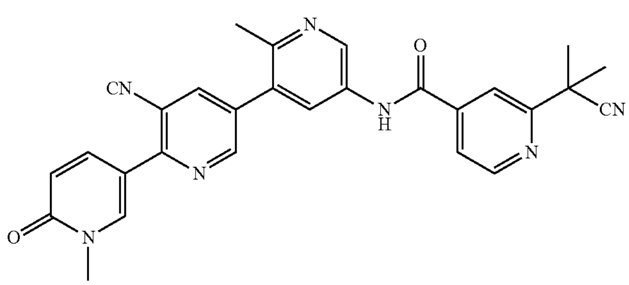 | N-(3'-cyano-1,2"-dimethyl-6-oxo-1,6-dihydro-[3,2':5',3"-terpyridin]-5'-yl)-2-(2-cyanopropan-2-yl)isonicotinamide | $^1$H NMR (400 MHz, <dmso>) δ ppm 1.76 (s, 6 H) 2.49-2.51 (m, 3 H) 3.56 (s, 3 H) 6.57 (d, J = 9.39 Hz, 1 H) 7.88 (d, J = 5.09 Hz, 1 H) 7.97-8.10 (m, 2 H) 8.19 (d, J = 1.96 Hz, 1 H) 8.45-8.63 (m, 2 H) 8.81-8.98 (m, 3 H) 10.90 (s, 1 H). LCMS (m/z) (M + H) = 490.1, Rt = 0.59 min. |
| 106 | 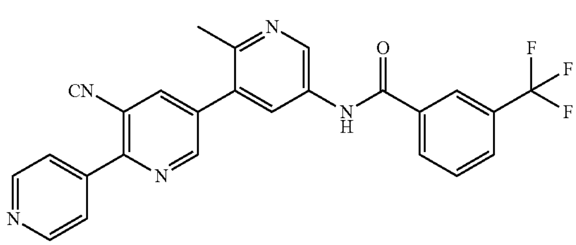 | N-(5'-cyano-2-methyl-[3,3':6',4"-terpyridin]-5'-yl)-3-(trifluoromethyl)benzamide | $^1$H NMR (400 MHz, <dmso>) δ ppm 2.50 (br. s., 3 H) 7.76-7.87 (m, 1 H) 7.99 (d, J = 5.87 Hz, 3 H) 8.32 (s, 3 H) 8.71 (d, J = 1.96 Hz, 1 H) 8.86 (d, J = 6.26 Hz, 2 H) 8.90-8.96 (m, 1 H) 9.10 (d, J = 1.96 Hz, 1 H) 10.79 (s, 1 H). LCMS (m/z) (M + H) = 460.0, Rt = 0.62 min. |
| 107 | 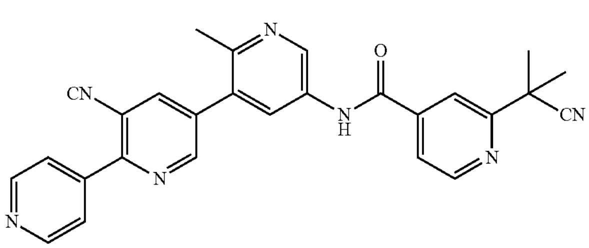 | N-(5'-cyano-2-methyl]-3,3':6',4"-terpyridin]-5'-yl)-2-(2-cyanopropan-2-yl)isonicotinamide | $^1$H NMR (400 MHz, <dmso>) δ ppm 1.76 (s, 6 H) 2.50-2.53 (m, 3 H) 7.81-7.92 (m, 1 H) 7.95-8.07 (m, 3 H) 8.22 (d, J = 1.96 Hz, 1 H) 8.71 (d, J = 1.96 Hz, 1 H) 8.80-8.95 (m, 4 H) 9.10 (d, J = 2.35 Hz, 1 H) 10.90 (s, 1 H). LCMS (m/z) (M + H) = 460.0, Rt = 0.52 min. |

TABLE 6-continued

| Example | Structure | Name | Physical Data |
|---|---|---|---|
| 108 | 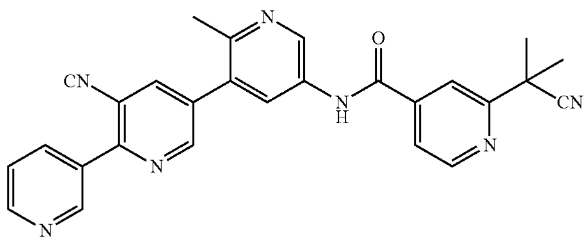 | N-(3'-cyano-2''-methyl-[3,2':5',3''-terpyridin]-5''-yl)-2-(2-cyanopropan-2-yl)isonicotinamide | $^1$H NMR (400 MHz, <dmso>) δ ppm 1.76 (s, 6 H) 2.51 (s, 3 H) 7.68 (dd, J = 7.83, 5.09 Hz, 1 H) 7.88 (dd, J = 4.89, 0.98 Hz, 1 H) 8.03 (s, 1 H) 8.23 (d, J = 2.35 Hz, 1 H) 8.40 (d, J = 8.22 Hz, 1 H) 8.69 (d, J = 1.96 Hz, 1 H) 8.76-8.88 (m, 2 H) 8.92 (d, J = 2.35 Hz, 1 H) 9.04-9.17 (m, 2 H) 10.91 (s, 1H). LCMS (m/z) (M + H) = 460.0, Rt = 0.52 min. |
| 109 | 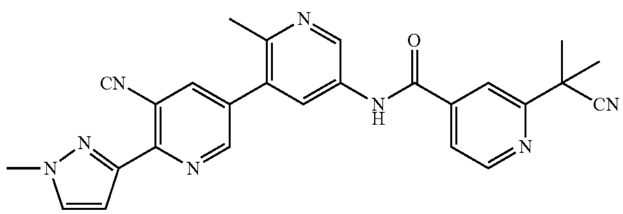 | N-(5'-cyano-2-methyl-6'-(1-methyl-1H-pyrazol-3-yl)-[3,3'-bipyridin]-5-yl)-2-(2-cyanopropan-2-yl)isonicotinamide | $^1$H NMR (400 MHz, <dmso>) δ ppm 1.76 (s, 6 H) 2.51-2.55 (m, 3 H) 4.04 (s, 3 H) 6.95 (d, J = 1.96 Hz, 1 H) 7.62 (d, J = 1.96 Hz, 1 H) 7.88 (d, J = 4.30 Hz, 1 H) 8.03 (s, 1 H) 8.22 (d, J = 1.96 Hz, 1 H) 8.66 (d, J = 1.96 Hz, 1 H) 8.79-8.95 (m, 2 H) 9.05 (d, J = 2.35 Hz, 1 H) 10.88 (s, 1 H). LCMS (m/z) (M + H) = 463.2, Rt = 0.66 min. |

Example 110

N-(5'-cyano-2-methyl-6'-(1-methyl-1H-pyrazol-4-yl)-[3,3'-bipyridin]-5-yl)-2-(2-cyanopropan-2-yl)isonicotinamide

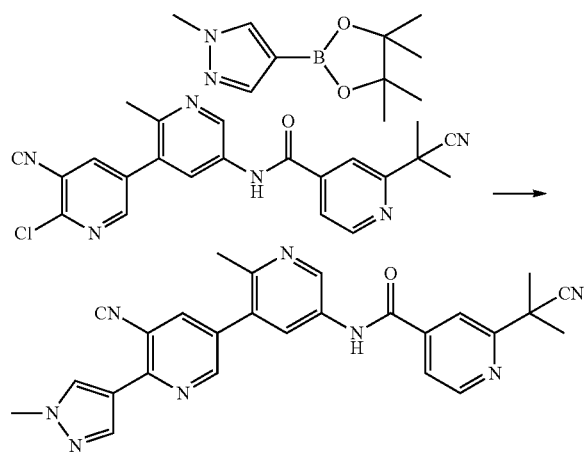

Method 8: A solution of N-(6'-chloro-5'-cyano-2-methyl-[3,3'-bipyridin]-5-yl)-2-(2-cyanopropan-2-yl)isonicotinamide (1.0 equiv.), 1-methyl-4-(4,4,5,5-tetramethyl-1,3,2-dioxaborolan-2-yl)-1H-pyrazole (2.0 equiv.), potassium carbonate (3.5 equiv., 3M aqueous solution) and Pd(PPh$_3$)$_4$ (0.05 equiv.) in toluene and ethanol (2.5:1, 0.06 M) was heated in the microwave at 120° C. for 20 minutes. The organic layer was separated and concentrated to dryness. The residue was dissolved in DMSO and purified via reverse-phase HPLC. The pure fractions were lyophilized to give N-(5'-cyano-2-methyl-6'-(1-methyl-1H-pyrazol-4-yl)-[3,3'-bipyridin]-5-yl)-2-(2-cyanopropan-2-yl)isonicotinamide as the TFA salt in 55% yield. $^1$H NMR (400 MHz, DMSO$_{d6}$) δ 10.91 (s, 1H), 8.94 (d, J=4.0, 1H), 8.90 (d, J=2.0, 1H), 8.84 (d, J=4.0, 1H), 8.54 (s, 1H), 8.48 (d, J=2.0, 1H), 8.22 (s, 1H), 8.19 (d, J=2.0, 1H), 8.04 (s, 1H), 7.89 (dd. J=8.0, 2.0, 1H), 3.98 (s, 3H), 2.51 (s, 3H), 1.77 (s, 6H). LCMS (m/z) (M+H)=463.1, Rt=0.64 min.

The compounds listed in Table 7, below, were prepared using methods similar to those described for the preparation of Example 110 (Method 8) using the appropriate starting materials.

TABLE 7

| Example | Structure | Name | Physical Data |
|---|---|---|---|
| 111 | 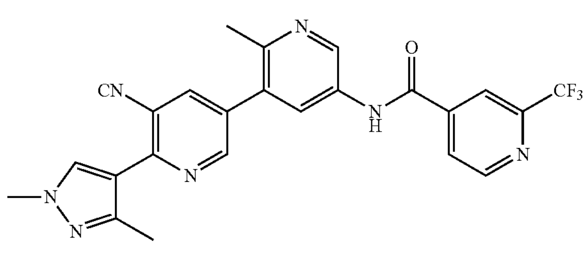 | N-(5'-cyano-6'-(1,3-dimethyl-1H-pyrazol-4-yl)-2-methyl-[3,3'-bipyridin]-5-yl)-2-(trifluoromethyl)isonicotinamide | $^1$H NMR (400 MHz, DMSO$_{d6}$) δ 11.01 (s, 1H), 9.04 (d, J = 4.0, 1H), 8.94 (d, J = 4.0, 2H), 8.50 (d, J = 4.0, 1H), 8.40 (s, 1H), 8.36 (s, 1H), 8.22 (d, J = 4.0, 8.22 (s, 1H), 3.89 (s, 3H), 2.52 (s, 3H), 2.42 (s, 3H). LCMS (m/z) (M + H) = 478.1, Rt = 0.68 min. |

TABLE 7-continued

| Example | Structure | Name | Physical Data |
|---|---|---|---|
| 112 | 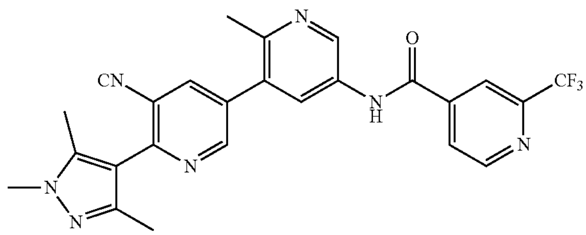 | N-(5'-cyano-2-methyl-6'-(1,3,5-trimethyl-1H-pyrazol-4-yl)-[3,3'-bipyridin]-5-yl)-2-(trifluoromethyl)isonicotinamide | $^1$H NMR (400 MHz, DMSO$_{d6}$) δ 11.02 (s, 1H), 9.04 (d, J = 4.0, 1H), 8.99 (d, J = 2.0, 1H), 8.92 (d, J = 2.0, 1H), 8.56 (d, J = 2.0, 1H), 8.40 (s, 1H), 8.24 (d, J = 2.0, 1H), 8.22 (d, J = 2.0, 1H), 3.77 (s, 3H), 2.53 (s, 3H), 2.30 (s, 3H), 2.21 (s, 3H). LCMS (m/z) (M + H) = 492.1, Rt = 0.66 min. |
| 113 | 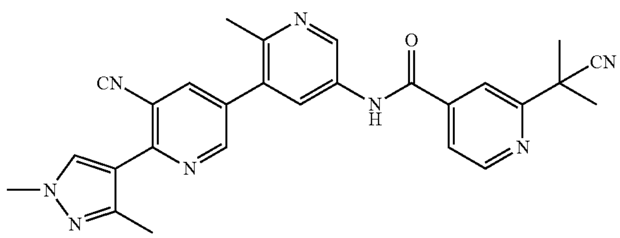 | N-(5'-cyano-6'-(1,3-dimethyl-1H-pyrazol-4-yl)-2-methyl-[3,3'-bipyridin]-5-yl)-2-(2-cyanopropan-2-yl)isonicotinamide | $^1$H NMR (400 MHz, DMSO$_{d6}$) δ 10.91 (s, 1H), 8.93-8.94 (m, 2H), 8.86 (d, J = 4.0, 1H), 8.50 (d, J = 2.0, 1H), 8.36 (s, 3H), 8.22 (d, J = 2.0, 1H), 8.05 (s, 1H), 7.90 (d, J = 8.0, 1H), 3.89 (s, 3H), 2.52 (s, 3H), 2.42 (s, 3H), 1.77 (s, 6H). LCMS (m/z) (M + H) = 477.1, Rt = 0.65 min. |
| 114 | 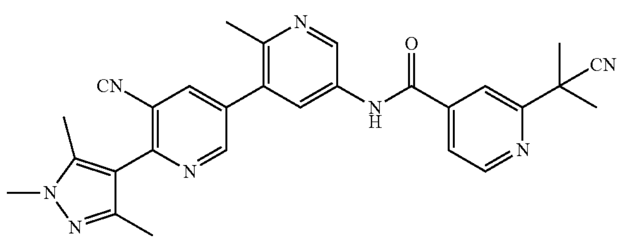 | N-(5'-cyano-2-methyl-6'-(1,3,5-trimethyl-1H-pyrazol-4-yl)-[3,3'-bipyridin]-5-yl)-2-(2-cyanopropan-2-yl)isonicotinainide | $^1$H NMR (400 MHz, DMSO$_{d6}$) δ 10.93 (s, 1H), 9.00 (d, J = 2.0, 1H), 8.94 (d, J = 2.0, 1H), 8.86 (d, J = 4.0, 1H), 8.56 (d, J = 2.0, 1H), 8.26 (d, J = 2.0, 1H), 8.05 (s, 1H), 7.90 (d, J = 4.0, 1H), 3.77 (s, 3H), 2.54 (s, 3H), 2.30 (s, 3H), 2.21 (s, 3H), 1.78 (s, 6H). LCMS (m/z) (M + H) = 491.1, Rt = 0.63 min. |
| 115 | 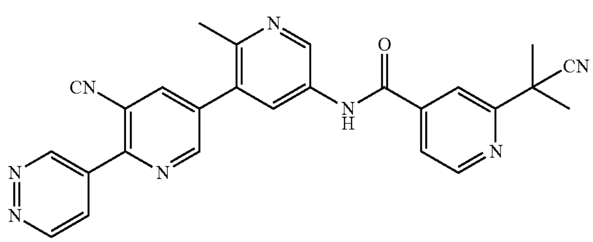 | N-(5'-cyano-2-methyl-6'-(pyridazin-4-yl)-3,3'-bipyridin]-5-yl)-2-(2-cyanopropan-2-yl)isonicotinamide | $^1$H NMR (400 MHz, DMSO$_{d6}$) δ 10.91 (s, 1H), 9.76 (s, 1H), 9.55 (d, J = 8.0, 1H), 9.16 (d, J = 4.0, 1H), 8.94 (d, J = 4.0, 1H), 8.86 (d, J = 4.0, 1H), 8.78 (d, J = 4.0, 1H), 8.28 (dd, J = 4.0, 2.0, 1 H), 8.24 (d, J = 2.0, 1H), 8.04 (s, 1H), 7.90 (dd, J = 4.0, 2.0, 1H), 2.52 (s, 3H), 1.78 (s, 6H). LCMS (m/z) (M + H) = 461.1, Rt = 0.57 min. |
| 116 | 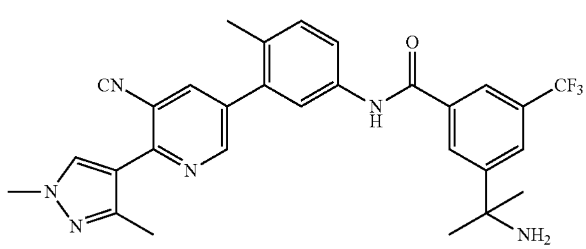 | 3-(2-aminopropan-2-yl)-N-(3-(5-cyano-6-(1,3-dimethyl-1H-pyrazol-4-yl)pyridin-3-yl)-4-methylphenyl)-5-(trifluoromethyl)benzamide | $^1$H NMR (400 MHz, <dmso>) δ ppm 1.70 (s, 6 H) 2.28 (s, 3 H) 2.40 (s, 3 H) 3.87 (s, 3 H) 7.38 (d, J = 8.61 Hz, 1 H) 7.71 (d, J = 2.35 Hz, 1 H) 7.74-7.82 (m, 1 H) 8.08 (s, 1 H) 8.32 (s, 1 H) 8.34-8.39 (m, 3 H) 8.54 (br. s., 2 H) 8.85 (d, J = 2.35 Hz, 1 H) 10.56 (s, 1 H). LCMS (m/z) (M + H) = 533.3, Rt = 0.83 min. |

Example 117

N-(3-(5-cyano-6-(1-methyl-1H-pyrazol-4-yl)pyridin-3-yl)-4-methylphenyl)-2-(1,1-difluoroethyl)isonicotinamide

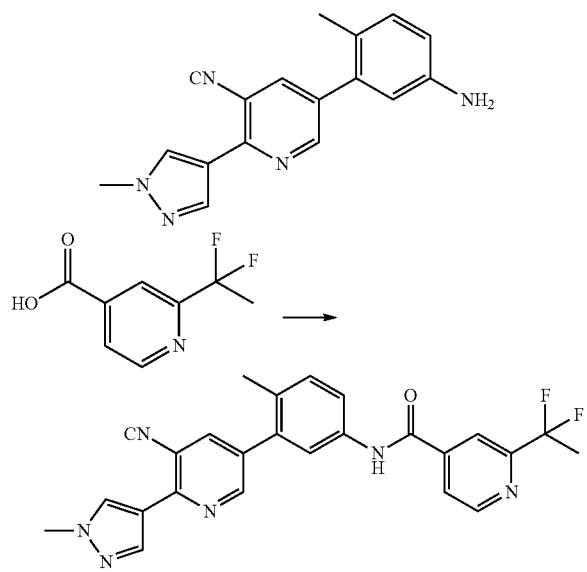

Method 9: To a solution of 5-(5-amino-2-methylphenyl)-2-(1-methyl-1H-pyrazol-4-yl)nicotinonitrile (1.0 equiv.) in DMF (0.2 M) was added EDC (1.3 equiv.), HOAt (1.3 equiv.), and 2-(1,1-difluoroethyl)isonicotinic acid (1.2 equiv.) at room temperature and the mixture was stirred for 3 hours. Diluted with water and extracted with ethyl acetate. The organic phase was washed with 1M aq NaOH and sat. NaCl, then dried with sodium sulfate, filtered and concentrated. The crude material was purified via reverse phase prep-HPLC and the pure fractions were lyophilized to give N-(3-(5-cyano-6-(1-methyl-1H-pyrazol-4-yl)pyridin-3-yl)-4-methylphenyl)-2-(1,1-difluoroethyl)isonicotinamide in 21% yield as the TFA salt. $^1$H NMR (400 MHz, <dmso>) δ ppm 1.99 (t, J=19.17 Hz, 3 H) 2.21 (s, 3H) 3.91 (s, 3 H) 7.33 (s, 1 H) 7.67 (d, J=1.96 Hz, 2 H) 7.92-8.01 (m, 1 H) 8.14 (d, J=9.00 Hz, 2 H) 8.31 (d, J=1.96 Hz, 1 H) 8.46 (s, 1 H) 8.77 (d, J=1.96 Hz, 2 H) 10.63 (s, 1 H). LCMS (m/z) (M+H)=459.1, Rt=0.98 min.

The compounds listed in Table 8, below, were prepared using methods similar to those described for the preparation of Example 117 (Method 9) using the appropriate starting materials. If a BOC protecting group was present, it was deprotected by stirring the crude material in TFA and DCM (1:2) until completion, then purified by concentrating under vacuo and purified via reverse phase prep-HPLC. The pure fractions were lyophilized to give the desired product as the TFA salt.

TABLE 8

| Example | Structure | Name | Physical Data |
|---|---|---|---|
| 118 | 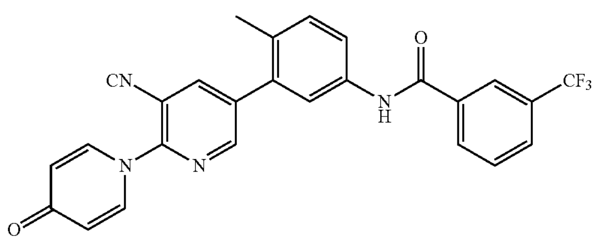 | N-(3-(3'-cyano-4-oxo-4H-[1,2'-bipyridin]-5'-yl)-4-methylphenyl)-3-(trifluoromethyl)benzamide | $^1$H NMR (400 MHz, <dmso>) δ ppm 2.28 (s, 3 H) 6.48 (d, J = 7.83 Hz, 2 H) 7.39 (d, J = 8.22 Hz, 1 H) 7.70-7.87 (m, 3 H) 7.97 (d, J = 7.83 Hz, 1 H) 8.21-8.40 (m, 4 H) 8.74 (d, J = 2.35 Hz, 1 H) 8.88 (d, J = 1.96 Hz, 1 H) 10.56 (s, 1 H). LCMS (m/z) (M + H) = 475.1, Rt = 0.89 min. |
| 119 | 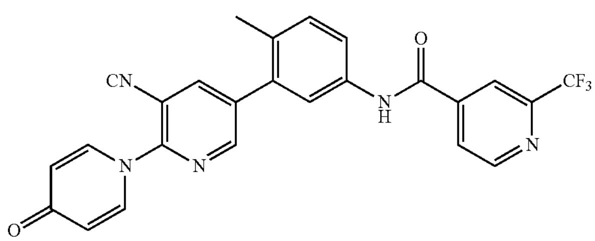 | N-(3-(3'-cyano-4-oxo-4H-[1,2'-bipyridin]-5'-yl)-4-methylphenyl)-2-(trifluoromethyl)isonicotinamide | $^1$H NMR (400 MHz, <dmso>) δ ppm 2.28 (s, 3 H) 6.33 (d, J = 7.83 Hz, 2 H) 7.42 (s, 1 H) 7.81 (d, J = 1.96 Hz, 2 H) 8.22 (d, J = 7.83 Hz, 3 H) 8.35 (s, 1 H) 8.72 (d, J = 1.96 Hz, 1 H) 8.86 (d, J = 2.35 Hz, 1 H) 8.98 (s, 1 H) 10.77 (s, 1 H). LCMS (m/z) (M + H) = 476.0, Rt = 0.80 min. |
| 120 | 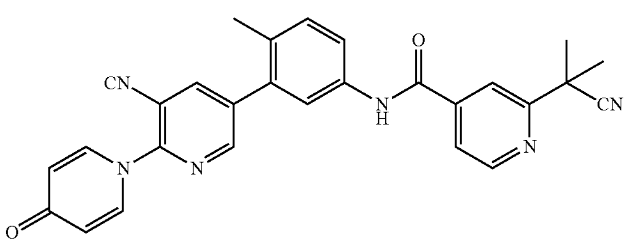 | N-(3-(3'-cyano-4-oxo-4H-[1,2'-bipyridin]-5'-yl)-4-methylphenyl)-2-(2-cyanopropan-2-yl)isonicotinamide | $^1$H NMR (400 MHz, <dmso>) δ ppm 1.75 (s, 6 H) 2.28 (s, 3 H) 6.29-6.50 (m, 2 H) 7.36-7.48 (m, 1 H) 7.71-7.89 (m, 3 H) 7.93-8.03 (m, 1 H) 8.22-8.33 (m, 2 H) 8.66-8.91 (m, 3 H) 10.58-10.70 (m, 1 H). LCMS (m/z) (M + H) = 475.2, Rt = 0.74 min. |

TABLE 8-continued

| Example | Structure | Name | Physical Data |
|---|---|---|---|
| 121 | 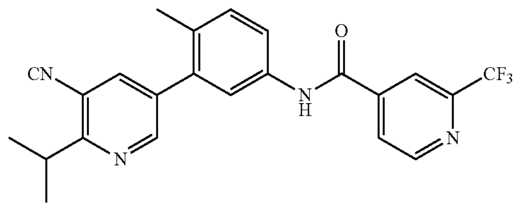 | N-(3-(5-cyano-6-isopropylpyridin-3-yl)-4-methylphenyl)-2-(trifluoromethyl)isonicotinamide | $^1$H NMR (400 MHz, DMSO$_{d6}$) δ 10.73 (s, 1H), 9.00 (d, J = 4.0, 1H), 8.83 (d, J = 2.0, 1H), 8.36 (s, 1H), 8.34 (d, J = 4.0, 1H), 8.19 (d, J = 8.0, 1H), 7.75 (dd, J = 8.0, 2.0, 1H), 7.73 *s, 1H), 7.39 (d, J = 8.0, 1H), 3.49 (septet, J = 8.0, 1H), 2.24 (s, 3H), 1.34 (d, J = 8.0, 6H). LCMS (m/z) (M + H) = 425.1, Rt = 1.09 min. |
| 122 | 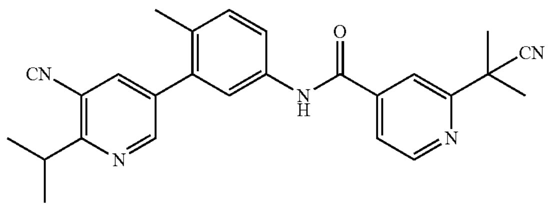 | N-(3-(5-cyano-6-isopropylpyridin-3-yl)-4-methylphenyl)-2-(2-cyanopropan-2-yl)isonicotinamide | $^1$H NMR (400 MHz, DMSO$_{d6}$) δ 10.60 (s, 1H), 8.83 (d, J = 2.0, 1H), 8.82 (d, J = 4.0, 1H), 8.34 (d, J = 4.0, 1H), 8.00 (s, 1H), 7.86 (dd, J = 4.0, 2.0, 1H), 7.73 (dd, J = 8.0, 2.0, 1H), 7.71 (s, 1H), 7.38 (d, J = 8.0, 1H), 3.49 (septet, J = 8.0, 1H), 2.24 (s, 3H), 1.76 (s, 6H), 1.34 (d, J = 8.0, 6H). LCMS (m/z) (M + H) = 424.1, Rt = 1.07 min. |
| 123 | 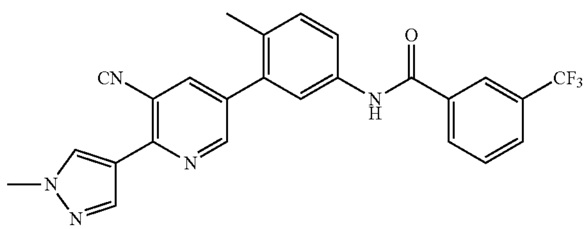 | N-(3-(5-cyano-6-(1-methyl-1H-pyrazol-4-yl)pyridin-3-yl)-4-methylphenyl)-3-(trifluoromethyl)benzamide | $^1$H NMR (400 MHz, <dmso>) δ ppm 2.26 (s, 3 H) 3.96 (s, 3 H) 7.35 (d, J = 8.61 Hz, 1 H) 7.69-7.85 (m, 3 H) 7.96 (d, J = 7.83 Hz, 1 H) 8.20 (s, 1 H) 8.22-8.32 (m, 2 H) 8.36 (d, J = 2.35 Hz, 1 H) 8.51 (s, 1H) 8.82 (d, J = 2.35 Hz, 1 H) 10.51 (s, 1 H) LCMS (m/z) (M + H) = 462.1, Rt = 1.07 min. |
| 124 | 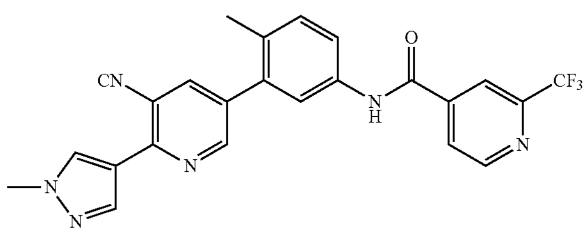 | N-(3-(5-cyano-6-(1-methyl-1H-pyrazol-4-yl)pyridin-3-yl)-4-methylphenyl)-2-(trifluoromethyl)isonicotinamide | $^1$H NMR (400 MHz, <dmso>) δ ppm 2.15-2.25 (m, 3 H) 3.91 (s, 3 H) 7.33 (d, J = 8.22 Hz, 1 H) 7.65-7.76 (m, 2 H) 8.09-8.19 (m, 2 H) 8.27-8.37 (m, 2 H) 8.46 (s, 1 H) 8.77 (d, J = 2.35 Hz, 1 H) 8.93 (d, J = 4.69 Hz, 1 H) 10.68 (s, 1H). LCMS (m/z) (M + H) = 463.1, Rt = 0.94 min. |
| 125 | 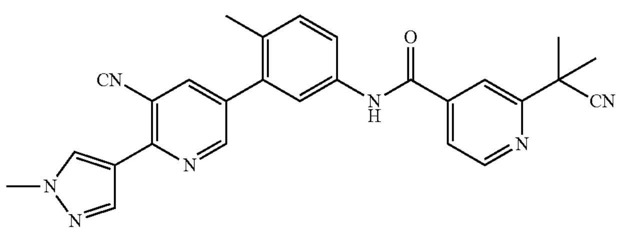 | N-(3-(5-cyano-6-(1-methyl-1H-pyrazol-4-yl)pyridin-3-yl)-4-methylphenyl)-2-(2-cyanopropan-2-yl)isonicotinamide | $^1$H NMR (400 MHz, <dmso>) δ ppm 1.75 (s, 6 H) 1.97 (s, 2 H) 2.26 (s, 3 H) 7.37 (d, J = 8.22 Hz, 1 H) 7.65-7.78 (m, 2 H) 7.85 (d, J = 3.91 Hz, 1 H) 8.00 (s, 1 H) 8.20 (s, 1 H) 8.36 (d, J = 1.96 Hz, 1 H) 8.51 (s, 1 H) 8.69-8.89 (m, 2 H) 10.60 (s, 1 H). LCMS (m/z) (M + H) = 462.2, Rt = 0.89 min. |
| 126 | 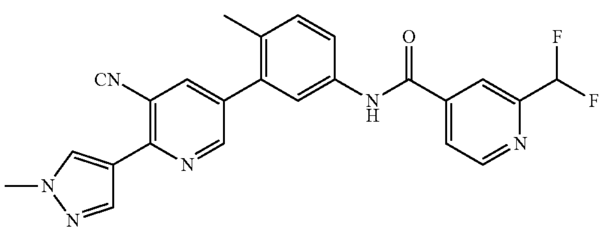 | N-(3-(5-cyano-6-(1-methyl-1H-pyrazol-4-yl)pyridin-3-yl)-4-methylphenyl)-2-(difluoromethyl)isonicotinamide | $^1$H NMR (400 MHz, <dmso>) δ ppm 2.21 (s, 3 H) 3.91 (s, 3 H) 7.02 (s, 1 H) 7.32 (d, J = 8.22 Hz, 1 H) 7.62-7.77 (m, 2H) 8.00 (d, J = 4.70, 1 H) 8.13 (d, J = 10.96 Hz, 2 H) 8.31 (d, J = 1.96 Hz, 1 H) 8.46 (s, 1 H) 8.77 (d, J = 2.35 Hz, 1 H) 8.84 (d, J = 5.09 Hz, 1 H) 10.64 (s, 1 H). LCMS (m/z) (M + H) = 445.1, Rt = 0.93 min. |

TABLE 8-continued

| Example | Structure | Name | Physical Data |
|---|---|---|---|
| 127 | 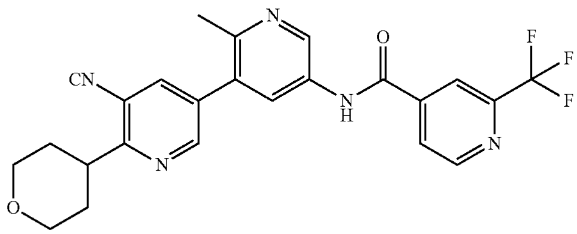 | N-(5'-cyano-2-methyl-6'-(tetrahydro-2H-pyran-4-yl)-[3,3'-bipyridin]-5-yl)-2-(trifluoromethyl)isonicotinamide | $^1$H NMR (400 MHz, <dmso>) δ ppm 1.70-1.82 (m, 2 H) 1.93 (dd, J = 12.33, 3.72 Hz, 2 H) 2.45 (s, 3 H) 3.39 (br. s., 1 H) 3.51 (t, J = 11.15 Hz, 2 H) 3.99 (dd, J = 10.96, 3.52 Hz, 2 H) 8.14-8.23 (m, 2 H) 8.37 (s, 1 H) 8.46 (d, J = 2.35 Hz, 1 H) 8.90 (dd, J = 5.09, 2.35 Hz, 2 H) 9.01 (d, J = 4.70 Hz, 1H) 10.99 (s, 1 H). LCMS (m/z) (M + H) = 468.2, Rt = 0.73 min. |
| 128 | 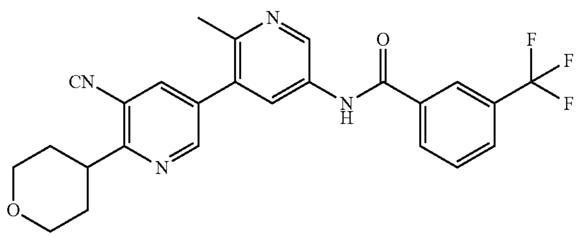 | N-(5'-cyano-2-methyl-6'-tetrahydro-2H-pyran-4-yl)-[3,3'-bipyridin]-5-yl)-3-(trifluoromethyl)benzamide | $^1$H NMR (400 MHz, <dmso>) δ ppm 1.79 (br. s., 2 H) 1.86-2.03 (m, 2 H) 2.45 (s, 3H) 3.51 (s, 3 H) 3.99 (dd, J = 11.15, 3.33 Hz, 2 H) 7.81 (s, 1 H) 7.99 (s, 1 H) 8.18 (s, 1 H) 8.31 (s, 2 H) 8.46 (d, J = 2.35 Hz, 1 H) 8.91 (d, J = 1.96 Hz, 2 H) 10.77 (s, 1 H). LCMS (m/z) (M + H) = 467.2, Rt = 0.80 min. |
| 129 | 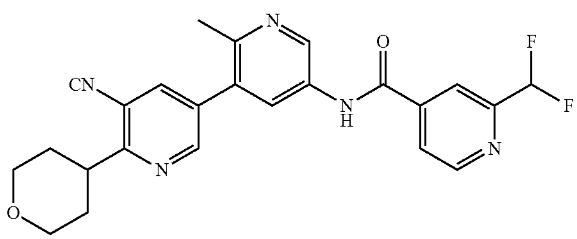 | N-(5'-cyano-2-methyl-6'-(tetrahydro-2H-pyran-4-yl)-[3,3'-bipyridin]-5-yl)-2-(difluoromethyl)isonicotinamide | $^1$H NMR (400 MHz, <dmso>) δ ppm 1.79 (br. s., 2 H) 1.86-2.03 (m, 2 H) 2.44 (s, 3 H) 3.32-3.45 (m, 1 H) 3.51 (s, 2 H) 3.98 (d, J = 3.52 Hz, 2 H) 7.08 (s, 1 H) 8.03-8.09 (m, 1 H) 8.13-8.24 (m, 2 H) 8.45 (d, J = 2.35 Hz, 1 H) 8.85-8.95 (m, 3 H) 10.93 (s, 1 H). LCMS (m/z) (M + H) = 450.2, Rt = 0.66 min. |
| 130 | 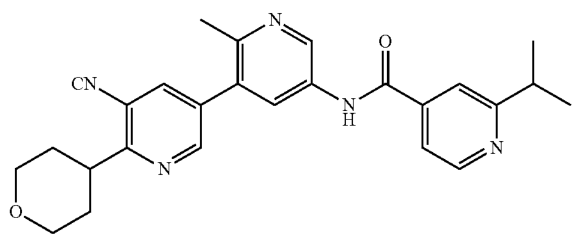 | N-(5'-cyano-2-methyl-6'-(tetrahydro-2H-pyran-4-yl)-[3,3'-bipyridin]-5-yl)-2-isopropyl-isonicotinamide | $^1$H NMR (400 MHz, <dmso>) δ ppm 1.28 (d, J = 7.04 Hz, 6 H) 1.73-1.82 (m, 2 H) 1.87-2.02 (m, 2 H) 2.44 (s, 3 H) 3.08-3.23 (m, 1 H) 3.33-3.44 (m, 1 H) 3.51 (s, 2 H) 3.97-4.03 (m, 2 H) 7.77 (s, 2 H) 8.08-8.20 (m, 1 H) 8.45 (d, J = 2.35 Hz, 1 H) 8.64-8.75 (m, 1 H) 8.90 (d, J = 1.96 Hz, 2 H) 10.71-10.77 (m, 1 H). LCMS (m/z) (M + H) = 442.2, Rt = 0.58 min. |
| 131 | 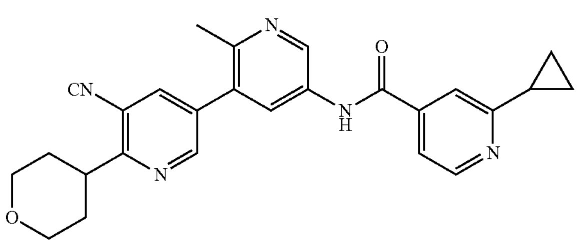 | N-(5'-cyano-2-methyl-6'-(tetrahydro-2H-pyran-4-yl)-[3,3'-bipyridin]-5-yl)-2-cyclopropyl-isonicotinamide | $^1$H NMR (400 MHz, <dmso>) δ ppm 0.98 (d, J = 1.57 Hz, 4 H) 1.69-1.84 (m, 2 H) 1.86-2.03 (m, 2 H) 2.16-2.27 (m, 1 H) 2.44 (s, 3 H) 3.33-3.46 (m, 1 H) 3.46-3.54 (m, 2 H) 3.96-4.04 (m, 2 H) 7.56-7.62 (m, 1 H) 7.75 (s, 1 H) 8.12-8.19 (m, 1 H) 8.45 (s, 1 H) 8.56-8.67 (m, 1 H) 8.90 (s, 2H) 10.71-10.78 (m, 1 H). LCMS (m/z) (M + H) = 440.3, Rt = 0.57 min. |
| 132 | 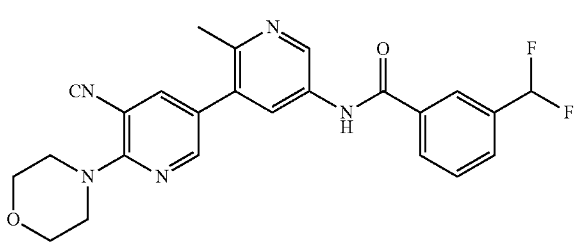 | N-(5'-cyano-2-methyl-6'-morpholino-[3,3'-bipyridin]-5-yl)-3-(difluoromethyl)benzamide | $^1$H NMR (400 MHz, <dmso>) δ ppm 2.52 (br. s., 3 H) 3.72 (dd, J = 18.19, 4.89 Hz, 8 H) 7.15 (s, 1 H) 7.65-7.86 (m, 2 H) 8.11-8.29 (m, 4 H) 8.51 (d, J = 2.35 Hz, 1 H) 8.91 (d, J = 1.96 Hz, 1 H) 10.72 (s, 1 H). LCMS (m/z) (M + H) = 450.1, Rt = 0.71 min. |

TABLE 8-continued

| Example | Structure | Name | Physical Data |
|---|---|---|---|
| 133 | 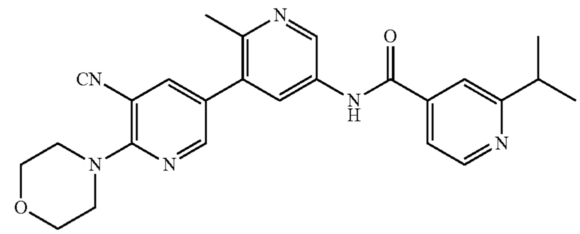 | N-(5'-cyano-2-methyl-6'-morpholino-[3,3'-bipyridin]-5-yl)-2-isopropyl-isonicotinamide | $^1$H NMR (400 MHz, <dmso>) δ ppm 1.28 (d, J = 7.04 Hz, 6 H) 2.47-2.47 (m, 3 H) 3.07-3.22 (m, 1 H) 3.72 (dd, J = 17.61, 5.09 Hz, 8 H) 7.71 (d, J = 5.09 Hz, 1 H) 7.78 (s, 1 H) 8.14 (s, 1 H) 8.25 (d, J = 2.35 Hz, 1 H) 8.51 (d, J = 2.35Hz, 1 H) 8.72 (d, J = 5.09 Hz, 1 H) 8.90 (d, J = 1.96 Hz, 1 H) 10.78 (s, 1 H). LCMS (m/z) (M + H) = 443.2, Rt = 0.55 min. |
| 134 | 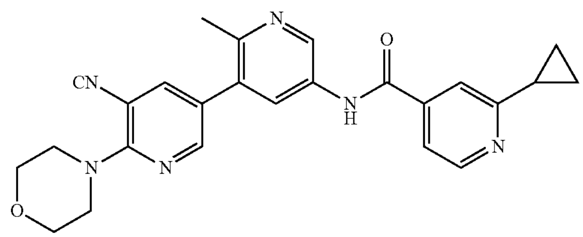 | N-(5'-cyano-2-methyl-6'-morpholino-[3,3'-bipyridin]-5-yl)-2-cyclopropyl-isonicotinamide | $^1$H NMR (400 MHz, <dmso>) δ ppm 0.94-1.08 (m, 4 H) 2.22 (s, 1 H) 2.44-2.47 (m, 3 H) 3.72 (dd, J = 17.02, 4.89 Hz, 8 H) 7.60 (dd, J = 5.09, 1.17 Hz, 1 H) 7.76 (s, 1 H) 8.16 (s, 1 H) 8.25 (d, J = 2.35 Hz, 1 H) 8.51 (d, J = 2.35 Hz, 1 H) 8.61 (d, J = 5.09 Hz, 1 H) 8.91 (d, J = 1.96 Hz, 1 H) 10.79 (s, 1 H). LCMS (m/z) (M + H) = 441.2, Rt = 0.53 min. |
| 135 | 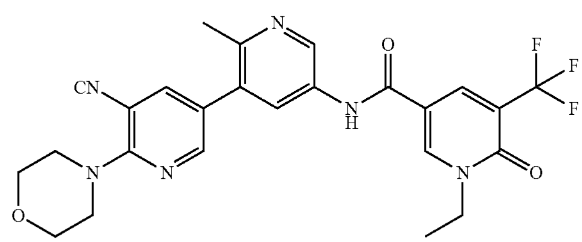 | N-(5'-cyano-2-methyl-6'-morpholino-[3,3'-bipyridin]-5-yl)-1-ethyl-6-oxo-5-(trifluoromethyl)-1,6-dihydropyridine-3-carboxamide | $^1$H NMR (400 MHz, <dmso>) δ ppm 1.30 (t, J = 7.04 Hz, 3 H) 2.45 (s, 3 H) 3.72 (dd, J = 19.17, 5.09 Hz, 8 H) 4.08 (d, J = 7.04 Hz, 2 H) 8.04 (s, 1 H) 8.23 (d, J = 2.35 Hz, 1 H) 8.49 (dd, J = 8.80, 2.15 Hz, 2 H) 8.83 (d, J = 1.96 Hz, 2H) 10.44 (s, 1 H). LCMS (m/z) (M + H) = 513.2, Rt = 0.69 min. |
| 136 | 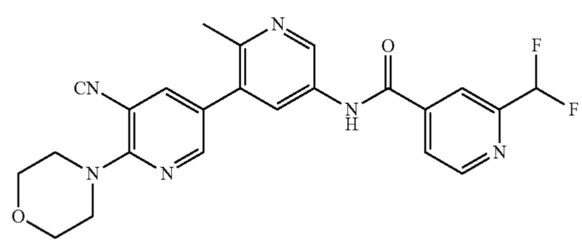 | N-(5'-cyano-2-methyl-6'-morpholino-[3,3'-bipyridin]-5-yl)-2-(difluoromethyl)isonicotinamide | $^1$H NMR (400 MHz, <dmso>) δ ppm 2.46 (br. s., 3 H) 3.74 (d, J = 5.09 Hz, 8 H) 7.08 (s, 1 H) 8.02-8.29 (m, 4 H) 8.50 (d, J = 2.35 Hz, 1 H) 8.83-8.99 (m, 2 H) 10.93 (s, 1 H). LCMS (m/z) (M + H) = 451.2, Rt = 0.63 min. |
| 137 | 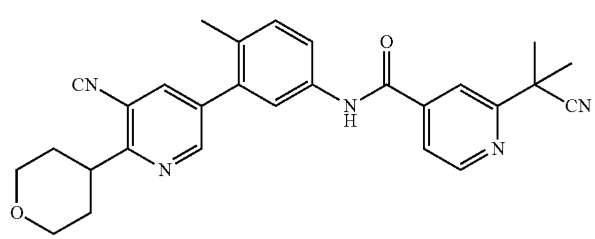 | N-(3-(5-cyano-6-(tetrahydro-2H-pyran-4-yl)pyridin-3-yl)-4-methylphenyl)-2-(2-cyanopropan-2-yl)isonicotinamide | $^1$H NMR (400 MHz, <dmso>) δ ppm 0.53-0.78 (m, 4 H) 1.75 (s, 6 H) 2.43 (s, 3 H) 2.76-2.91 (m, 1 H) 7.43-7.56 (m, 1 H) 7.82-7.91 (m, 1 H) 7.96-8.07 (m, 3 H) 8.32-8.44 (m, 1 H) 8.75-8.86 (m, 2 H) 10.70-10.82 (m, 1 H). LCMS (m/z) (M + H) = 466.2, Rt = 0.97 min. |
| 138 | 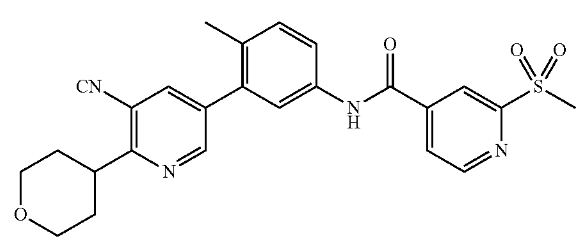 | N-(3-(5-cyano-6-(tetrahydro-2H-pyran-4-yl)pyridin-3-yl)-4-methylphenyl)-2-(methylsulfonyl)isonicotinamide | $^1$H NMR (400MHz, <dmso>) δ ppm 1.79 (br. s., 2 H) 1.84-2.03 (m, 2 H) 2.23 (s, 3 H) 3.33 (s, 3 H) 3.49 (d, J = 11.35 Hz, 3 H) 3.97 (d, J = 3.52 Hz, 2 H) 7.37 (d, J = 8.22 Hz, 1 H) 7.73 (d, J = 2.35 Hz, 2 H) 8.20 (dd, J = 4.89, 1.37 Hz, 1 H) 8.35 (d, J = 2.35 Hz, 1 H) 8.52 (s, 1 H) 8.83 (d, J = 2.35 Hz, 1 H) 8.99 (d, J = 5.09 Hz, 1 H) 10.81 (s, 1 H). LCMS (m/z) (M + H) = 477.1, Rt = 0.84 min. |

TABLE 8-continued

| Example | Structure | Name | Physical Data |
|---|---|---|---|
| 139 | 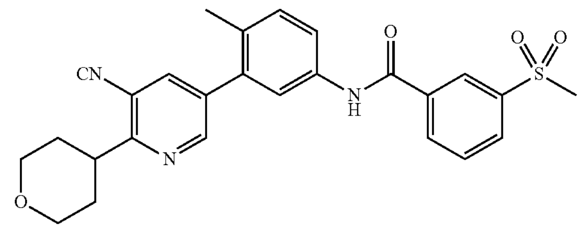 | N-(3-(5-cyano-6-(tetrahydro-2H-pyran-4-yl)pyridin-3-yl)-4-methylphenyl)-3-(methylsulfonyl)benzamide | $^1$H NMR (400 MHz, <dmso>) δ ppm 1.79 (br. s., 2 H) 1.92 (br. s., 2 H) 2.23 (s, 3 H) 3.27 (s, 3 H) 3.38 (d, J = 3.91 Hz, 3 H) 3.91-4.04 (m, 2 H) 7.35 (d, J = 8.22 Hz, 1 H) 7.69-7.86 (m, 3 H) 8.08-8.18 (m, 1 H) 8.21-8.32 (m, 1 H) 8.35 (d, J = 2.35 Hz, 1 H) 8.46 (s, 1 H) 8.84 (d, J = 1.96 Hz, 1 H) 10.55 (s, 1 H). LCMS (m/s) (M + H) = 476.2, Rt = 0.88 min. |
| 140 | 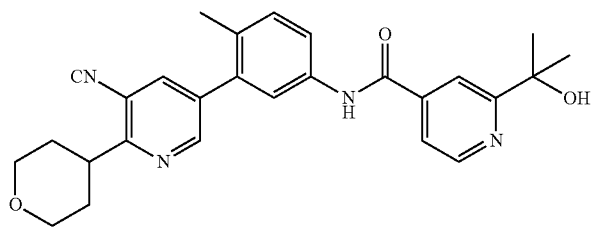 | N-(3-(5-cyano-6-(tetrahydro-2H-pyran-4-yl)pyridin-3-yl)-4-methylphenyl)-2-(2-hydroxypropan-2-yl)isonicotinamide | $^1$H NMR (400 MHz, <dmso>) δ ppm 1.47 (s, 6 H) 1.79 (br. s., 2 H) 1.84-2.02 (m, 2H) 2.22 (s, 3H) 3.31-3.44 (m, 1 H) 3.50 (s, 2 H) 3.93-4.05 (m, 2 H) 7.35 (d, J = 8.22 Hz, 1 H) 7.72 (t, J = 3.91 Hz, 3 H) 8.13 (s, 1 H) 8.35 (d, J = 2.35 Hz, 1 H) 8.67 (d, J = 5.09 Hz, 1 H) 8.83 (d, J = 1.96 Hz, 1 H) 10.55 (s, 1 H). LCMS (m/z) (M + H) = 457.2, Rt = 0.73 min. |
| 141 | 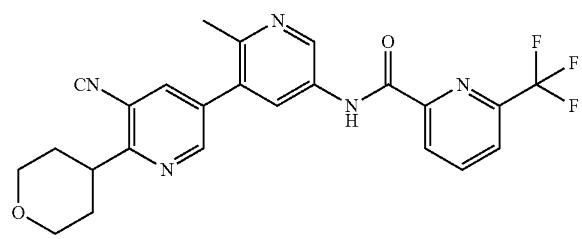 | N-(5'-cyano-2-methyl-6'-(tetrahydro-2H-pyran-4-yl)-[3,3'-bipyridin]-5-yl)-6-(trifluoromethyl)picolinamide | $^1$H NMR (400 MHz, <dmso>) δ ppm 1.79 (br. s., 2 H) 1.92 (br. s., 2 H) 2.49-2.53 (m, 3 H) 3.34-3.46 (m, 1 H) 3.47-3.58 (m, 2 H) 3.99 (dd, J = 10.76, 3.72 Hz, 2 H) 8.20 (dd, J = 7.24, 0.98 Hz, 1 H) 8.27 (d, J = 1.96 Hz, 1 H) 8.33-8.44 (m, 2 H) 8.47 (d, J = 2.35 Hz, 1 H) 8.93 (d, J = 2.35 Hz, 3 H) 9.08 (d, J = 2.35 Hz, 1 H) 10.73 (s, 1 H). LCMS (m/z) (M + H) = 468.2, Rt. = 0.76 min. |
| 142 | 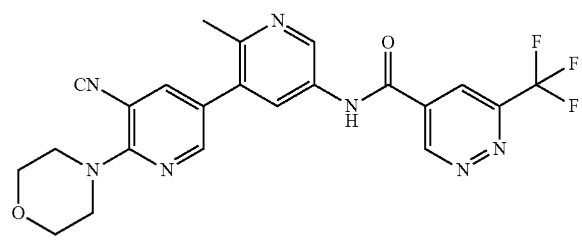 | N-(5'-cyano-2-methyl-6'-morpholino-[3,3'-bipyridin]-5-yl)-6-(trifluoromethyl)pyridazine-4-carboxamide | $^1$H NMR (400 MHz, <dmso>) δ ppm 2.46 (s, 3 H) 3.68-3.76 (m, 8 H) 8.02-8.13 (m, 1 H) 8.20-8.28 (m, 1 H) 8.44-8.55 (m, 1 H) 8.62-8.72 (m, 1H) 8.81-8.90 (m, 1 H) 9.87-9.96 (m, 1 H) 11.07-11.15 (m, 1 H). LCMS (m/z) (M + H) = 470.2, Rt = 0.64 min. |
| 143 | 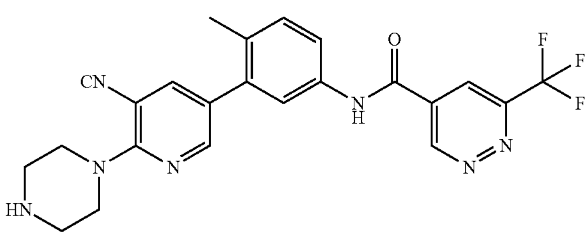 | N-(3-(5-cyano-6-(piperazin-1-yl)pyridin-3-yl)-4-methylphenyl)-6-(trifluoromethyl)pyridazine-4-carboxamide | $^1$H NMR (400 MHz, <dmso>) δ ppm 2.24 (s, 3 H) 3.33-3.43 (m, 4 H) 3.77-3.90 (m, 4 H) 7.29-7.43 (m, 1 H) 7.61-7.75 (m, 2 H) 8.17-8.29 (m, 1 H) 8.43-8.53 (m, 1 H) 8.62-8.69 (m, 1 H) 8.74-8.84 (m, 1 H) 9.86-9.93 (m, 1 H) 10.81-10.94 (m, 1 H). LCMS (m/z) (M + H) = 468.2, Rt = 0.76 min. |
| 144 | 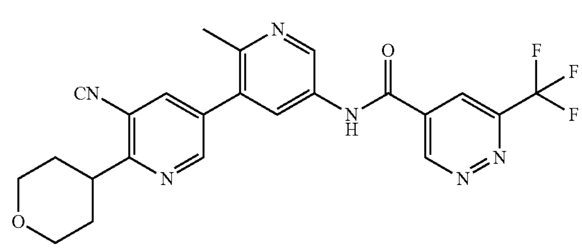 | N-(5'-cyano-2-methyl-6'-(tetrahydro-2H-pyran-4-yl)-[3,3'-bipyridin]-5-yl)-6-(trifluoromethyl)pyridazine-4-carboxamide | $^1$H NMR (400 MHz, <dmso>) δ ppm 1.73-1.82 (m, 2H) 1.85-2.02 (m, 2 H) 2.44 (s, 3 H) 3.34-3.47 (m, 3 H) 3.94-4.04 (m, 2 H) 8.09-8.15 (m, 1 H) 8.41-8.56 (m, 1 H) 8.66-8.74 (m, 1 H) 8.82-8.92 (m, 2 H) 9.84-9.95 (m, 1 H) 11.08-11.18 (m, 1 H). LCMS (m/z) (M + H) = 469.2, Rt = 0.65 min. |

TABLE 8-continued

| Example | Structure | Name | Physical Data |
|---|---|---|---|
| 145 | 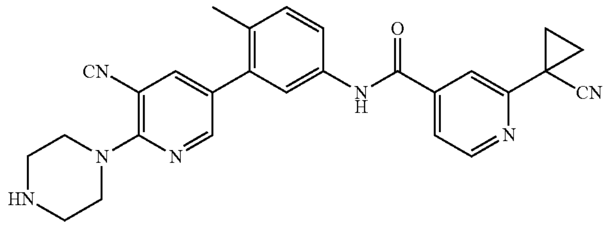 | N-(3-(5-cyano-6-(piperazin-1-yl)pyridin-3-yl)-4-methylphenyl)-2-(1-cyanocyclopropyl)isonicotinamide | ¹H NMR (400 MHz, <dmso>) δ ppm 1.75 (d, J = 3.52 Hz, 2 H) 1.87 (d, J = 3.52 Hz, 2 H) 2.23 (s, 3 H) 3.29 (br. s., 4 H) 3.74-3.89 (m, 4 H) 7.27-7.39 (m, 1 H) 7.60-7.68 (m, 1 H) 7.71 (s, 2 H) 7.91 (s, 1 H) 8.23 (d, J = 2.35 Hz, 1 H) 8.48 (d, J = 2.35 Hz, 1 H) 8.67-8.72 (m, 1 H) 8.74-8.85 (m, 1 H) 10.60 (s, 1 H) LCMS (m/z) (M + H) = 464.3, Rt = 0.72 min. |
| 146 | 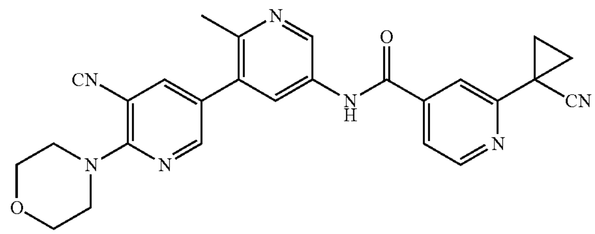 | N-(5'-cyano-2-methyl-6'-morpholino-[3,3'-bipyridin]-5-yl)-2-(1-cyanocyclopropyl)isonicotinamide | ¹H NMR (400 MHz, <dmso>) δ ppm 1.71-1.79 (m, 2H) 1.85-1.93 (m, 2 H) 2.47 (br. s., 3 H) 3.72 (dd, J = 19.17, 5.09 Hz, 8 H) 7.79 (dd, J = 5.09, 1.17 Hz, 1 H) 7.95 (s, 1 H) 8.12 (d, J = 2.35 Hz, 1 H) 8.25 (d, J = 2.35 Hz, 1 H) 8.51 (d, J = 2.35 Hz, 1 H) 8.73 (d, J = 5.09 Hz, 1 H) 8.87 (d, J = 2.35 Hz, 1 H) 10.88 (s, 1 H). LCMS (m/z) (M + H) = 466.3, Rt = 0.66 min. |
| 147 | 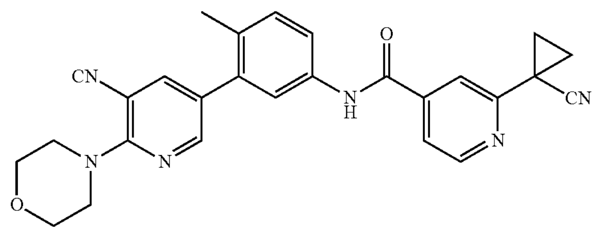 | N-(3-(5-cyano-6-morpholinopyridin-3-yl)-4-methylphenyl)-2-(1-cyanocyclopropyl)isonicotinamide | ¹H NMR (400 MHz, <dmso>) δ ppm 1.70-1.79 (m, 2 H) 1.87 (d, J = 3.13 Hz, 2 H) 2.23 (s, 3 H) 3.62-3.71 (m, 8 H) 7.32 (d, J = 8.22 Hz, 3 H) 7.65 (d, J = 1.96 Hz, 2 H) 7.74-7.80 (m, 1 H) 7.91 (s, 1 H) 8.14 (d, J = 2.35 Hz, 1 H) 8.44 (d, J = 2.35 Hz, 1 H) 8.69 (d, J = 5.09 Hz, 1 H) 10.57 (s, 1 H). LCMS (m/z) (M + H) = 465.3, Rt = 0.96 min. |
| 148 | 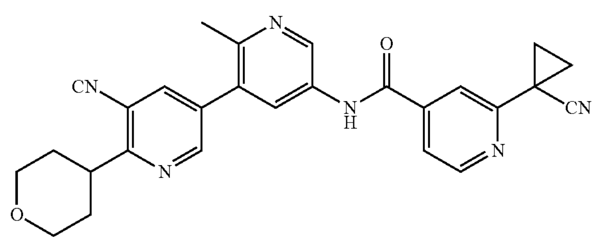 | N-(5'-cyano-2-methyl-6'-(tetrahydro-2H-pyran-4-yl)-[3,3'-bipyridin]-5-yl)-2-(1-cyanocyclopropyl)isonicotinamide | ¹H NMR (400 MHz, <dmso>) δ ppm 1.76 (d, J = 3.52 Hz, 4 H) 1.87 (br. s., 4 H) 2.44 (s, 3 H) 3.32-3.53 (m, 3 H) 3.91-4.05 (m, 2 H) 7.75-7.84 (m, 1 H) 7.92-8.01 (m, 1 H) 8.09-8.19 (m, 1 H) 8.41-8.50 (m, 1 H) 8.68-8.76 (m, 1 H) 8.82-8.95 (m, 2 H) 10.82-10.89 (m, 1 H). LCMS (m/z) (M + H) = 465.3, Rt = 0.66 min. |
| 149 | 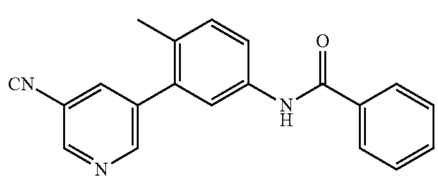 | N-(3-(5-cyanopyridin-3-yl)-4-methylphenyl)benzamide | ¹H NMR (400 MHz, <dmso>) δ ppm 2.21 (s, 3 H) 7.33 (d, J = 8.61 Hz, 1 H) 7.46-7.62 (m, 3 H) 7.71-7.81 (m, 2 H) 7.94 (d, J = 7.04 Hz, 2 H) 8.40 (t, J = 1.96 Hz, 1 H) 8.87 (d, J = 1.96 Hz, 1 H) 9.04 (d, J = 1.96 Hz, 1 H) 10.29 (s, 1 H). LCMS (m/z) (M + H) = 314.1, Rt = 0.78 min. |
| 150 | 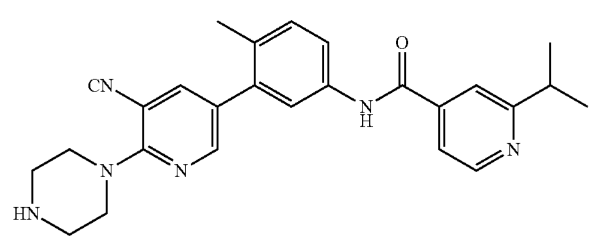 | N-(3-(5-cyano-6-(piperazin-1-yl)pyridin-3-yl)-4-methylphenyl)-2-isopropyl-isonicotinamide | ¹H NMR (400 MHz, DMSO$_{d6}$) δ 10.50 (s, 1H), 8.88 (bs, 2H), 8.70 (d, J = 4.0, 1H), 8.50 (d, J = 2.0, 1H), 8.24 (d, J = 2.0, 1H), 7.67-7.75 (m, 4H), 7.34 (d, J = 8H, 1H), 3.84-3.86 (m, 4H), 3.30 (bs, 4H), 3.14 (septet, J = 8.0, 1H), 2.24 (s, 3H), 1.29 (d, J = 8.0, 6H). LCMS (m/z) (M + H) = 441.1, Rt = 0.58 min. |

| Example | Structure | Name | Physical Data |
|---|---|---|---|
| 151 | 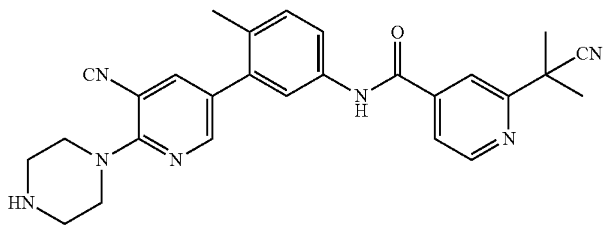 | N-(3-(5-cyano-6-(piperazin-1-yl)pyridin-3-yl)-4-methylphenyl)-2-(2-cyanopropan-2-yl)isonicotinamide | $^1$H NMR (400 MHz, DMSO$_{d6}$) δ 10.60 (s, 1H), 8.82 (d, J = 4.0, 1H), 8.50 (d, J = 2.0, 1H), 8.24 (d, J = 4.0, 1H), 8.00 (s, 1H), 7.86 (d, J = 4.0, 1H), 7.72 (d, J = 4.0, 1H), 7.67 (dd, J = 8.0, 2.0, 1H), 7.35 (d, J = 8.0, 1H), 3.83-3.86 (m, 4H), 3.31 (bs, 4H), 2.25 (s, 3H), 1.77 (s, 6H). LCMS (m/z) (M + H) = 466.1, Rt = 0.72 min. |
| 152 | 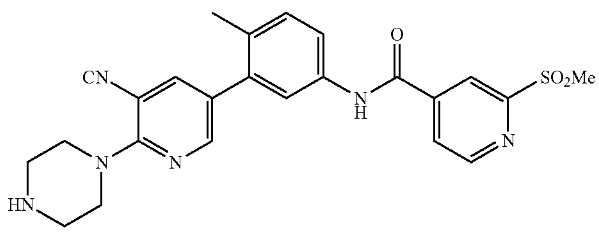 | N-(3-(5-cyano-6-(piperazin-1-yl)pyridin-3-yl)-4-methylphenyl)-2-(methylsulfonyl)isonicotinamide | $^1$H NMR (400 MHz, DMSO$_{d6}$) δ 10.82 (s, 1H), 9.01 (d, J = 8.0, 1H), 8.52 (s, 1H), 8.50 (d, J = 2.6, 1H), 8.24 (d, J = 4.0, 1H), 8.22 (d, J = 4.0, 1H), 7.74 (s, 1H), 7.70 (d, J = 8.0, 1H), 7.36 (d, J = 8.0, 1H), 3.84-3.86 (m, 4H), 3.35 (s, 3H), 3.31 (bs, 4H), 2.25 (s, 3H). LCMS (m/z) (M + H) = 477.1, Rt = 0.62 min. |
| 153 | 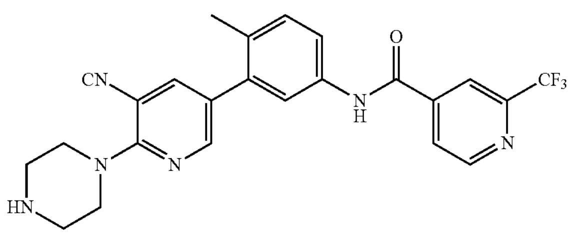 | N-(3-(5-cyano-6-(piperazin-1-yl)pyridin-3-yl)-4-methylphenyl)-2-(trifluoromethyl)isonicotinamide | $^1$H NMR (400 MHz, DMSO$_{d6}$) δ 10.73 (s, 1H), 9.00 (d, J = 8.0, 1H), 8.50 (d, J = 4.0, 1H), 8.36 (s, 1H), 8.24 (d, J = 4.0, 1H), 8.19 (d, J = 8.0, 1H), 7.74 (d, J = 4.0, 1H), 7.68 (dd, J = 8.0, 2.0, 1H), 7.36 (d, J = 8.0, 1H), 3.84-3.86 (m, 4H), 3.31 (bs, 4H), 2.25 (s, 3H). LCMS (m/z) (M + H) = 467.1, Rt = 0.76 min. |
| 154 | 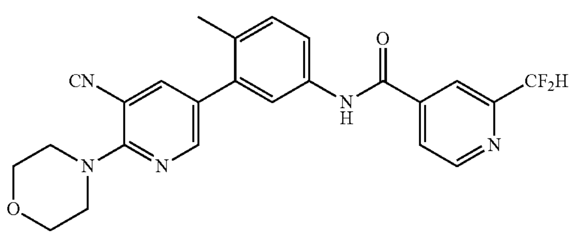 | N-(3-(5-cyano-6-morpholinopyridin-3-yl)-4-methylphenyl)-2-(difluoromethyl)isonicotinamide | $^1$H NMR (400 MHz, DMSO$_{d6}$) δ 10.66 (s, 1H), 8.90 (d, J = 4.0, 1H), 8.46 (d, J = 2.0, 1H), 8.18 (s, 1H), 8.16 (d, J = 2.0, 1H), 8.06 (d, J = 4.0, 1H), 7.73 (dd, J = 8.0, 2.0, 1H), 7.68 (d, J = 4.0, 1H), 7.34 (d, J = 8.0, 1H), 7.08 (t, J = 56.0, 1H), 3.75-3.78 (m, 4H), 3.66-3.68 (m, 4H), 2.25 (s, 3H). LCMS (m/z) (M + H) = 450.0, Rt = 0.94 min. |
| 155 | 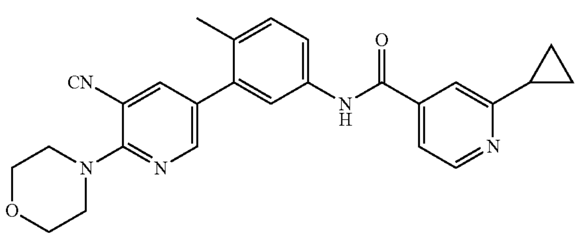 | N-(3-(5-cyano-6-morpholinopyridin-3-yl)-4-methylphenyl)-2-cyclopropyl-isonicotinamide | $^1$H NMR (400 MHz, DMSO$_{d6}$) δ 10.48 (s, 1H), 8.60 (d, J = 4.0, 1H), 8.46 (d, J = 4.0, 1H), 8.15 (d, J = 2.0, 1H), 7.76 (s, 1H), 7.70 (dd, J = 8.0, 2.0, 1H), 7.68 (d, J = 4.0, 1H), 7.62 (d, J = 4.0, 1H), 7.32 (d, J = 8.0, 1H), 3.75-3.78 (m, 4H), 3.66-3.68 (m, 4H), 2.24 (s, 3H), 2.21-2.25 (m, 1H), 1.00-1.07 (m, 4H). LCMS (m/z) (M + H) = 440.0, Rt = 0.76 min. |
| 156 | 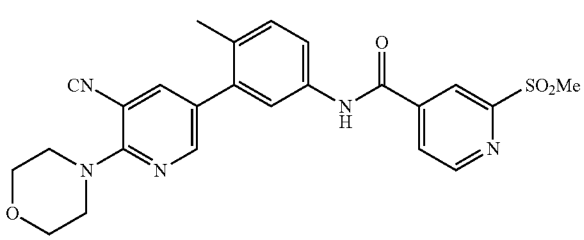 | N-(3-(5-cyano-6-morpholinopyridin-3-yl)-4-methylphenyl)-2-(methylsulfonyl)isonicotinamide | $^1$H NMR (400 MHz, DMSO$_{d6}$) δ 10.80 (s, 1H), 9.00 (d, J = 4.0, 1H), 8.53 (s, 1H), 8.46 (d, J = 2.0, 1H), 8.22 (d, J = 4.0, 1H), 8.16 (d, J = 2.0, 1H), 7.74 (dd, J = 8.0, 2.0, 1H), 7.69 (d, J = 2.0, 1H), 7.35 (d, J = 8.0, 1H), 3.75-3.78 (m, 4H), 3.66-3.68 (m, 4H), 3.35 (s, 3H), 2.25 (s, 3H). LCMS (m/z) (M + H) = 478.0, Rt = 0.85 min. |

TABLE 8-continued

| Example | Structure | Name | Physical Data |
|---------|-----------|------|---------------|
| 157 | 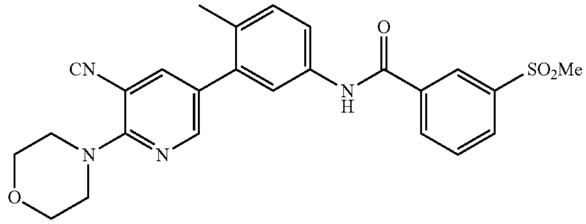 | N-(3-(5-cyano-6-morpholinopyridin-3-yl)-4-methylphenyl)-3-(methylsulfonyl)benzamide | ¹H NMR (400 MHz, DMSO$_{d6}$) δ 10.54 (s, 1H), 8.46-8.50 (m, 2H), 8.29 (d, J = 8.0, 1H), 8.16 (d, J = 2.0, 1H), 8.14 (d, J = 8.0, 1H), 7.83 (t, J = 8.0, 1H), 7.73 (dd, J = 8.0, 2.0, 1H), 7.68 (d, J = 2.0, 1H), 7.33 (d, J = 8.0, 1H), 3.75-3.78 (m, 4H), 3.66-3.68 (m, 4H), 3.29 (s, 3H), 2.24 (s, 3H). LCMS (m/z) (M + H) = 477.0, Rt = 0.88 min. |
| 158 | 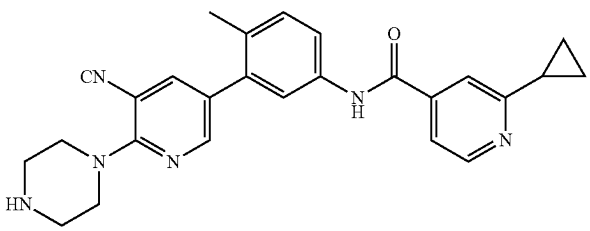 | N-(3-(5-cyano-6-(piperazin-1-yl)pyridin-3-yl)-4-methylphenyl)-2-cyclopropyl isonicotinamide | ¹H NMR (400 MHz, DMSO$_{d6}$) δ 10.48 (s, 1H), 8.58 (d, J = 4.0, 1H), 8.50 (d, J = 4.0, 1H), 8.24 (d, J = 2.0, 1H), 7.73-7.74 (m, 2H), 7.66 (dd, J = 8.0, 4.0, 1H), 7.56 (dd, J = 8.0, 4.0, 1H), 7.33 (d, J = 8.0, 1H), 3.83-3.86 (m, 4H), 3.30 (bs, 4H), 2.24 (s, 3H), 2.21-2.25 (m, 1H), 0.98-1.03 (m, 4H). LCMS (m/z) (M + H) = 439.1, Rt = 0.56 min. |
| 159 | 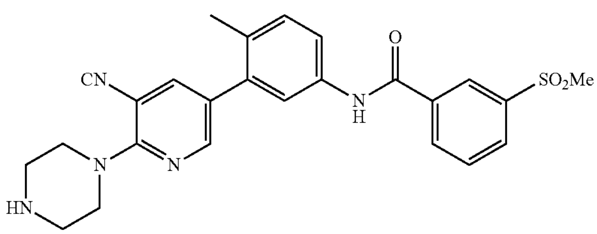 | N-(3-(5-cyano-6-(piperazin-1-yl)pyridin-3-yl)-4-methylphenyl)-3-(methylsulfonyl)benzamide | ¹H NMR (400 MHz, DMSO$_{d6}$) δ 10.56 (s, 1H), 8.50 (d, J = 4.0, 1H), 8.47 (s, 1H), 8.28 (d, J = 8.0, 1H), 8.24 (d, J = 4.0, 1H), 8.15 (d, J = 8.0, 1H), 7.83 (t, J = 8.0, 1H), 7.74 (d, J = 4.0, 1H), 7.69 (dd, J = 8.0, 4.0, 1H), 7.34 (d, J = 8.0, 1H), 3.84-3.86 (m, 4H), 3.31 (bs, 4H), 3.29 (s, 3H), 2.25 (s, 3H). LCMS (m/z) (M + H) = 476.1, Rt = 0.66 min. |
| 160 | 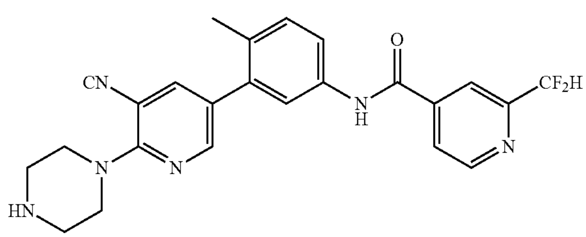 | N-(3-(5-cyano-6-(piperazin-1-yl)pyridin-3-yl)-4-methylphenyl)-2-(difluoromethyl)isonicotinamide | ¹H NMR (400 MHz, DMSO$_{d6}$) δ 10.72 (s, 1H), 8.91 (d, J = 8.0, 1H), 8.86 (bs, 1H), 8.50 (s, 1H), 8.24 (d, J = 4.0, 1H), 8.19 (s, 1H), 8.07 (d, J = 8.0, 1H), 7.93 (d, J = 2.0, 1H), 7.79 (dd, J = 8.0, 2.0, 1H), 7.38 (d, J = 2.0, 1H), 7.09 (t, J = 56.0, 1H), 3.80-3.82 (m, 4H), 3.75-3.77 (m, 4H), 2.32 (s, 3H). LCMS (m/z) (M + H) = 449.1, Rt = 0.69 min. |
| 161 | 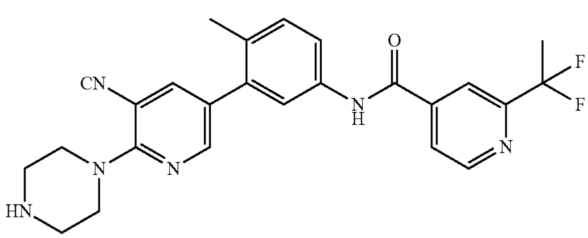 | N-(3-(5-cyano-6-(piperazin-1-yl)pyridin-3-yl)-4-methylphenyl)-2-(1,1-difluoroethyl)isonicotinamide | ¹H NMR (400 MHz, DMSO$_{d6}$) δ 10.67 (s, 1H), 8.88 (d, J = 4.0, 1H), 8.50 (d, J = 2.0, 1H), 8.24 (d, J = 4.0, 1H), 8.17 (s, 1H), 8.02 (d, J = 4.0, 1H), 7.74 (s, 1H), 7.69 (d, J = 8.0, 1H), 7.35 (d, J = 8.0, 1H), 3.83-3.86 (m, 4H), 3.30 (bs, 4H), 2.25 (s, 3H), 2.05 (t, J = 20.0, 3H) LCMS (m/z) (M + H) = 463.2, Rt = 0.77 min. |
| 162 | 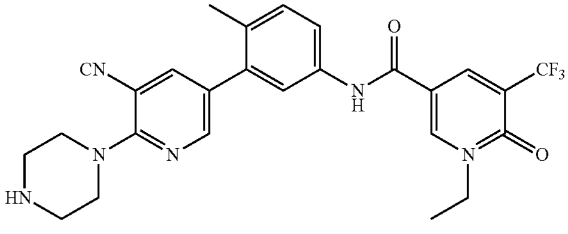 | N-(3-(5-cyano-6-(piperazin-1-yl)pyridin-3-yl)-4-methylphenyl)-1-ethyl-6-oxo-5-(trifluoromethyl)-1,6-dihydropyridine-3-carboxamide | ¹H NMR (400 MHz, DMSO$_{d6}$) δ 10.19 (s, 1H), 8.80 (d, J = 2.0, 1H), 8.49 (d, J = 2.0, 1H), 8.46 (d, J = 2.0, 1H), 8.24 (d, J = 4.0, 1H), 7.63 (s, 1H), 7.62 (dd, J = 8.0, 4.0, 1H), 7.33 (d, J = 8.0, 1H), 4.08 (quartet, J = 8.0, 2H), 3.83-3.86 (m, 4H), 3.30 (bs, 4H), 2.23 (s, 3H), 1.31 (triplet, J = 8.0, 3H). LCMS (m/z) (M + H) = 511.2, Rt = 0.77 min. |

TABLE 8-continued

| Example | Structure | Name | Physical Data |
|---|---|---|---|
| 163 | 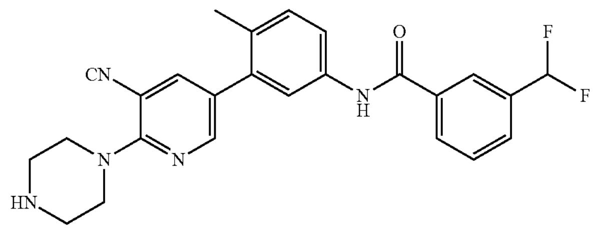 | N-(3-(5-cyano-6-(piperazin-1-yl)pyridin-3-yl)-4-methylphenyl)-3-(difluoromethyl)benzamide | $^1$H NMR (400 MHz, DMSO$_{d6}$) δ 10.44 (s, 1H), 8.50 (d, J = 4.0, 1H), 8.24 (d, J = 4.0, 1H), 8.15 (s, 1H), 8.12 (d, J = 8.0, 1H), 7.90 (d, J = 8.0, 1H), 7.74 (d, J = 2.0, 1H), 7.67-7.71 (m, 2H), 7.33 (d, J = 8.0, 1H), 7.15 (t, J = 56.0, 1H), 3.83-3.86 (m, 4H), 3.29 (bs, 4H), 2.24 (s, 3H). LCMS (m/z) (M + H) = 448.2, Rt = 0.80 min. |
| 164 | 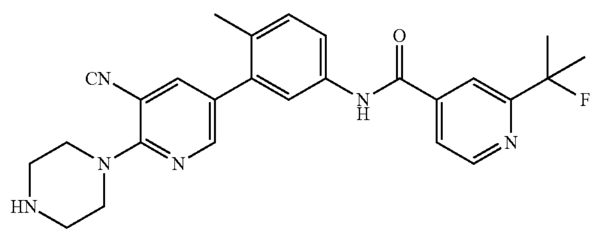 | N-(3-(5-cyano-6-(piperazin-1-yl)pyridin-3-yl)-4-methylphenyl)-2-(2-fluoropropan-2-yl)isonicotinamide | $^1$H NMR (400 MHz, DMSO$_{d6}$) δ 10.60 (s, 1H), 8.88 (bs, 2H), 8.76 (d, J = 8.0, 1H), 8.50 (d, J = 2.0, 1H), 8.24 (d, J = 4.0, 1H), 8.02 (s, 1H), 7.82 (d, J = 4.0, 1H), 7.74 (d, J = 4.0, 1H), 7.69 (dd, J = 8.0, 4.0, 1H), 7.34 (d, J = 8.0, 1H), 3.84-3.86 (m, 4H), 3.30 (bs, 4H), 2.24 (s, 3H), 1.71 (d, J = 20.0, 6H). LCMS (m/z) (M + H) = 459.2, Rt = 0.76 min. |
| 165 | 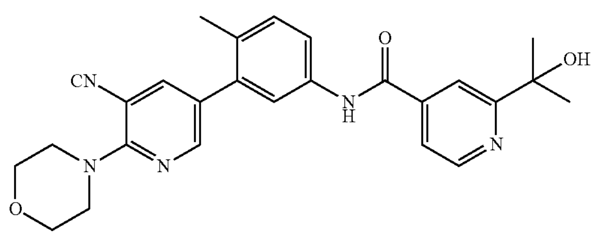 | N-(3-(5-cyano-6-morpholinopyridin-3-yl)-4-methylphenyl)-2-(2-hydroxypropan-2-yl)isonicotinamide | $^1$H NMR (400 MHz, DMSO$_{d6}$) δ 10.55 (s, 1H), 8.70 (d, J = 4.0, 1H), 8.46 (d, J = 2.0, 1H), 8.16 (s, 1H), 8.16 (d, J = 4.0, 1H), 7.71-7.74 (m, 2H), 7.68 (d, J = 4.0, 1H), 7.33 (d, J = 12.0, 1H), 3.75-3.78 (m, 4H), 3.65-3.68 (m, 4H), 2.24 (s, 3H), 1.49 (s, 6H). LCMS (m/z) (M + H) = 458.1, Rt = 0.72 min. |
| 166 | 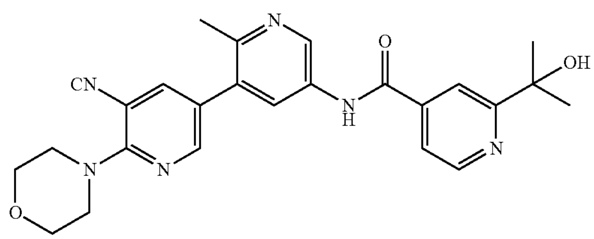 | N-(5'-cyano-2-methyl-6'-morpholino-[3,3'-bipyridin]-5-yl)-2-(2-hydroxypropan-2-yl)isonicotinamide | $^1$H NMR (400 MHz, DMSO$_{d6}$) δ 10.90 (s, 1H), 8.94 (d, J = 4.0, 1H), 8.72 (d, J = 4.0, 1H), 8.53 (d, J = 2.0, 1H), 8.28 (d, J = 4.0, 1H), 8.19-8.20 (bs, 2H), 7.75 (dd, J = 8.0, 2.0, 1H), 3.75-3.78 (m, 4H), 3.69-3.72 (m, 4H), 2.50 (s, 3H), 1.50 (s, 6H). LCMS (m/z) (M + H) = 459.1, Rt = 0.50 min. |
| 167 | 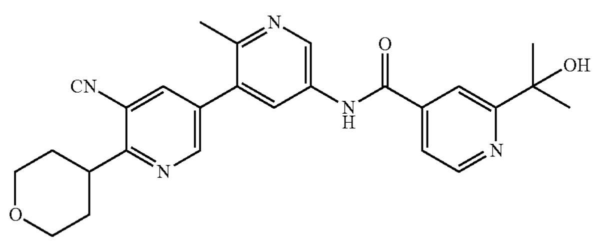 | N-(5'-cyano-2-methyl-6'-(tetrahydro-2H-pyran-4-yl)-[3,3'-bipyridin]-5-yl)-2-(2-hydroxypropan-2-yl)isonicotinamide | $^1$H NMR (400 MHz, DMSO$_{d6}$) δ 10.86 (s, 1H), 8.92-8.93 (m, 2H), 8.72 (d, J = 8.0, 1H), 8.48 (d, J = 4.0, 1H), 8.19-8.20 (m, 2H), 7.74 (dd, J = 8.0, 2.0, 1H), 4.00 (dd, J = 12.0, 4.6, 2H), 3.50 (triplet, 12.0, 2H), 3.38-3.44 (m, 1H), 2.47 (s, 3H), 1.95 (quartet of doublets, J = 12.0, 4.0, 2H), 1.79 (dd, J = 12.0, 4.0, 2H), 1.49 (s, 6H). LCMS (m/z) (M + H) = 458.1, Rt = 0.50 min. |
| 168 | 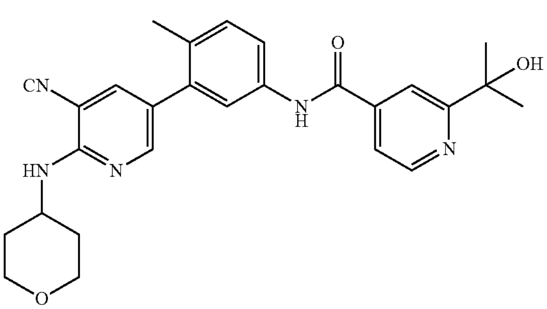 | N-(3-(5-cyano-6-((tetrahydro-2H-pyran-4-yl)amino)pyridin-3-yl)-4-methylphenyl)-2-(2-hydroxypropan-2-yl)isonicotinamide | $^1$H NMR (400 MHz, DMSO$_{d6}$) δ 10.52 (s, 1H), 8.69 (d, J = 8.0, 1H), 8.31 (d, J = 2.0, 1H), 8.16 (s, 1H), 7.97 (d, J = 2.0, 1H), 7.74 (dd, J = 4.0, 2.0, 1H), 7.70 (dd, J = 8.0, 2.0, 1H), 7.62 (d, J = 4.0, 1H), 7.30 (d, J = 8.0, 1H), 7.02 (d, J = 8.0, 1H). 4.19-4.27 (m, 1H), 3.88-3.91 (m, 2H), 3.36-3.42 (m, 2H), 2.23 (s, 3H), 1.74-1.83 (m, 2H), 1.65-1.73 (m, 2H), 1.49 (s, 6H). LCMS (m/z) (M + H) = 472.2, Rt = 0.70 min. |

TABLE 8-continued

| Example | Structure | Name | Physical Data |
|---|---|---|---|
| 169 | 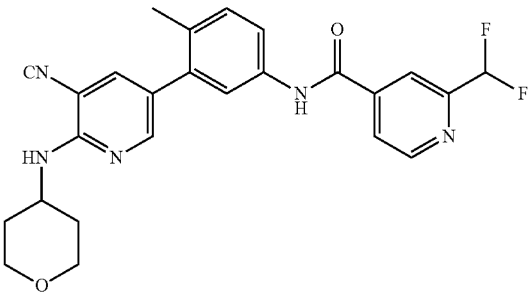 | N-(3-(5-cyano-6-((tetrahydro-2H-pyran-4-yl)amino)pyridin-3-yl)-4-methylphenyl)-2-(difluoromethyl)isonicotinamide | $^1$H NMR (400 MHz, DMSO$_{d6}$) δ 10.63 (s, 1H), 8.90 (d, J = 4.0, 1H), 8.32 (d, J = 4.0, 1H), 8.18 (s, 1H), 8.06 (d, J = 4.0, 1H), 7.98 (d, J = 4.0, 1H), 7.70 (dd, J = 8.0, 4.0, 1H), 7.63 (d, J = 2.0, 1H), 7.31 (d, J = 8.0, 1H), 7.08 (triplet, J = 56.0, 1H), 7.02 (d, J = 8.0, 1H), 4.19-4.27 (m, 1H), 3.88-3.91 (m, 2H), 3.36-3.42 (m, 2H), 2.24 (s, 3H), 1.80-1.83 (m, 2H), 1.65-1.73 (m, 2H). LCMS (m/z) (M + H) = 464.1, Rt = 0.89 min. |
| 170 | 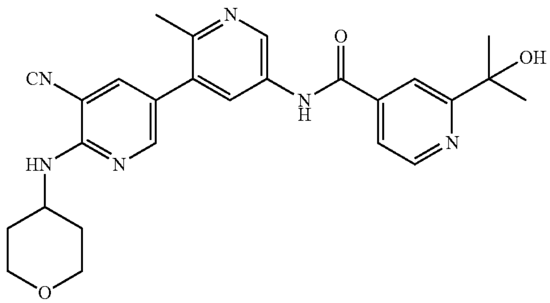 | N-(5'-cyano-2-methyl-6'-((tetrahydro-2H-pyran-4-yl)amino)-[3,3'-bipyridin]-5-yl)-2-(2-hydroxypropan-2-yl)isonicotinamide | $^1$H NMR (400 MHz, DMSO$_{d6}$) δ 10.91 (s, 1H), 8.96 (d, J = 4.0, 1H), 8.73 (dd, J = 8.0, 2.0, 1H), 8.40 (d, J = 4.0, 1H), 8.18-8.20 (m, 2H), 8.10 (d, J = 4.0, 1 H), 7.74 (dd, J = 4.0, 2.0, 1H), 7.21 (d, J = 8.0, 1H), 4.21-4.29 (m, 1H), 3.88-3.92 (m, 2H), 3.36-3.42 (m, 2H), 2.51 (s, 3H), 1.79-1.83 (m, 2H), 1.69-1.75 (m, 2H), 1.77 (s, 6H). LCMS (m/z) (M + H) = 473.1, Rt = 0.48 min. |
| 171 | 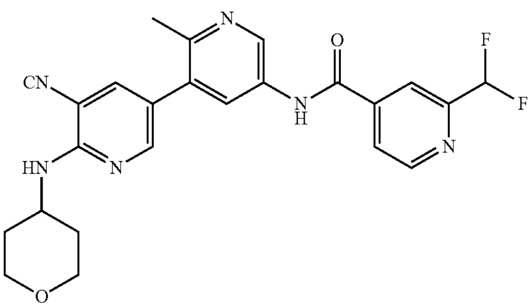 | N-(5'-cyano-2-methyl-6'-((tetrahydro-2H-pyran-4-yl)amino)-[3,3'-bipyridin]-5-yl)-2-(difluoromethyl)isonicotinamide | $^1$H NMR (400 MHz, DMSO$_{d6}$) δ 11.00 (s, 1H), 8.94 (d, J = 4.0, 1H), 8.92 (d, J = 4.0, 1H), 8.40 (d, J = 4.0, 1H), 8.21 (s, 1H), 8.16 (d, J = 4.0, 1H), 8.10 (d, J = 2.0, 1H), 8.08 (d, J = 4.0, 1H), 7.20 (d, J = 8.0, 1H), 7.10 (triplet, J = 56.0, 1H), 4.21-4.29 (m, 1H), 3.88-3.92 (m, 2H), 3.36-3.42 (m, 2H), 2.51 (s, 3H), 1.79-1.83 (m, 2H), 1.67-1.75 (m, 2H). LCMS (m/z) (M + H) = 465.1, Rt = 0.60 min. |
| 172 | 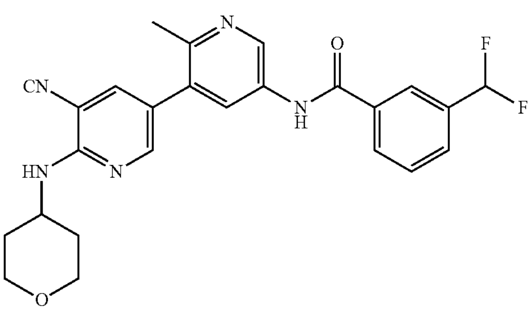 | N-(5'-cyano-2-methyl-6'-((tetrahydro-2H-pyran-4-yl)amino)-[3,3'-bipyridin]-5-yl)-3-(difluoromethyl)benzamide | $^1$H NMR (400 MHz, DMSO$_{d6}$) δ 10.76 (s, 1H), 8.94 (d, J = 2.0, 1H), 8.40 (d, J = 4.0, 1H), 8.15-8.19 (m, 3H), 8.10 (d, J = 2.0, 1H), 7.84 (d, J = 8.0, 1H), 7.73 (triplet, J = 8.0, 1H), 7.17 (triplet, J = 56.0, 1H), 7.20 (d, J = 8.0, 1H), 4.21-4.29 (m, 1H), 3.88-3.92 (m, 2H), 3.36-3.42 (m, 2H), 2.51 (s, 3H), 1.79-1.83 (m, 2H), 1.67-1.76 (m, 2H). LCMS (m/z) (M + H) = 464.1, Rt = 0.68 min. |
| 173 | 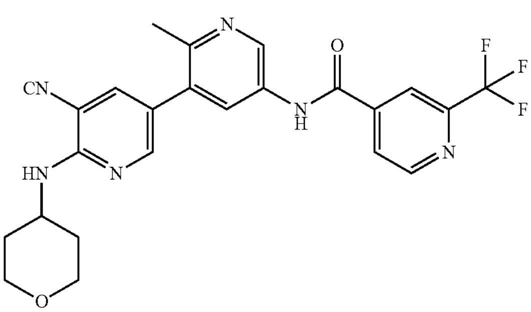 | N-(5'-cyano-2-methyl-6'-((tetrahydro-2H-pyran-4-yl)amino)-[3,3'-bipyridin]-5-yl)-2-(trifluoromethyl)isonicotinamide | $^1$H NMR (400 MHz, DMSO$_{d6}$) δ 10.98 (s, 1H), 9.03 (d, J = 8.0, 1H), 8.88 (d, J = 4.0, 1H), 8.39 (s, 1H), 8.38 (d, J = 4.0, 1H), 8.21 (d, J = 4.0, 1H), 8.10 (d, J = 2.0, 1H), 8.09 (d, J = 2.0, 1H), 7.18 (d, J = 8.0, 1H), 4.21-4.29 (m, 1H), 3.90 (dd, J = 12.0, 4.0, 2H), 3.39 (triplet of doublets, J = 12.0, 2.0, 2H), 2.51 (s, 3H), 1.81 (dd, J = 12.0, 4.0, 2H), 1.72 (quartet of doublets, J = 8.0, 4.0, 2H). LCMS (m/z) (M + H) = 483.1, Rt = 0.66 min. |

TABLE 8-continued

| Example | Structure | Name | Physical Data |
|---|---|---|---|
| 174 | 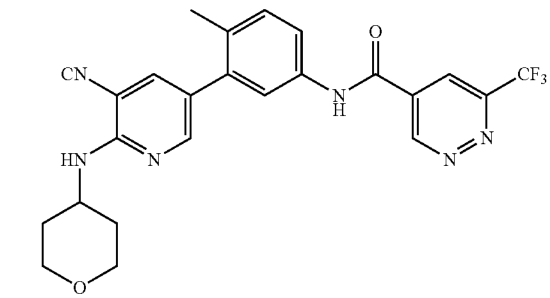 | N-(3-(5-cyano-6-((tetrahydro-2H-pyran-4-yl)amino)pyridin-3-yl)-4-methylphenyl)-6-(trifluoromethyl)pyridazine-4-carboxamide | $^1$H NMR (400 MHz, DMSO$_{d6}$) δ 10.85 (s, 1H), 9.92 (d, J = 4.0, 1H), 8.68 (d, J = 4.0, 1H), 8.32 (d, J = 4.0, 1H), 7.98 (d, J = 4.0, 1H), 7.70 (dd, J = 8.0, 2.0, 1H), 7.62 (d, J = 4.0, 1H), 7.34 (d, J = 8.0, 1H), 7.04 (d, J = 8.0, 1H), 4.18-4.28 (m, 1H), 3.88-3.90 (m, 2H), 3.39 (triplet of doublets, J = 12.0, 2.0, 2H), 2.24 (s, 3H), 1.82 (dd, J = 12.0, 2.0, 2H), 1.70 (quartet of doublets, J = 12.0, 4.0, 2H). LCMS (m/z) (M + H) = 483.1, Rt = 0.91 min. |
| 175 | 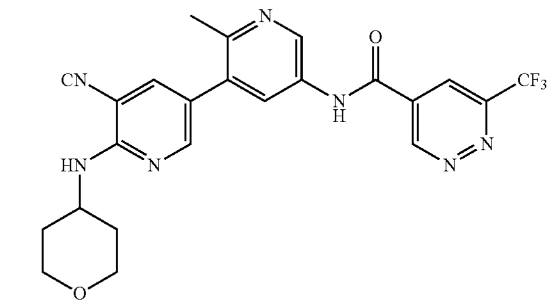 | N-(5'-cyano-2-methyl-6'-((tetrahydro-2H-pyran-4-yl)amino)-[3,3'-bipyridin]-5-yl)-6-(trifluoromethyl)pyridazine-4-carboxamide | $^1$H NMR (400 MHz, DMSO$_{d6}$) δ 11.16 (s, 1H), 9.94 (d, J = 4.0, 1H), 8.88 (d, J = 4.0, 1H), 8.70 (d, J = 2.0, 1H), 8.38 (d, J = 2.0, 1H), 8.08-8.09 (m, 2H), 7.18 (d, J = 8.0, 1H), 4.21-4.28 (m, 1H), 3.90 (dd, J = 12.0, 4.0, 2H), 3.39 (triplet of doublets, J = 12.0, 2.0, 2H), 2.54 (s, 3H), 1.81 (dd, J = 12.0, 2.0, 2H), 1.71 (quartet of doublets, J = 12.0, 4.0, 2H). LCMS (m/z) (M + H) = 484.1, Rt = 0.62 min. |
| 176 | 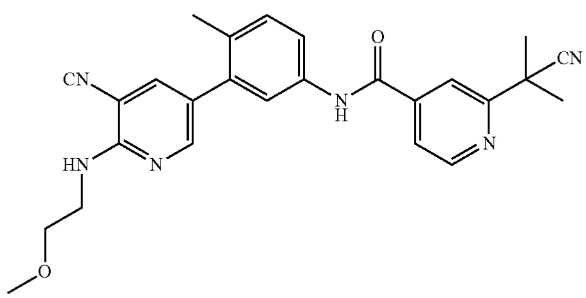 | N-(3-(5-cyano-6-((2-methoxyethyl)amino)pyridin-3-yl)-4-methylphenyl)-2-(2-cyanopropan-2-yl)isonicotinamide | $^1$H NMR (400 MHz, <dmso>) δ ppm 1.77 (s, 6 H) 2.24 (s, 3 H) 2.50 (dt, J = 3.74, 1.90 Hz, 16 H) 3.28 (s, 3 H) 3.49-3.55 (m, 2 H) 3.56-3.64 (m, 2 H) 7.31 (d, J = 9.10 Hz, 1 H) 7.61 (d, J = 2.40 Hz, 1 H) 7.69 (dd, J = 8.22, 2.30 Hz, 1 H) 7.86 (dd, J = 5.04, 1.56 Hz, 1 H) 7.98 (d, J = 2.45 Hz, 1 H) 7.99-8.01 (m, 1 H) 8.31 (d, J = 2.45 Hz, 1 H) 8.81 (dd, J = 5.04, 0.88 Hz, 1 H) 10.54 (s, 1 H). LCMS (m/z) (M + H) = 455.2, Rt = 0.89 min. |
| 177 | 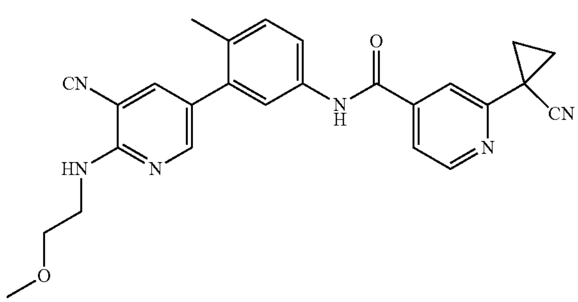 | N-(3-(5-cyano-6-((2-methoxyethyl)amino)pyridin-3-yl)-4-methylphenyl)-2-(1-cyanocyclopropyl)isonicotinamide | $^1$H NMR (400 MHz, <dmso>) δ ppm 1.75-1.79 (m, 2 H) 1.86-1.91 (m, 2 H) 2.24 (s, 3 H) 3.27-3.34 (m, 3 H) 3.49-3.54 (m, 2 H) 3.60 (d, J = 5.77 Hz, 2H) 7.31 (d, J = 9.05 Hz, 1 H) 7.62 (d, J = 2.30 Hz, 1 H) 7.68 (dd, J = 8.27, 2.30 Hz, 1 H) 7.78 (dd, J = 5.09, 3.56 Hz, 1 H) 7.91-7.94 (m, 1 H) 7.98 (d, J = 2.45 Hz, 1 H) 8.31 (d, J = 2.45 Hz, 1 H) 8.71 (dd, J = 5.04, 0.88 Hz, 1 H) 10.56 (s, 1 H). LCMS (m/z) (M + H) = 453.1, Rt = 0.89 min. |

TABLE 8-continued

| Example | Structure | Name | Physical Data |
|---|---|---|---|
| 178 | 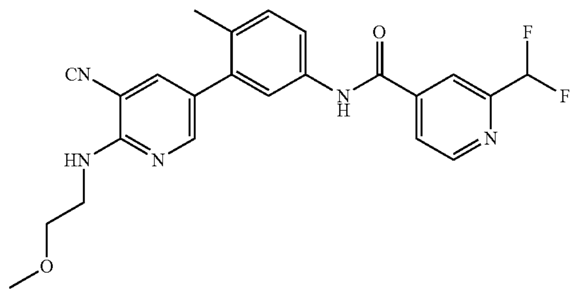 | N-(3-(5-cyano-6-((2-methoxyethyl)amino)pyridin-3-yl)-4-methylphenyl)-2-(difluoromethyl)isonicotinamide | $^1$H NMR (400 MHz, <dmso>) δ ppm 2.24 (s, 3 H) 3.28 (s, 3 H) 3.50-3.54 (m, 2 H) 3.56-3.66 (m, 2 H) 7.08 (t, J = 56.0, 1H), 7.16-7.19 (m, 1H) 7.31 (d, J = 9.15 Hz, 1 H) 7.63 (d, J = 2.30 Hz, 1 H) 7.71 (dd, J = 8.24, 2.37 Hz, 1 H) 7.98 (d, J = 2.45 Hz, 1 H) 8.06 (dt, J = 5.01, 0.87 Hz, 1 H) 8.17-8.19 (m, 1 H) 8.31 (d, J = 2.40 Hz, 1 H) 8.90 (dd, J = 5.04, 0.73 Hz, 1 H). LCMS (m/z) (M + H) = 438.1, Rt = 0.87 min. |
| 179 | 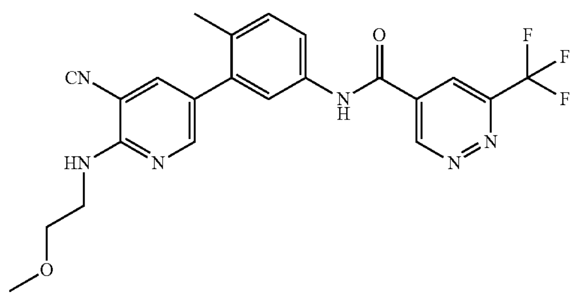 | N-(3-(5-cyano-6-((2-methoxyethyl)amino)pyridin-3-yl)-4-methylphenyl)-6-(trifluoromethyl)pyridazine-4-carboxamide | $^1$H NMR (400 MHz, <dmso>) δ ppm 2.25 (s, 3 H) 3.28 (s, 3 H) 3.51-3.63 (m, 4 H) 7.34 (d, J = 9.00 Hz, 1 H) 7.62 (d, J = 2.35 Hz, 1 H) 7.70 (dd, J = 8.22, 2.30 Hz, 1 H) 7.98 (d, J = 2.45 Hz, 1 H) 8.31 (d, J = 2.45 Hz, 1 H) 8.68 (d, J = 2.05 Hz, 1 H) 9.91 (d, J = 2.05 Hz, 1 H) 10.85 (s, 1 H). LCMS (m/z) (M + H) = 457.1, Rt = 0.89 min. |
| 180 | 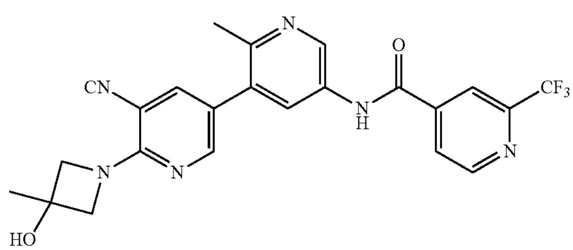 | N-(5'-cyano-6'-(3-hydroxy-3-methylazetidin-1-yl)-2-methyl-[3,3'-bipyridin]-5-yl)-2-(trifluoromethyl)isonicotinamide | $^1$H NMR (400 MHz, <dmso>) δ ppm 1.47 (s, 3 H) 2.48 (s, 3 H) 4.10-4.15 (m, 2 H) 4.17-4.20 (m, 2 H) 8.12 (d, J = 2.45 Hz, 1 H) 8.13 (d, J = 2.40 Hz, 1 H) 8.21 (dd, J = 4.99, 2.20 Hz, 1 H) 8.38-8.40 (m, 1 H) 8.41 (d, J = 2.40 Hz, 1 H) 8.91 (d, J = 2.45 Hz, 1 H) 9.03 (dt, J = 4.99, 0.71 Hz, 1 H) 11.01 (s, 1 H). LCMS (m/z) (M + H) = 469.1, Rt = 0.62 min. |
| 181 | 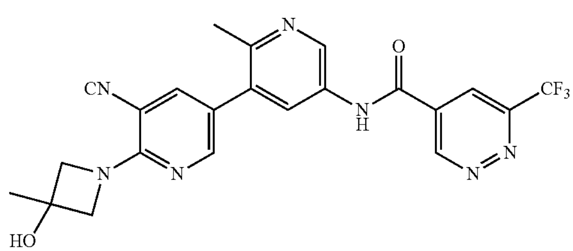 | N-(5'-cyano-6'-(3-hydroxy-3-methylazetidin-1-yl)-2-methyl-[3,3'-bipyridin]-5-yl)-6-(trifluoromethyl)pyridazine-4-carboxamide | $^1$H NMR (400 MHz, <dmso>) δ ppm 1.47 (s, 3 H) 2.47 (s, 3 H) 4.10-4.15 (m, 2 H) 4.17-4.20 (m, 2 H) 8.07 (d, J = 2.45 Hz, 1 H) 8.12 (d, J = 2.40 Hz, 1 H) 8.40 (d, J = 2.40 Hz, 1 H) 8.70 (d, J = 2.01 Hz, 1 H) 8.87 (d, J = 2.49 Hz, 1 H) 9.93 (d, J = 2.01 Hz, 1 H) 11.14 (s, 1 H). LCMS (m/z) (M + H) = 470.1, Rt = 0.57 min. |
| 182 | 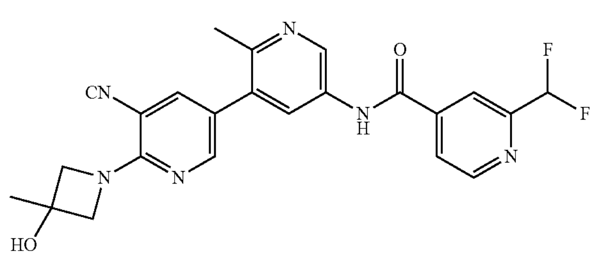 | N-(5'-cyano-6'-(3-hydroxy-3-methylazetidin-1-yl)-2-methyl-[3,3'-bipyridin]-5-yl)-2-(difluoromethyl)isonicotinamide | $^1$H NMR (400 MHz, <dmso>) δ ppm 1.47 (s, 3 H) 2.47 (s, 3 H) 4.11-4.15 (m, 2 H) 4.17-4.20 (m, 2 H) 7.10 (t, J = 56.0, 1H) 8.08 (d, J = 8.0 Hz, 1H) 8.13 (d, J = 2.35Hz, 1 H) 8.14 (d, J = 2.40 Hz, 1 H) 8.20-8.22 (m, 1 H) 8.41 (d, J = 2.40 Hz, 1 H) 8.92 (d, J = 2.45 Hz, 1 H) 8.94 (dd, J = 5.04, 0.78 Hz, 1 H) 10.98 (s, 1H). LCMS (m/z) (M + H) = 451.1, Rt = 0.55 min. |

TABLE 8-continued

| Example | Structure | Name | Physical Data |
|---|---|---|---|
| 183 | 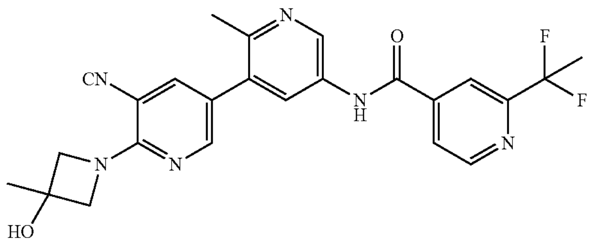 | N-(5'-cyano-6'-(3-hydroxy-3-methylazetidin-1-yl)-2-methyl-[3,3'-bipyridin]-5-yl)-2-(1,1-difluoroethyl)isonicotinamide | ¹H NMR (400 MHz, <dmso>) δ 1.47 (s, 3 H) 2.06 (t, J = 20.0 Hz, 3 H) 2.48 (s, 3 H) 4.10-4.21 (m, 4H) 8.05 (dd, J = 5.04, 1.71 Hz, 1 H) 8.10-8.16 (m, 2 H) 8.21-8.23 (m, 1 H) 8.41 (d, J = 2.40 Hz, 1 H) 8.90-8.95 (m, 2 H) 10.97 (s, 1 H). LCMS (m/z) (M + H) = 465.1, Rt = 0.60 min. |
| 184 | 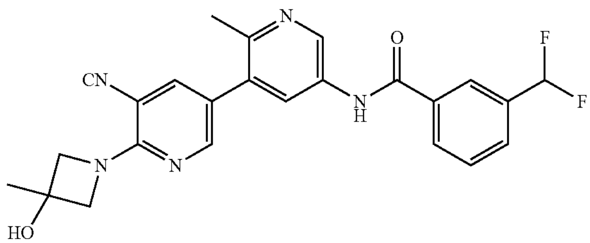 | N-(5'-cyano-6'-(3-hydroxy-3-methylazetidin-1-yl)-2-methyl-[3,3'-bipyridin]-5-yl)-3-(difluoromethyl)benzamide | ¹H NMR (400 MHz, <dmso>) δ ppm 1.47 (s, 3 H) 2.48 (s, 3 H) 4.11-4.15 (m, 2 H) 4.17-4.21 (m, 2 H) 7.17 (t, J = 56.0 Hz, 3H) 7.71-7.76 (m, 1 H) 7.83-7.85 (m, 1 H) 8.12-8.21 (m, 4H) 8.42 (d, J = 2.40 Hz, 1 H) 8.95 (d, J = 2.35 Hz, 1 H) 10.77 (s, 1 H). LCMS (m/z) (M + H) = 450.1, Rt = 0.63 min. |
| 185 | 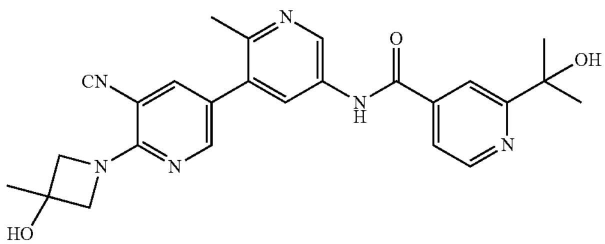 | N-(5'-cyano-6'-(3-hydroxy-3-methylazetidin-1-yl)-2-methyl-[3,3'-bipyridin]-5-yl)-2-(2-hydroxypropan-2-yl)isonicotinamide | ¹H NMR (400 MHz, <dmso>) δ ppm 1.47 (s, 3H) 1.50 (s, 6H) 2.50 (s, 3H) 4.11-4.15 (m, 2 H) 4.17-4.21 (m, 2 H) 7.75 (dd, J = 5.09, 1.76 Hz, 1H) 8.14 (d, J = 2.40 Hz, 1 H) 8.19-8.23 (m, 2 H) 8.42 (d, J = 2.40 Hz, 1 H) 8.73 (dd, J = 5.11, 0.86 Hz, 1 H) 8.98 (d, J = 2.40 Hz, 1 H) 10.95 (s, 1 H). LCMS (m/z) (M + H) = 459.1, Rt = 0.45 min. |
| 186 | 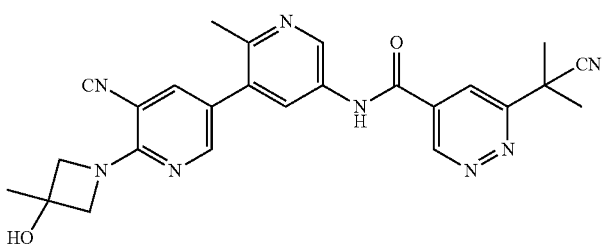 | N-(5'-cyano-6'-(3-hydroxy-3-methylazetidin-1-yl)-2-methyl-[3,3'-bipyridin]-5-yl)-6-(2-cyanopropan-2-yl)pyridazine-4-carboxamide | ¹H NMR (400 MHz, <dmso>) δ ppm 1.47 (s, 3 H) 1.86 (s, 6 H) 2.47 (s, 3 H) 4.10-4.15 (m, 2 H) 4.17-4.20 (m, 2 H) 8.07 (d, J = 2.15 Hz, 1 H) 8.12 (d, J = 2.40 Hz, 1 H) 8.33 (d, J = 2.01 Hz, 1 H) 8.40 (d, J = 2.40 Hz, 1 H) 8.87 (d, J = 2.45 Hz, 1 H) 9.67 (d, J = 2.00 Hz, 1 H) 11.06 (s, 1 H). LCMS (m/z) (M + H) = 469.2, Rt = 0.54 min. |
| 187 | 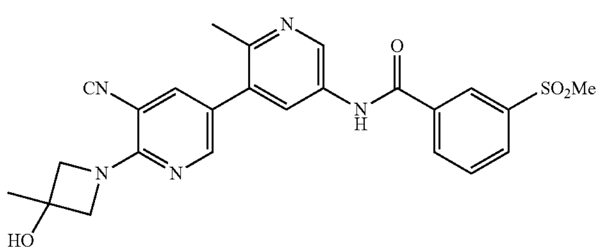 | N-(5'-cyano-6'-(3-hydroxy-3-methylazetidin-1-yl)-2-methyl-[3,3'-bipyridin]-5-yl)-3-(methylsulfonyl)benzamide | ¹H NMR (400 MHz, <dmso>) δ ppm 1.47 (s, 3 H) 2.49 (s, 3H) 3.30 (s, 3H) 4.11-4.15 (m, 2 H) 4.17-4.21 (m, 2 H) 7.87 (t, J = 7.83 Hz, 1 H) 8.13-8.21 (m, 3 H) 8.30-8.34 (m, 1 H) 8.42 (d, J = 2.40 Hz, 1 H) 8.52 (t, J = 1.83 Hz, 1 H) 8.96 (d, J = 2.49 Hz, 1 H) 10.90 (s, 1 H). LCMS (m/z) (M + H) = 478.1, Rt = 0.52 min. |
| 188 | 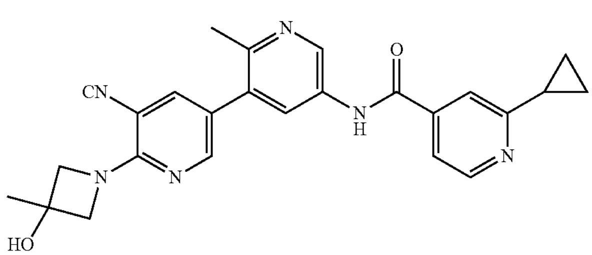 | N-(5'-cyano-6'-(3-hydroxy-3-methylazetidin-1-yl)-2-methyl-[3,3'-bipyridin]-5-yl)-2-cyclopropyl-isonicotinamide | ¹H NMR (400 MHz, <dmso>) δ ppm 0.99-1.07 (m, 4H) 1.47 (s, 3 H) 2.22-2.25 (m, 1H) 2.50 (s, 3H) 4.10-4.15 (m, 2 H) 4.17-4.21 (m, 2 H) 7.62 (dd, J = 5.16, 1.74 Hz, 1 H) 7.78 (dd, J = 1.74, 0.86 Hz, 1 H) 8.13 (d, J = 2.40 Hz, 1 H) 8.17 (d, J = 2.40 Hz, 1 H) 8.41 (d, J = 2.40 Hz, 1 H) 8.61-8.64 (m, 1 H) 8.94 (d, J = 2.45 Hz, 1 H) 10.84 (s, 1 H). LCMS (m/z) (M + H) = 441.1, Rt = 0.47 min. |

TABLE 8-continued

| Example | Structure | Name | Physical Data |
|---|---|---|---|
| 189 | 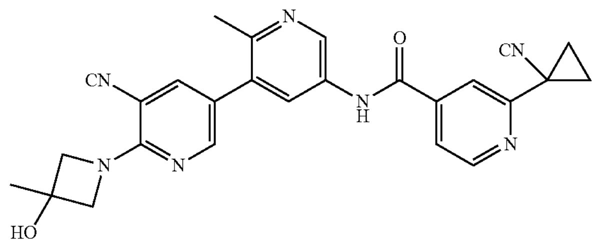 | N-(5'-cyano-6'-(3-hydroxy-3-methylazetidin-1-yl)-2-methyl-[3,3'-bipyridin]-5-yl)-2-(1-cyanocyclopropyl)isonicotinamide | $^1$H NMR (400 MHz, <dmso>) δ ppm 1.47 (s, 3 H) 1.75-1.80 (m, 2H) 1.87-1.92 (m, 2 H) 2.43 (s, 3 H) 4.10-4.15 (m, 2 H) 4.16-4.18 (m, 2 H) 7.81 (dd, J = 5.09, 1.57 Hz, 1 H) 7.95-7.97 (m, 1 H) 8.02 (d, J = 2.45 Hz, 1 H) 8.10 (d, J = 2.40 Hz, 1 H) 8.40 (d, J = 2.40 Hz, 1 H) 8.73 (dd, J = 5.04, 0.88 Hz, 1 H), 8.82 (d, J = 2.40 Hz, 1 H), 10.79 (s, 1H). LCMS (m/z) (M + H) = 466.1, Rt = 0.60 min. |
| 190 | 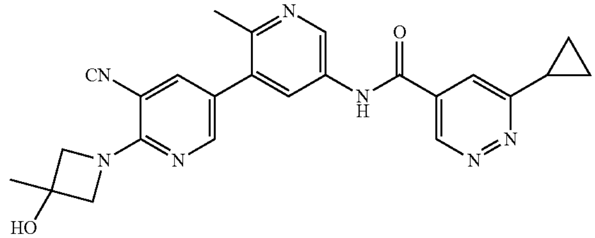 | N-(5'-cyano-6'-(3-hydroxy-3-methylazetidin-1-yl)-2-methyl-[3,3'-bipyridin]-5-yl)-6-cyclopropylpyridazine-4-carboxamide | $^1$H NMR (400 MHz, <dmso>) δ ppm 1.12-1.22 (m, 4 H) 1.47 (s, 3 H) 2.39 (s, 1 H) 2.37-2.41 (m, 1 H) 2.48 (s, 3H) 4.10-4.15 (m, 2 H) 4.17-4.20 (m, 2 H) 7.92 (d, J = 2.10 Hz, 1 H) 8.10 (d, J = 2.49 Hz, 1 H) 8.12 (d, J = 2.40 Hz, 1 H) 8.40 (d, J = 2.40 Hz, 1 H) 8.89 (d, J = 2.40 Hz, 1 H) 9.41 (d, J = 2.05 Hz, 1 H) 10.98 (s, 1 H). LCMS (m/z) (M + H) = 442.1, Rt = 0.52 min. |
| 191 | 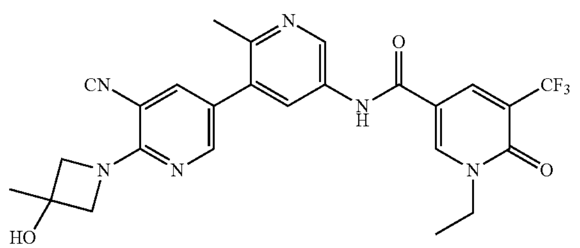 | N-(5'-cyano-6'-(3-hydroxy-3-methylazetidin-1-yl)-2-methyl-[3,3'-bipyridin]-5-yl)-1-ethyl-6-oxo-5-(trifluoromethyl)-1,6-dihydropyridine-3-carboxamide | $^1$H NMR (400 MHz, <dmso>) δ ppm 1.31 (t, J = 7.16 Hz, 3H) 1.47 (s, 3 H) 2.47 (s, 3 H) 4.06-4.15 (m, 4 H) 4.17-4.21 (m, 2 H) 8.04 (d, J = 2.30 Hz, 1 H) 8.12 (d, J = 2.40 Hz, 1 H) 8.40 (d, J = 2.40 Hz, 1 H) 8.49 (d, J = 3.47 Hz, 1 H) 8.85 (dd, J = 6.09, 2.62 Hz, 2 H) 10.48 (s, 1 H). LCMS (m/z) (M + H) = 513.1, Rt = 0.61 min |
| 192 | 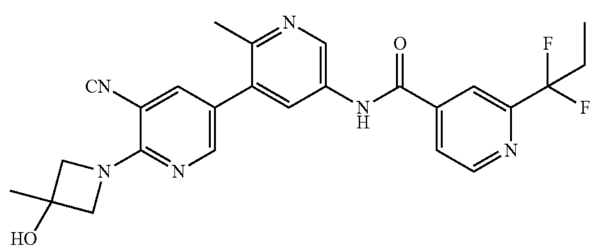 | N-(5'-cyano-6'-(3-hydroxy-3-methylazetidin-1-yl)-2-methyl-[3,3'-bipyridin]-5-yl)-2-(1,1-difluoropropyl)isonicotinamide | $^1$H NMR (400 MHz, <dmso>) δ ppm 0.95 (t, J = 7.48 Hz, 3 H) 1.47 (s, 3 H) 2.33-2.39 (m, 2 H) 4.10-4.22 (m, 4 H) 8.05 (dd, J = 5.06, 1.69 Hz, 1 H) 8.13 (d, J = 2.40 Hz, 2 H) 8.19-8.21 (m, 1 H) 8.41 (d, J = 2.40 Hz, 1 H) 8.91-8.95 (m, 2 H) 10.96 (s, 1 H). LCMS (m/z) (M + H) = 479.1, Rt = 0.65 min. |
| 193 | 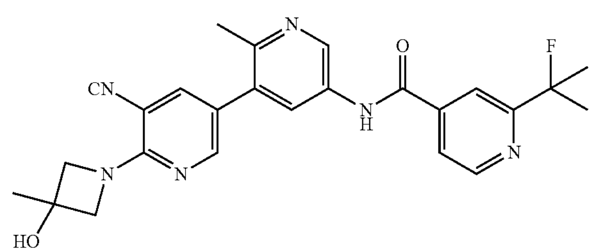 | N-(5'-cyano-6'-(3-hydroxy-3-methylazetidin-1-yl)-2-methyl-[3,3'-bipyridin]-5-yl)-2-(2-fluoropropan-2-yl)isonicotinamide | $^1$H NMR (400 MHz, <dmso>) δ ppm 1.47 (s, 4 H) 1.71 (d, J = 20.0 Hz, 6 H) 1.74 (s, 4 H) 2.50 (s, 3H) 4.10-4.22 (m, 4 H) 7.85 (dd, J = 5.04, 1.71 Hz, 1 H) 8.06-8.08 (m, 1 H) 8.14 (d, J = 2.40 Hz, 1 H) 8.18 (d, J = 2.49 Hz, 1 H) 8.42 (d, J = 2.40 Hz, 1 H) 8.80 (dt, J = 5.04, 1.00 Hz, 1 H) 8.96 (d, J = 2.40 Hz, 1 H) 10.94 (s, 1 H). LCMS (m/z) (M + H) = 461.1, Rt = 0.60 min. |

TABLE 8-continued

| Example | Structure | Name | Physical Data |
|---|---|---|---|
| 194 | 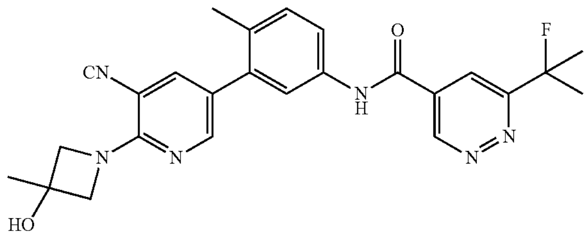 | N-(3-(5-cyano-6-(3-hydroxy-3-methylazetidin-1-yl)pyridin-3-yl)-4-methylphenyl)-6-(2-fluoropropan-2-yl)pyridazine-4-carboxamide | $^1$H NMR (400 MHz, <dmso>) δ ppm 1.47 (s, 3 H) 1.83 (d, J = 20.0 Hz, 6) 2.23 (s, 3 H) 4.09-4.13 (m, 2 H) 4.15-4.17 (m, 2 H) 7.33 (d, J = 9.10 Hz, 1 H) 7.62 (d, J = 2.40 Hz, 1 H) 7.70 (s, 1 H) 8.01 (d, J = 2.40 Hz, 1 H) 8.28 (dd, J = 2.13, 0.81 Hz, 1 H) 8.34 (d, J = 2.40 Hz, 1 H) 9.61 (d, J = 2.10 Hz, 1 H) 10.78 (s, 1 H). LCMS (m/z) (M + H) = 461.2, Rt = 0.81 min. |
| 195 | 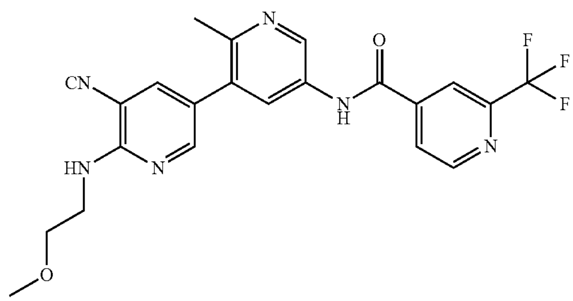 | N-(5'-cyano-6'-((2-methoxyethyl)amino)-2-methyl-[3,3'-bipyridin]-5-yl)-2-(trifluoromethyl)isonicotinamide | $^1$H NMR (400 MHz, <dmso>) δ ppm 2.46 (s, 3 H) 3.27 (s, 3H) 3.51 (d, J = 5.87 Hz, 2 H) 3.59 (d, J = 5.87 Hz, 2 H) 7.25-7.36 (m, 1 H) 8.07 (d, J = 2.35 Hz, 2 H) 8.17-8.24 (m, 1 H) 8.32-8.40 (m, 2 H) 8.86 (d, J = 2.35 Hz, 1 H) 9.01 (d, J = 4.70 Hz, 1 H) 10.95 (s, 1 H). LCMS (m/z) (M + H) = 457.1, Rt = 0.65 min. |
| 196 | 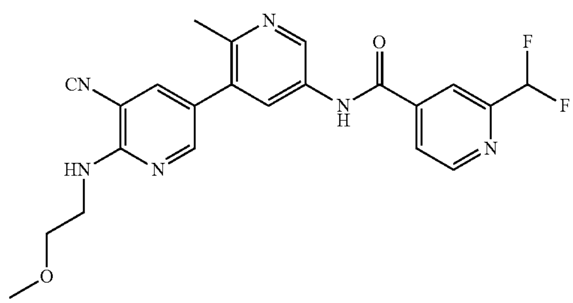 | N-(5'-cyano-6'-((2-methoxyethyl)amino)-2-methyl-[3,3'-bipyridin]-5-yl)-2-(difluoromethyl)isonicotinamide | $^1$H NMR (400 MHz, <dmso>) δ ppm 2.46-2.47 (m, 3 H) 3.27 (s, 3 H) 3.51 (d, J = 5.48 Hz, 2 H) 3.60 (d, J = 5.48 Hz, 2 H) 7.09 (s, 1 H) 7.27-7.35 (m, 1 H) 8.02-8.14 (m, 3 H) 8.19 (s, 1 H) 8.36 (d, J = 2.35 Hz, 1 H) 8.81-8.99 (m, 2 H) 10.93 (s, 1 H). LCMS (m/z) (M + H) = 439.1, Rt = 0.59 min. |
| 197 | 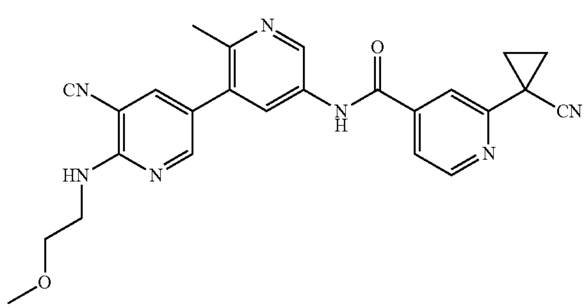 | N-(5'-cyano-6'-((2-methoxyethyl)amino)-2-methyl-[3,3'-bipyridin]-5-yl)-2-(1-cyanocyclopropyl)isonicotinamide | $^1$H NMR (400 MHz, <dmso>) δ ppm 1.62-1.76 (m, 2 H) 1.80-1.89 (m, 2 H) 2.41-2.42 (m, 3 H) 3.22 (s, 3 H) 3.46 (d, J = 5.87 Hz, 2 H) 3.55 (d, J = 5.48 Hz, 2 H) 7.20-7.32 (m, 1 H) 7.75 (dd, J = 5.09, 1.17 Hz, 1 H) 7.90 (s, 1 H) 8.04 (dd, J = 6.46, 2.15 Hz, 2 H) 8.32 (d, J = 2.35 Hz, 1 H) 8.68 (d, J = 5.09 Hz, 1 H) 8.83 (d, J = 2.35 Hz, 1 H) 10.83 (s, 1 H). LCMS (m/z) (M + H) = 454.1, Rt = 0.63 min. |
| 198 | 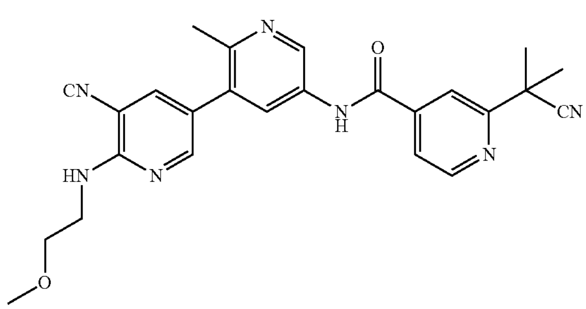 | N-(5'-cyano-6'-((2-methoxyethyl)amino)-2-methyl-[3,3'-bipyridin]-5-yl)-2-(2-cyanopropan-2-yl)isonicotinamide | $^1$H NMR (400 MHz, <dmso>) δ ppm 1.75 (s, 6 H) 2.46-2.47 (m, 3 H) 3.27 (s, 3 H) 3.42-3.53 (m, 2 H) 3.55-3.62 (m, 2 H) 7.32 (s, 1 H) 7.88 (dd, J = 4.89, 1.37 Hz, 1 H) 8.02 (s, 1 H) 8.10 (dd, J = 9.59, 2.15 Hz, 2 H) 8.37 (d, J = 2.35 Hz, 1 H) 8.78-8.96 (m, 2 H) 10.88 (s, 1 H). LCMS (m/z) (M + H) = 456.1, Rt = 0.63 min. |

| Example | Name | Physical Data |
|---|---|---|
| 199 | N-(5'-cyano-6'-((2-methoxyethyl)amino)-2-methyl-[3,3'-bipyridin]-5-yl)-3-(difluoromethyl)benzamide | ¹H NMR (400 MHz, <dmso>) δ ppm 3.75 (s, 6 H) 2.46-2.47 (m, 3 H) 3.27 (s, 3 H) 3.42-3.53 (m, 2 H) 3.55-3.62 (m, 2 H) 7.32 (s, 1 H) 7.88 (dd, J = 4.89, 1.37 Hz, 1 H) 8.02 (s, 1 H) 8.10 (dd, J = 9.59, 2.15 Hz, 2 H) 8.37 (d, J = 2.35 Hz, 1H) 8.78-8.96 (m, 2 H) 10.88 (s, 1 H). LCMS (m/z) (M + H) = 438.1, Rt = 0.67 min. |
| 200 | N-(5'-cyano-2-methyl-6'-((tetrahydro-2H-pyran-4-yl)amino)-[3,3'-bipyridin]-5-yl)-6-cyclopropylpyridazine-4-carboxamide | ¹H NMR (400 MHz, <dmso>) δ ppm 1.04-1.27 (m, 4H) 1.58-1.86 (m, 4 H) 2.32-2.42 (m, 1 H) 2.46 (s, 3 H) 3.34 (br. s., 2 H) 3.75-3.96 (m, 2 H) 4.12-4.35 (m, 1 H) 7.08-7.24 (m, 1 H) 7.83-7.96 (m, 1 H) 8.01-8.12 (m, 2 H) 8.29-8.40 (m, 1 H) 8.77-8.89 (m, 1 H) 9.32-9.44 (m, 3 H) 10.82-10.98 (m, 1 H). LCMS (m/z) (M + H) = 456.1, Rt = 0.56 min. |
| 201 | N-(3-(5-cyano-6-((2-methoxyethyl)amino)pyridin-3-yl)-4-methylphenyl)-6-(2-cyanopropan-2-yl)pyridazine-4-carboxamide | ¹H NMR (400 MHz, <dmso>) δ ppm 1.83 (s, 6 H) 2.22 (s, 3 H) 3.26 (s, 3 H) 3.55-3.63 (m, 4H) 7.10-7.21 (m, 1 H) 7.32 (d, J = 8.22 Hz, 1 H) 7.58 (d, J = 1.96 Hz, 2 H) 7.96 (d, J = 2.35 Hz, 1 H) 8.28 (dd, J = 4.30, 1.96 Hz, 2 H) 9.62 (d, J = 1.57 Hz, 1 H) 10.73 (s, 1 H). LCMS (m/z) (M + H) = 456.4, Rt = 0.81 min. |
| 202 | N-(5'-cyano-6'-((2-methoxyethyl)amino)-2-methyl-[3,3'-bipyridin]-5-yl)-6-(2-cyanopropan-2-yl)pyridazine-4-carboxamide | ¹H NMR (400 MHz, <dmso>) δ ppm 1.84 (s, 6 H) 2.46 (br. s., 3 H) 3.26 (s, 3 H) 3.50 (br. s., 4 H) 7.23-7.40 (m, 1 H) 8.06 (dd, J = 13.50, 2.15 Hz, 2 H) 8.33 (dd, J = 18.59, 2.15 Hz, 2 H) 8.84 (d, J = 2.35 Hz, 1 H) 9.65 (d, J = 1.96 Hz, 1 H) 11.02 (s, 1 H). LCMS (m/z) (M + H) = 457.4, Rt = 0.56 min. |
| 203 | N-(5'-cyano-6'-((2-methoxyethyl)amino)-2-methyl-[3,3'-bipyridin]-5-yl)-6-(trifluoromethyl)pyridazine-4-carboxamide | ¹H NMR (400 MHz, <dmso>) δ ppm 2.46 (br. s., 3 H) 3.26 (s, 3 H) 3.60 (br. s., 4 H) 7.19-7.34 (m, 1 H) 8.06 (dd, J = 11.93, 2.15 Hz, 2 H) 8.35 (d, J = 2.35 Hz, 1 H) 8.68 (d, J = 1.96 Hz, 1 H) 8.84 (d, J = 2.35 Hz, 1 H) 9.92 (d, J = 1.57 Hz, 1 H) 11.11 (s, 1 H). LCMS (m/z) (M + H) = 458.1, Rt = 0.60 min. |

TABLE 8-continued

| Example | Structure | Name | Physical Data |
|---|---|---|---|
| 204 | 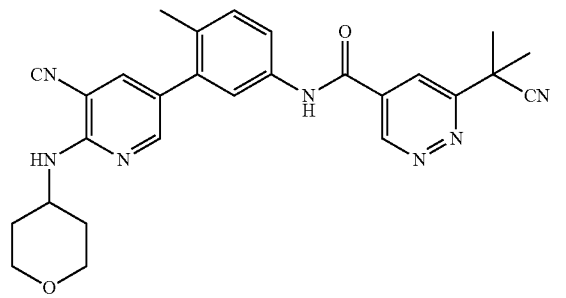 | N-(3-(5-cyano-6-((tetrahydro-2H-pyran-4-yl)amino)pyridin-3-yl)-4-methylphenyl)-6-(2-cyanopropan-2-yl)pyridazine-4-carboxamide | $^1$H NMR (400 MHz, <dmso>) δ ppm 1.60-1.75 (m, 2 H) 1.83 (s, 8 H) 2.22 (s, 3 H) 3.37 (br. s., 3 H) 3.79-3.95 (m, 2 H) 6.93-7.11 (m, 1 H) 7.25-7.38 (m, 1 H) 7.58 (d, J = 1.96 Hz, 2 H) 7.96 (d, J = 2.35 Hz, 1 H) 8.28 (dd, J = 7.63, 2.15 Hz, 2 H) 9.62 (d, J = 1.96 Hz, 1 H) 10.73 (s, 1 H). LCMS (m/z) (M + H) = 482.2, Rt = 0.84 min. |
| 205 | 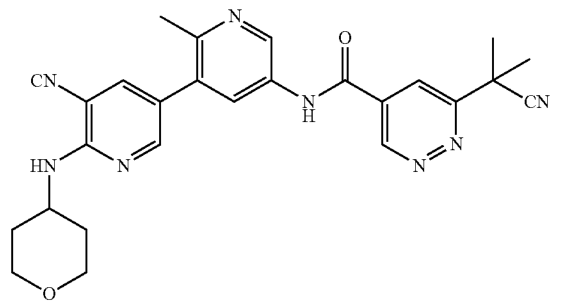 | N-(5'-cyano-2-methyl-6'-((tetrahydro-2H-pyran-4-yl)amino)-[3,3'-bipyridin]-5-yl)-6-(2-cyanopropan-2-yl)pyridazine-4-carboxamide | $^1$H NMR (400 MHz, <dmso>) δ ppm 1.84 (s, 10 H) 2.45 (s, 3 H) 3.34 (br. s., 3 H) 3.81-3.94 (m, 2 H) 7.04-7.24 (m, 1 H) 7.99-8.12 (m, 2 H) 8.26-8.43 (m, 2 H) 8.78-8.85 (m, 1 H) 9.57-9.67 (m, 1 H) 10.92-11.04 (m, 1 H). LCMS (m/z) (M + H) = 483.1, Rt = 0.58 min. |
| 206 | 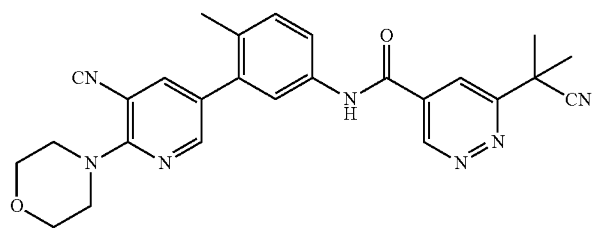 | N-(3-(5-cyano-6-morpholinopyridin-3-yl)-4-methylphenyl)-6-(2-cyanopropan-2-yl)pyridazine-4-carboxamide | $^1$H NMR (400 MHz, <dmso>) δ ppm 1.83 (s, 6 H) 2.23 (s, 3 H) 3.63-3.78 (m, 8 H) 7.36 (s, 1 H) 7.63 (d, J = 1.96 Hz, 2 H) 8.14 (d, J = 2.35 Hz, 1 H) 8.28 (d, J = 1.96 Hz, 1 H) 8.44 (d, J = 2.35 Hz, 1 H) 9.62 (d, J = 1.96 Hz, 1 H) 10.75 (s, 1 H). LCMS (m/z) (M + H) = 468.1, Rt = 6.86 min. |
| 207 | 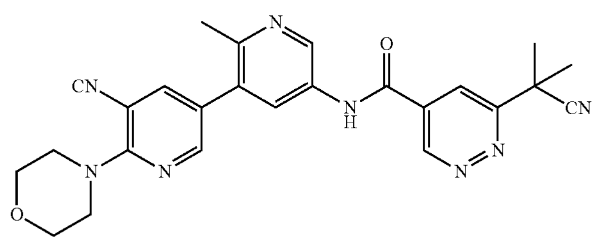 | N-(5'-cyano-2-methyl-6'-morpholino-[3,3'-bipyridin]-5-yl)-6-(2-cyanopropan-2-yl)pyridazine-4-carboxamide | $^1$H NMR (400 MHz, <dmso>) δ ppm 1.81-1.88 (m, 6 H) 2.45 (s, 3 H) 3.66-3.77 (m, 8 H) 8.06 (d, J = 2.35 Hz, 1 H) 8.20-8.35 (m, 2 H) 8.50 (d, J = 2.74 Hz, 1 H) 8.83 (d, J = 1.96 Hz, 1 H) 9.65 (d, J = 1.96 Hz, 1 H) 11.02 (s, 1 H). LCMS (m/z) (M + H) = 469.1, Rt = 0.59 min. |
| 208 | 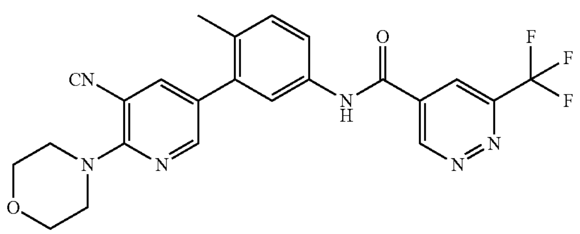 | N-(3-(5-cyano-6-morpholinopyridin-3-yl)-4-methylphenyl)-6-(trifluoromethyl)pyridazine-4-carboxamide | $^1$H NMR (400 MHz, <dmso>) δ ppm 2.24 (s, 3 H) 3.67-3.78 (m, 8 H) 7.35 (d, J = 8.61 Hz, 1 H) 7.52-7.78 (m, 2 H) 8.14 (d, J = 2.35 Hz, 1 H) 8.44 (d, J = 2.35 Hz, 1 H) 8.66 (d, J = 1.96 Hz, 1 H) 9.90 (d, J = 1.96 Hz, 1 H) 10.86 (s, 1 H). LCMS (m/z) (M + H) = 469.0, Rt = 0.92 min. |
| 209 | 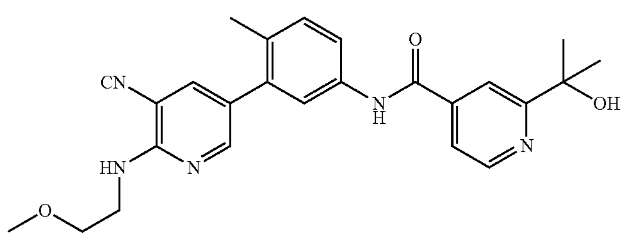 | N-(3-(5-cyano-6-((2-methoxyethyl)amino)pyridin-3-yl)-4-methylphenyl)-2-(2-hydroxypropan-2-yl)isonicotinamide | $^1$H NMR (400 MHz, <dmso>) δ ppm 1.47 (s, 6 H) 2.21 (s, 3 H) 3.26 (s, 3 H) 3.50 (br. s., 4 H) 7.08-7.21 (m, 1 H) 7.28 (d, J = 8.61 Hz, 1 H) 7.61 (d, J = 1.96 Hz, 1 H) 7.65-7.79 (m, 2 H) 7.96 (d, J = 2.35 Hz, 1 H) 8.15 (s, 1 H) 8.29 (d, J = 2.35 Hz, 1 H) 8.67 (d, J = 5.09 Hz, 3 H) 10.51 (s, 1 H). LCMS (m/z) (M + H) = 446.2, Rt = 0.68 min. |

TABLE 8-continued

| Example | Structure | Name | Physical Data |
|---|---|---|---|
| 210 | 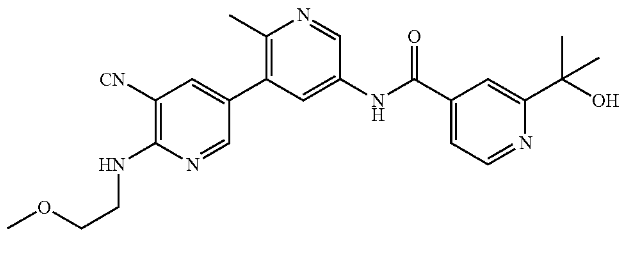 | N-(5'-cyano-6'-((2-methoxyethyl)amino)-2-methyl-[3,3'-bipyridin]-5-yl)-2-(2-hydroxypropan-2-yl)isonicotinamide | $^1$H NMR (400 MHz, <dmso>) δ ppm 1.48 (s, 6 H) 2.51 (s, 3 H) 3.26 (s, 3 H) 3.46-3.55 (m, 2 H) 3.60 (q, J = 5.35 Hz, 2 H) 7.37 (br. s., 1 H) 7.74 (dd, J = 5.09, 1.57 Hz, 1 H) 8.10 (d, J = 2.35 Hz, 1 H) 8.16-8.27 (m, 2 H) 8.38 (d, J = 2.35 Hz, 1 H) 8.72 (d, J = 5.09 Hz, 1 H) 8.98 (d, J = 1.96 Hz, 2 H) 10.96 (s, 1 H). LCMS (m/z) (M + H) = 447.1, Rt = 0.47 min. |
| 211 | 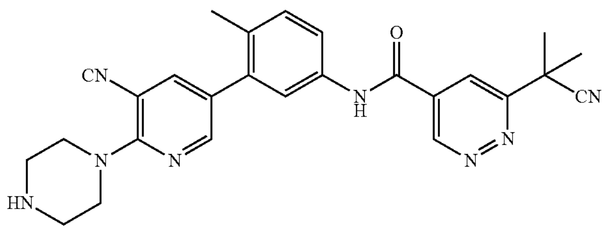 | N-(3-(5-cyano-6-(piperazin-1-yl)pyridin-3-yl)-4-methylphenyl)-6-(2-cyanopropan-2-yl)pyridazine-4-carboxamide | $^1$H NMR (400 MHz, <dmso>) δ ppm 1.83 (s, 6 H) 2.23 (s, 3 H) 3.25-3.29 (m, 4 H) 3.83 (br. s., 4H) 7.30-7.41 (m, 1 H) 7.69 (s, 2 H) 8.18-8.30 (m, 2 H) 8.45-8.52 (m, 1 H) 8.70-8.90 (m, 1 H) 9.57-9.69 (m, 1 H) 9.59-9.60 (m, 1 H) 10.74-10.83 (m, 1 H). LCMS (m/z) (M + H) = 467.1, Rt = 0.65 min. |
| 212 | 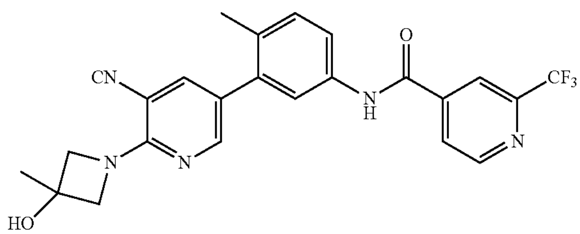 | N-(3-(5-cyano-6-(3-hydroxy-3-methylazetidin-1-yl)pyridin-3-yl)-4-methylphenyl)-2-(trifluoromethyl)isonicotinamide | $^1$H NMR (400 MHz, <dmso>) δ ppm 3.45 (s, 3 H) 2.21 (s, 3 H) 4.02-4.22 (m, 4 H) 7.31 (d, J = 8.61 Hz, 1 H) 7.61 (d, J = 1.56 Hz, 1 H) 7.69 (dd, J = 8.22, 2.35 Hz, 1 H) 7.99 (d, J = 2.35 Hz, 1 H) 8.17 (d, J = 4.70 Hz, 1 H) 8.28-8.39 (m, 2 H) 8.97 (d, J = 5.09 Hz, 1 H) 10.66 (s, 1 H). LCMS (m/z) (M + H) = 468.1, Rt = 0.86 min. |
| 213 | 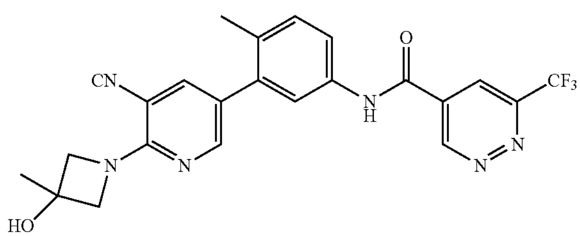 | N-(3-(5-cyano-6-(3-hydroxy-3-methylazetidin-1-yl])pyridin-3-yl)-4-methylphenyl)-6-(trifluoromethyl)pyridazine-4-carboxamide | $^1$H NMR (400 MHz, <dmso>) δ ppm 1.45 (s, 3 H) 2.22 (s, 3 H) 3.96-4.20 (m, 4 H) 7.33 (d, J = 8.61 Hz, 1 H) 7.60 (d, J = 1.96 Hz, 1 H) 7.68 (dd, J = 8.41, 2.15 Hz, 1 H) 7.99 (d, J = 2.35 Hz, 1 H) 8.32 (d, J = 2.35 Hz, 1 H) 8.66 (d, J = 1.57 Hz, 1 H) 9.89 (d, J = 1.57 Hz, 1 H) 10.84 (s, 1 H). LCMS (m/z) (M + H) = 469.2, Rt = 0.79 min. |
| 214 | 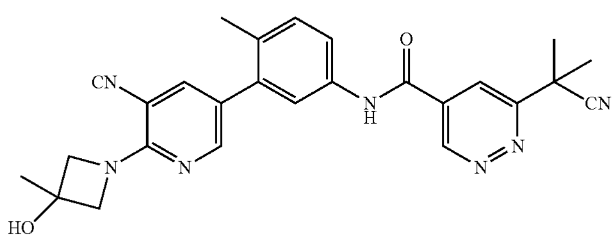 | N-(3-(5-cyano-6-(3-hydroxy-3-methylazetidin-1-yl)pyridin-3-yl)-4-methylphenyl)-6-(2-cyanopropan-2-yl)pyridazine-4-carboxamide | $^1$H NMR (400 MHz, <dmso>) δ ppm 1.45 (s, 3 H) 1.83 (s, 6 H) 2.21 (s, 3 H) 4.06-4.21 (m, 4H) 7.33 (d, J = 8.22 Hz, 1 H) 7.58 (d, J = 1.96 Hz, 1 H) 7.67 (dd, J = 8.41, 2.15 Hz, 1 H) 7.99 (d, J = 2.35 Hz, 1 H) 8.30 (dd, J = 18.98, 2.15 Hz, 2 H) 9.62 (d, J = 1.96 Hz, 1 H) 10.74 (s, 1 H). LCMS (m/z) (M + H) = 468.3, Rt = 0.74 min. |
| 215 | 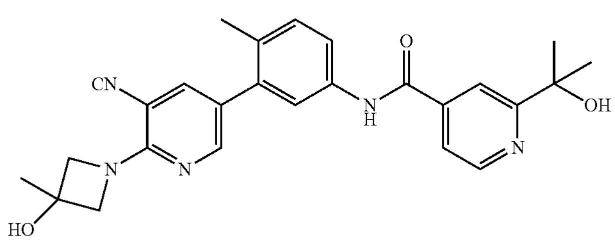 | N-(3-(5-cyano-6-(3-hydroxy-3-methylazetidin-1-yl)pyridin-3-yl)-4-methylphenyl)-2-(2-hydroxypropan-2-yl)isonicotinamide | $^1$H NMR (400 MHz, <dmso>) δ ppm 1.41-1.52 (m, 9 H) 2.20 (s, 3 H) 4.04-4.21 (m, 6 H) 7.29 (d, J = 8.22 Hz, 1 H) 7.61 (d, J = 1.96 Hz, 1 H) 7.65-7.80 (m, 2 H) 7.99 (d, J = 2.35 Hz, 1 H) 8.14 (s, 1 H) 8.32 (d, J = 2.35 Hz, 1 H) 8.67 (d, J = 5.09 Hz, 1 H) 10.52 (s, 1 H). LCMS (m/z) (M + H) = 458.3, Rt = 0.62 min. |

TABLE 8-continued

| Example | Structure | Name | Physical Data |
|---|---|---|---|
| 216 | 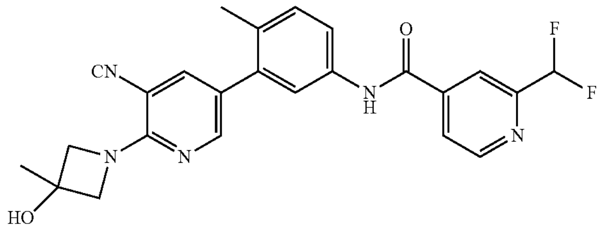 | N-(3-(5-cyano-6-(3-hydroxy-3-methylazetidin-1-yl)pyridin-3-yl)-4-methylphenyl)-2-(difluoromethyl)isonicotinamide | $^1$H NMR (400 MHz, <dmso>) δ ppm 1.45 (s, 3 H) 2.21 (s, 3 H) 4.09-4.18 (m, 4 H) 6.88-7.24 (m, 1 H) 7.30 (d, J = 8.61 Hz, 1 H) 7.62 (d, J = 1.96 Hz, 1 H) 7.69 (dd, J = 8.41, 2.15 Hz, 1 H) 7.95-8.10 (m, 2 H) 8.16 (s, 1 H) 8.32 (d, J = 2.35 Hz, 1 H) 8.88 (d, J = 5.09 Hz, 1 H) 10.62 (s, 1 H). LCMS (m/z) (M + H) = 450.2, Rt = 0.77 min. |
| 217 | 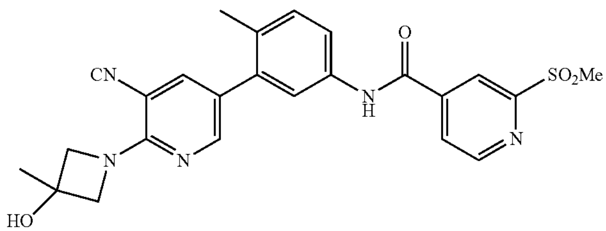 | N-(3-(5-cyano-6-(3-hydroxy-3-methylazetidin-1-yl)pyridin-3-yl)-4-methylphenyl)-2-(methylsulfonyl)isonicotinamide | $^1$H NMR (400 MHz, <dmso>) δ ppm 1.45 (s, 3 H) 2.21 (s, 3 H) 3.33 (s, 3 H) 4.04-4.20 (m, 4 H) 7.31 (d, J = 8.22 Hz, 1 H) 7.62 (d, J = 1.96 Hz, 1 H) 7.70 (dd, J = 8.41, 2.15 Hz, 1 H) 7.99 (d, J = 2.35 Hz, 1 H) 8.20 (dd, J = 4.89, 1.37 Hz, 1 H) 8.33 (d, J = 1.96 Hz, 1 H) 8.51 (s, 1 H) 8.98 (d, J = 5.09 Hz, 1 H) 10.76 (s, 1 H). LCMS (m/z) (M + H) = 478.3, Rt = 0.69 min. |
| 218 | 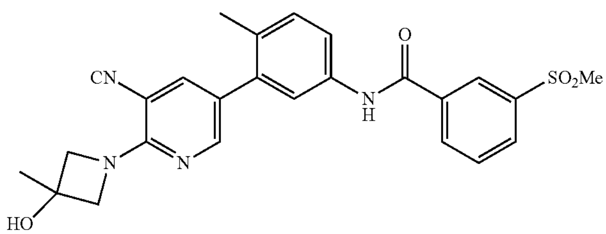 | N-(3-(5-cyano-6-(3-hydroxy-3-methylazetidin-1-yl)pyridin-3-yl)-4-methylphenyl)-3-(methylsulfonyl)benzamide | $^1$H NMR (400 MHz, <dmso>) δ ppm 1.45 (s, 3 H) 2.21 (s, 3 H) 3.27 (s, 3 H) 4.05-4.18 (m, 4 H) 7.29 (d, J = 8.61 Hz, 1 H) 7.61 (d, J = 1.96 Hz, 1 H) 7.66-7.74 (m, 1 H) 7.81 (s, 1 H) 7.99 (d, J = 2.35 Hz, 1 H) 8.08-8.17 (m, 1 H) 8.33 (d, J = 2.35 Hz, 2 H) 8.46 (s, 1 H) 10.50 (s, 1 H). LCMS (m/z) (M + H) = 477.2, Rt = 0.72 min. |
| 219 | 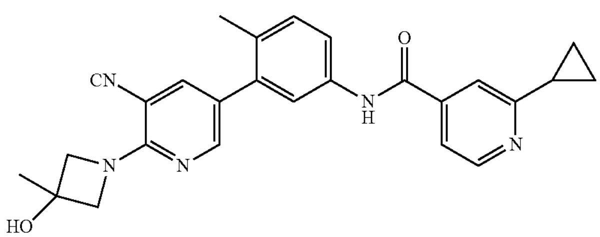 | N-(3-(5-cyano-6-(3-hydroxy-3-methylazetidin-1-yl)pyridin-3-yl)-4-methylphenyl)-2-cyclopropyl-isonicotinamide | $^1$H NMR (400 MHz, <dmso>) δ ppm 0.86-1.04 (m, 4 H) 1.40 (s, 3 H) 2.15 (s, 4 H) 4.01-4.13 (m, 4 H) 7.14-7.28 (m, 1 H) 7.48-7.70 (m, 4 H) 7.93 (d, J = 2.35 Hz, 1 H) 8.27 (d, J = 2.35 Hz, 1 H) 8.46-8.57 (m, 1 H) 10.37 (s, 1 H). LCMS (m/z) (M + H) = 440.2, Rt = 0.66 min. |
| 220 | 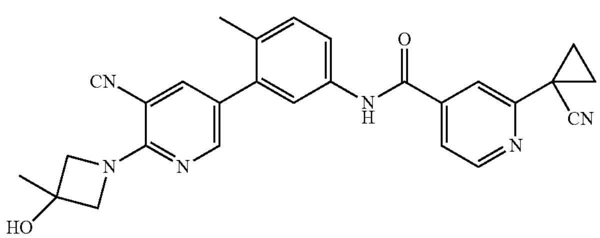 | N-(3-(5-cyano-6-(3-hydroxy-3-methylazetidin-1-yl)pyridin-3-yl)-4-methylphenyl)-2-(1-cyanocyclopropyl)isonicotinamide | $^1$H NMR (400 MHz, <dmso>) δ ppm 1.45 (s, 3 H) 1.69-1.78 (m, 2 H) 1.83-1.90 (m, 2H) 2.21 (s, 3 H) 4.06-4.18 (m, 4 H) 7.30 (d, J = 8.61 Hz, 1 H) 7.60 (d, J = 1.96 Hz, 1 H) 7.63-7.72 (m, 1 H) 7.76 (dd, J = 5.09, 1.17 Hz, 1 H) 7.90 (s, 1 H) 7.99 (d, J = 2.35 Hz, 1 H) 8.32 (d, J = 2.35 Hz, 1 H) 8.69 (d, J = 5.09 Hz, 1 H) 10.55 (s, 1 H). LCMS (m/z) (M + H) = 465.1, Rt = 0.82 min. |
| 221 | 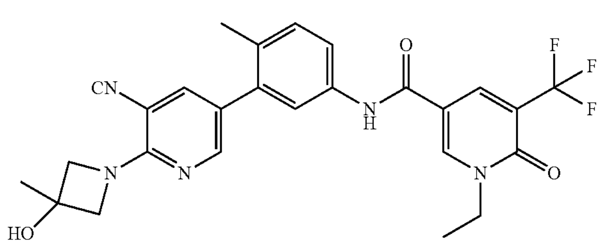 | N-(3-(5-cyano-6-(3-hydroxy-3-methylazetidin-1-yl)pyridin-yl)-4-methylphenyl)-1-ethyl-6-oxo-5-(trifluoromethyl)-1,6-dihydropyridine-3-carboxamide | $^1$H NMR (400 MHz, <dmso>) δ ppm 1.29 (t, J = 7.04 Hz, 3 H) 1.45 (s, 3 H) 2.20 (s, 3 H) 4.01-4.17 (m, 6 H) 7.27 (d, J = 8.22 Hz, 1 H) 7.51 (d, J = 2.35 Hz, 1 H) 7.61 (s, 1 H) 7.98 (d, J = 2.35 Hz, 1 H) 8.32 (d, J = 2.35 Hz, 1 H) 8.44 (d, J = 1.96 Hz, 1 H) 8.78 (d, J = 2.35 Hz, 1 H) 10.13 (s, 1 H). LCMS (m/z) (M + H) = 512.1, Rt = 0.84 min. |

TABLE 8-continued

| Example | Structure | Name | Physical Data |
| --- | --- | --- | --- |
| 222 | 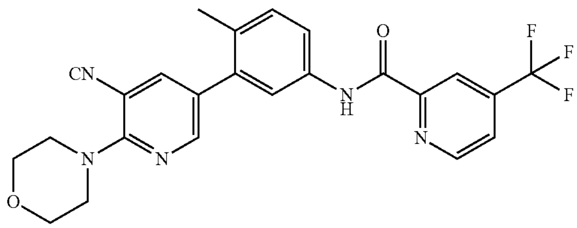 | N-(3-(5-cyano-6-morpholinopyridin-3-yl)-4-methylphenyl)-4-(trifluoromethyl)picolinamide | $^1$H NMR (400 MHz, <dmso>) δ ppm 2.23 (s, 3 H) 3.61-3.69 (m, 4 H) 3.71-3.79 (m, 4 H) 7.30 (d, J = 8.61 Hz, 1 H) 7.78-7.92 (m, 2 H) 8.07 (d, J = 5.09 Hz, 1 H) 8.14 (d, J = 2.35 Hz, 1 H) 8.32 (s, 1 H) 8.45 (d, J = 2.35 Hz, 1 H) 9.01 (d, J = 4.70 Hz, 1 H) 10.79 (s, 1 H). LCMS (m/z) (M + H) = 468.3, Rt = 1.12 min. |
| 223 | 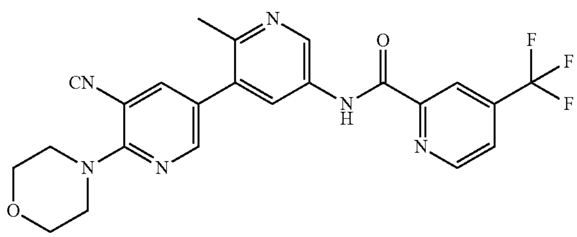 | N-(5'-cyano-2-methyl-6'-morpholino-[3,3'-bipyridin]-5-yl)-4-(trifluoromethyl)picolinamide | $^1$H NMR (400 MHz, <dmso>) δ ppm 2.52 (br. s., 3 H) 3.67-3.77 (m, 8 H) 8.11 (d, J = 5.09 Hz, 1 H) 8.25 (d, J = 2.35 Hz, 1 H) 8.33 (d, J = 10.56 Hz, 2 H) 8.51 (d, J = 2.35 Hz, 1 H) 9.00-9.11 (m, 2H) 11.19 (s, 1 H). LCMS (m/z) (M + H) = 469.2, Rt = 0.75 min. |
| 224 | 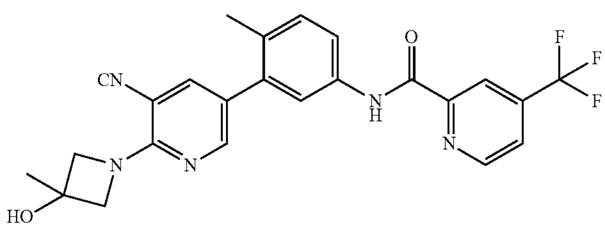 | N-(3-(5-cyano-6-(3-hydroxy-3-methylazetidin-1-yl)pyridin-3-yl)-4-methylphenyl)-4-(trifluoromethyl)picolinamide | $^1$H NMR (400 MHz, <dmso>) δ ppm 1.45 (s, 3 H) 2.21 (s, 3 H) 4.05-4.18 (m, 4 H) 7.29 (d, J = 8.61 Hz, 1 H) 7.77 (d, J = 1.96 Hz, 1 H) 7.84 (dd, J = 8.41, 2.15 Hz, 1 H) 7.99 (d, J = 1.96 Hz, 1 H) 8.07 (d, J = 4.70 Hz, 1 H) 8.28-8.39 (m, 2 H) 9.01 (d, J = 5.09 Hz, 1 H) 10.77 (s, 1 H). LCMS (m/z) (M + H) = 468.3, Rt = 1.00 min. |
| 225 | 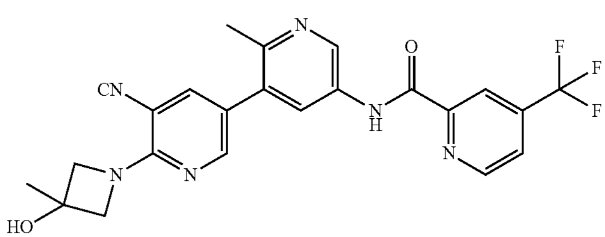 | N-(5'-cyano-6'-(3-hydroxy-3-methylazetidin-1-yl)-2-methyl-[3,3'-bipyridin]-5-yl)-4-(trifluoromethyl)picolinamide | $^1$H NMR (400 MHz, <dmso>) δ ppm 1.45 (s, 3 H) 2.49-2.53 (m, 3 H) 4.08-4.14 (m, 2 H) 4.15-4.20 (m, 2 H) 8.11 (d, J = 2.35 Hz, 2 H) 8.29-8.46 (m, 3 H) 8.99-9.15 (m, 2 H) 11.22 (s, 1 H). LCMS (m/z) (M + H) = 469.3, Rt = 0.70 min. |
| 226 | 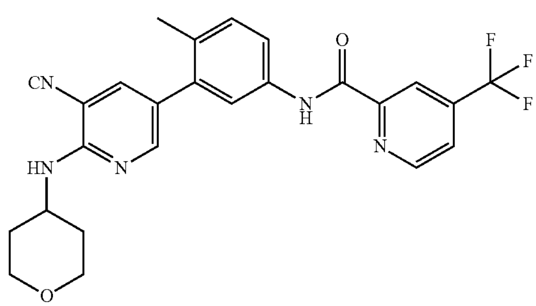 | N-(3-(5-cyano-6-((tetrahydro-2H-pyran-4-yl)amino)pyridin-3-yl)-4-methylphenyl)-4-(trifluoromethyl)picolinamide | $^1$H NMR (400 MHz, <dmso>) δ ppm 1.67 (dd, J = 11.93, 4.11 Hz, 2 H) 1.76-1.84 (m, 2 H) 2.22 (s, 3 H) 3.31-3.43 (m, 2 H) 3.87 (dd, J = 11.35, 2.74 Hz, 2 H) 4.18-4.27 (m, 1 H) 7.00 (d, J = 7.83 Hz, 1 H) 7.28 (d, J = 8.61 Hz, 1 H) 7.76 (d, J = 1.96 Hz, 1 H) 7.83 (dd, J = 8.22, 2.35 Hz, 1 H) 7.96 (d, J = 2.74 Hz, 1 H) 8.07 (d, J = 3.91 Hz, 1 H) 8.28-8.36 (m, 2 H) 9.01 (d, J = 4.70 Hz, 1 H) 10.76 (s, 1 H). LCMS (m/z) (M + H) = 482.3, Rt = 1.11 min. |

TABLE 8-continued

| Example | Structure | Name | Physical Data |
|---|---|---|---|
| 227 | 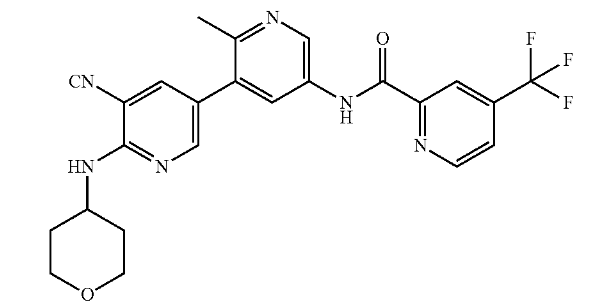 | N-(5'-cyano-2-methyl-6'-((tetrahydro-2H-pyran-4-yl)amino)-[3,3'-bipyridin]-5-yl)-4-(trifluoromethyl)picolinamide | ¹H NMR (400 MHz, <dmso>) δ ppm 1.63-1.85 (m, 4 H) 2.52 (br. s., 3 H) 3.32-3.44 (m, 2 H) 3.74-3.95 (m, 2 H) 4.18-4.30 (m, 1 H) 7.18 (d, J = 7.83 Hz, 1 H) 8.04-8.17 (m, 2 H) 8.29-8.41 (m, 3H) 8.99-9.11 (m, 2 H) 11.22 (s, 1 H). LCMS (m/z) (M + H) = 483.3, Rt = 0.76 min. |
| 228 | 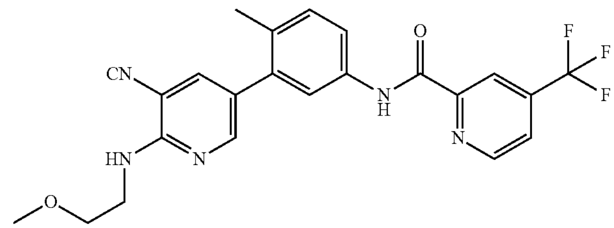 | N-(3-(5-cyano-6-((2-methoxyethyl)amino)pyridin-3-yl)-4-methylphenyl)-4-(trifluoromethyl)picolinamide | ¹H NMR (400 MHz, <dmso>) δ ppm 2.22 (s, 3 H) 3.27 (s, 3 H) 3.44-3.53 (m, 2 H) 3.55-3.65 (m, 2 H) 7.15 (br. s., 1 H) 7.28 (d, J = 8.61 Hz, 1 H) 7.77 (d, J = 2.35 Hz, 1 H) 7.83 (dd, J = 8.22, 2.35 Hz, 1 H) 7.96 (d, J = 2.74 Hz, 1 H) 8.07 (d, J = 4.69 Hz, 1 H) 8.25-8.39 (m, 2 H) 9.01 (d, J = 5.09 Hz, 1 H) 10.76 (s, 1 H). LCMS (m/z) (M + H) = 456.2, Rt = 1.09 min. |
| 229 | 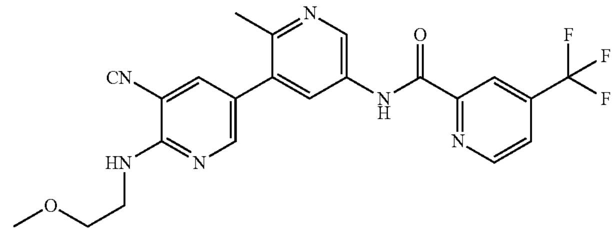 | N-(5'-cyano-6'-((2-methoxyethyl)amino)-2-methyl-[3,3'-bipyridin]-5-yl)-4-(trifluoromethyl)picolinamide | ¹H NMR (400 MHz, <dmso>) δ ppm 2.49 (br. s., 3 H) 3.26 (s, 3 H) 3.46-3.54 (m, 2 H) 3.56-3.64 (m, 2 H) 7.34 (s, 1 H) 8.02-8.17 (m, 2 H) 8.28-8.42 (m, 3 H) 9.00-9.13 (m, 2 H) 11.24 (s, 1 H). LCMS (m/z) (M + H) = 457.3, Rt = 0.74 min. |
| 230 | 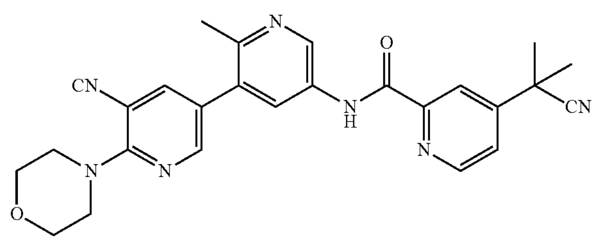 | N-(5'-cyano-2-methyl-6'-morpholino-[3,3'-bipyridin]-5-yl)-4-(2-cyanopropan-2-yl)picolinamide | ¹H NMR (400 MHz, <dmso>) δ ppm 1.70 (s, 6 H) 2.47 (s, 3 H) 3.59-3.74 (m, 8 H) 7.81 (dd, J = 5.09, 1.96 Hz, 1 H) 8.22 (dd, J = 7.83, 1.96 Hz, 2 H) 8.31 (s, 1 H) 8.47 (d, J = 2.35 Hz, 1 H) 8.76 (d, J = 5.09 Hz, 1 H) 9.05 (d, J = 1.96 Hz, 1 H) 11.07 (8, 1 H). LCMS (m/z) (M + H) = 468.1, Rt = 0.70 min. |
| 231 | 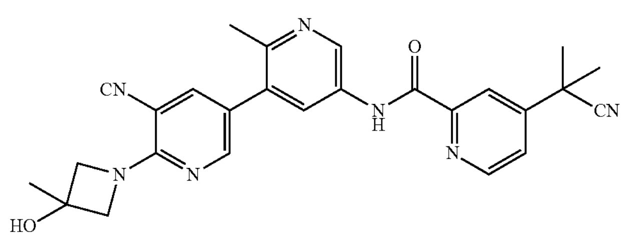 | N-(5'-cyano-6'-(3-hydroxy-3-methylazetidin-1-yl)-2-methyl-[3,3'-bipyridin]-5-yl)-4-(2-cyanopropan-2-yl)picolinamide | ¹H NMR (400 MHz, <dmso>) δ ppm 1.45 (s, 3 H) 1.70-1.82 (m, 6 H) 2.52 (br. s., 3 H) 4.09-4.22 (m, 4 H) 7.78-7.93 (m, 1 H) 8.11 (d, J = 2.35 Hz, 1 H) 8.22-8.46 (m, 3 H) 8.81 (d, J = 5.09 Hz, 1 H) 9.09 (d, J = 1.96 Hz, 1 H) 11.09-11.19 (m, 1 H). LCMS (m/z) (M + H) = 468.0, Rt = 0.64 min. |
| 232 | 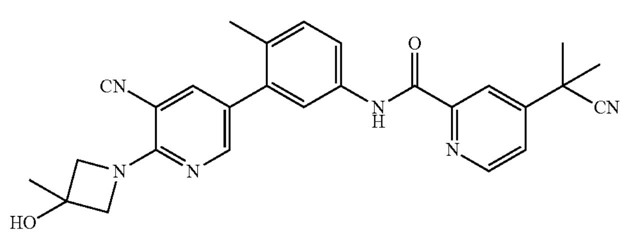 | N-(3-(5-cyano-6-(3-hydroxy-3-methylazetidin-1-yl)pyridin-3-yl)-4-methylphenyl)-4-(2-cyanopropan-2-yl)picolinamide | ¹H NMR (400 MHz, <dmso>) δ ppm 1.45 (s, 3 H) 1.74 (s, 6 H) 2.21 (s, 3 H) 4. 12 (d, J = 15.65 Hz, 4 H) 7.23-7.34 (m, 1 H) 7.74-7.89 (m, 3 H) 7.99 (d, J = 2.35 Hz, 1 H) 8.18-8.28 (m, 1 H) 8.34 (d, J = 2.35 Hz, 1 H) 8.72-8.81 (m, 1 H) 10.66 (s, 1 H). LCMS (m/z) (M + H) = 467.1, Rt = 0.89 min. |

TABLE 8-continued

| Example | Structure | Name | Physical Data |
|---|---|---|---|
| 233 | 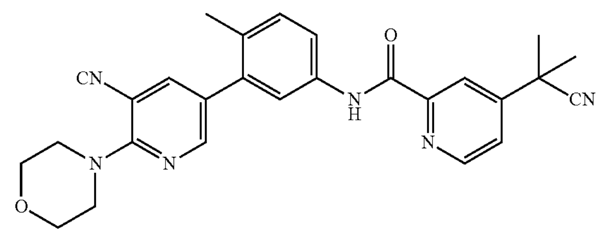 | N-(3-(5-cyano-6-morpholinopyridin-3-yl)-4-methylphenyl)-4-(2-cyanopropan-2-yl)picolinamide | ¹H NMR (400 MHz, <dmso>) δ ppm 1.74 (s, 6 H) 2.23 (s, 3 H) 3.65 (d, J = 4.70 Hz, 4 H) 3.72-3.78 (m, 4 H) 7.25-7.35 (m, 1 H) 7.81 (d, J = 1.96 Hz, 3 H) 8.14 (d, J = 2.35 Hz, 1 H) 8.21-8.28 (m, 1 H) 8.46 (d, J = 2.35 Hz, 1 H) 8.73-8.82 (m, 1 H) 10.68 (s, 1 H). LCMS (m/z) (M + H) = 467.1, Rt = 1.02 min. |
| 234 | 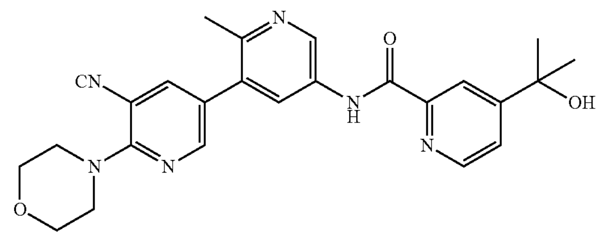 | N-(5'-cyano-2-methyl-6'-morpholino-[3,3'-bipyridin]-5-yl)-4-(2-hydroxypropan-2-yl)picolinamide | ¹H NMR (400 MHz, <dmso>) δ ppm 1.45 (s, 6 H) 2.49-2.51 (m, 3 H) 3.70 (d, J = 5.09 Hz, 4 H) 3.74 (d, J = 5.09 Hz, 4 H) 7.65-7.79 (m, 1 H) 8.20-8.28 (m, 2 H) 8.28-8.39 (m, 1 H) 8.51 (d, J = 2.35 Hz, 1 H) 8.62-8.71 (m, 1 H) 9.02-9.13 (m, 1 H) 10.93-11.06 (m, 1 H). LCMS (m/z) (M + H) = 459.1, Rt = 0.61 min. |
| 235 | 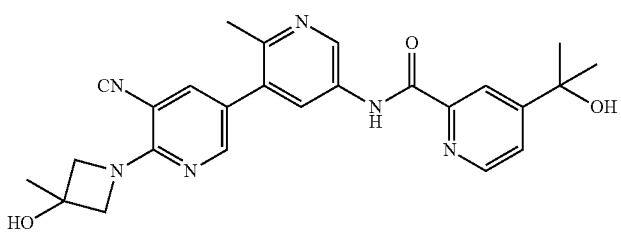 | N-(5'-cyano-6'-(3-hydroxy-3-methylazetidin-1-yl)-2-methyl-[3,3'-bipyridin]-5-yl)-4-(2-hydroxypropan-2-yl)picolinamide | ¹H NMR (400 MHz, <dmso>) δ ppm 1.45 (s, 9 H) 2.49-2.53 (m, 3 H) 4.14 (d, J = 18.00 Hz, 4 H) 7.65-7.80 (m, 1 H) 8.12 (d, J = 2.35 Hz, 1 H) 8.25 (s, 1 H) 8.41 (d, J = 2.35 Hz, 2 H) 8.62-8.70 (m, 1 H) 9.06-9.14 (m, 1 H) 10.99-11.11 (m, 1 H). LCMS (m/z) (M + H) = 459.1, Rt = 0.56 min. |
| 236 | 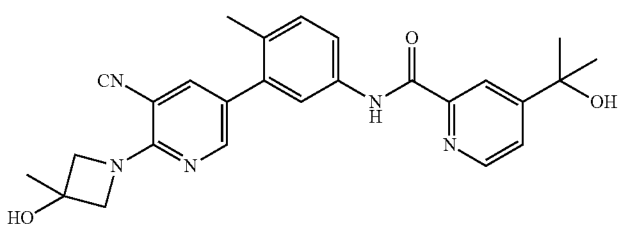 | N-(3-(5-cyano-6-(3-hydroxy-3-methylazetidin-1-yl)pyridin-3-yl)-4-methylphenyl)-4-(2-hydroxypropan-2-yl)picolinamide | ¹H NMR (400 MHz, <dmso>) δ ppm 1.41-1.50 (m, 9 H) 2.21 (s, 3 H) 4.12 (d, J = 15.65 Hz, 4 H) 7.18-7.33 (m, 1 H) 7.64-7.79 (m, 2 H) 7.79-7.89 (m, 1 H) 7.96-8.03 (m, 1 H) 8.20-8.26 (m, 1 H) 8.30-8.38 (m, 1 H) 8.58-8.67 (m, 1 H) 10.52-10.61 (m, 1 H). LCMS (m/z) (M + H) = 458.2, Rt = 0.79 min. |
| 237 | 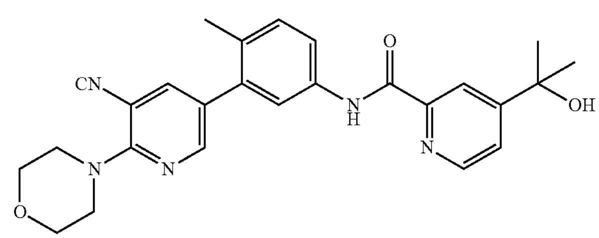 | N-(3-(5-cyano-6-morpholinopyridin-3-yl)-4-methylphenyl)-4-(2-hydroxypropan-2-yl)picolinamide | ¹H NMR (400 MHz, <dmso>) δ ppm 1.44 (s, 6 H) 2.22 (s, 3 H) 3.64-3.67 (m, 4 H) 3.75 (d, J = 4.30 Hz, 4 H) 7.24-7.34 (m, 1 H) 7.65-7.73 (m, 1 H) 7.78-7.91 (m, 2 H) 8.15 (s, 1 H) 8.19-8.29 (m, 1 H) 8.46 (s, 1 H) 8.60-8.67 (m, 1 H) 10.60 (s, 1 H). LCMS (m/z) (M + H) = 458.2, Rt = 0.90 min. |
| 238 | 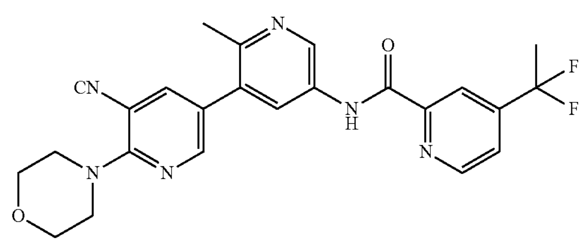 | N-(5'-cyano-2-methyl-6'-morpholino-[3,3'-bipyridin]-5-yl)-4-(1,1-difluoroethyl)picolinamide | ¹H NMR (400 MHz, <dmso>) δ ppm 2.03 (t, J = 19.17 Hz, 3 H) 2.49-2.50 (m, 3 H) 3.72 (dd, J = 16.63, 4.89 Hz, 8 H) 7.89 (d, J = 5.09 Hz, 1 H) 8.20-8.28 (m, 2 H) 8.33 (br. s., 1 H) 8.51 (d, J = 2.35 Hz, 1 H) 8.91 (d, J = 5.09 Hz, 1 H) 9.07 (d, J = 2.35 Hz, 1 H) 11.13 (s, 1 H). LCMS (m/z) (M + H) = 465.2, Rt = 0.73 min. |

TABLE 8-continued

| Example | Structure | Name | Physical Data |
|---|---|---|---|
| 239 | 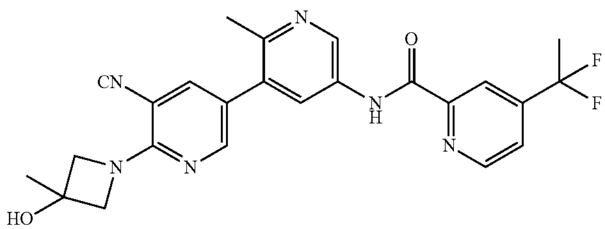 | N-(5'-cyano-6'-3-hydroxy-3-methylazetidin-1-yl)-2-methyl-[3,3'-bipyridin]-5-yl)-4-(1,1-difluoroethyl)picolinamide | $^1$H NMR (400 MHz, <dmso>) δ ppm 1.45 (s, 3 H) 2.03 (t, J = 19.37 Hz, 3 H) 2.45 (br. s., 3 H) 4.06-4.22 (m, 4 H) 7.85-7.94 (m, 1 H) 8.11 (d, J = 2.35 Hz, 1 H) 8.23 (s, 2 H) 8.40 (d, J = 2.35 Hz, 1 H) 8.87-8.95 (m, 1 H) 9.01-9.09 (m, 1 H) 11.05-11.14 (m, 1 H). LCMS (m/z) (M + H) = 465.2, Rt = 0.68 min. |
| 240 | 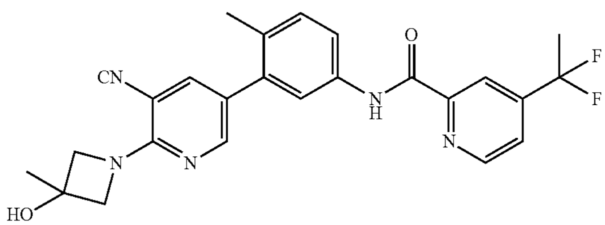 | N-(3-(5-cyano-6-(3-hydroxy-3-methylazetidin-1-yl)pyridin-3-yl)-4-methylphenyl)-4-(1,1-difluoroethyl)picolinamide | $^1$H NMR (400 MHz, <dmso>) δ ppm 1.45 (s, 3 H) 2.03 (t, J = 19.17 Hz, 3 H) 2.21 (s, 3 H) 4.05-4.21 (m, 4 H) 7.28 (d, J = 8.22 Hz, 1 H) 7.77 (d, J = 1.96 Hz, 1 H) 7.80-7.89 (m, 2 H) 7.99 (d, J = 2.35 Hz, 1 H) 8.21 (s, 1 H) 8.34 (d, J = 2.35 Hz, 1 H) 8.87 (d, J = 5.09 Hz, 1 H) 10.70 (s, 1 H). LCMS (m/z) (M + H) = 464.2, Rt = 0.95 min. |
| 241 | 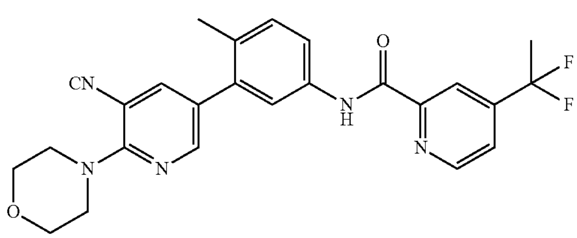 | N-(3-(5-cyano-6-morpholinopyridin-3-yl)-4-methylphenyl)-4-(1,1-difluoroethyl)picolinamide | $^1$H NMR (400 MHz, <dmso>) δ ppm 2.03 (t, J = 19.37 Hz, 3 H) 2.23 (s, 3 H) 3.64-3.67 (m, 4 H) 3.75 (d, J = 3.91 Hz, 4 H) 7.30 (d, J = 8.22 Hz, 1 H) 7.77-7.92 (m, 3 H) 8.10-8.27 (m, 2 H) 8.45 (d, J = 2.35 Hz, 1 H) 8.87 (d, J = 4.70 Hz, 1 H) 10.72 (s, 1 H). LCMS (m/z) (M + H) = 464.2, Rt = 1.08 min. |
| 242 | 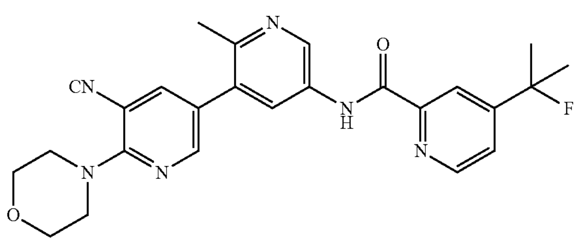 | N-(5'-cyano-2-methyl-6'-morpholino-[3,3'-bipyridin]-5-yl)-4-(2-fluoropropan-2-yl)picolinamide | $^1$H NMR (400 MHz, <dmso>) δ ppm 1.64-1.76 (m, 6 H) 2.52 (br. s., 3 H) 3.70-3.76 (m, 8 H) 7.72 (dd, J = 5.09, 1.57 Hz, 1 H) 8.15 (d, J = 1.17 Hz, 1 H) 8.25 (d, J = 2.35 Hz, 1 H) 8.35 (br. s., 1 H) 8.52 (d, J = 2.35 Hz, 1 H) 8.76 (d, J = 5.09 Hz, 1 H) 9.09 (d, J = 1.96 Hz, 1 H) 11.09 (s, 1 H). LCMS (m/z) (M + H) = 461.2, Rt = 0.76 min. |
| 243 | 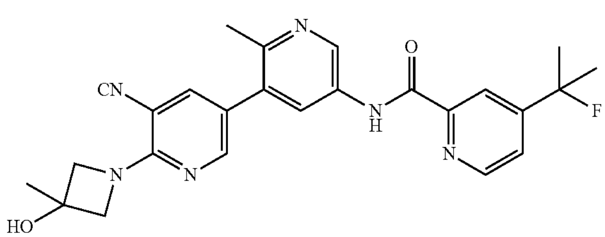 | N-(5'-cyano-6'-(3-hydroxy-3-methylazetidin-1-yl)-2-methyl-[3,3'-bipyridin]-5-yl)-4-(2-fluoropropan-2-yl)picolinamide | $^1$H NMR (400 MHz, <dmso>) δ ppm 1.45 (s, 3 H) 1.66 (s, 3 H) 1.72 (s, 3 H) 2.50 (s, 3 H) 3.99-4.28 (m, 4 H) 7.73 (dd, J = 5.09, 1.57 Hz, 1 H) 8.14 (dd, J = 12.72, 1.76 Hz, 2 H) 8.41 (d, J = 2.35 Hz, 2 H) 8.76 (d, J = 5.09 Hz, 1 H) 9.13 (d, J = 1.96 Hz, 1 H) 11.18 (s, 1 H). LCMS (m/z) (M + H) = 461.3, Rt = 0.69 min. |
| 244 | 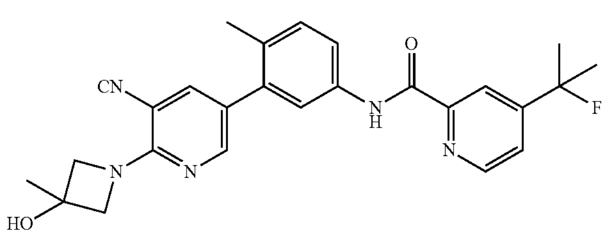 | N-(3-(5-cyano-6-(3-hydroxy-3-methylazetidin-1-yl)pyridin-3-yl)-4-methylphenyl)-4-(2-fluoropropan-2-yl)picolinamide | $^1$H NMR (400 MHz, <dmso>) δ ppm 1.45 (s, 3 H) 1.65 (s, 3 H) 1.68-1.74 (m, 3 H) 2.21 (s, 3 H) 4.05-4.21 (m, 4 H) 7.27 (d, J = 8.22 Hz, 1 H) 7.63-7.90 (m, 3 H) 7.99 (d, J = 2.35 Hz, 1 H) 8.12 (d, J = 1.17 Hz, 1 H) 8.34 (d, J = 2.35 Hz, 1 H) 8.72 (d, J = 5.09 Hz, 1 H) 10.63 (s, 1 H). LCMS (m/z) (M + H) = 460.2, Rt = 0.97 min. |

TABLE 8-continued

| Example | Structure | Name | Physical Data |
|---|---|---|---|
| 245 | 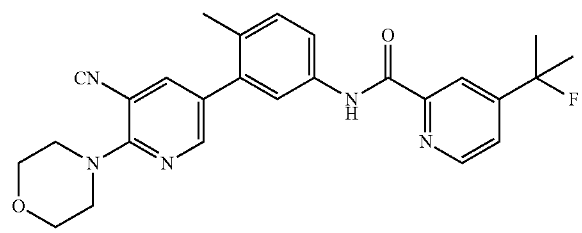 | N-(3-(5-cyano-6-morpholinopyridin-3-yl)-4-methylphenyl)-4-(2-fluoropropan-2-yl)picolinamide | $^1$H NMR (400 MHz, <dmso>) δ ppm 1.66 (s, 3 H) 1.68-1.73 (m, 3 H) 2.23 (s, 3 H) 3.56-3.70 (m, 4 H) 3.71-3.78 (m, 4 H) 7.29 (d, J = 8.22 Hz, 1 H) 7.68 (dd, J = 5.09, 1.96 Hz, 1 H) 7.77-7.92 (m, 2 H) 8.13 (dd, J = 6.85, 1.76 Hz, 2 H) 8.45 (d, J = 2.35 Hz, 1 H) 8.72 (d, J = 5.09 Hz, 1 H) 10.65 (s, 1 H). LCMS (m/z) (M + H) = 460.2, Rt = 1.10 min. |
| 246 | 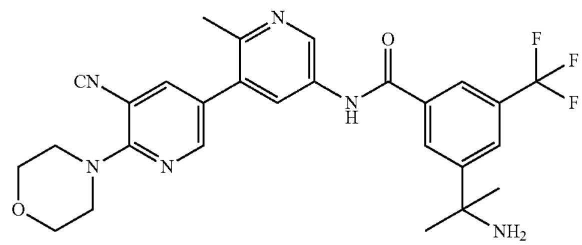 | 3-(2-aminopropan-2-yl)-N-(5'-cyano-2-methyl-6'-morpholino-[3,3'-bipyridin]-5-yl)-5-(trifluoromethyl)benzamide | $^1$H NMR (400 MHz, <dmso>) δ ppm 1.70 (s, 6 H) 2.45 (s, 3 H) 3.69 (d, J = 4.70 Hz, 4 H) 3.75 (br. s., 4 H) 8.01-8.13 (m, 2 H) 8.24 (d, J = 2.35 Hz, 1 H) 8.38 (d, J = 3.91 Hz, 2 H) 8.47-8.66 (m, 4 H) 8.88 (d, J = 2.35 Hz, 1 H) 10.78 (s, 1 H). LCMS (m/z) (M + H) = 525.3, Rt = 0.63 min. |
| 247 | 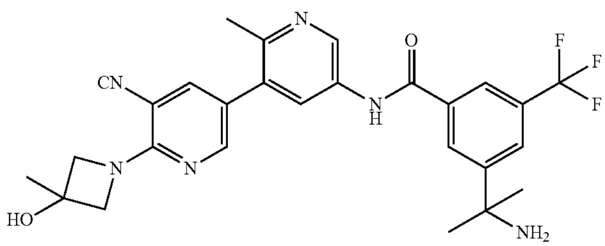 | 3-(2-aminopropan-2-yl)-N-(5'-cyano-6'-(3-hydroxy-3-methylazetidin-1-yl)-2-methyl-[3,3'-bipyridin]-5-yl)-5-(trifluoromethyl)benzamide | $^1$H NMR (400 MHz, <dmso>) δ ppm 1.46 (s, 3 H) 1.70 (s, 6 H) 2.43 (s, 3 H) 4.14 (d, J = 16.82 Hz, 4 H) 7.96-8.02 (m, 1 H) 8.09 (br. s., 2 H) 8.39 (d, J = 1.96 Hz, 3 H) 8.48-8.61 (m, 3H) 8.81-8.90 (m, 1 H) 10.68-10.79 (m, 1 H). LCMS (m/z) (M + H) = 525.3, Rt = 0.57 min. |
| 248 | 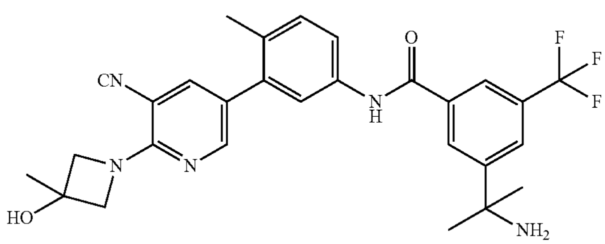 | 3-(2-aminopropan-2-yl)-N-(3-(5-cyano-6-(3-hydroxy-3-methylazetidin-1-yl)pyridin-3-yl)-4-methylphenyl)-5-(trifluoromethyl)benzamide | $^1$H NMR (400 MHz, <dmso>) δ ppm 1.46 (s, 3 H) 1.69 (s, 6 H) 2.22 (s, 3 H) 4.05-4.22 (m, 4 H) 7.21-7.39 (m, 1 H) 7.58 (d, J = 1.96 Hz, 1 H) 7.66-7.75 (m, 1 H) 7.99 (d, J = 1.96 Hz, 1 H) 8.07 (s, 1 H) 8.28-8.39 (m, 3 H) 8.53 (br. s., 2H) 10.50 (s, 1 H). LCMS (M + H) = 524.3, Rt = 0.77 min. |
| 249 | 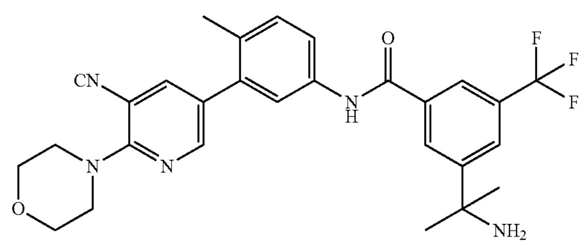 | 3-(2-aminopropan-2-yl)-N-(3-(5-cyano-6-morpholinopyridin-3-yl)-4-methylphenyl)-5-(trifluoromethyl)benzamide | $^1$H NMR (400 MHz, <dmso>) δ ppm 1.69 (s, 6 H) 2.24 (s, 3 H) 3.61-3.70 (m, 4 H) 3.72-3.79 (m, 4 H) 7.34 (s, 1 H) 7.63 (d, J = 1.96 Hz, 1 H) 7.67-7.75 (m, 1 H) 8.08 (s, 1 H) 8.14 (d, J = 2.35 Hz, 1 H) 8.35 (s, 2 H) 8.45 (d, J = 2.35 Hz, 1 H) 8.53 (br. s., 2 H) 10.52 (s, 1 H). LCMS (m/z) (M + H) = 524.3, Rt = 0.85 min. |
| 250 | 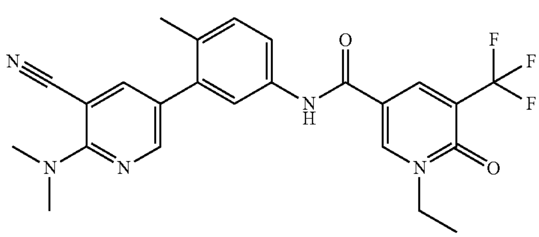 | N-(3-(5-cyano-6-(dimethylamino)pyridin-3-yl)-4-methylphenyl)-1-ethyl-6-oxo-5-(trifluoromethyl)-1,6-dihydropyridine-3-carboxamide | $^1$H NMR (400 MHz, <cd3od>) δ ppm 1.42 (t, J = 7.04 Hz, 3 H) 2.27 (s, 3 H) 3.34 (s, 6 H) 4.16 (q, J = 7.17 Hz, 2 H) 7.30 (d, J = 8.22 Hz, 1 H) 7.49-7.62 (m, 2 H) 7.91 (d, J = 2.35 Hz, 1 H) 8.30 (d, J = 2.35 Hz, 1 H) 8.48 (d, J = 1.57 Hz, 1 H) 8.70 (d, J = 2.35 Hz, 1 H). LCMS (m/z) (M + H) = 470.2, Rt = 0.98 min |

TABLE 8-continued

| Example | Structure | Name | Physical Data |
|---|---|---|---|
| 251 | 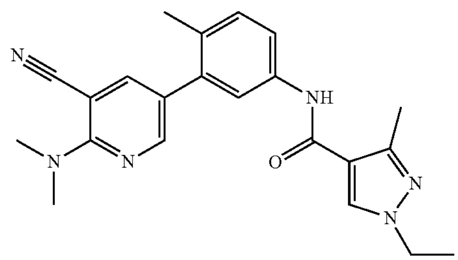 [SMILES: CCn1cc(C(=O)Nc2ccc(C)c(-c3cnc(N(C)C)c(C#N)c3)c2)c(C)n1] | N-(3-(5-cyano-6-(dimethylamino)pyridin-3-yl)-4-methylphenyl)-1-ethyl-3-methyl-1H-pyrazole-4-carboxamide | $^1$H NMR (500 MHz, DMSO-$d_6$) δ ppm 1.39 (t, J = 7.25 Hz, 3 H) 2.21 (s, 3 H) 2.35 (s, 3 H) 3.27 (s, 6 H) 4.10 (q, J = 7.25 Hz, 2 H) 7.24 (d, J = 8.20 Hz, 1 H) 7.54-7.65 (m, 2 H) 7.99 (d, J = 2.52 Hz, 1 H) 8.33 (s, 1 H) 8.36 (d, J = 2.52 Hz, 1 H) 9.65 (s, 1 H). LCMS (m/z) (M + H) = 389.1, Rt = 0.86 min. |
| 252 | 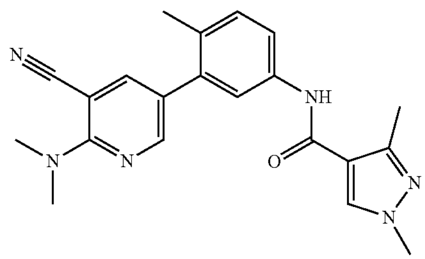 [SMILES: Cc1ccc(NC(=O)c2cn(C)nc2C)cc1-c1cnc(N(C)C)c(C#N)c1] | N-(3-(5-cyano-6-(dimethylamino)pyridin-3-yl)-4-methylphenyl)-1,3-dimethyl-1H-pyrazole-4-carboxamide | $^1$H NMR (500 MHz, DMSO-$d_6$) δ ppm 2.20 (s, 3 H) 2.33 (s, 3 H) 3.26 (s, 6 H) 3.81 (s, 3 H) 7.23 (d, J = 8.83 Hz, 1 H) 7.51-7.67 (m, 2 H) 7.99 (d, J = 2.52 Hz, 1 H) 8.27 (s, 1 H) 8.35 (d, J = 2.52 Hz, 1 H) 9.65 (s, 1 H). LCMS (m/z) (M + H) = 375.1, Rt = 0.81 min. |
| 253 | 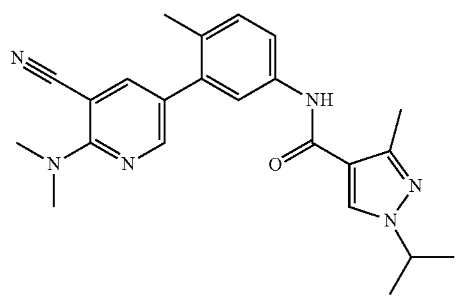 [SMILES: Cc1ccc(NC(=O)c2cn(C(C)C)nc2C)cc1-c1cnc(N(C)C)c(C#N)c1] | N-(3-(5-cyano-6-(dimethylamino)pyridin-3-yl)-4-methylphenyl)-1-isopropyl-3-methyl-1H-pyrazole-4-carboxamide | $^1$H NMR (500 MHz, DMSO-$d_6$) δ ppm 1.42 (d, J = 6.62 Hz, 6 H) 2.21 (s, 3 H) 2.35 (s, 3 H) 3.26 (s, 6 H) 4.44 (spt, J = 6.67 Hz, 1 H) 7.24 (d, J = 8.20 Hz, 1 H) 7.52-7.64 (m, 2 H) 7.99 (dd, J = 2.52, 0.63 Hz, 1 H) 8.36 (d, J = 2.21 Hz, 1 H) 8.38 (s, 1 H) 9.62 (s, 1 H). LCMS (m/z) (M + H) = 403.1, Rt = 0.92 min. |
| 254 | 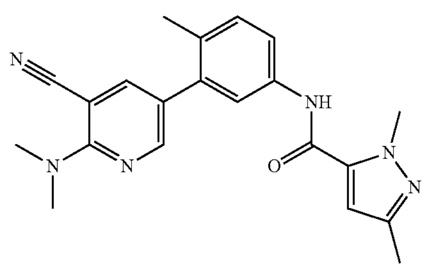 [SMILES: Cc1cc(C(=O)Nc2ccc(C)c(-c3cnc(N(C)C)c(C#N)c3)c2)n(C)n1] | N-(3-(5-cyano-6-(dimethylamino)pyridin-3-yl)-4-methylphenyl)-1,3-dimethyl-1H-pyrazole-5-carboxamide | $^1$H NMR (500 MHz, DMSO-$d_6$) δ ppm 2.19 (s, 3 H) 2.22 (s, 3 H) 3.27 (s, 6 H) 3.99 (s, 3 H) 6.82 (s, 1 H) 7.28 (d, J = 8.20 Hz, 1 H) 7.56-7.71 (m, 2 H) 8.00 (d, J = 2.52 Hz, 1 H) 8.36 (d, J = 2.52 Hz, 1 H) 10.12 (s, 1 H). LCMS (m/z) (M + H) = 375.1, Rt = 0.90 min. |
| 255 | 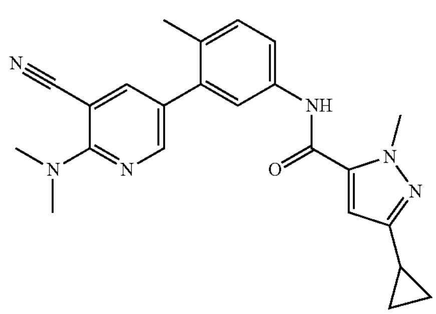 [SMILES: Cc1ccc(NC(=O)c2cc(C3CC3)nn2C)cc1-c1cnc(N(C)C)c(C#N)c1] | N-(3-(5-cyano-6-(dimethylamino)pyridin-3-yl)-4-methylphenyl)-3-cyclopropyl-1-methyl-1H-pyrazole-5-carboxamide | LCMS (m/z) (M + H) = 401.1, Rt = 0.98 min. |

TABLE 8-continued

| Example | Structure | Name | Physical Data |
|---------|-----------|------|---------------|
| 256 | 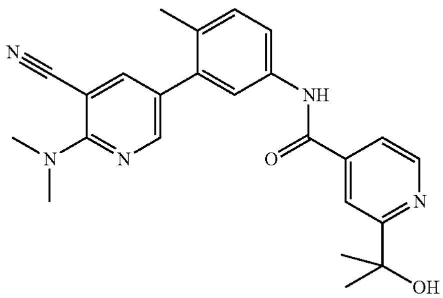 [SMILES: Cc1ccc(NC(=O)c2ccnc(C(C)(C)O)c2)cc1-c1cnc(N(C)C)c(C#N)c1] | N-(3-(5-cyano-6-(dimethylamino)pyridin-3-yl)-4-methylphenyl)-2-(2-hydroxypropan-2-yl)isonicotinamide | $^1$H NMR (500 MHz, DMSO-$d_6$) δ ppm 1.50 (s, 6 H) 2.24 (s, 3 H) 3.27 (s, 6 H) 7.31 (d, J = 8.20 Hz, 1 H) 7.66 (d, J = 2.21 Hz, 1 H) 7.72 (dd, J = 8.20, 2.21 Hz, 1 H) 7.76 (d, J = 4.10 Hz, 1 H) 8.02 (d, J = 2.21 Hz, 1 H) 8.18 (s, 1 H) 8.38 (d, J = 2.52 Hz, 1 H) 8.71 (d, J = 5.04 Hz, 1 H) 10.56 (s, 1 H). LCMS (m/z) (M + H) = 416.1, Rt = 0.74 min. |
| 257 | 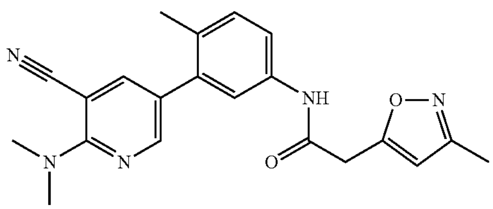 | N-(3-(5-cyano-6-(dimethylamino)pyridin-3-yl)-4-methylphenyl)-2-(3-methylisoxazol-5-yl)acetamide | $^1$H NMR (500 MHz, DMSO-$d_6$) δ ppm 2.20 (d, J = 5.36 Hz, 6 H) 3.26 (s, 6 H) 3.87 (s, 2 H) 6.26 (s, 1 H) 7.24 (d, J = 8.20 Hz, 1 H) 7.41-7.55 (m, 2 H) 7.98 (d, J = 2.52 Hz, 1 H) 8.33 (d, J = 2.52 Hz, 1 H) 10.30 (s, 1 H). LCMS (m/z) (M + H) = 376.1, Rt = 0.86 min. |
| 258 | 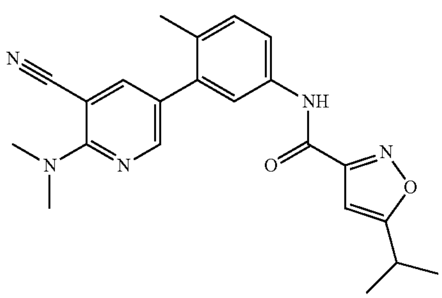 [SMILES: Cc1ccc(NC(=O)c2cc(C(C)C)on2)cc1-c1cnc(N(C)C)c(C#N)c1] | N-(3-(5-cyano-6-(dimethylamino)pyridin-3-yl)-4-methylphenyl)-5-isopropylisoxazole-3-carboxamide | $^1$H NMR (500 MHz, DMSO-$d_6$) δ ppm 1.29 (d, J = 6.94 Hz, 6 H) 2.23 (s, 3 H) 3.18 (spt, J = 6.94 Hz, 1 H) 3.27 (s, 6 H) 6.67 (s, 1 H) 7.29 (d, J = 8.51 Hz, 1 H) 7.66 (d, J = 2.21 Hz, 1 H) 7.70 (dd, J = 8.20, 2.21 Hz, 1 H) 8.00 (d, J = 2.52 Hz, 1 H) 8.36 (d, J = 2.52 Hz, 1 H) 10.62 (s, 1 H). LCMS (m/z) (M + H) = 390.1, Rt = 1.12 min. |
| 259 | 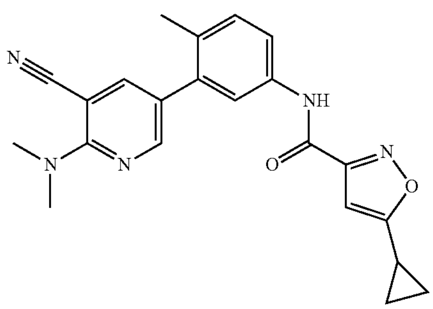 [SMILES: Cc1ccc(NC(=O)c2cc(C3CC3)on2)cc1-c1cnc(N(C)C)c(C#N)c1] | N-(3-(5-cyano-6-(dimethylamino)pyridin-3-yl)-4-methylphenyl)-5-cyclopropylisoxazole-3-carboxamide | $^1$H NMR (500 MHz, DMSO-$d_6$) δ ppm 0.93-0.99 (m, 2 H) 1.09-1.15 (m, 2 H) 2.19-2.27 (m, 4 H) 3.26 (s, 6 H) 6.61 (s, 1 H) 7.28 (d, J = 8.51 Hz, 1 H) 7.65 (d, J = 2.21 Hz, 1 H) 7.69 (dd, J = 8.20, 2.21 Hz, 1 H) 8.00 (d, J = 2.21 Hz, 3 H) 8.35 (d, J = 2.52 Hz, 1 H) 10.59 (s, 1 H). LCMS (m/z) (M + H) = 388.1, Rt = 1.07 min. |
| 260 | 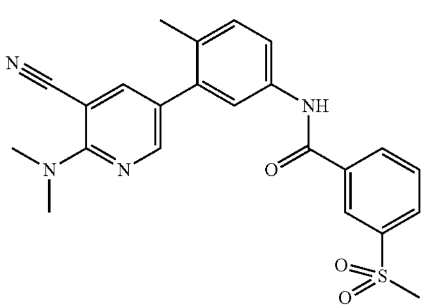 | N-(3-(5-cyano-6-(dimethylamino)pyridin-3-yl)-4-methylphenyl)-3-(methylsulfonyl)benzamide | $^1$H NMR (500 MHz, DMSO-$d_6$) δ ppm 2.24 (s, 3 H) 3.27 (s, 6 H) 3.30 (s, 3 H) 7.31 (d, J = 8.20 Hz, 1 H) 7.65 (d, J = 1.89 Hz, 1 H) 7.72 (dd, J = 8.20, 2.21 Hz, 1 H) 7.83 (t, J = 7.72 Hz, 1 H) 8.02 (d, J = 2.21 Hz, 1 H) 8.14 (d, J = 7.88 Hz, 1 H) 8.29 (d, J = 7.88 Hz, 1 H) 8.38 (d, J = 2.21 Hz, 1 H) 8.48 (s, 1 H) 10.53 (s, 1 H). LCMS (m/z) (M + H) = 435.0, Rt = 0.91 min. |

TABLE 8-continued

| Example | Structure | Name | Physical Data |
|---|---|---|---|
| 261 | 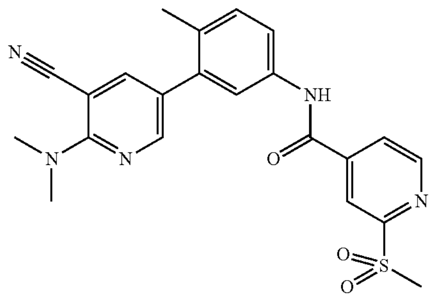 | N-(3-(5-cyano-6-(dimethylamino)pyridin-3-yl)-4-methylphenyl)-2-(methylsulfonyl)isonicotinamide | $^1$H NMR (500 MHz, DMSO-$d_6$) δ ppm 2.25 (s, 3 H) 3.27 (s, 6 H) 3.35 (s, 3 H) 7.33 (d, J = 8.51 Hz, 1 H) 7.66 (d, J = 2.21 Hz, 1 H) 7.72 (dd, J = 8.35, 2.05 Hz, 1 H) 8.02 (d, J = 2.52 Hz, 1 H) 8.22 (dd, J = 4.89, 1.42 Hz, 1 H) 8.38 (d, J = 2.52 Hz, 1 H) 8.53 (s, 1 H) 9.01 (d, J = 5.04 Hz, 1 H) 10.79 (s, 1 H). LCMS (m/z) (M + H) = 436.0, Rt = 0.84 min. |
| 262 | 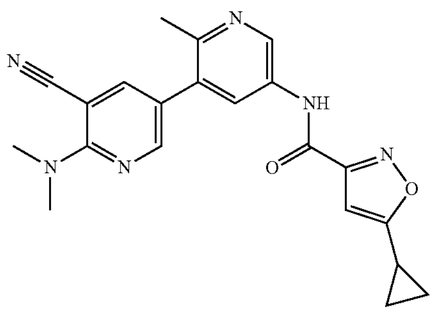 [SMILES: Cc1ncc(NC(=O)c2cc(C3CC3)on2)cc1-c1cnc(N(C)C)c(C#N)c1] | N-(5'-cyano-6'-(dimethylamino)-2-methyl-[3,3'-bipyridin]-5-yl)-5-cyclopropylisoxazole-3-carboxamide | LCMS (m/z) (M + H) = 389.2, Rt = 0.71 min. |
| 263 | 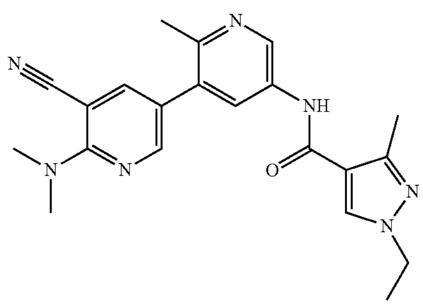 [SMILES: CCn1cc(C(=O)Nc2cnc(C)c(-c3cnc(N(C)C)c(C#N)c3)c2)c(C)n1] | N-(5'-cyano-6'-(dimethylamino)-2-methyl-[3,3'-bipyridin]-5-yl)-1-ethyl-3-methyl-1H-pyrazole-4-carboxamide | $^1$H NMR (500 MHz, DMSO-$d_6$) δ ppm 1.40 (t, J = 7.25 Hz, 3 H) 2.37 (s, 3 H) 3.29 (s, 6 H) 4.13 (q, J = 7.25 Hz, 2 H) 8.15 (d, J = 2.52 Hz, 1 H) 8.19 (s, 1 H) 8.37 (s, 1 H) 8.45 (d, J = 2.52 Hz, 1 H) 8.93 (s, 1 H) 10.15 (br. s., 1 H). LCMS (m/z) (M + H) = 390.1, Rt = 0.60 min. |
| 264 | 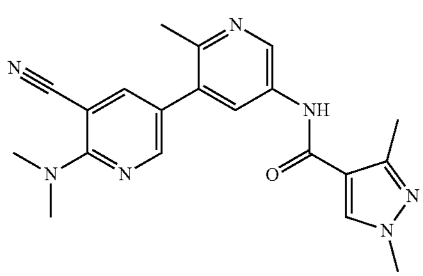 [SMILES: Cc1nn(C)cc1C(=O)Nc1cnc(C)c(-c2cnc(N(C)C)c(C#N)c2)c1] | N-(5'-cyano-6'-(dimethylamino)-2-methyl-[3,3'-bipyridin]-5-yl)-1,3-dimethyl-1H-pyrazole-4-carboxamide | LCMS (m/z) (M + H) = 376.1, Rt = 0.56 min. |
| 265 | 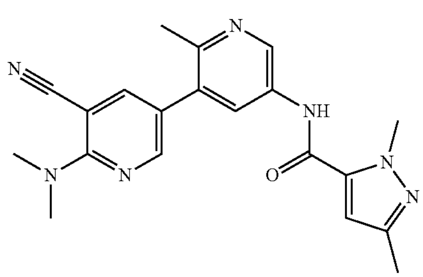 [SMILES: Cc1cc(C(=O)Nc2cnc(C)c(-c3cnc(N(C)C)c(C#N)c3)c2)n(C)n1] | N-(5'-cyano-6'-(dimethylamino)-2-methyl-[3,3'-bipyridin]-5-yl)-1,3-dimethyl-1H-pyrazole-5-carboxamide | $^1$H NMR (500 MHz, DMSO-$d_6$) δ ppm 2.21 (s, 3 H) 3.29 (s, 6 H) 4.01 (s, 3 H) 6.87 (s, 1 H) 8.08-8.21 (m, 2 H) 8.44 (d, J = 2.52 Hz, 1 H) 8.88 (d, J = 1.89 Hz, 1 H) 10.49 (s, 1 H). LCMS (m/z) (M + H) = 376.2, Rt = 0.64 min. |

TABLE 8-continued

| Example | Structure | Name | Physical Data |
|---|---|---|---|
| 266 | 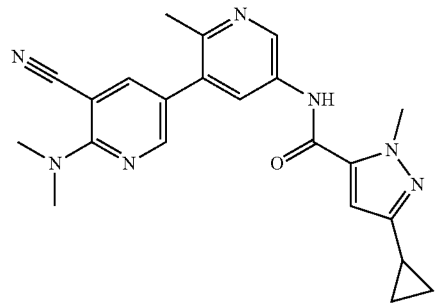 [SMILES: Cc1ncc(NC(=O)c2cc(C3CC3)nn2C)cc1-c1cnc(N(C)C)c(C#N)c1] | N-(5'-cyano-6'-(dimethylamino)-2-methyl-[3,3'-bipyridin]-5-yl)-3-cyclopropyl-1-methyl-1H-pyrazole-5-carboxamide | ¹H NMR (500 MHz, DMSO-d₆) δ ppm 0.56-0.76 (m, 2 H) 0.83-1.00 (m, 2 H) 1.83-2.02 (m, 1 H) 2.51-2.54 (m, 4 H) 3.29 (s, 6 H) 4.00 (s, 3 H) 6.80 (s, 1 H) 8.15 (d, J = 2.52 Hz, 1 H) 8.21 (s, 1 H) 8.45 (dd, J = 2.52, 0.63 Hz, 1 H) 8.92 (d, J = 1.89 Hz, 1 H) 10.54 (s, 1 H). LCMS (m/z) (M + H) = 402.2, Rt = 0.68 min. |
| 267 | 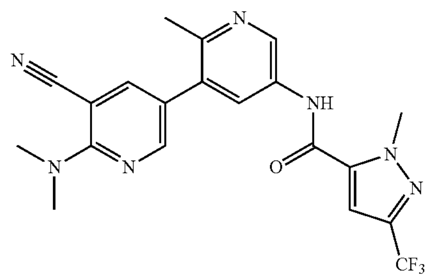 [SMILES: Cc1ncc(NC(=O)c2cc(C(F)(F)F)nn2C)cc1-c1cnc(N(C)C)c(C#N)c1] | N-(5'-cyano-6'-(dimethylamino)-2-methyl-[3,3'-bipyridin]-5-yl)-1-methyl-3-(trifluoromethyl)-1H-pyrazole-5-carboxamide | ¹H NMR (500 MHz, DMSO-d₆) δ ppm 2.48 (s, 3 H) 3.29 (s, 6 H) 4.18 (s, 3 H) 7.54 (s, 1 H) 8.09 (s, 1 H) 8.12-8.14 (m, 1 H) 8.38-8.49 (m, 1 H) 8.83 (d, J = 2.21 Hz, 1 H) 10.71 (s, 1 H). LCMS (m/z) (M + H) = 430.2, Rt = 0.75 min. |
| 268 | 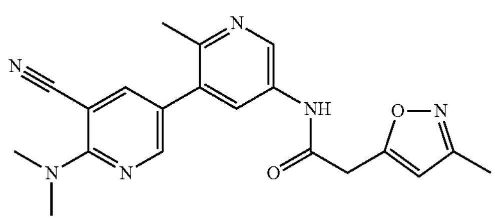 | N-(5'-cyano-6'-(dimethylamino)-2-methyl-[3,3'-bipyridin]-5-yl)-2-(3-methylisoxazol-5-yl)acetamide | LCMS (m/z) (M + H) = 377.2, Rt = 0.56 min. |
| 269 | 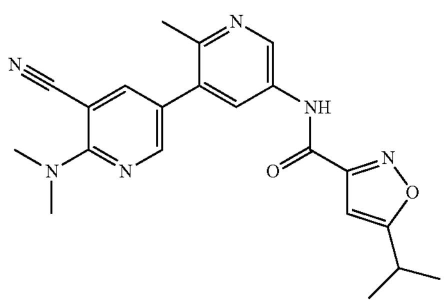 [SMILES: Cc1ncc(NC(=O)c2cc(C(C)C)on2)cc1-c1cnc(N(C)C)c(C#N)c1] | N-(5'-cyano-6'-(dimethylamino)-2-methyl-[3,3'-bipyridin]-5-yl)-5-isopropylisoxazole-3-carboxamide | ¹H NMR (500 MHz, DMSO-d₆) δ ppm 1.30 (d, J = 6.94 Hz, 6 H) 3.20 (spt, J = 6.88 Hz, 1 H) 3.29 (s, 6 H) 6.73 (s, 1 H) 8.14 (d, J = 2.52 Hz, 1 H) 8.20 (s, 1 H) 8.43 (d, J = 2.52 Hz, 1 H) 8.94 (d, J = 1.89 Hz, 1 H) 11.07 (s, 1 H). LCMS (m/z) (M + H) = 391.2, Rt = 0.74 min. |
| 270 | 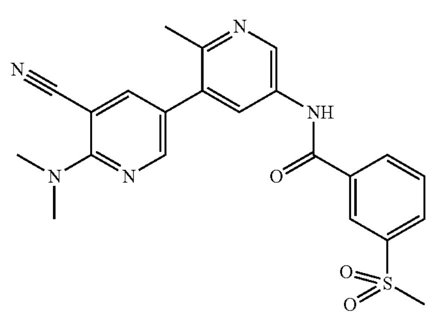 | N-(5'-cyano-6'-(dimethylamino)-2-methyl-[3,3'-bipyridin]-5-yl)-3-(methylsulfonyl)benzamade | LCMS (m/z) (M + H) = 436.1, Rt = 0.61 min. |

TABLE 8-continued

| Example | Structure | Name | Physical Data |
|---|---|---|---|
| 271 | 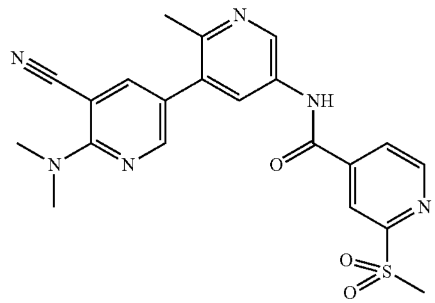 | N-(5'-cyano-6'-(dimethylamino)-2-methyl-[3,3'-bipyridin]-5-yl)-2-(methylsulfonyl)isonicotinamide | $^1$H NMR (500 MHz, DMSO-$d_6$) δ ppm 2.52 (s, 3 H) 3.29 (s, 6 H) 3.37 (s, 3 H) 8.16 (d, J = 2.52 Hz, 1 H) 8.20 (d, J = 1.58 Hz, 1 H) 8.25 (dd, J = 4.89, 1.10 Hz, 1 H) 8.46 (d, J = 2.52 Hz, 1 H) 8.58 (s, 1 H) 8.96 (d, J = 1.89 Hz, 1 H) 9.05 (d, J = 4.73 Hz, 1 H) 11.17 (s, 1 H). LCMS (m/z) (M + H) = 437.1, Rt = 0.58 min. |
| 272 | 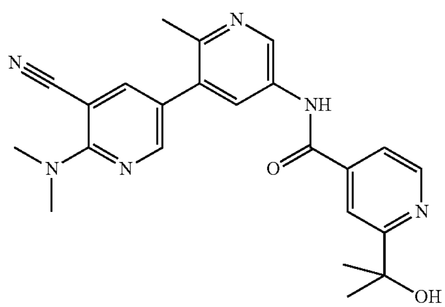 [SMILES: Cc1ncc(NC(=O)c2ccnc(C(C)(C)O)c2)cc1-c1cnc(N(C)C)c(C#N)c1] | N-(5'-cyano-6'-(dimethylamino)-2-methyl-[3,3'-bipyridin]-5-yl)-2-(2-hydroxypropan-2-yl)isonicotinamide | $^1$H NMR (500 MHz, DMSO-$d_6$) δ ppm 1.50 (s, 7 H) 2.55 (s, 3 H) 3.30 (s, 7 H) 7.77 (dd, J = 5.04, 1.58 Hz, 1 H) 8.17 (d, J = 2.21 Hz, 1 H) 8.22 (s, 1 H) 8.30 (s, 1 H) 8.47 (d, J = 2.21 Hz, 1 H) 8.75 (d, J = 5.04 Hz, 1 H) 9.03 (d, J = 1.89 Hz, 1 H) 11.04 (s, 1 H). LCMS (m/z) (M + H) = 417.1, R.t = 0.52 min. |
| 273 | 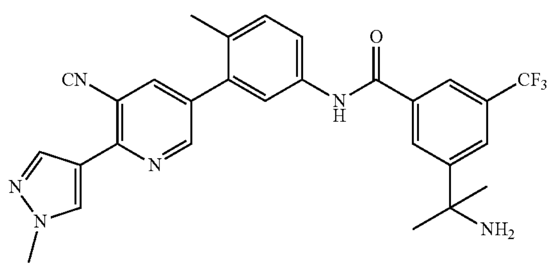 | 3-(2-aminopropan-2-yl)-N-(3-(5-cyano-6-(1-methyl-1H-pyrazol-4-yl)pyridin-3-yl)-4-methylphenyl)-5-(trifluoromethyl)benzamide | LCMS (m/z) (M + H) = 519.2, Rt = 0.84 min. $^1$H NMR (400 MHz, <dmso>) δ ppm 1.69 (s, 6 H) 2.27 (s, 3 H) 3.96 (s, 3 H) 7.34-7.42 (m, 1 H) 7.66-7.72 (m, 1 H) 7.75-7.81 (m, 1H) 8.03-8.13 (m, 1 H) 8.20 (d, J = 0.78 Hz, 1 H) 8.36 (d, J = 2.35 Hz, 3 H) 8.51 (s, 1 H) 8.52-8.57 (m, 2 H) 8.82 (d, J = 2.35 Hz, 1 H) 10.55-10.60 (m, 1 H). |

Example 274

N-(5'-cyano-6'-isopropyl-2-methyl-[3,3'-bipyridin]-5-yl)-2-(trifluoromethyl)isonicotinamide

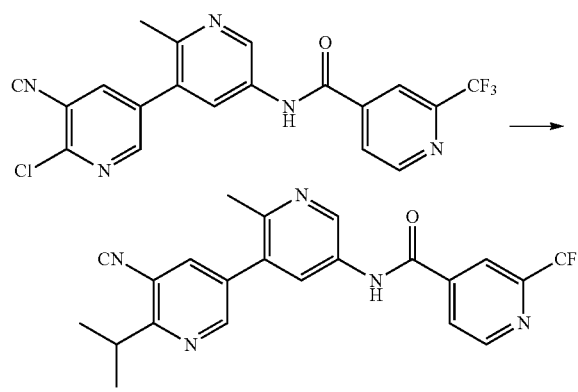

To a solution of N-(6'-chloro-5'-cyano-2-methyl-[3,3'-bipyridin]-5-yl)-2-(trifluoromethyl)isonicotinamide (1.0 equiv.) and 4,4,5,5-tetramethyl-2-(prop-1-en-2-yl)-1,3,2-dioxaborolane (3.0 equiv.) in toluene and ethanol (2.5:1, 0.07M) was added Pd(PPh$_3$)$_4$ and potassium carbonate (3.0 equiv., 3M aqueous sln). The reaction was heated in the microwave at 120° C. for 20 min. Partitioned between water and sat. NaCl, mixed, separated the layers, dried the organic phase with MgSO$_4$, filtered, concentrated and dried on the high vacuum overnight. The crude material was dissolved in methanol and the homogeneous solution was degassed by pulling a house vacuum and purged to Argon. Pd/C (Degussa type, 0.1 equiv.) was added, followed by a hydrogen balloon. The reaction was stirred under hydrogen overnight. Filtered through a 1 μM HPLC filter, rinsed with ethyl acetate, concentrated the filtrate, dissolved in DMSO and purified via reverse phase-HPLC. The pure fractions were lyophilized to yield N-(5'-cyano-6'-isopropyl-2-methyl-[3,3'-bipyridin]-5-yl)-2-(trifluoromethyl)isonicotinamide in 45% yield. $^1$H NMR (400 MHz, DMSO$_{d6}$) δ 11.02 (s, 1H), 9.04 (d, J=4.0, 1H), 8.92 (d, J=2.0, 1H), 8.90 (d, J=2.0, 1H), 8.44 (d, J=2.0, 1H), 8.39 (s, 1H), 8.22 (d, J=4.0, 1H), 8.19 (d, J=2.0, 1H), 3.40 (septet, J=8.0, 1H), 2.47 (s, 3H), 1.34 (d, J=8.0, 6H). LCMS (m/z) (M+H)=426.1, Rt=0.78 min.

Example 275

N-(5'-cyano-6'-isopropyl-2-methyl-[3,3'-bipyridin]-5-yl)-2-(2-cyanopropan-2-yl)isonicotinamide

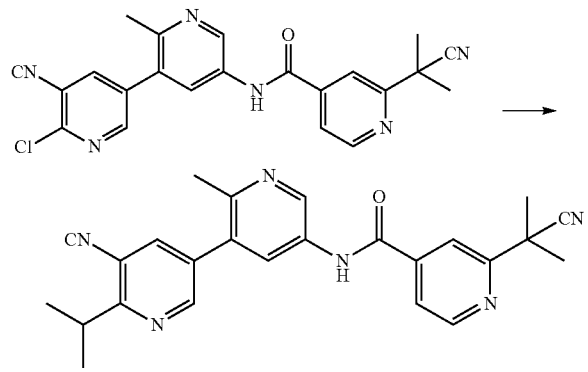

To a solution of N-(6'-chloro-5'-cyano-2-methyl-[3,3'-bipyridin]-5-yl)-2-(2-cyanopropan-2-yl)isonicotinamide (1.0 equiv.) and 4,4,5,5-tetramethyl-2-(prop-1-en-2-yl)-1,3,2-dioxaborolane (3.0 equiv.) in toluene and ethanol (2.5:1, 0.07M) was added Pd(PPh₃)₄ and potassium carbonate (3.0 equiv., 3M aqueous sln). The reaction was heated in the microwave at 120° C. for 20 min. Partitioned between water and sat. NaCl, mixed, separated the layers, dried the organic phase with MgSO₄, filtered, concentrated and dried on the high vacuum overnight. The crude material was dissolved in methanol and the homogeneous solution was degassed by pulling a house vacuum and purged to Argon. Pd/C (Degussa type, 0.1 equiv.) was added, followed by a hydrogen balloon. The reaction was stirred under hydrogen overnight. Filtered through a 1 µM HPLC filter, rinsed with ethyl acetate, concentrated the filtrate, dissolved in DMSO and purified via reverse phase-HPLC. The pure fractions were lyophilized to yield N-(5'-cyano-6'-isopropyl-2-methyl-[3,3'-bipyridin]-5-yl)-2-(2-cyanopropan-2-yl)isonicotinamide in 43% yield. ¹H NMR (400 MHz, DMSO$_{d6}$) δ ppm 10.90 (s, 1H), 8.92 (d, J=4.0, 1H), 8.90 (d, J=4.0, 1H), 8.85 (d, J=8.0, 1H), 8.44 (d, J=2.0, 1H), 8.18 (d, J=2.0, 1H), 8.04 (s, 1H), 7.89 (d, J=8.0, 1H), 3.50 (septet, J=8.0, 1H), 2.47 (s, 3H), 1.77 (s, 6H), 1.34 (d, J=8.0, 6H). LCMS (m/z) (M+H)=425.1, Rt=0.74 min.

Example 276

N-(5'-cyano-2-methyl-6'-(tetrahydro-2H-pyran-4-yl)-[3,3'-bipyridin]-5-yl)-2-(2-cyanopropan-2-yl)isonicotinamide

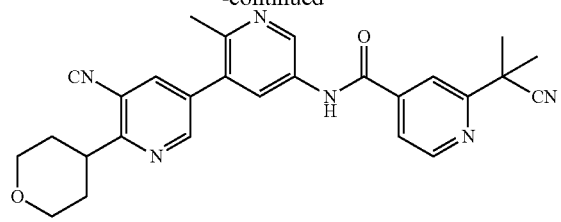

To a solution of N-(6'-chloro-5'-cyano-2-methyl-[3,3'-bipyridin]-5-yl)-2-(2-cyanopropan-2-yl)isonicotinamide (1.0 equiv.), 2-(3,6-dihydro-2H-pyran-4-yl)-4,4,5,5-tetramethyl-1,3,2-dioxaborolane (2.0 equiv.) and sodium carbonate (1.0 equiv., 2 M aqueous solution) in DME (0.2 M) was added PdCl₂(dppf)-DCM adduct (0.2 equiv.) and the reaction was heated in the microwave at 110° C. for 15 min. The reaction mixture was diluted with ethyl acetate and washed with water, then sat. NaCl. The organic layer was dried with sodium sulfate, filtered and concentrated. The residue was purified via silica gel chromatography (ISCO, 0-100% ethyl acetate/heptanes) to give N-(5'-cyano-6'-(3,6-dihydro-2H-pyran-4-yl)-2-methyl-[3,3'-bipyridin]-5-yl)-2-(2-cyanopropan-2-yl)isonicotinamide. This product was dissolved in MeOH/Ethyl acetate (3:1) and Pd/C (0.8 equiv.) was added. The reaction was stirred at rt under a hydrogen balloon for 16 hours. The solution was filtered through Celite and washed with ethyl acetate and concentrated. The crude was purified via reverse phase prep-HPLC and the pure fractions were lyophilized to give N-(5'-cyano-2-methyl-6'-(tetrahydro-2H-pyran-4-yl)-[3,3-'bipyridin]-5-yl)-2-(2-cyanopropan-2-yl)isonicotinamide in 5% yield as the TFA salt. ¹H NMR (400 MHz, <dmso>) δ ppm 1.73-1.81 (m, 8 H) 1.86-2.02 (m, 2 H) 2.44 (s, 3 H) 3.34-3.44 (m, 1 H) 3.45-3.57 (m, 2 H) 3.95-4.04 (m, 2 H) 7.76-7.91 (m, 1 H) 8.02 (s, 1 H) 8.08-8.16 (m, 1 H) 8.45 (d, J=2.35 Hz, 1 H) 8.90 (d, J=1.96 Hz, 3 H) 10.84 (s, 1 H). LCMS (m/z) (M+H)=467.2, Rt=0.67 min.

Example 277

4-(aminomethyl)-N-(3-(5-cyano-6-(dimethylamino)pyridin-3-yl)-4-methylphenyl)-3-(trifluoromethyl)benzamide

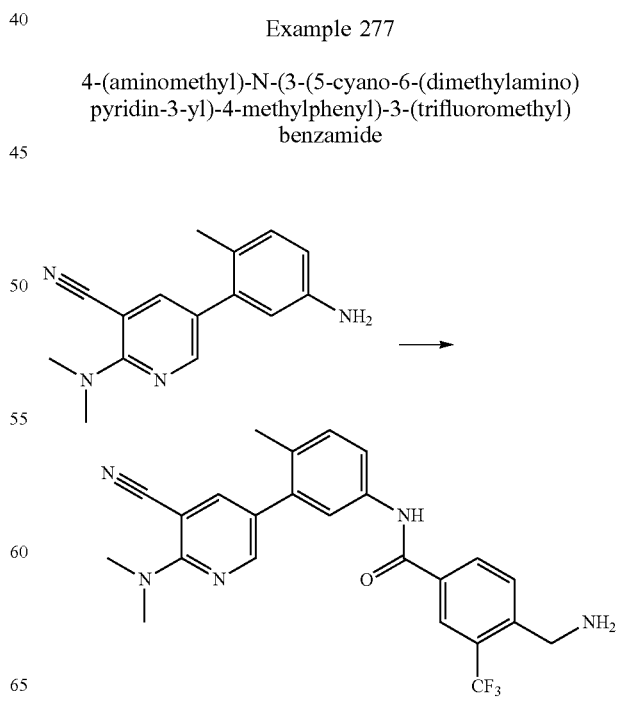

A solution of 5-(5-amino-2-methylphenyl)-2-(dimethylamino)nicotinonitrile (1.0 equiv.), 4-(bromomethyl)-3-(trifluoromethyl)benzoic acid (1.1 equiv.), EDC (1.0 equiv.) and HOAt (1.0 equiv.) in DMF (0.15 M) was stirred at rt overnight. To this reaction as added ammonia in methanol (24 equiv, 7 M solution) and heated to 50° C. Upon completion, the reaction was purified via reverse phase prep-HPLC and the pure fractions were lyophilized to provide 4-(aminomethyl)-N-(3-(5-cyano-6-(dimethylamino)pyridin-3-yl)-4-methylphenyl)-3-(trifluoromethyl)benzamide in 3% yield as the TFA salt. LCMS (m/z) (M+H)=454.3. Rt=0.78 min.

Example 278

3-(5-cyano-6-(piperazin-1-yl)pyridin-3-yl)-4-methyl-N-(2-(trifluoromethyl)pyridin-4-yl)benzamide

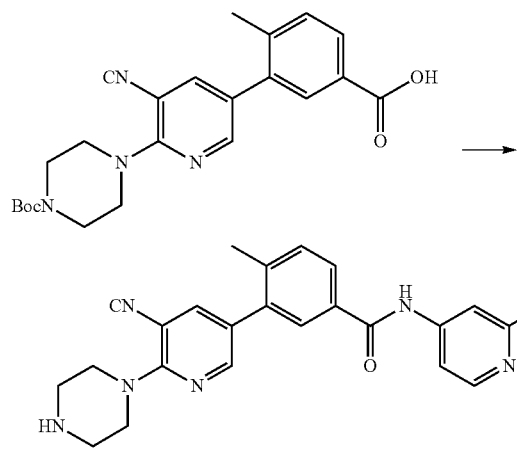

To a stirred solution of 3-(6-(4-(tert-butoxycarbonyl)piperazin-1-yl)-5-cyanopyridin-3-yl)-4-methylbenzoic acid (1.0 equiv.) in DCM (0.06 M) at 0° C. was added 1-chloro-N,N,2-trimethyl-1-propenylamine (1.6 equiv.) and the mixture was allowed to stir at 0° C. for 1 h. The solution was subsequently added to a solution of 4-amino-2-(trifluoromethyl)pyridine (1.7 equiv.) and Et$_3$N (2.0 equiv.) in DCM and the reaction was allowed to warm to rt and stirred for 1 h. Concentrated and dissolved in DCM and washed with sat. NaHCO$_3$. The organic layer was washed with brine, dried over sodium sulfate and concentrated. Redissolved in DCM and TFA (2:1) and stirred at rt for 2 hr. The reaction was concentrated and purified by prep HPLC. Upon lyophilization, isolated 3-(5-cyano-6-(piperazin-1-yl)pyridin-3-yl)-4-methyl-N-(2-(trifluoromethyl)pyridin-4-yl)benzamide in 17% yield. LCMS (m/z) (M+H)=467.2, Rt=0.77 min. $^1$H NMR (400 MHz, <dmso> δ ppm 2.34 (s, 3 H) 3.29 (br. s., 4 H) 3.81-3.86 (m, 4 H) 7.49-7.58 (m, 1 H) 7.88 (d, J=1.96 Hz, 1 H) 7.92-8.00 (m, 1 H) 8.03-8.08 (m, 1 H) 8.27 (d, J=1.57 Hz, 1 H) 8.32 (d, J=2.35 Hz, 1 H) 8.56 (d, J=2.35 Hz, 1 H) 8.63-8.70 (m, 1 H) 8.74-8.89 (m, 2 H) 10.84 (s, 1 H).

Example 279

3-(5-cyano-6-(piperazin-1-yl)pyridin-3-yl)-4-methyl-N-(2-(methylsulfonyl)pyridin-4-yl)benzamide

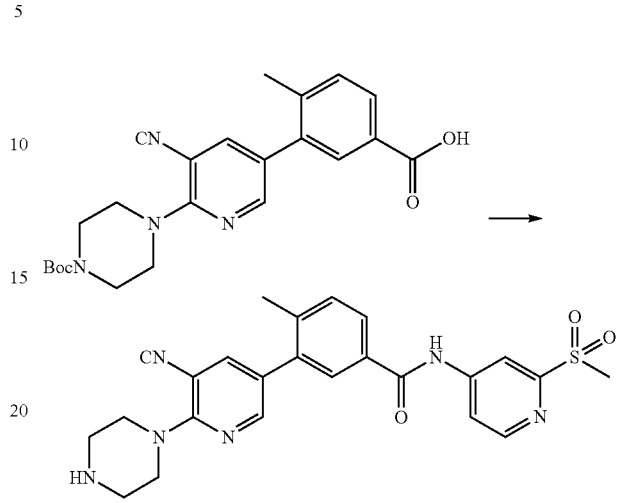

To a stirred solution of 3-(6-(4-(tert-butoxycarbonyl)piperazin-1-yl)-5-cyanopyridin-3-yl)-4-methylbenzoic acid (1.0 equiv.) in DCM (0.06 M) at 0° C. was added 1-chloro-N,N,2-trimethyl-1-propenylamine (1.6 equiv.) and the mixture was allowed to stir at 0° C. for 1 h. The solution was subsequently added to a solution of 2-(methylsulfonyl)pyridin-4-amine (1.7 equiv.) and Et$_3$N (2.0 equiv.) in DCM and the reaction was allowed to warm to rt and stirred for 1 h. Concentrated and dissolved in DCM and washed with sat. NaHCO$_3$. The organic layer was washed with brine, dried over sodium sulfate and concentrated. Redissolved in DCM and TFA (2:1) and stirred at rt for 2 hr. The reaction was concentrated and purified by prep HPLC. Upon lyophilization, isolated 3-(5-cyano-6-(piperazin-1-yl)pyridin-3-yl)-4-methyl-N-(2-(methylsulfonyl)pyridin-4-yl)benzamide in 16% yield. LCMS (m/z) (M+H)=477.1, Rt=0.63 min. 1H NMR (400 MHz, <dmso>) δ ppm 2.35 (s, 3 H) 3.25-3.31 (m, 7 H) 3.82-3.87 (m, 4 H) 7.55 (s, 1 H) 7.90 (d, J=1.96 Hz, 1 H) 7.94-7.98 (m, 1 H) 8.11 (dd, J=5.48, 1.96 Hz, 1 H) 8.32 (d, J=2.74 Hz, 1 H) 8.47 (d, J=1.57 Hz, 1 H) 8.56 (d, J=2.35 Hz, 1 H) 8.67 (d, J=5.48 Hz, 1 H) 8.77-8.84 (m, 2 H) 10.90 (s, 1 H).

ASSAYS

The activity of a compound according to the present invention can be assessed by well-known in vitro & in vivo methods. Raf inhibition data provided herein was obtained using the following procedures.

In Vitro Raf Activity Determination: The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf TR refers to a truncated C-Raf protein, a Δ1-324 deletion mutant. C-Raf FL refers to the full-length C-Raf protein.

Full length MEK1 with an inactivating K97R ATP binding site mutation is utilized as a RAF substrate. The MEK1 cDNA was subcloned with an N-terminal $(his)_6$ tag into a vector for *E. Coli* expression. The MEK1 substrate was purified from *E. Coli* lysate by nickel affinity chromatography followed by anion exchange. The final MEK1 preparation was biotinylated (Pierce EZ-Link Sulfo-NHS-LC-Biotin) and concentrated.

Assay Materials: Assay buffer is 50 mM Tris, pH 7.5, 15 mM $MgCl_2$, 0.01% Bovine Serum Albumin (BSA) and 1 mM dithiothreitol (DTT); Stop buffer is 60 mM ethylenediaminetetraacetic acid (EDTA) and 0.01% Tween® 20; b-Raf (V600E), active; biotinylated Mek, kinase dead; Alpha Screen detection kit (available from PerkinElmer™, #6760617R); Anti phospho-MEK1/2 (available from Cell Signaling Technology, Inc. #9121); 384 well low volume assay plates (White Greiner® plates).

Assay conditions: b-Raf (V600E) approximately 4 pM; c-Raf approximately 4 nM; biotinylated Mek, kinase dead approximately 10 nM; ATP 10 μM for BRAF (V600E) and 1 μM for CRAF; Pre-incubation time with compounds 60 minutes at room temperature; Reaction time 1 or 3 hours at room temperature.

Assay protocol: Raf and biotinylated Mek (kinase dead) were combined at 2× final concentrations in assay buffer (50 mM Tris, pH 7.5, 15 mM $MgCl_2$, 0.01% BSA and 1 mM DTT) and dispensed 5 ml per well in assay plates (Greiner white 384 well assay plates #781207) containing 0.25 ml of 40× of a Raf kinase inhibitor test compound diluted in 100% DMSO. The plate was incubated for 60 minutes at room temperature. The Raf kinase activity reaction was started by the addition of 5 mL per well of 2×ATP diluted in assay buffer. After 3 hours (b-Raf(V600E)) or 1 hour (c-Raf). The reactions were stopped and the phosphorylated product was measured using a rabbit anti-p-MEK (Cell Signaling, #9121) antibody and the Alpha Screen IgG (ProteinA) detection Kit (PerkinElmer #6760617R), by the addition of 10 mL to the well of a mixture of the antibody (1:2000 dilution) and detection beads (1:2000 dilution of both beads) in Stop/bead buffer (25 mM EDTA, 50 mM Tris, pH 7.5, 0.01% Tween20). The additions were carried out under dark conditions to protect the detection beads from light. A lid was placed on top of the plate and incubated for 1 hour at room temperature, after which the luminescence was read on a PerkinElmer Envision instrument. The concentration of each compound for 50% inhibition ($IC_{50}$) was calculated by non-linear regression using XL Fit data analysis software.

Using the assays described above, compounds of the invention exhibit inhibitory efficacy for C-Raf and B-Raf. Table 9 details IC50 data for compounds of the invention.

TABLE 9

| Example No. | C-RAF IC50 μM | B-RAF IC50 μM |
| --- | --- | --- |
| 2 | 6.61E-04 | 0.003072 |
| 3 | 1.25E-04 | 9.91E-04 |
| 4 | 2.11E-04 | 0.001626 |
| 5 | 1.80E-04 | 0.001327 |
| 6 | 3.79E-04 | 0.002179 |
| 7 | 5.66E-04 | 0.004444 |
| 8 | 2.50E-04 | 0.001979 |
| 9 | 0.006555 | 0.060774 |
| 10 | 0.006555 | 0.060774 |
| 11 | 6.06E-04 | 0.009789 |
| 12 | 0.001815 | 0.027814 |
| 13 | 2.84E-04 | 0.005614 |
| 14 | 6.14E-04 | 0.011191 |
| 15 | 7.34E-05 | 5.66E-04 |
| 16 | 2.16E-04 | 0.001532 |
| 17 | 3.23E-04 | 0.002276 |
| 18 | 3.86E-04 | 0.003444 |
| 19 | 3.97E-04 | 0.002154 |
| 20 | 4.67E-04 | 0.001667 |
| 21 | 1.03E-04 | 5.75E-04 |
| 22 | 3.14E-04 | 0.001248 |
| 23 | 2.47E-04 | 0.001464 |
| 24 | 1.23E-04 | 8.05E-04 |
| 25 | 1.27E-04 | 9.00E-04 |
| 26 | 0.001778 | 0.015016 |
| 27 | 0.001652 | 0.02112 |
| 28 | 0.002551 | 0.009824 |
| 29 | 6.71E-04 | 0.004055 |
| 30 | 0.003693 | 0.028781 |
| 32 | 0.001034 | 0.005733 |
| 33 | 4.32E-04 | 0.003396 |
| 34 | 6.16E-04 | 0.0039 |
| 35 | 0.001947 | 0.01112 |
| 36 | 4.79E-04 | 0.002762 |
| 37 | 1.60E-04 | 0.001304 |
| 38 | 0.001809 | 0.016409 |
| 39 | 4.29E-04 | 0.004023 |
| 40 | 2.33E-04 | 0.001574 |
| 41 | 0.001084 | 0.016425 |
| 42 | 6.72E-04 | 0.010234 |
| 43 | 25.00034 | 25.00034 |
| 44 | 0.0028 | 0.017278 |
| 45 | 0.001126 | 0.005948 |
| 46 | 0.002107 | 0.010532 |
| 51 | 0.101293 | 0.447067 |
| 52 | 0.00928 | 0.027183 |
| 53 | 0.064021 | 0.284651 |
| 54 | 0.007882 | 0.034705 |
| 55 | 0.002364 | 0.011587 |
| 60 | 3.67E-04 | 0.001084 |
| 61 | 1.94E-04 | 5.09E-04 |
| 62 | 1.58E-04 | 4.77E-04 |
| 63 | 1.21E-04 | 4.88E-04 |
| 64 | 8.32E-04 | 0.003704 |
| 65 | 0.002699 | 0.014474 |
| 66 | 2.03E-04 | 8.52E-04 |
| 67 | 2.25E-04 | 0.001243 |
| 68 | 2.23E-04 | 9.02E-04 |
| 69 | 4.60E-04 | 0.002563 |
| 70 | 4.18E-04 | 9.94E-04 |
| 71 | 0.001974 | 0.004034 |
| 72 | 0.001528 | 0.006472 |
| 73 | 0.00209 | 0.008659 |
| 74 | 0.001636 | 0.005537 |
| 75 | 0.001198 | 0.003793 |
| 76 | 0.001532 | 0.009007 |
| 77 | 0.002531 | 0.009279 |
| 78a | 0.003164 | 0.012318 |
| 78b | 0.002412 | 0.010269 |
| 79 | 0.001512 | 0.004336 |
| 80 | 0.001928 | 0.012561 |
| 81 | 0.015118 | 0.090632 |
| 82 | 0.002041 | 0.010802 |
| 83 | 0.004888 | 0.023713 |
| 84 | 0.005103 | 0.025057 |
| 85 | 2.27E-04 | 0.001333 |
| 86 | 4.38E-04 | 0.002983 |
| 87 | 0.001153 | 0.003024 |
| 88 | 6.12E-04 | 0.002039 |
| 89 | 0.001017 | 0.003422 |
| 90 | 0.002098 | 0.008935 |
| 91 | 0.001005 | 0.003619 |
| 93 | 0.001745 | 0.006844 |
| 94 | 0.005979 | 0.023602 |
| 95 | 0.002341 | 0.012815 |
| 96 | 0.003526 | 0.011856 |
| 97 | | |
| 98 | 0.009211 | 0.074312 |

TABLE 9-continued

| Example No. | C-RAF IC50 μM | B-RAF IC50 μM |
| --- | --- | --- |
| 99 | 7.12E−04 | 0.0058 |
| 102 | 6.60E−04 | 0.003144 |
| 103 | 0.00421 | 0.022519 |
| 104 | 5.94E−04 | 0.003159 |
| 105 | 0.002755 | 0.018031 |
| 106 | 3.91E−04 | 0.002185 |
| 107 | 0.002157 | 0.009067 |
| 108 | 0.002657 | 0.0137 |
| 109 | 0.002743 | 0.019994 |
| 111 | 3.97E−04 | 0.001456 |
| 112 | 0.003515 | 0.017581 |
| 113 | 0.001789 | 0.006257 |
| 114 | 0.008185 | 0.032077 |
| 115 | 0.011466 | 0.070554 |
| 116 | | |
| 118 | 7.68E−04 | 0.005574 |
| 119 | 0.001653 | 0.012228 |
| 120 | 0.006843 | 0.034619 |
| 121 | 3.07E−04 | 8.71E−04 |
| 122 | 9.94E−04 | 0.002801 |
| 123 | 1.50E−04 | 0.00118 |
| 124 | 7.46E−05 | 4.27E−04 |
| 125 | 2.54E−04 | 0.001459 |
| 126 | 4.23E−05 | 3.04E−04 |
| 127 | 4.64E−04 | 0.003109 |
| 128 | 2.02E−04 | 0.001342 |
| 129 | 0.002553 | 0.023847 |
| 130 | 8.79E−04 | 0.004826 |
| 131 | 7.45E−04 | 0.004264 |
| 132 | 1.17E−04 | 5.42E−04 |
| 133 | 3.30E−04 | 0.002046 |
| 134 | 2.36E−04 | 0.001465 |
| 135 | 9.69E−04 | 0.004786 |
| 136 | 1.53E−04 | 0.001157 |
| 137 | 4.76E−04 | 0.001979 |
| 138 | 5.11E−04 | 0.004139 |
| 139 | 3.77E−04 | 0.002402 |
| 140 | 7.92E−04 | 0.003613 |
| 141 | 0.005127 | 0.056228 |
| 142 | 3.44E−04 | 0.002793 |
| 143 | 8.42E−04 | 0.005632 |
| 144 | 0.012596 | 0.076037 |
| 145 | 1.48E−04 | 5.60E−04 |
| 146 | 2.62E−04 | 0.001334 |
| 147 | 1.16E−04 | 5.03E−04 |
| 148 | 7.31E−04 | 0.003338 |
| 149 | 2.370096 | 15.05676 |
| 150 | 1.58E−04 | 5.91E−04 |
| 151 | 3.53E−04 | 0.001411 |
| 152 | 7.02E−04 | 0.005683 |
| 153 | 1.50E−04 | 7.00E−04 |
| 154 | 6.75E−05 | 3.42E−04 |
| 155 | 3.95E−05 | 2.63E−04 |
| 156 | 5.97E−05 | 3.50E−04 |
| 157 | 5.59E−05 | 3.04E−04 |
| 158 | 1.99E−04 | 0.00109 |
| 159 | 1.97E−04 | 0.001493 |
| 160 | 1.57E−04 | 0.00159 |
| 161 | 1.53E−04 | 5.77E−04 |
| 162 | 5.22E−04 | 0.002485 |
| 163 | 1.25E−04 | 9.01E−04 |
| 164 | 2.22E−04 | 6.83E−04 |
| 165 | 3.56E−04 | 0.001237 |
| 166 | 0.00159 | 0.006909 |
| 167 | 0.006861 | 0.032967 |
| 168 | 4.87E−04 | 0.001442 |
| 169 | 1.54E−04 | 5.07E−04 |
| 170 | 0.003157 | 0.012082 |
| 171 | 9.25E−04 | 0.004178 |
| 172 | 3.56E−04 | 0.001089 |
| 173 | 4.78E−04 | 0.001633 |
| 174 | 1.77E−04 | 5.76E−04 |
| 175 | 0.001254 | 0.004736 |
| 176 | 3.98E−04 | 0.001581 |
| 177 | 1.69E−04 | 9.40E−04 |
| 178 | 1.92E−04 | 0.001505 |
| 179 | 5.88E−04 | 0.004106 |
| 180 | 0.001314 | 0.008456 |
| 181 | 0.016769 | 0.112357 |
| 182 | 0.007494 | 0.05882 |
| 183 | 8.24E−04 | 0.005786 |
| 184 | 0.001137 | 0.007876 |
| 185 | 0.011025 | 0.060998 |
| 186 | 0.010232 | 0.05264 |
| 187 | 0.0042 | 0.026642 |
| 188 | 0.001755 | 0.009918 |
| 189 | 3.90E−04 | 0.003407 |
| 190 | 0.029093 | 0.177729 |
| 191 | 0.005213 | 0.030618 |
| 192 | 0.001148 | 0.005133 |
| 193 | 0.001745 | 0.007913 |
| 194 | 2.85E−04 | 0.001528 |
| | 7.95E−04 | 0.004057 |
| 196 | 0.002142 | 0.01611 |
| 197 | 8.18E−04 | 0.005231 |
| 198 | 0.004061 | 0.013356 |
| 199 | 3.86E−04 | 0.002618 |
| 200 | 0.002378 | 0.015154 |
| 201 | 4.47E−04 | 0.003042 |
| 202 | 0.004821 | 0.032602 |
| 203 | 0.008173 | 0.048181 |
| 204 | 2.19E−04 | 0.001454 |
| 205 | 0.001819 | 0.01093 |
| 206 | 1.99E−04 | 0.001227 |
| 207 | 0.001352 | 0.006145 |
| 208 | 9.67E−05 | 3.97E−04 |
| 209 | 7.77E−04 | 0.004169 |
| 210 | 0.005969 | 0.03596 |
| 211 | 8.86E−04 | 0.003066 |
| 212 | 3.20E−04 | 0.001145 |
| 213 | 0.00178 | 0.008794 |
| 214 | 7.41E−04 | 0.004723 |
| 215 | 0.001285 | 0.00805 |
| 216 | 6.91E−04 | 0.004731 |
| 217 | 0.00107 | 0.006782 |
| 218 | 6.17E−04 | 0.003579 |
| 219 | 1.71E−04 | 0.001313 |
| 220 | 1.83E−04 | 9.39E−04 |
| 221 | 5.91E−04 | 0.003654 |
| 222 | 2.19E−04 | 0.001 |
| 223 | 3.04E−04 | 0.001 |
| 224 | 4.90E−04 | 0.002 |
| 225 | 0.001077 | 0.005 |
| 226 | 6.95E−04 | 0.002 |
| 227 | 7.96E−04 | 0.003 |
| 228 | 4.09E−04 | 0.002 |
| 229 | 0.00137 | 0.005 |
| 230 | 3.84E−04 | 0.002617 |
| 231 | 0.001959 | 0.015818 |
| 232 | 4.20E−04 | 0.003181 |
| 233 | 1.87E−04 | 0.001344 |
| 234 | 0.002235 | 0.003869 |
| 235 | 0.005798 | 0.027926 |
| 236 | 0.001549 | 0.00578 |
| 237 | 6.95E−04 | 0.002252 |
| 238 | 3.33E−04 | 0.00225 |
| 239 | 7.11E−04 | 0.006376 |
| 240 | 5.19E−04 | 0.003509 |
| 241 | 2.79E−04 | 0.001504 |
| 242 | 5.39E−04 | 0.003183 |
| 243 | 0.001027 | 0.00983 |
| 244 | 8.76E−04 | 0.007181 |
| 245 | 5.33E−04 | 0.003243 |
| 246 | 0.001854 | 0.007674 |
| 247 | 0.004959 | 0.030733 |
| 248 | 0.002016 | 0.010636 |
| 249 | 6.53E−04 | 0.002535 |
| 250 | 4.01E−04 | 0.001962 |
| 251 | 0.007282 | 0.059732 |
| 252 | 0.017586 | 0.195976 |
| 253 | 0.002502 | 0.016532 |
| 254 | 0.038397 | 0.278296 |
| 255 | 0.004839 | 0.035553 |
| 256 | 3.53E−04 | 0.001516 |
| 257 | 0.001364 | 0.012924 |
| 258 | 1.58E−04 | 0.001184 |

TABLE 9-continued

| Example No. | C-RAF IC50 μM | B-RAF IC50 μM |
|---|---|---|
| 259 | 4.35E-04 | 0.003785 |
| 260 | 1.15E-04 | 2.97E-04 |
| 261 | 1.06E-04 | 7.10E-04 |
| 262 | 0.002157 | 0.010856 |
| 263 | 0.055265 | 0.884278 |
| 264 | 0.148337 | 1.971938 |
| 265 | 0.311684 | 25.00034 |
| 266 | 0.030823 | 0.403702 |
| 267 | 0.196173 | 1.658233 |
| 268 | 0.008 | 0.094214 |
| 269 | 6.36E-04 | 0.006146 |
| 270 | 4.90E-04 | 0.005406 |
| 271 | 0.001153 | 0.011237 |
| 272 | 0.002164 | 0.018378 |
| 273 | 0.001 | 0.004 |

We claim:

1. A compound of formula I or II:

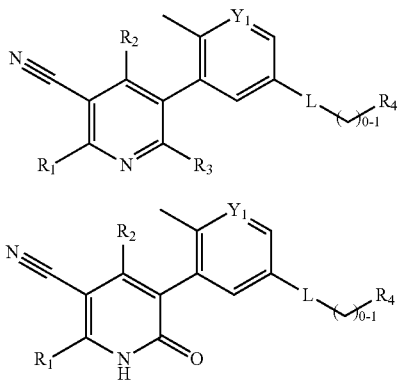

in which:

L is selected from —NHC(O)— and —C(O)NH—;

$Y_1$ is selected from N and CH;

$R_1$ is selected from H, halo, isopropyl, methyl-sulfonyl, $OR_6$, $NR_5R_6$, methoxy-ethoxy, 2-oxa-5-azabicyclo[2.2.1]heptan-5-yl, 3-oxa-8-azabicyclo[3.2.1]octan-8-yl, 8-oxa-3-azabicyclo[3.2.1]octan-3-yl, 2-oxo-1,2-dihydropyridin-4-yl, tetrahydro-2H-pyranyl, 4-oxopyridin-1(4H)-yl, pyrazolyl, pyridazinyl and azetidinyl; wherein said azetidinyl, pyrazolyl or 2-oxo-1,2-dihydropyridin-4-yl is unsubstituted or substituted with 1 to 3 groups independently selected from methyl and hydroxy;

$R_2$ is selected from H and methyl;

$R_3$ is selected from H, methyl and amino;

$R_4$ is selected from:

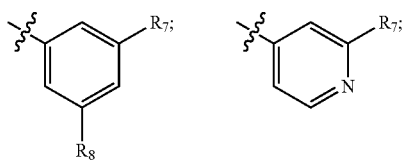

-continued

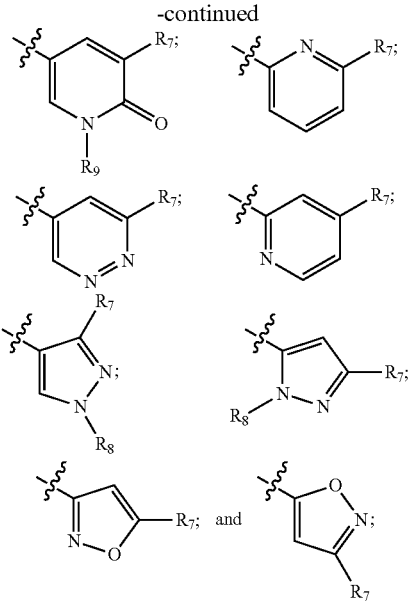

wherein

indicates the point of attachment with L;

$R_5$ is selected from H and methyl;

$R_6$ is selected from H and methyl, ethyl, propyl, isopropyl, cyclopropyl, methoxy, hydroxy-ethyl, methoxy-ethyl, tetrahydro-2H-pyranyl, pyridinyl, tetrahydrofuranyl and oxetanyl; or $R_5$ and $R_6$, together with the nitrogen to which $R_5$ and $R_6$ are attached form a group selected from morpholino, 2-oxopyridin-1(2H)-yl, 1,1-dioxido-thiomorpholino, piperazinyl, pyrrolidinyl, imidazolyl and pyrazolyl; wherein said morpholino, pyrazolyl or imidazolyl can be unsubstituted or substituted with 1 to 2 methyl groups;

$R_7$ is selected from H, methyl, —$CF_3$, —$C(CH_3)_2CN$, —$C(CH_3)_2OH$, —$C(CH_3)_2F$, —$CF_2CH_3$, —$CF_2H$, isopropyl, cyclopropyl and methyl-sulfonyl; wherein said cyclopropyl is unsubstituted or substituted with cyano;

$R_8$ is selected from H, methyl, ethyl, isopropyl, —$C(CH_3)_2$ OH and —$C(CH_3)_2NH_2$;

$R_9$ is selected from H and ethyl; or a pharmaceutically acceptable salt thereof.

2. The compound of claim 1 of formula Ia:

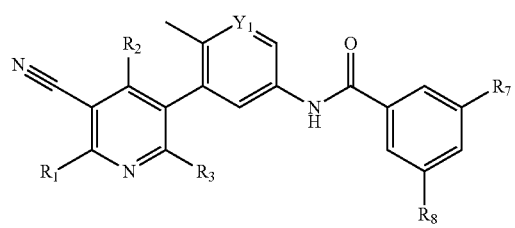

in which:

$Y_1$ is selected from N and CH;

$R_1$ is selected from H, halo, isopropyl, methyl-sulfonyl, $OR_6$, $NR_5R_6$, methoxy-ethoxy, 2-oxa-5-azabicyclo [2.2.1]heptan-5-yl, 3-oxa-8-azabicyclo [3.2.1]octan-8-yl, 8-oxa-3-azabicyclo[3.2.1]octan-3-yl, 2-oxo-1,2-dihydropyridin-4-yl, tetrahydro-2H-pyranyl, 4-oxopyridin-1(4H)-yl, pyrazolyl, pyridazinyl and azetidinyl; wherein said azetidinyl, pyrazolyl or 2-oxo-1,2-dihydropyridin-4-yl is unsubstituted or substituted with 1 to 3 groups independently selected from methyl and hydroxy;

$R_2$ is selected from H and methyl;

$R_3$ is selected from H, methyl and amino;

$R_7$ is selected from H, methyl, —$CF_3$, —$C(CH_3)_2CN$, —$C(CH_3)_2OH$, —$C(CH_3)_2F$, —$CF_2CH_3$, —$CF_2H$, isopropyl, cyclopropyl and methyl-sulfonyl; wherein said cyclopropyl is unsubstituted or substituted with cyano;

$R_8$ is selected from H, methyl, ethyl, isopropyl, —$C(CH_3)_2OH$ and —$C(CH_3)_2NH_2$; and the pharmaceutically acceptable salt thereof.

3. The compound of claim 2 selected from:

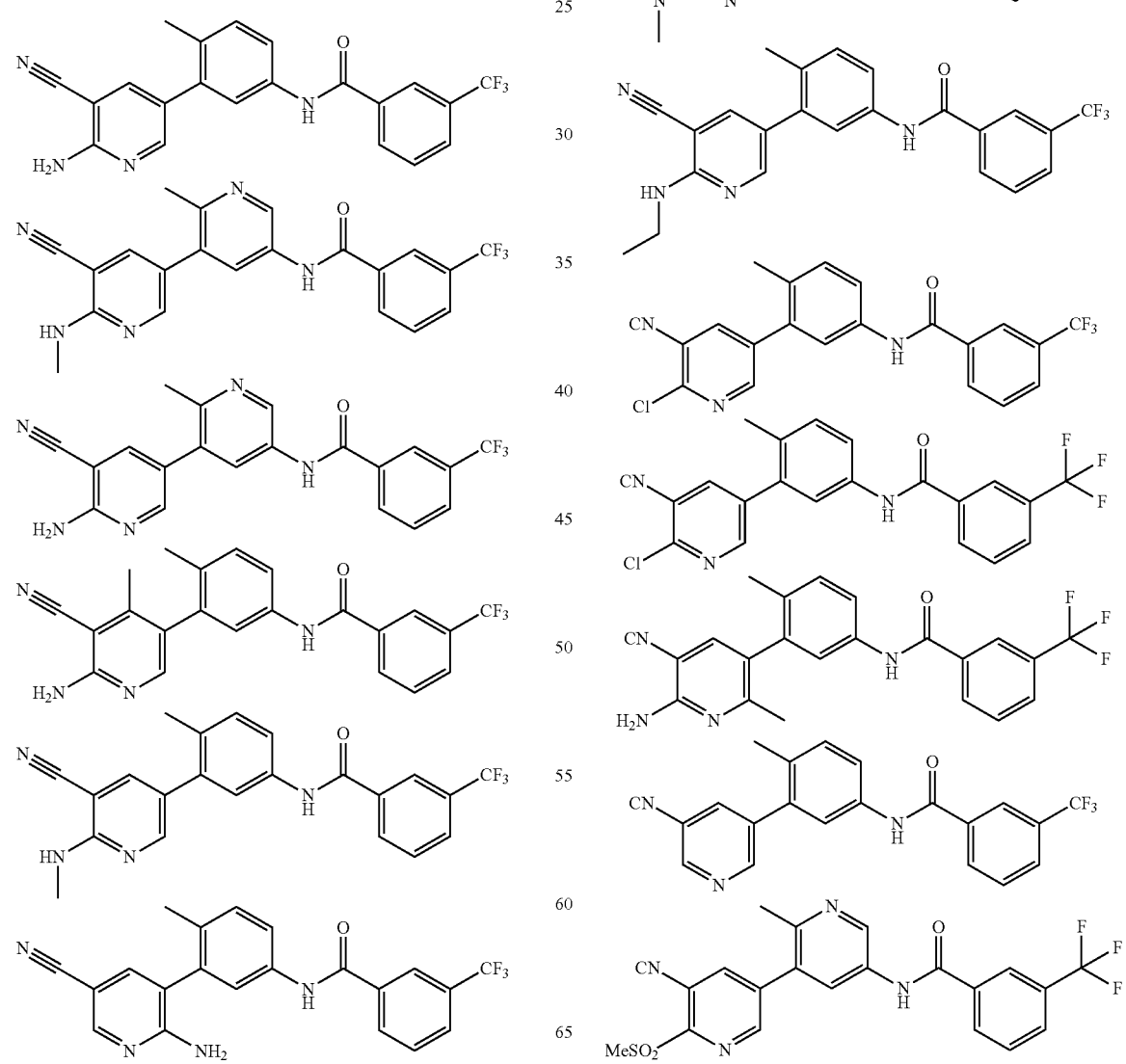

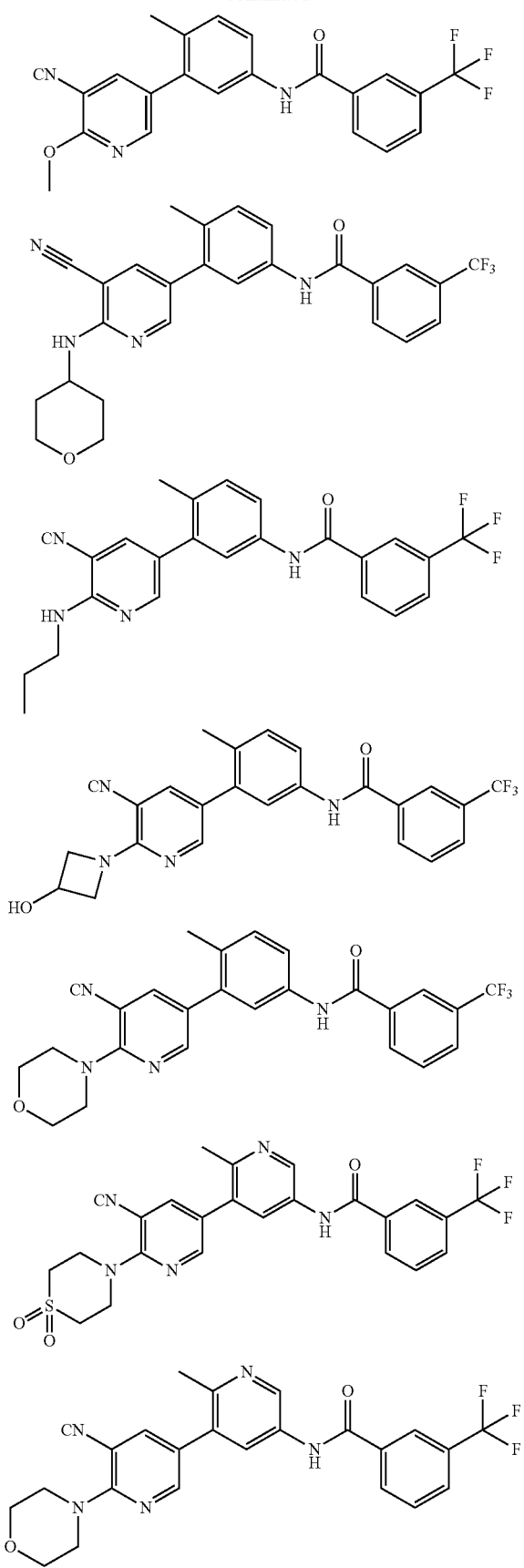
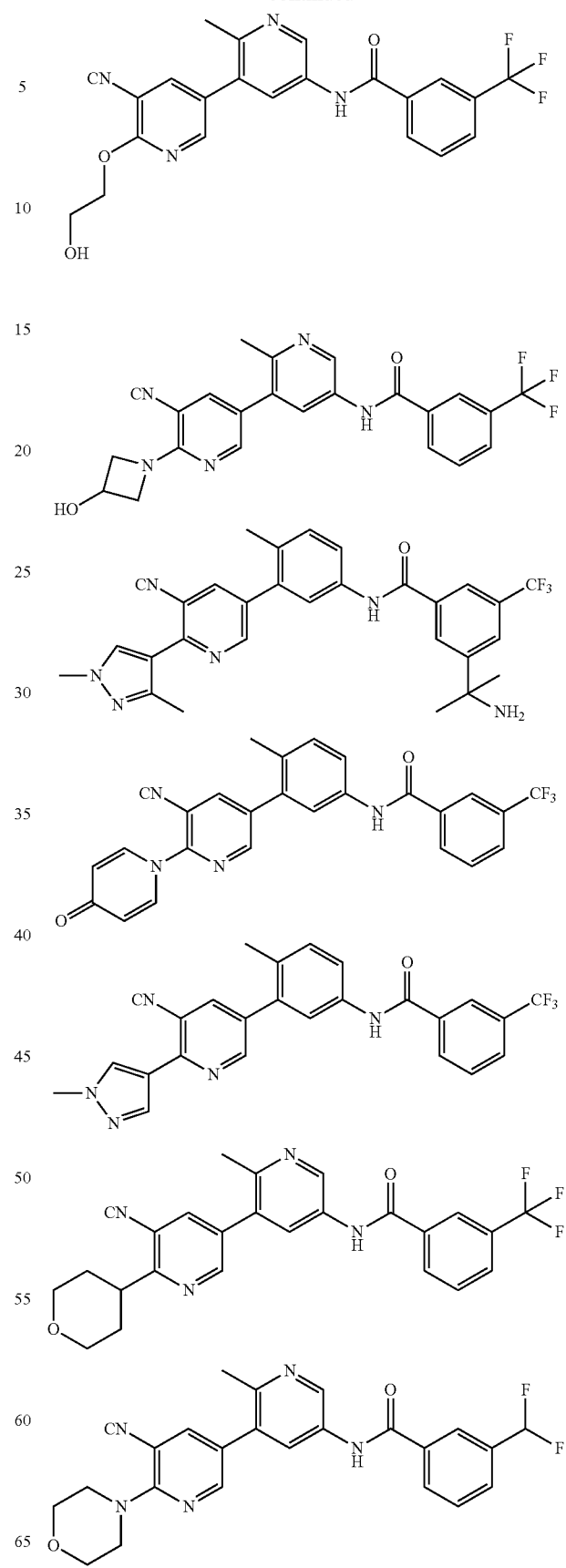

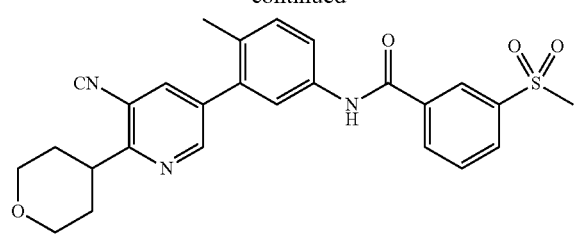
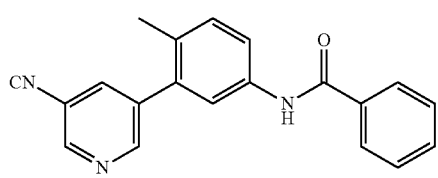
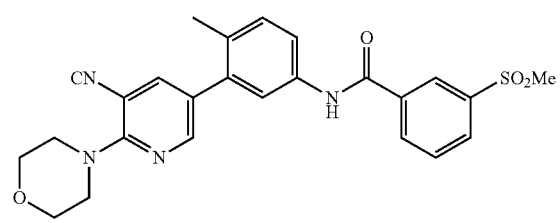
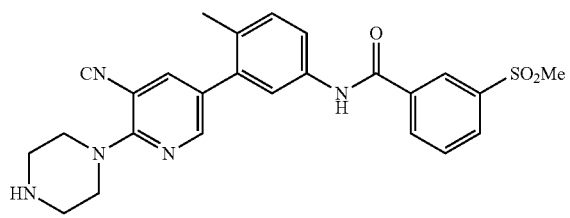
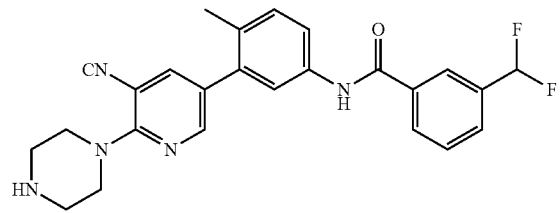
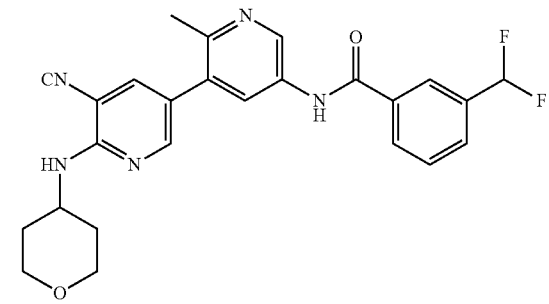
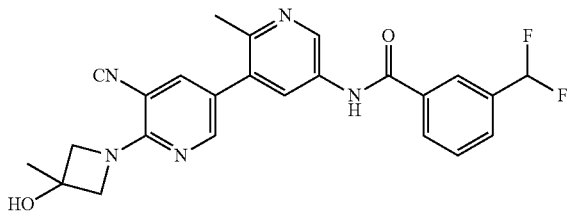
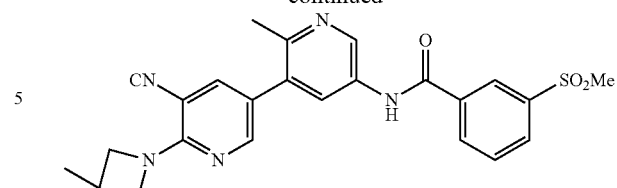
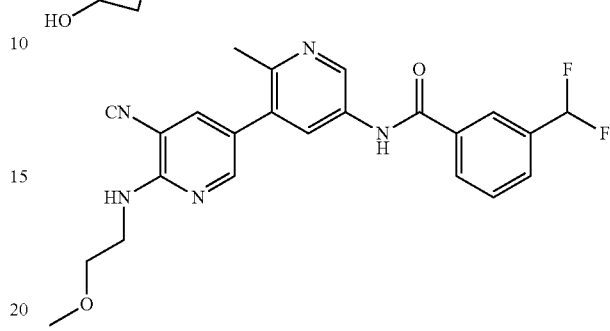
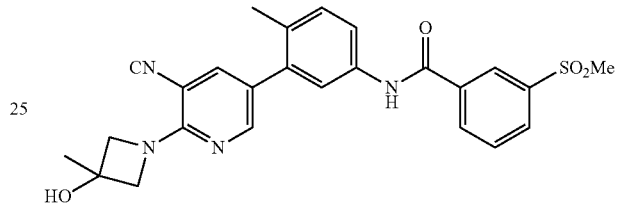
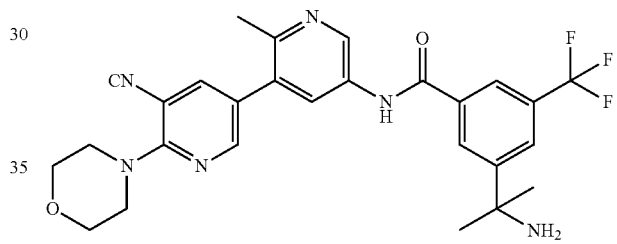
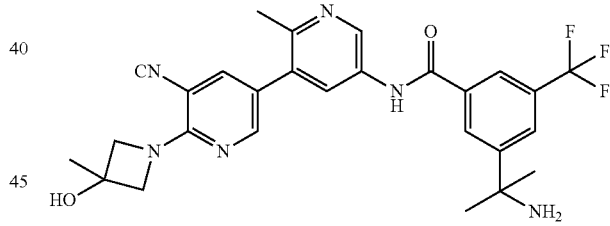
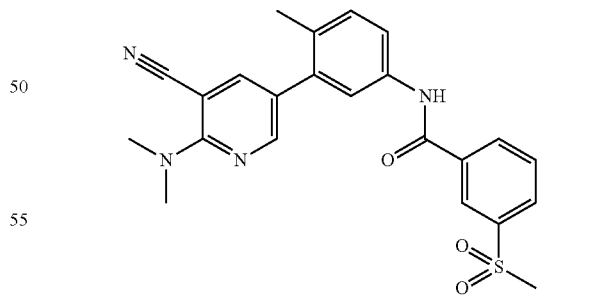
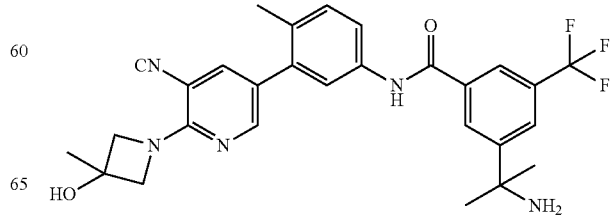

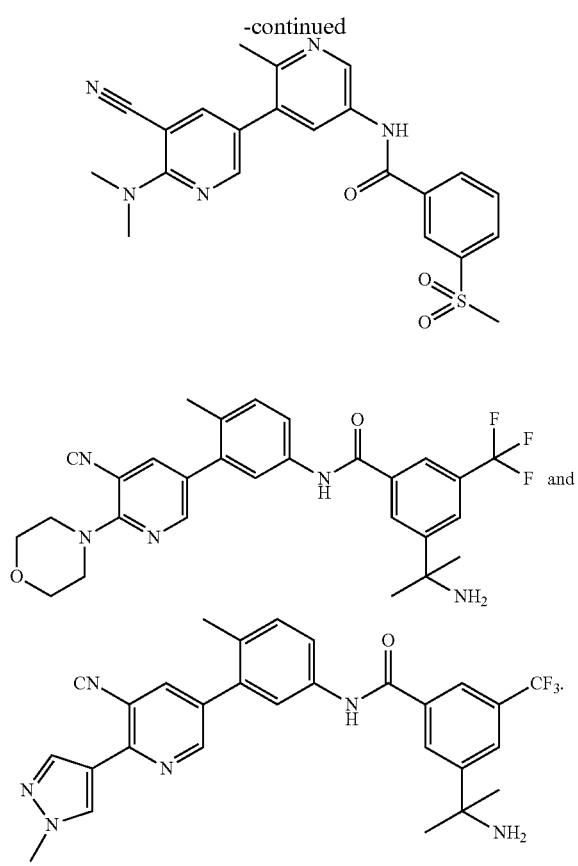

4. The compound of claim 1 of formula Ib:

Ib in which:

Y₁ is selected from N and CH;

R₁ is selected from H, halo, isopropyl, methyl-sulfonyl, OR₆, NR₅R₆, methoxy-ethoxy, 2-oxa-5-azabicyclo[2.2.1]heptan-5-yl, 3-oxa-8-azabicyclo[3.2.1]octan-8-yl, 8-oxa-3-azabicyclo[3.2.1]octan-3-yl, 2-oxo-1,2-dihydropyridin-4-yl, tetrahydro-2H-pyranyl, 4-oxopyridin-1(4H)-yl, pyrazolyl, pyridazinyl and azetidinyl; wherein said azetidinyl, pyrazolyl or 2-oxo-1,2-dihydropyridin-4-yl is unsubstituted or substituted with 1 to 3 groups independently selected from methyl and hydroxy;

R₂ is selected from H and methyl;

R₃ is selected from H, methyl and amino;

R₇ is selected from H, methyl, —CF₃, —C(CH₃)₂CN, —C(CH₃)₂OH, —C(CH₃)₂F, —CF₂CH₃, —CF₂H, isopropyl, cyclopropyl and methyl-sulfonyl; wherein said cyclopropyl is unsubstituted or substituted with cyano; and the pharmaceutically acceptable salt thereof.

5. A compound selected from:

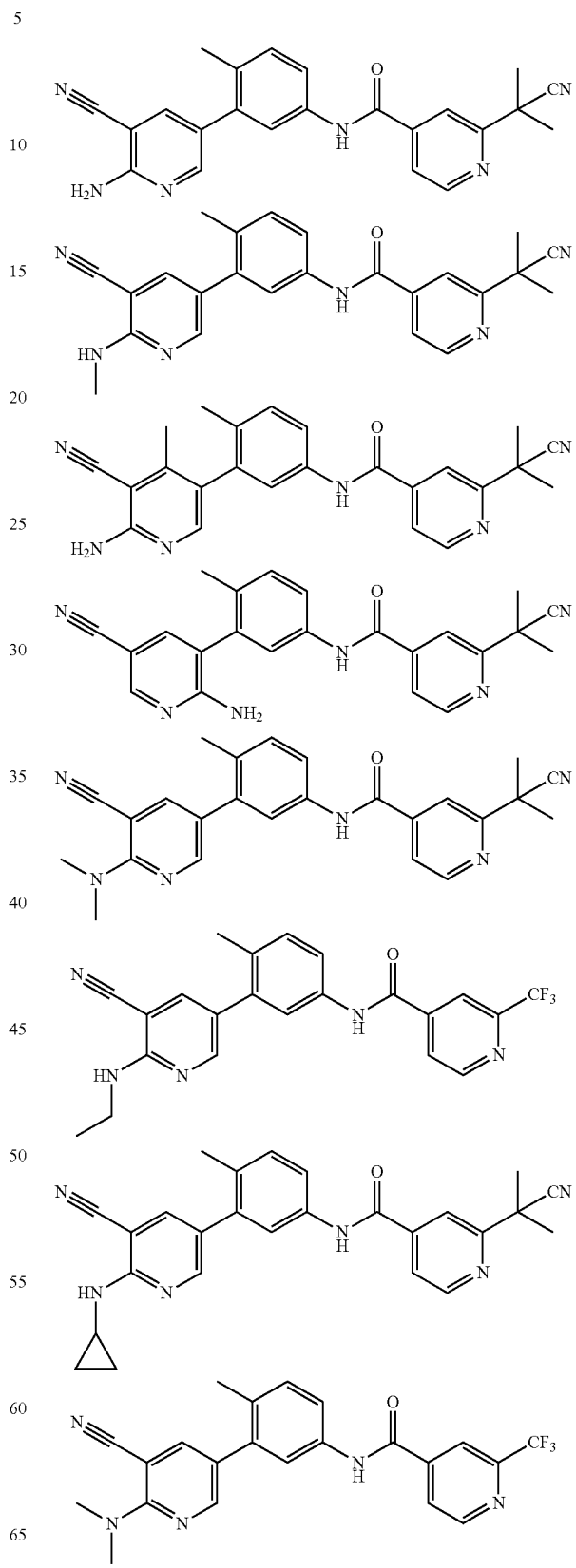

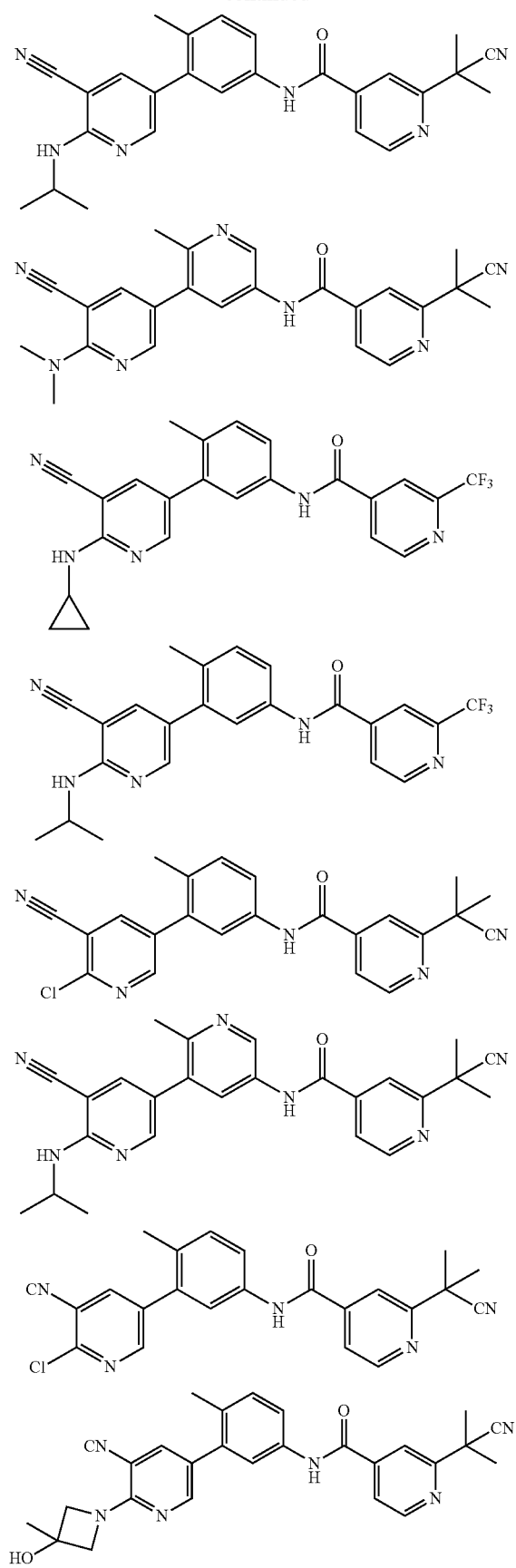
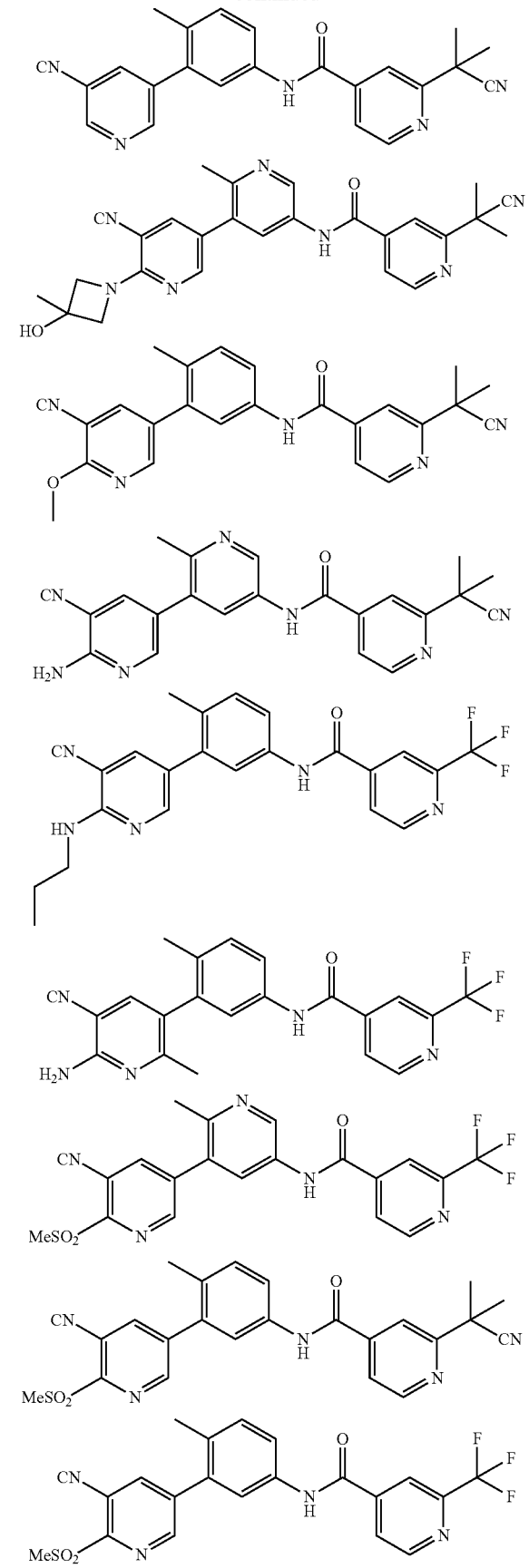

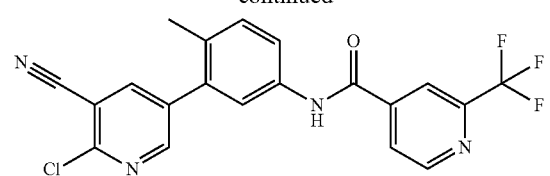
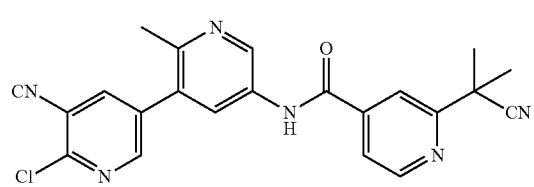
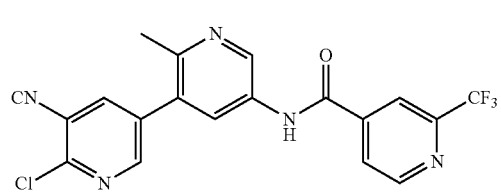
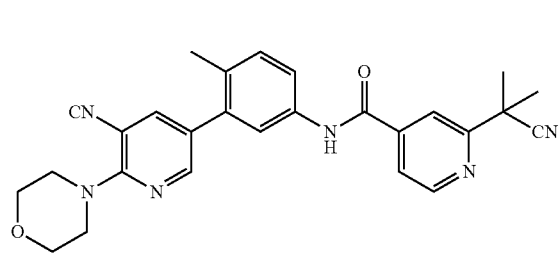
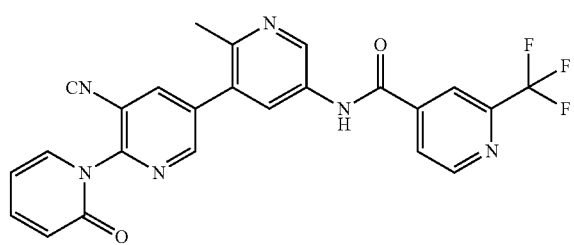
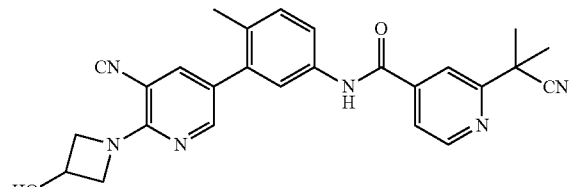
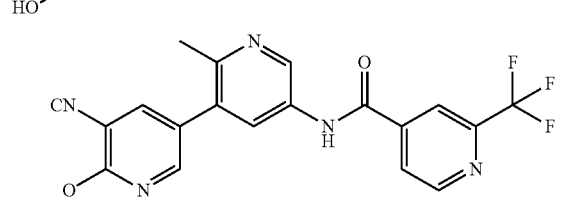
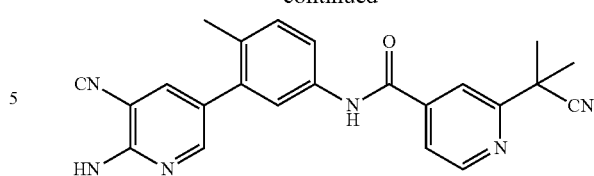
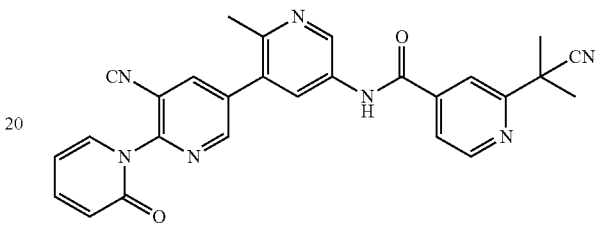
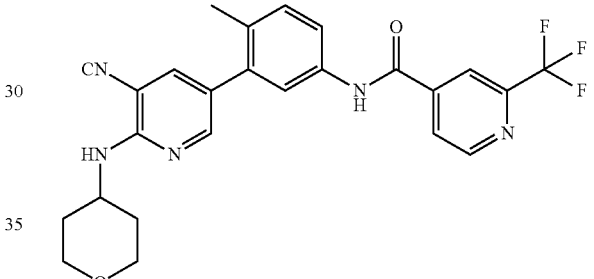
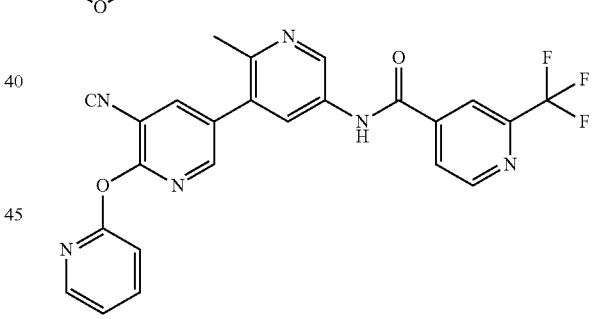
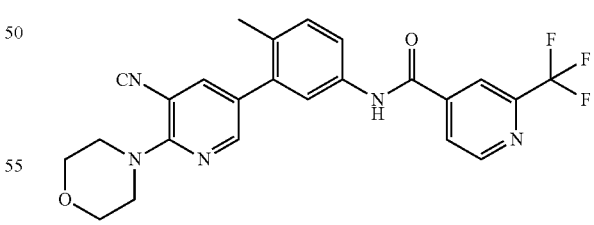
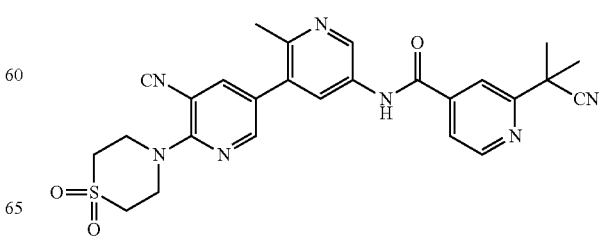

205
-continued
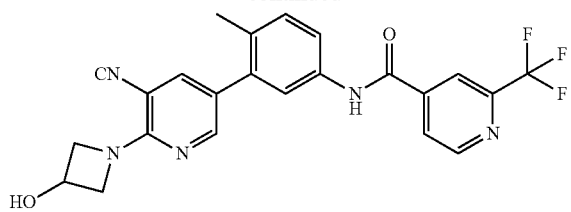
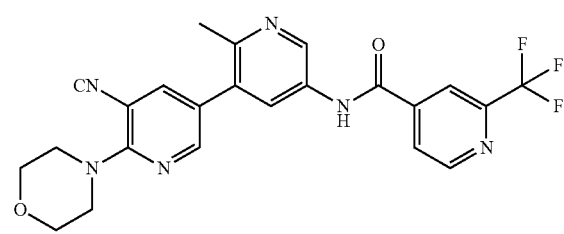
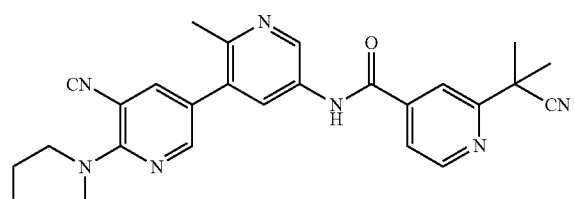
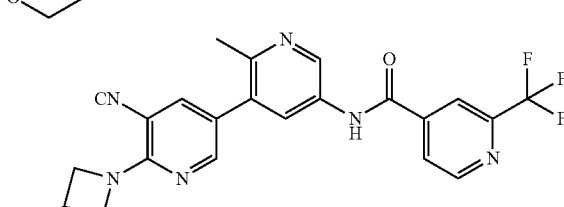
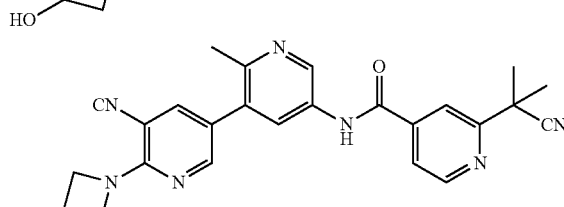
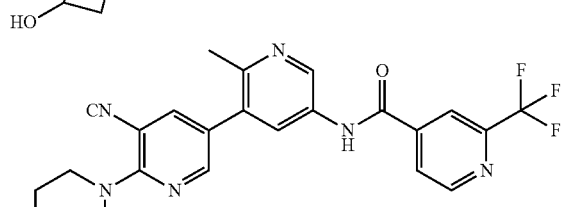
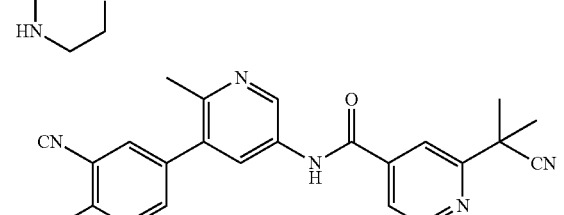
206
-continued
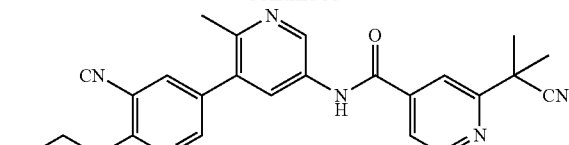
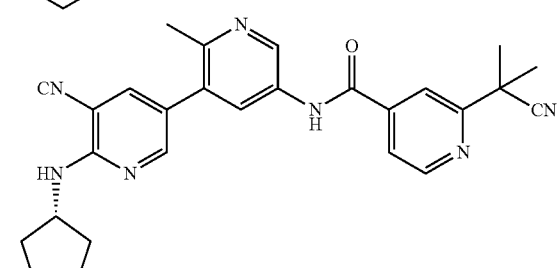
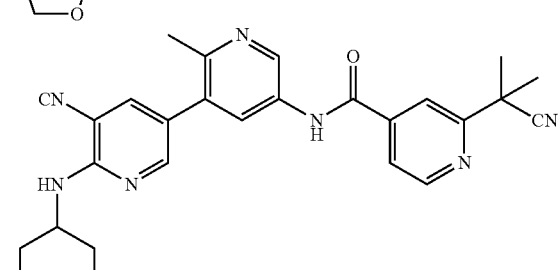
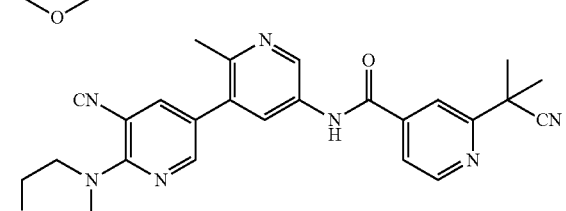
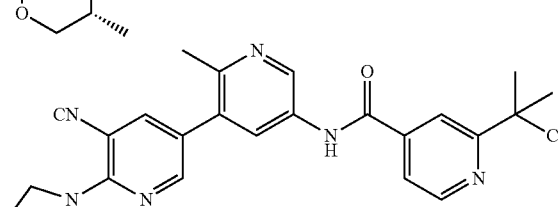
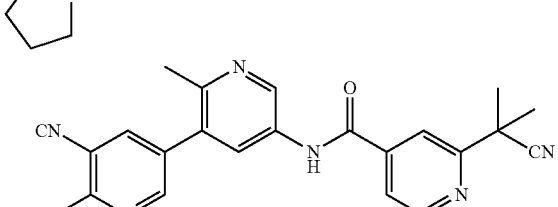
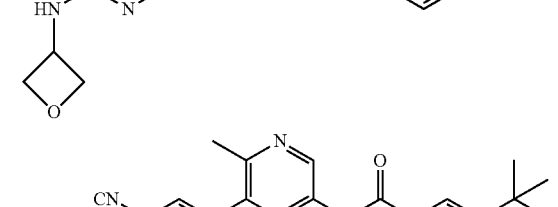

207
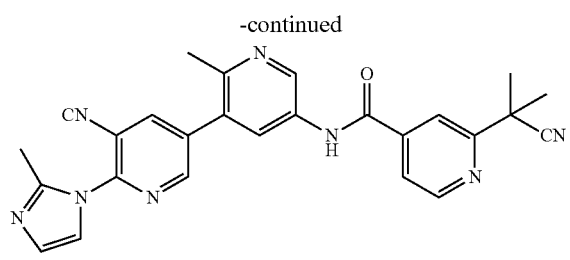
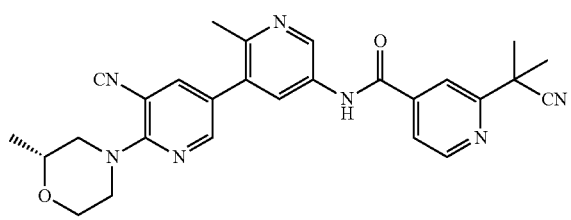
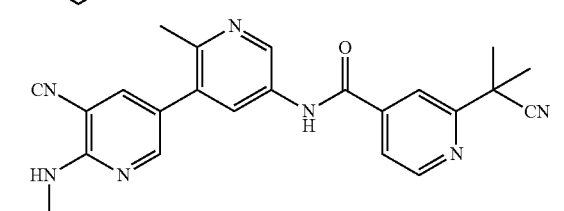
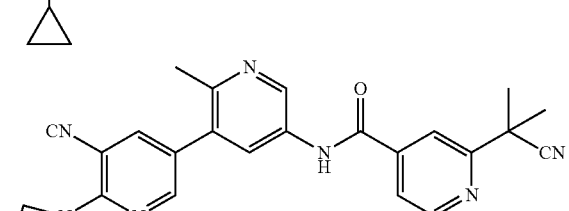
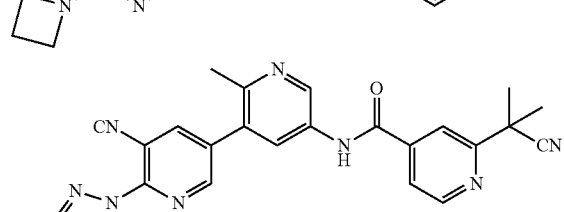
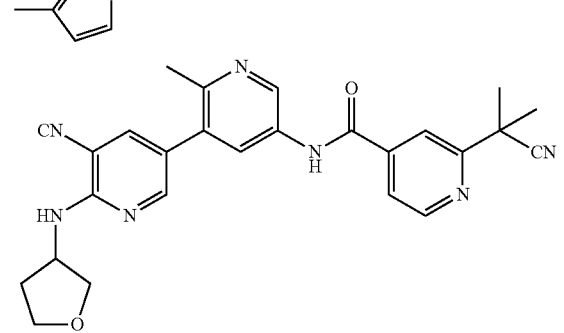
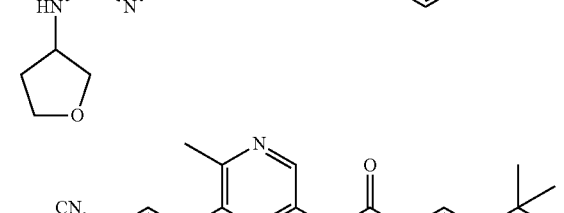
208
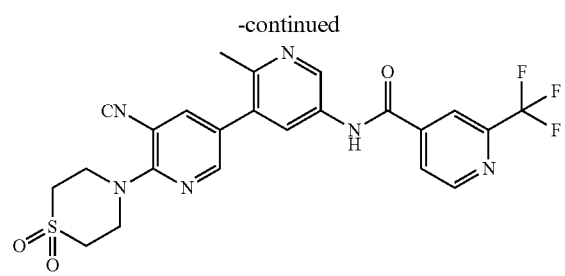
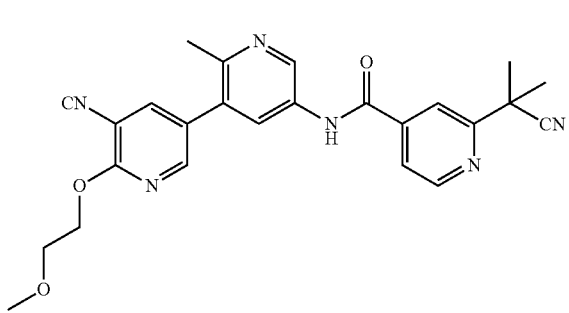
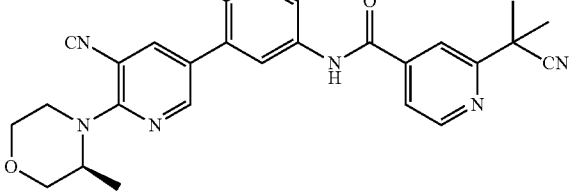
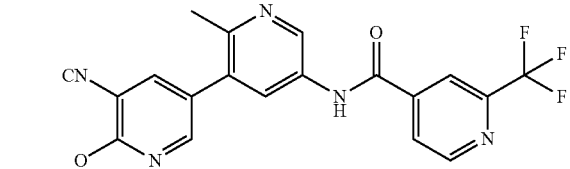
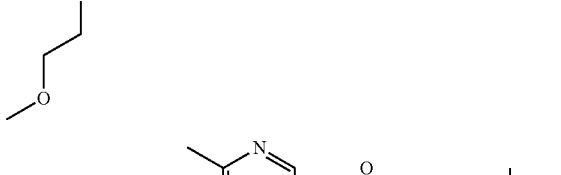
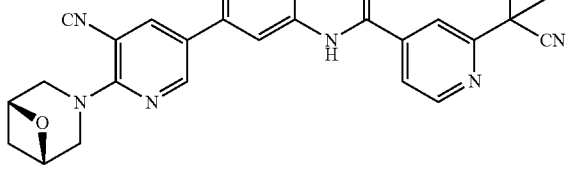

209
-continued
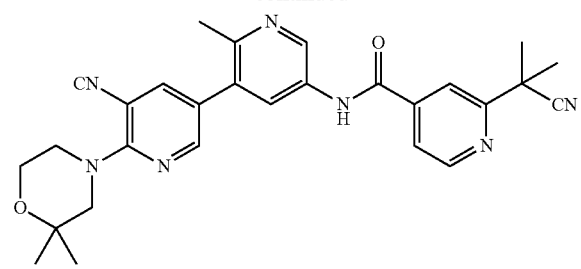
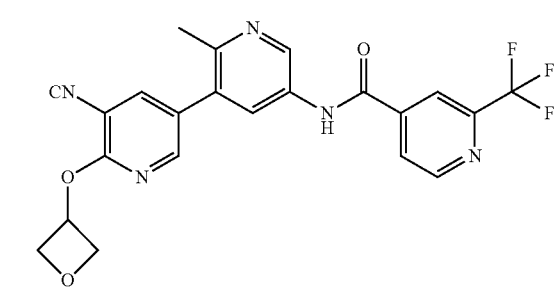
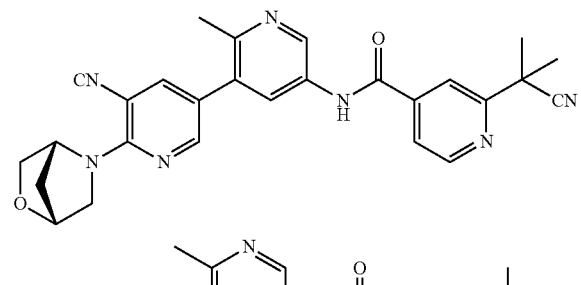
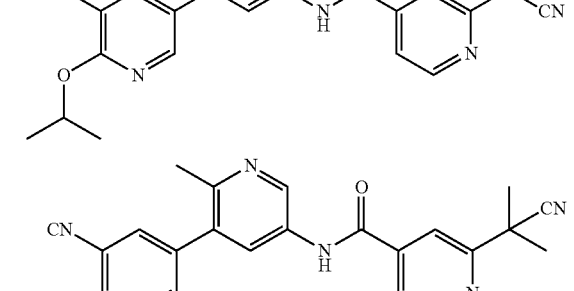
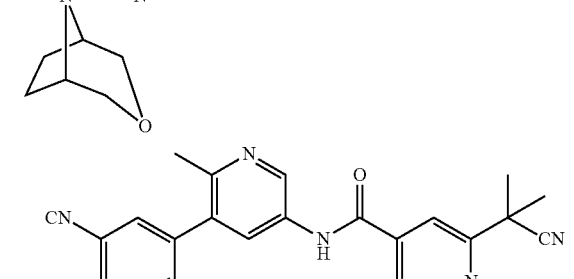
210
-continued
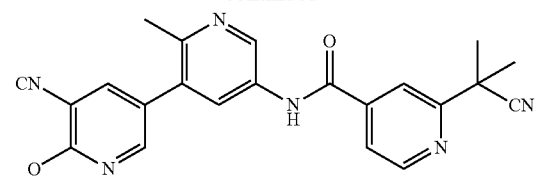
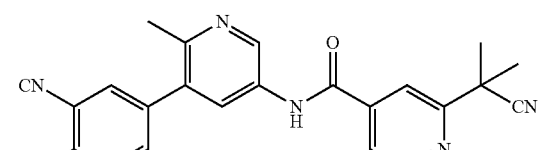
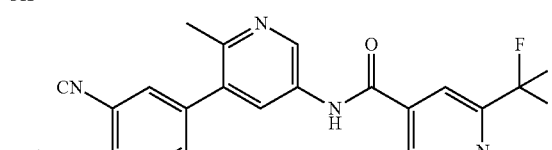
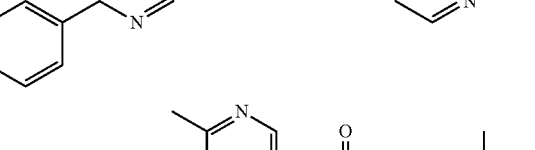
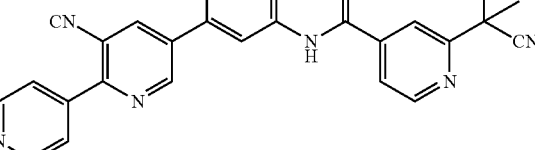
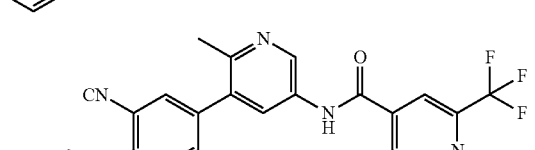
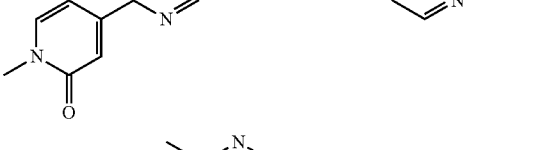
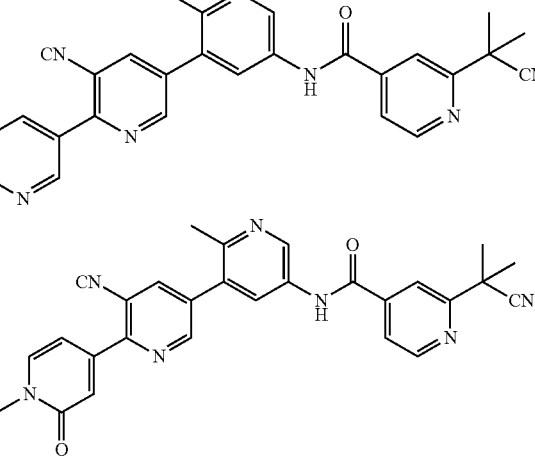

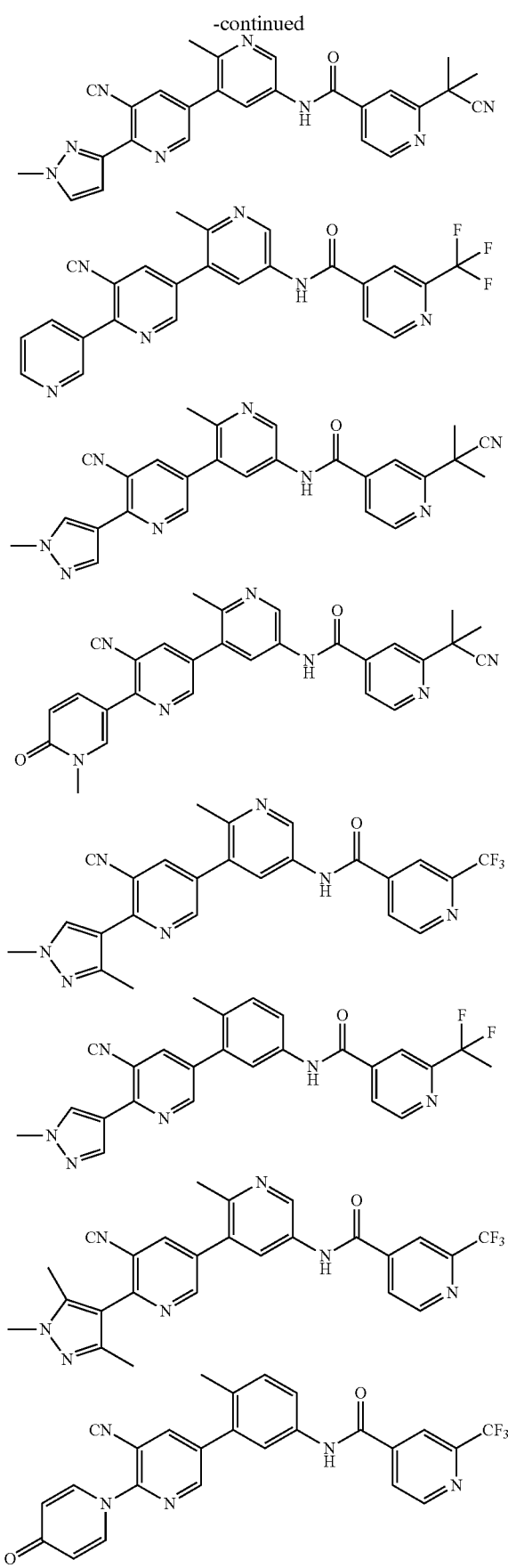

213
-continued
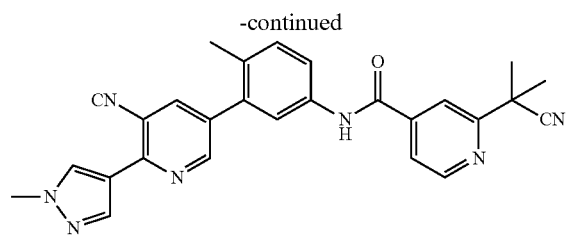
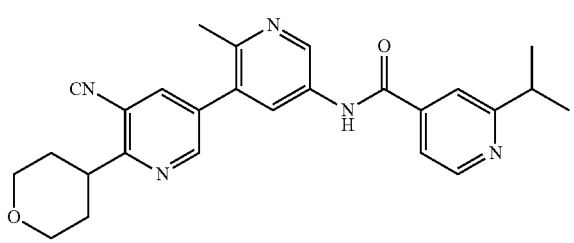
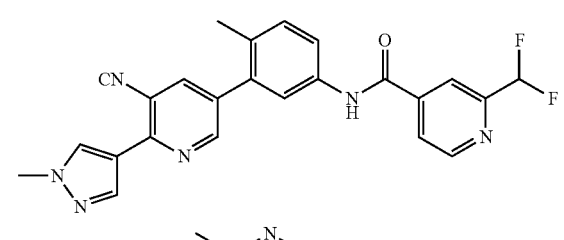
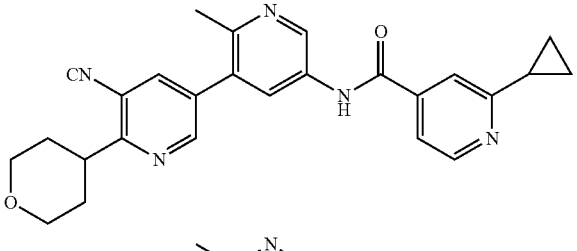
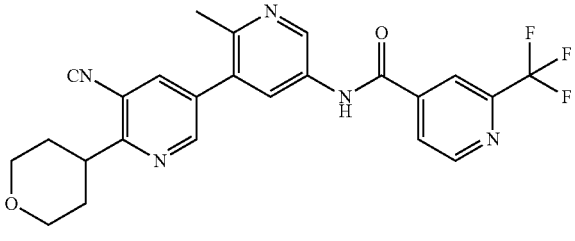
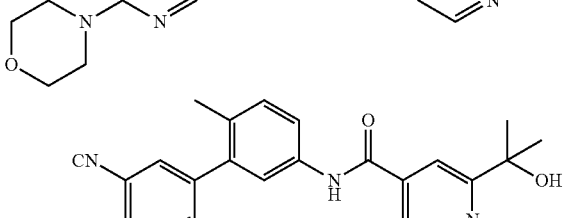
214
-continued
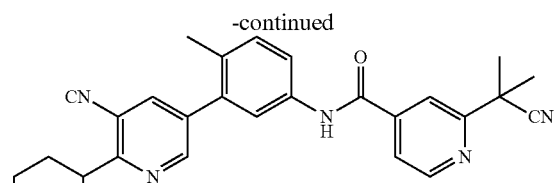
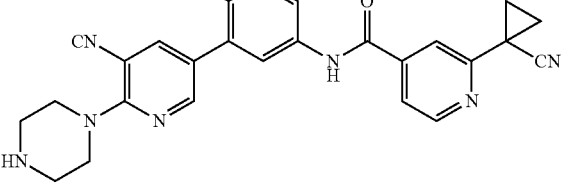
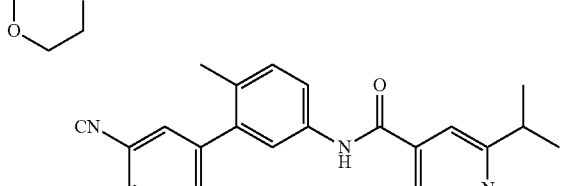
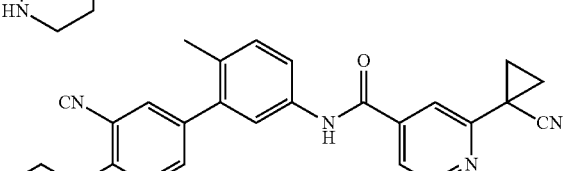
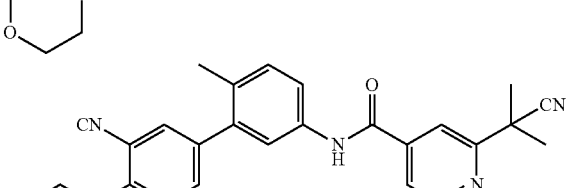
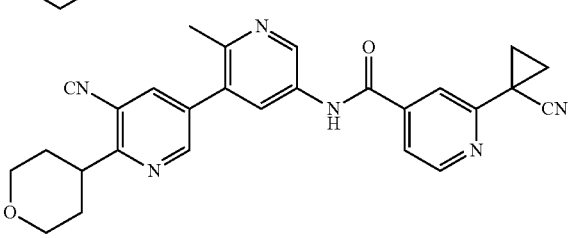

-continued
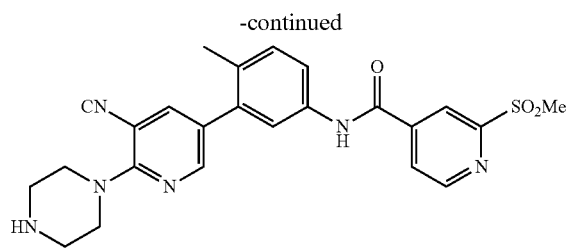
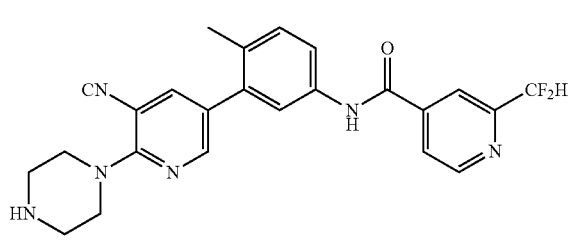
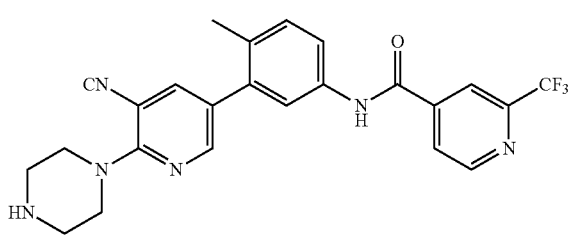
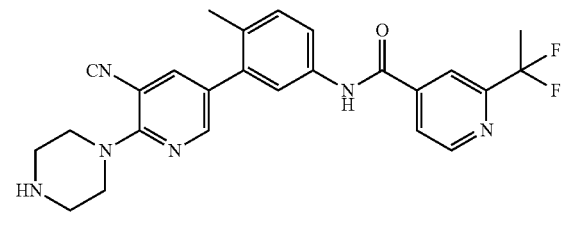
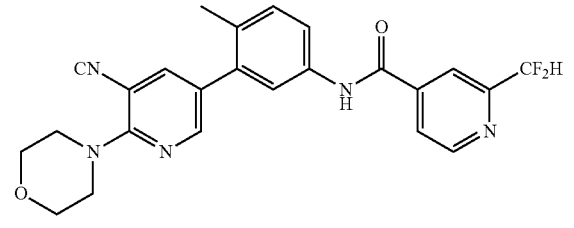
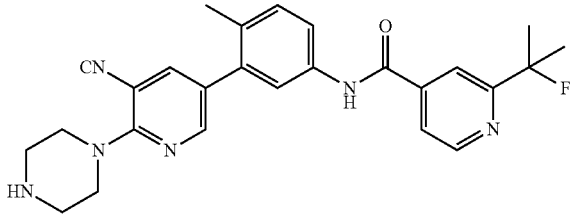
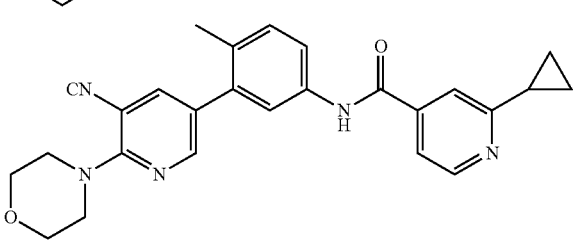
-continued
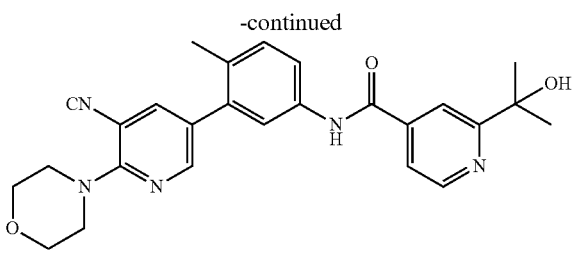
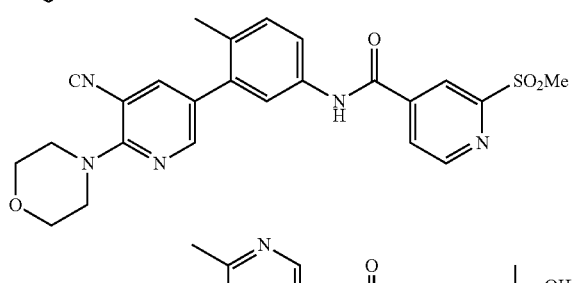
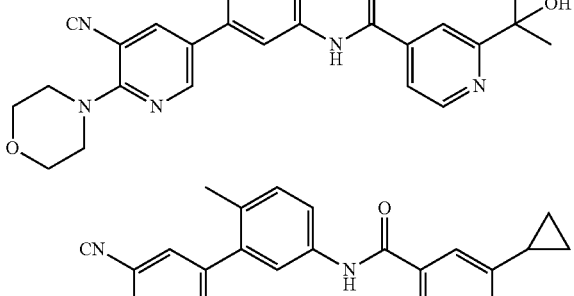
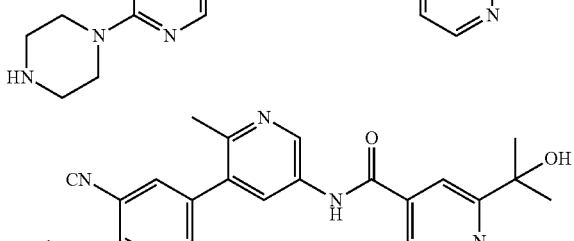
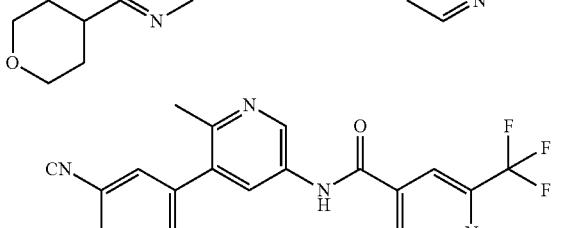
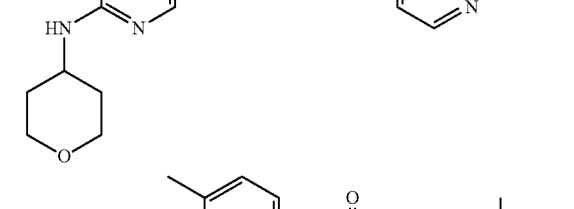
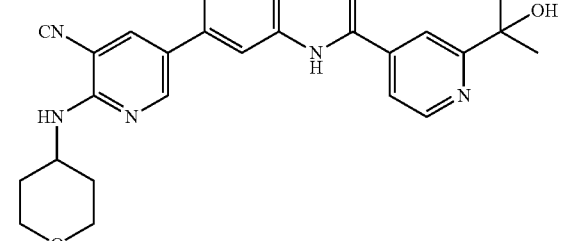

-continued

219
-continued
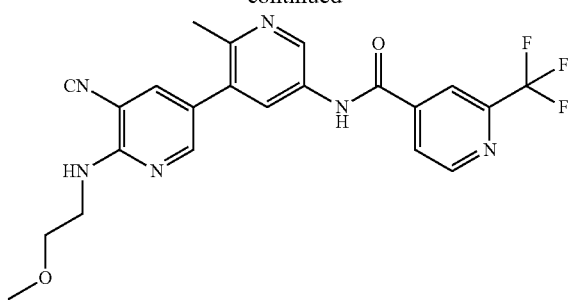
220
-continued
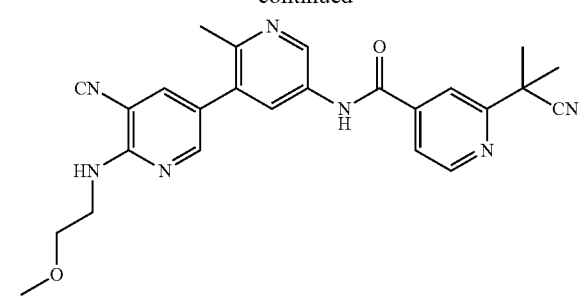
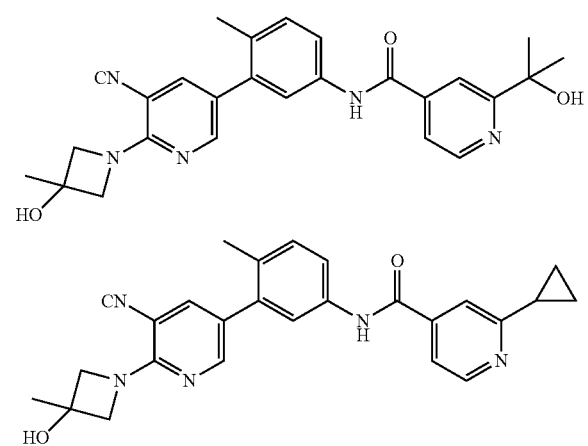
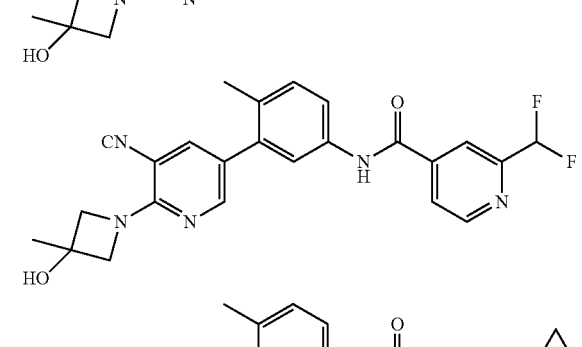
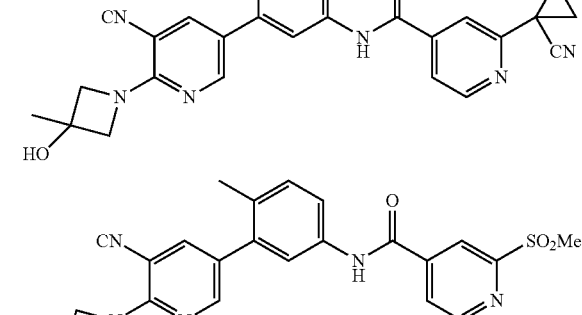
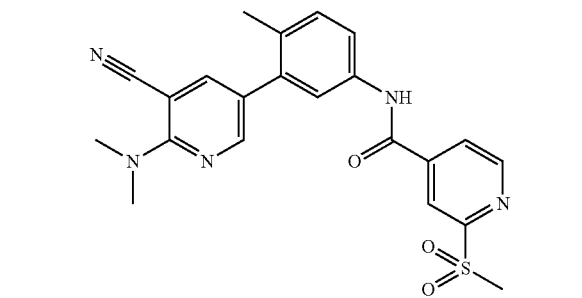

-continued
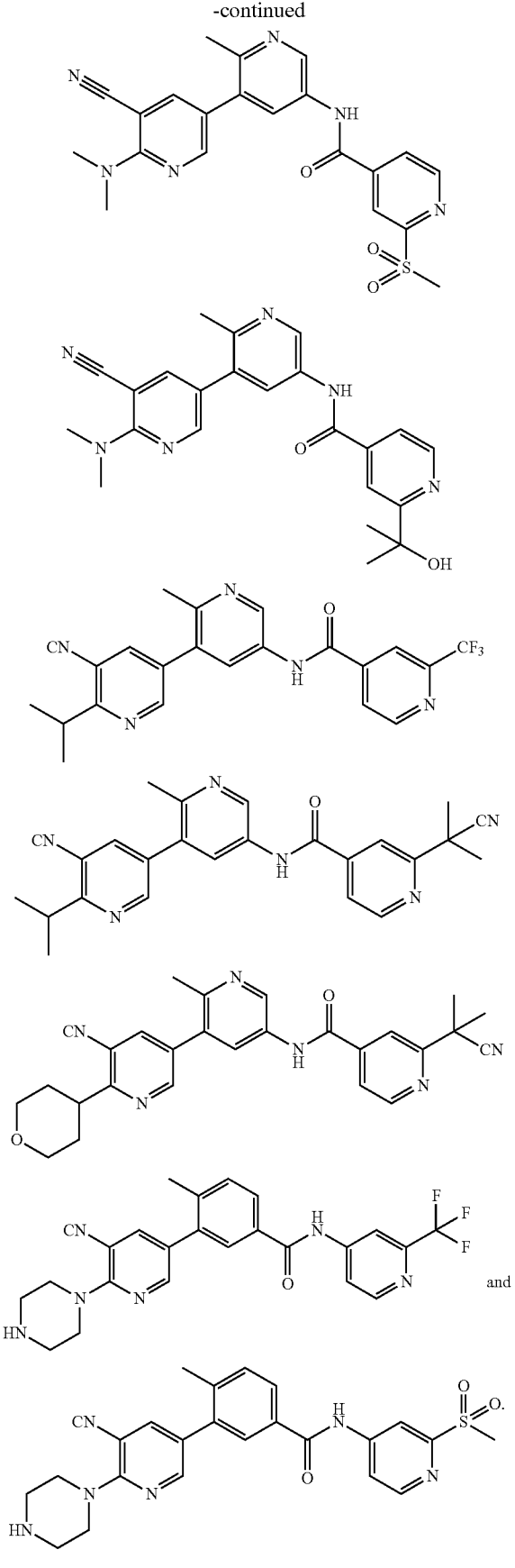
6. The compound of claim 1 selected from:
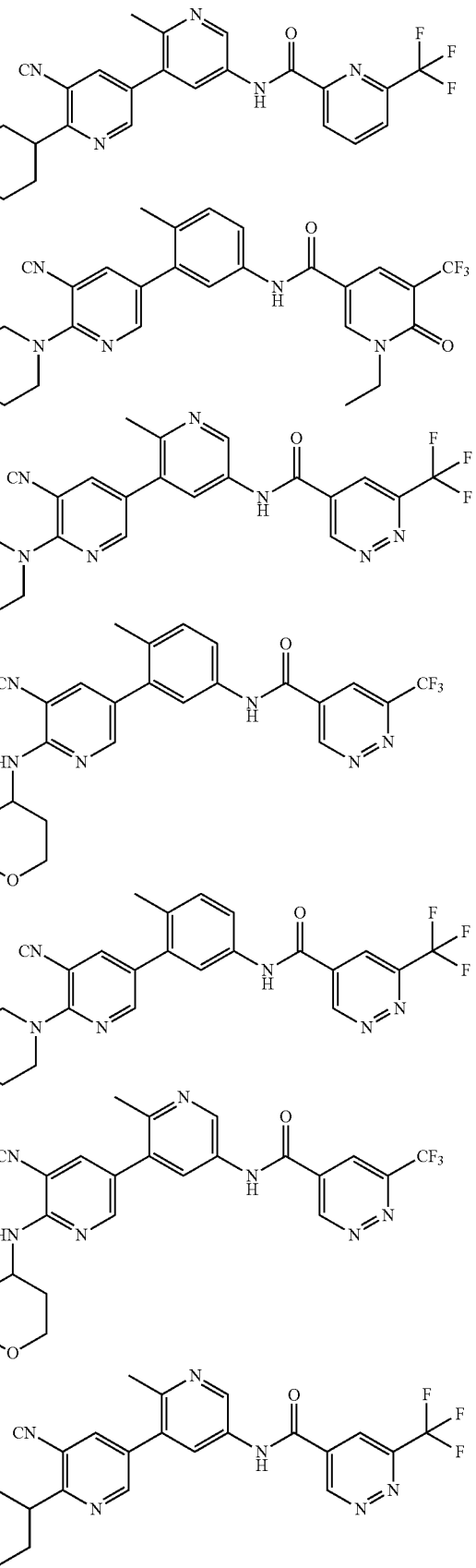

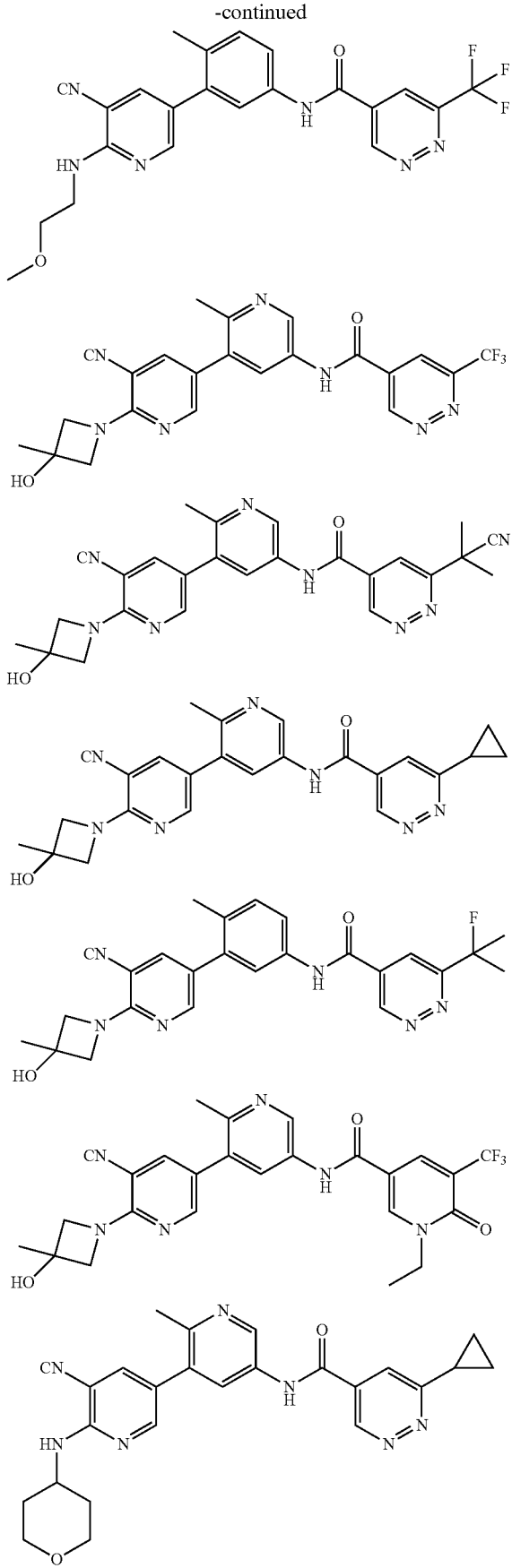
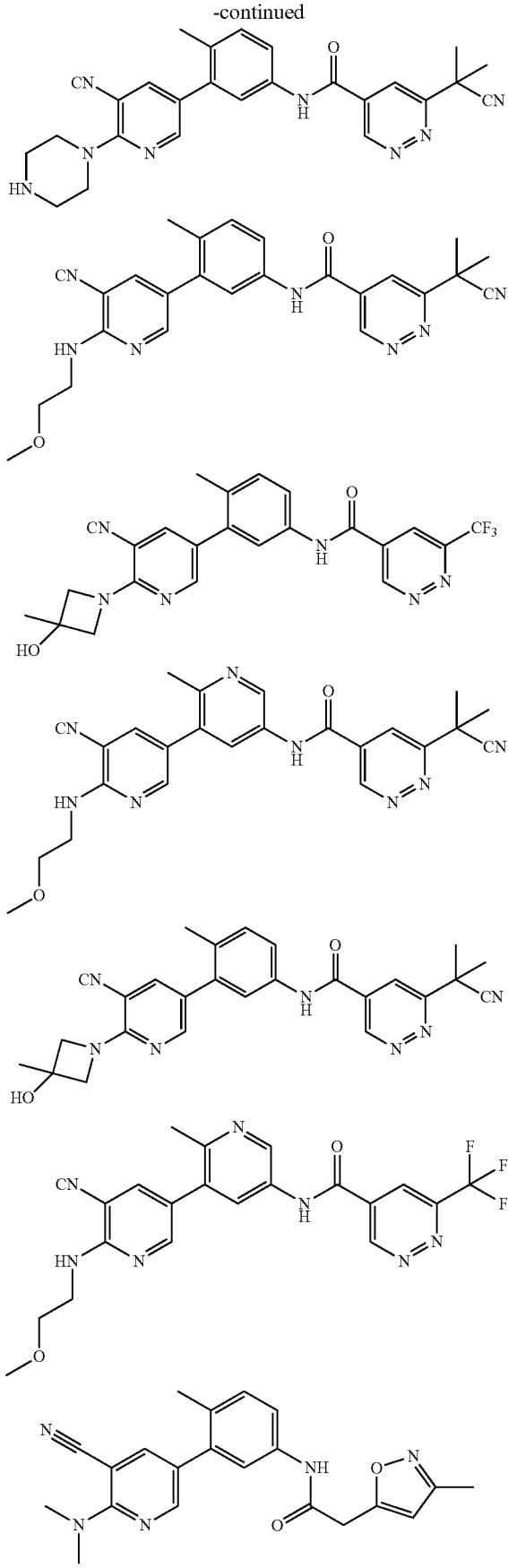

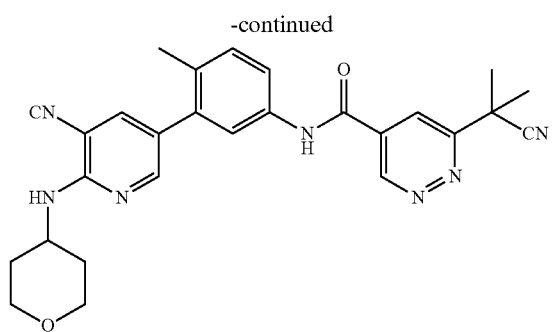
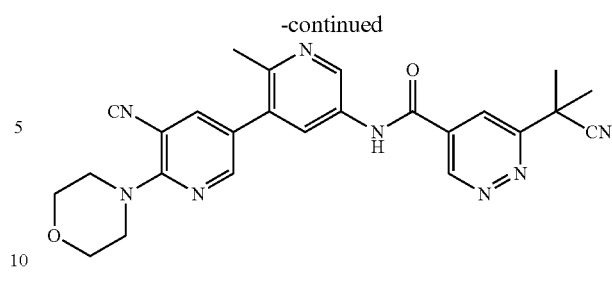
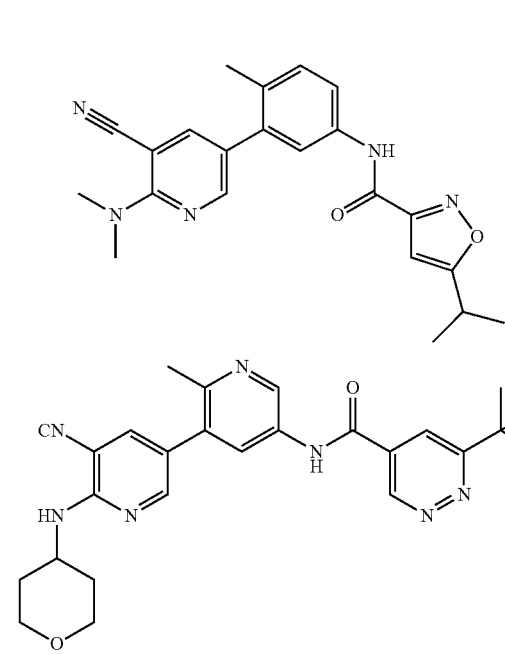
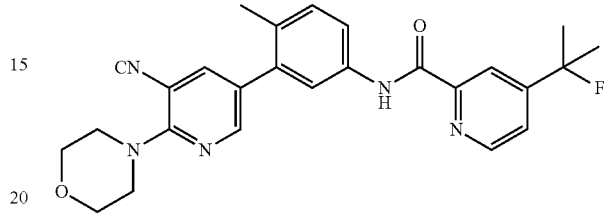
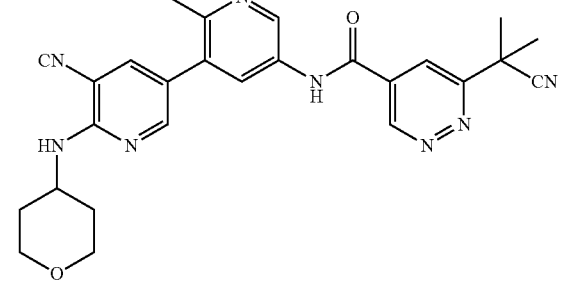
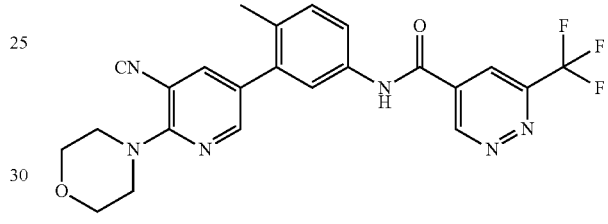
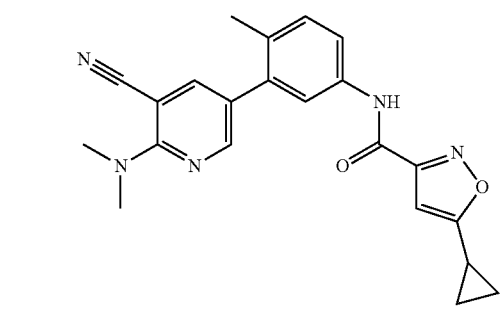
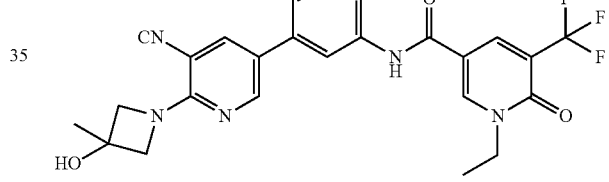
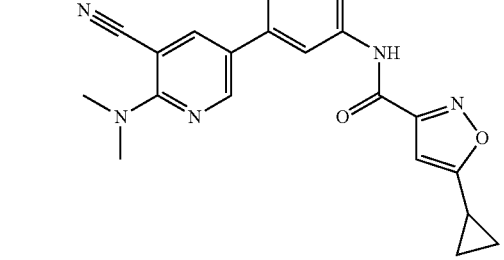
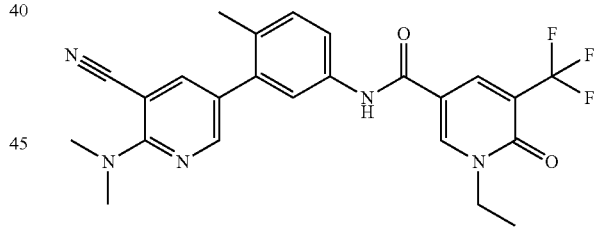
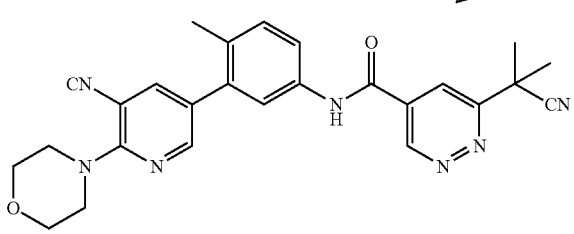
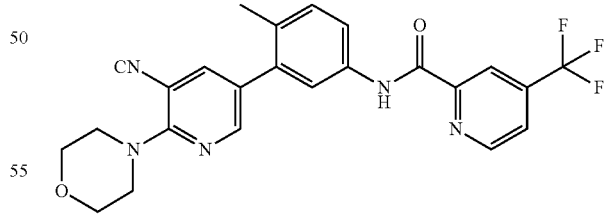
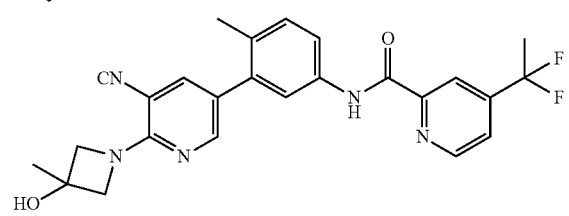
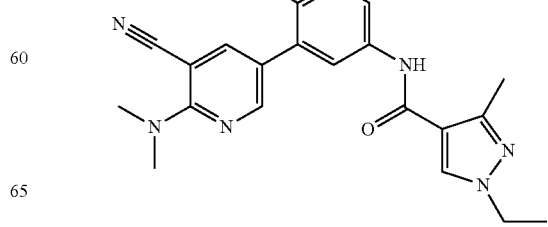

227
-continued
228
-continued
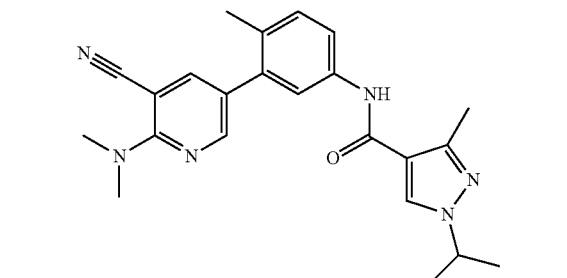
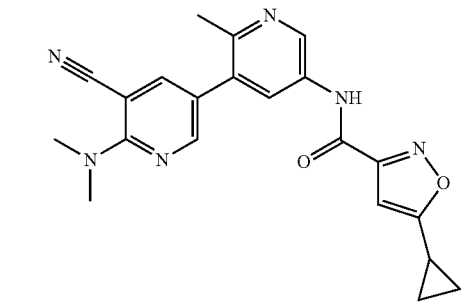
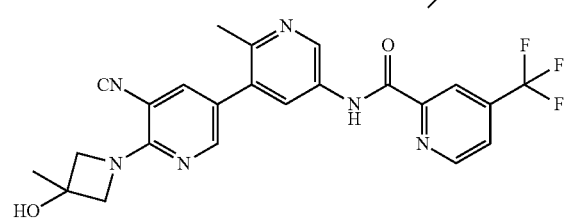
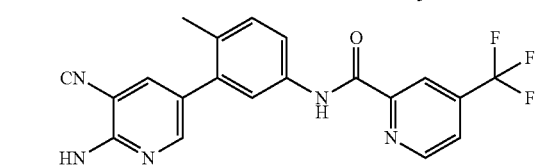
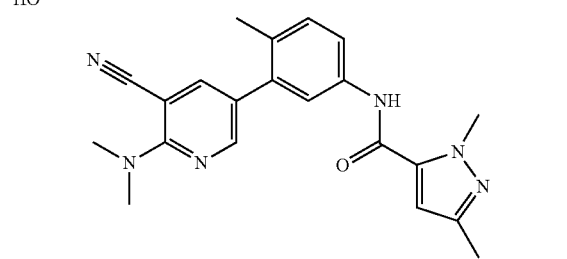
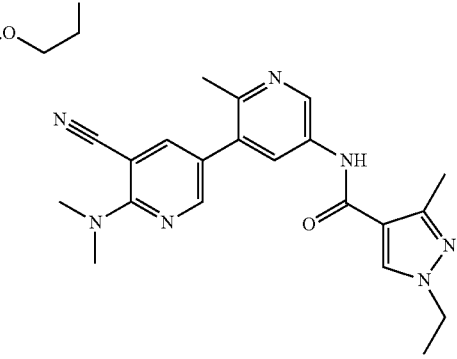
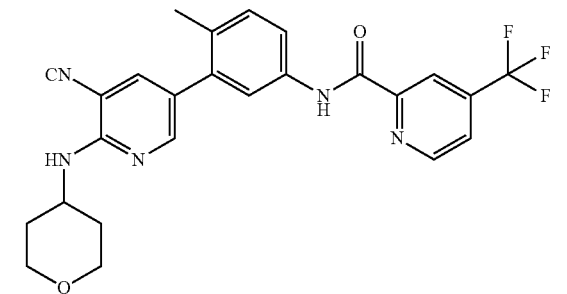
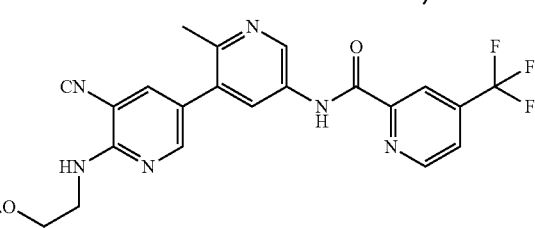

229
-continued
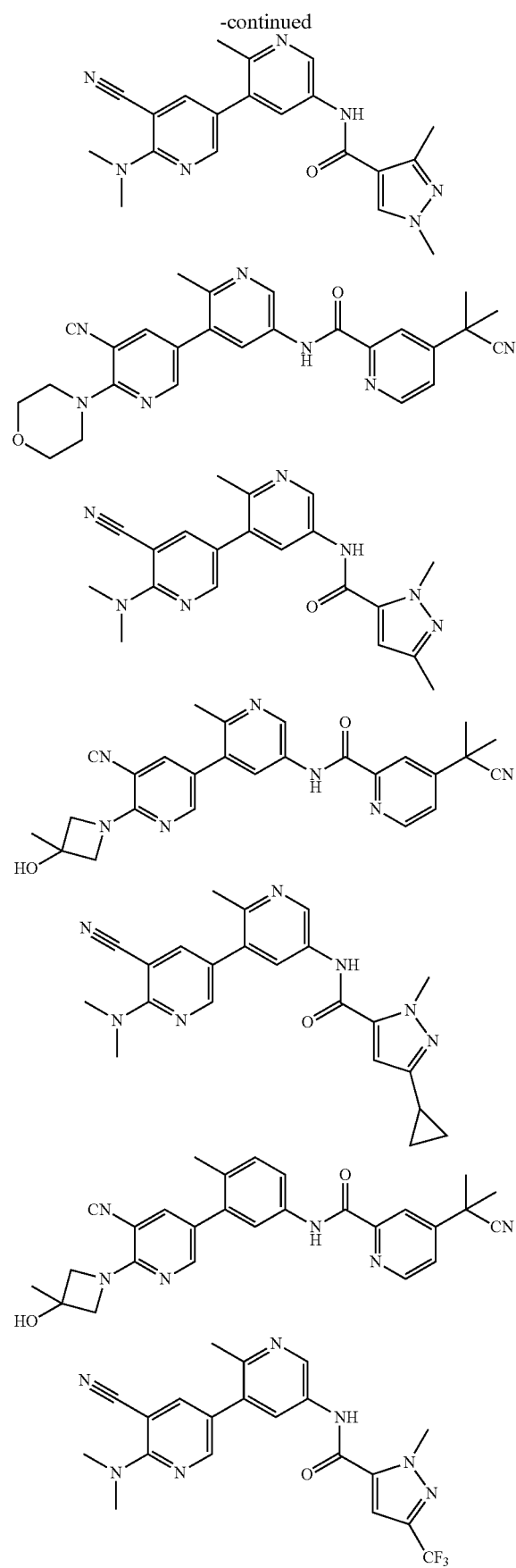
230
-continued
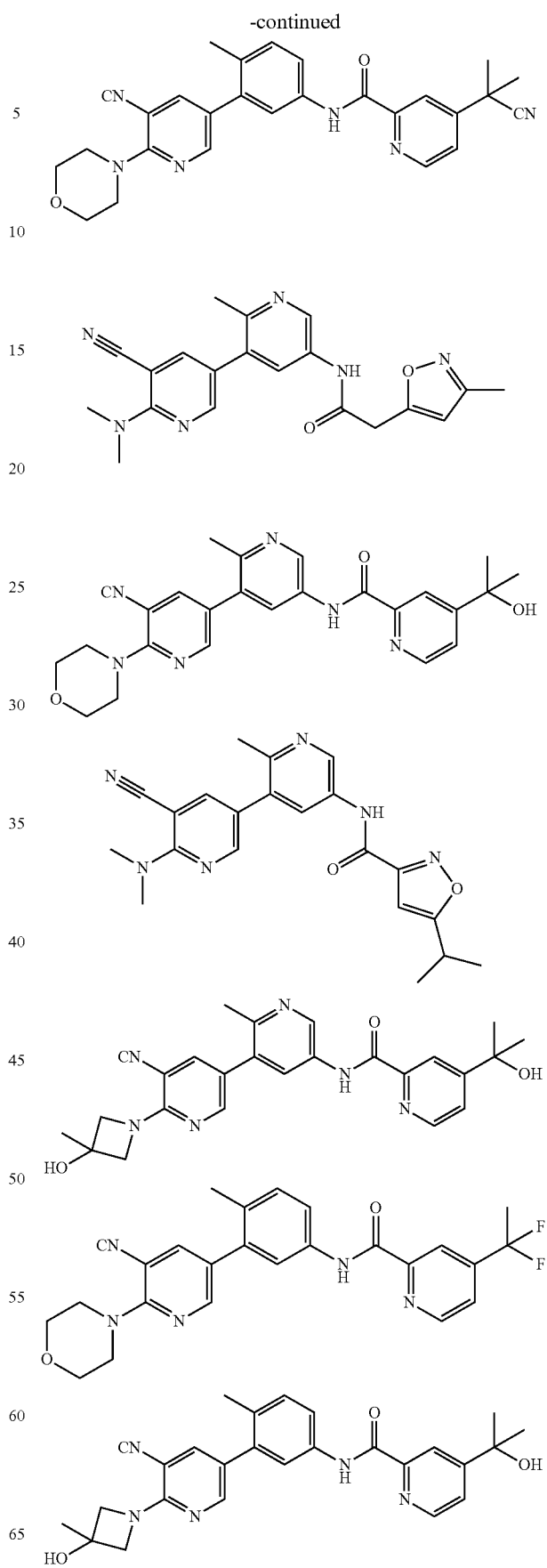

-continued

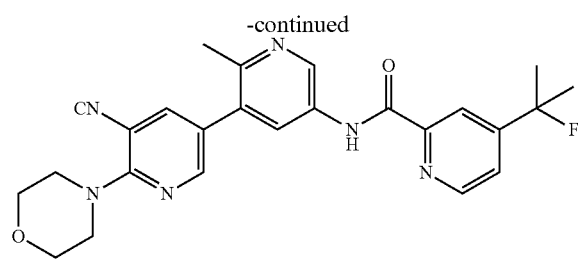

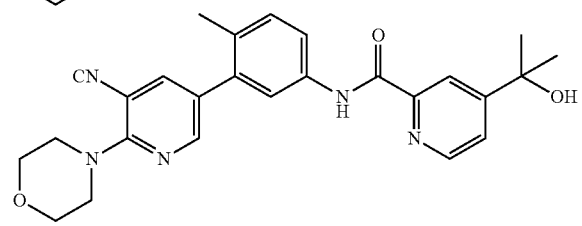

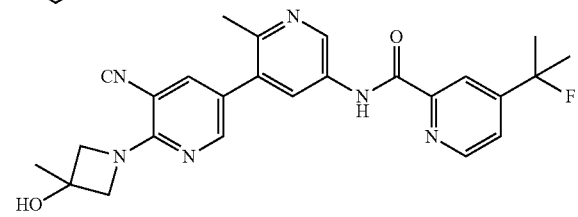

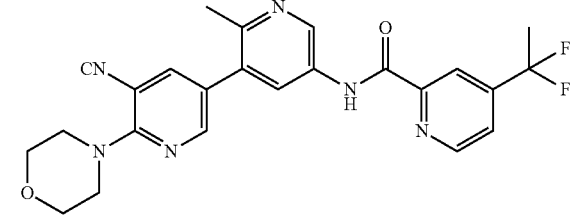

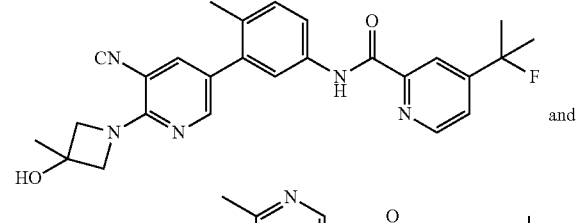

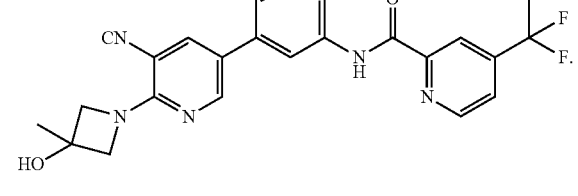

7. A pharmaceutical composition comprising a compound of claim 1 or a pharmaceutically acceptable salt thereof and one or more pharmaceutically acceptable carriers.

8. A combination comprising a therapeutically effective amount of a compound according to claim 1 or a pharmaceutically acceptable salt thereof and one or more therapeutically active co-agents.

9. A method of treating melanoma, comprising administering to a subject in need thereof a therapeutically effective amount of a compound of claim 1 or a pharmaceutically acceptable salt thereof.

10. A compound, or pharmaceutically acceptable salt thereof, selected from:

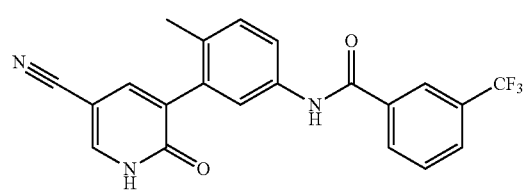

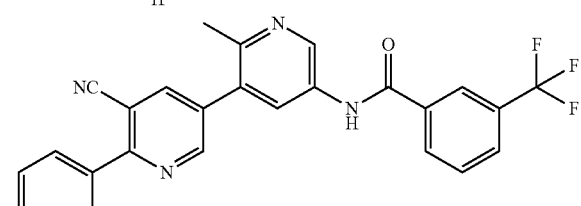

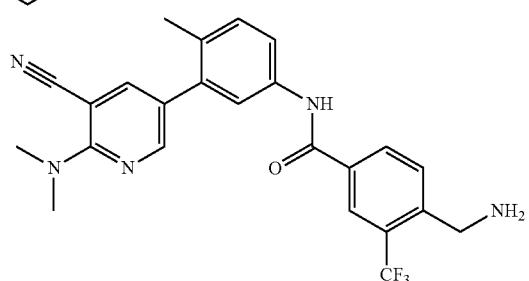

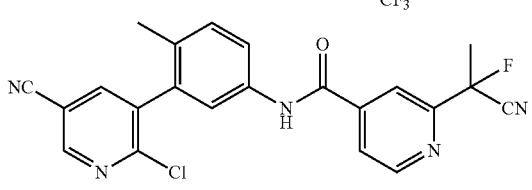

and

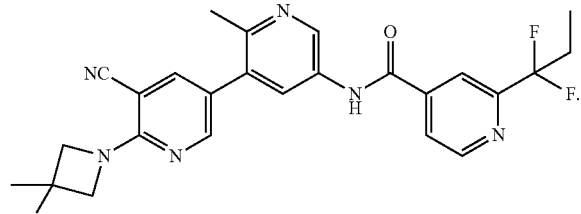

* * * * *